(12) United States Patent
Zhou et al.

(10) Patent No.: US 11,987,575 B2
(45) Date of Patent: May 21, 2024

(54) TRICYCLIC COMPOUNDS AS BCR-ABL INHIBITORS

(71) Applicants: ASCENTAGE PHARMA (SUZHOU) CO., LTD., Suzhou (CN); ASCENTAGE PHARMA GROUP CORP LIMITED

(72) Inventors: Yunlong Zhou, Suzhou (CN); Guozhi Tang, Suzhou (CN); Chao Li, Suzhou (CN); Fang Liu, Suzhou (CN); Yu Jing, Suzhou (CN); Renlin Wang, Suzhou (CN)

(73) Assignees: ASCENTAGE PHARMA (SUZHOU) CO., LTD. (CN); ASCENTAGE PHARMA GROUP CORP, LIMITED (CN)

( * ) Notice: Subject to any disclaimer, the term of this patent is extended or adjusted under 35 U.S.C. 154(b) by 293 days.

(21) Appl. No.: 17/262,586

(22) PCT Filed: Jul. 29, 2020

(86) PCT No.: PCT/CN2020/105522
§ 371 (c)(1),
(2) Date: Jan. 22, 2021

(87) PCT Pub. No.: WO2021/018195
PCT Pub. Date: Feb. 4, 2021

(65) Prior Publication Data
US 2022/0306608 A1     Sep. 29, 2022

(30) Foreign Application Priority Data

Jul. 29, 2019    (WO) ............... PCT/CN2019/098227
Apr. 27, 2020    (WO) ............... PCT/CN2020/087277

(51) Int. Cl.
| | |
|---|---|
| *C07D 403/04* | (2006.01) |
| *A61P 35/02* | (2006.01) |
| *C07D 209/94* | (2006.01) |
| *C07D 401/04* | (2006.01) |
| *C07D 401/14* | (2006.01) |
| *C07D 403/14* | (2006.01) |
| *C07D 405/14* | (2006.01) |
| *C07D 413/14* | (2006.01) |
| *C07D 417/14* | (2006.01) |
| *C07D 471/04* | (2006.01) |
| *C07D 495/04* | (2006.01) |

(52) U.S. Cl.
CPC ............ *C07D 403/04* (2013.01); *A61P 35/02* (2018.01); *C07D 209/94* (2013.01); *C07D 401/04* (2013.01); *C07D 401/14* (2013.01); *C07D 403/14* (2013.01); *C07D 405/14* (2013.01); *C07D 413/14* (2013.01); *C07D 417/14* (2013.01); *C07D 471/04* (2013.01); *C07D 495/04* (2013.01)

(58) Field of Classification Search
CPC .. C07D 403/04; C07D 209/94; C07D 401/04; C07D 401/14; C07D 403/14; C07D 405/14; C07D 413/14; C07D 417/14; C07D 471/04; C07D 495/04; A61P 35/02
See application file for complete search history.

(56) References Cited

U.S. PATENT DOCUMENTS 9,278,981 B2 *   3/2016   Furet ............... C07D 401/04
2016/0102077 A1   4/2016   Boral et al.

FOREIGN PATENT DOCUMENTS

| WO | WO00/62778 A1 | 10/2000 |
| WO | WO13/171641 A1 | 11/2013 |
| WO | WO19/119145 A1 | 6/2019 |

OTHER PUBLICATIONS

Skorski, Tomasz BCR-ABL1 Kinase: Hunting an Elusive Target with New Weapons. Chem Biol., vol. 18, Nov. 23. 2011 pp. 1352-1353.
Wylie, Andrew A., et al. The allosteric inhibitor ABL001 enables dual targeting of BCR-ABL1. Nature, vol. 543, Mar. 30, 2017, pp. 1-10 doi: 10.1038/nature21702.
Zhang, Jianming, et al. Targeting Bcr-Abl by combining allosteric with ATP-binding-site-inhibitors. Nature, vol. 463, No. 7280, Jan. 28, 2010 pp. 501-507, doi: 10.1038/nature08675.

* cited by examiner

*Primary Examiner* — Bahar Craigo
*Assistant Examiner* — Manahil Mirghani Ali Abdalhameed
(74) *Attorney, Agent, or Firm* — Honigman LLP; Lucy Yang; Jonathan P. O'Brien

(57) ABSTRACT

The present disclosure provides compounds represented by Formula I, or an enantiomer or diastereomer, or a pharmaceutically acceptable salt thereof, wherein X, Y, Z, L, Ar, $R^1$, $R^2$, $R^3$, $R^4$, $R^5$, $R^6$, m, and p are defined herein. Compounds of Formula I are BCR-ABL inhibitors. BCR-ABL inhibitors are useful for the treatment of cancer and other diseases.

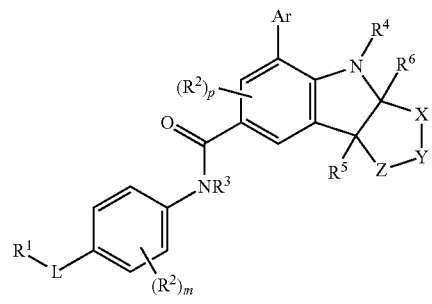

30 Claims, No Drawings

TRICYCLIC COMPOUNDS AS BCR-ABL INHIBITORS

FIELD OF THE INVENTION

The present disclosure provides heterocyclic compounds that inhibit the enzymatic activity of the Abelson protein (ABL1), Abelson-related protein (ABL2), and related chimeric proteins, in particular BCR-ABL1. The disclosure also provides processes for preparing these compounds, pharmaceutical compositions comprising these compounds, and methods of using these compounds to treat diseases, disorders, or conditions responsive to inhibition of BCR-ABL1.

BACKGROUND OF THE INVENTION

Abelson murine leukemia viral oncogene homolog 1 also known as ABL1 is a protein that, in humans, is encoded by the ABL1 gene located on chromosome 9. The ABL1 proto-oncogene encodes a cytoplasmic and nuclear protein tyrosine kinase that is involved in processes of cell differentiation, cell division, cell adhesion and stress response. Activity of ABL1 protein is self-inhibited by its SH3 domain, and deletion of the SH3 domain turns ABL1 into an oncogene. The hallmark of chronic myelogenous leukemia (CML) is the Philadelphia chromosome (Ph), formed by the t(9;22) translocation which causes the expression of the BCR-ABL tyrosine kinase fusion gene. This fusion gene encodes the chimeric BCR-ABL protein, that loses the self-regulatory of the SH3 domain.

Although there are effective drugs in the treatment of CML by inhibiting the tyrosine kinase activity of BCR-ABL via an ATP-competitive mechanism, such as Imatinib, Nilotinib, Dasatinib, and Bosutinib, some patients relapse due to the emergence of drug-resistant clones, in which mutations in the SH1 comprise inhibitor binding. Thus compounds that inhibit the BCR-ABL protein activities via a different binding mode have the potential to overcome the resistance and expanding the treatment choice for AML patients.

Agents targeting the myristoyl binding site (referred to as allosteric inhibitors) have potential for the treatment of BCR-ABL disorders (Zhang et al., Nature, 2010, 463:501-6). Potentially, an allosteric inhibitor that binds to the myristoyl binding site might be useful to prevent the emergence of drug resistance from ATP inhibitors. More importantly, a combination treatment using both types of inhibitors can be developed for the treatment of BCR-ABL related disorders (Wylie et al., Nature, 2017, 543: 733-7).

There exists a need in the art for BCR-ABL inhibitors.

SUMMARY OF THE INVENTION

In one aspect, the present disclosure provides novel tricyclic compounds that are BCR-ABL inhibitors.

In some embodiments, the present disclosure provides a compound of formula I:

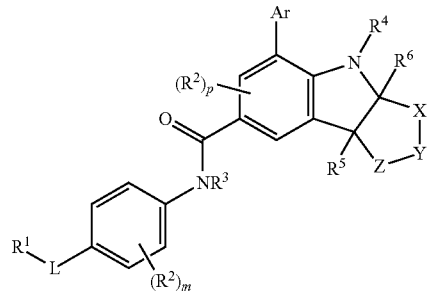

or an enantiomer or diastereomer, or a pharmaceutically acceptable salt thereof, wherein X, Y, Z, L, Ar, $R^1$, $R^2$, $R^3$, $R^4$, $R^5$, $R^6$, m and p are defined herein.

In some embodiments, the present disclosure provides a compound of formula II, IIa, or IIb as defined herein.

In some embodiments, the present disclosure provides a compound of formula IIA.

In some embodiments, the present disclosure provides a compound of formulas from IIA-1 to IIA-22 as defined herein.

In some embodiments, the present disclosure provides a compound of formula IIB.

In some embodiments, the present disclosure provides a compound of formulas from IIB-1 to IIB23 as defined herein.

In some embodiments, the present disclosure provides a compound of formula III, IIIA, IIIB, or IIID as defined herein.

In some embodiments, the present disclosure provides a compound of formulas from IIIB-1 to IIIB6 as defined herein.

In some embodiments, the present disclosure provides a compound of formulas from IIIC-1 to IIIC-4 as defined herein.

In some embodiments, the present disclosure provides a compound of formulas from IIB-1 to IIB-24 as defined herein.

In some embodiments, the present disclosure provides a compound of formula III, IIIA, IIIB, IIIC, or IIID as defined herein.

In some embodiments, the present disclosure provides a compound of formulas from IIIB-1 to IIIB-7 as defined herein.

In some embodiments, the present disclosure provides a compound of formulas from IIIC-1 to IIIC-6 as defined herein.

In some embodiments, the present disclosure provides a compound of formulas from IIID-1 to IIID-6 as defined herein.

In some embodiments, the present disclosure provides a method of treating or preventing conditions or diseases associated with enzymatic activity of ABL1 or ABL2, and in particular BCR-ABL1.

In some embodiments, the present disclosure provides a medical use for preventing conditions or diseases associated with enzymatic activity of ABL1 or ABL2, and in particular BCR-ABL1.

In some embodiments, the conditions or diseases associated with enzymatic activity of ABL1 or ABL2, in particular BCR-ABL1, are unwanted cell proliferations.

In some embodiments, the conditions or diseases associated with enzymatic activity of ABL1 or ABL2, in particular BCR-ABL1, are cancer.

In some embodiments, the conditions or diseases associated with enzymatic activity of ABL1 or ABL2, in particular BCR-ABL1, are chronic myeloid leukemia.

In some embodiments, the present disclosure provides a method of inhibiting BCR-ABL for therapeutic benefits in a subject in need thereof.

In some embodiments, the present disclosure provides a pharmaceutical composition comprising a compound of the disclosure and an excipient and/or pharmaceutically acceptable carrier.

In some embodiments, the present disclosure provides a pharmaceutical composition comprising a compound of the disclosure and an excipient and/or pharmaceutically acceptable carrier for treating or preventing conditions or diseases associated with enzymatic activity of ABL1 or ABL2, and in particular BCR-ABL1.

In some embodiments, the present disclosure provides methods of preparing compounds and intermediates of the present disclosure.

It shall be understood that both the foregoing summary and the following description are exemplary and explanatory only, and are not restrictive of the invention as claimed.

DETAILED DESCRIPTION OF THE INVENTION

As used herein, all technical and scientific terms have the same meaning as commonly understood by one of ordinary skill in the art to which this invention belongs. All publications, patent applications, patents, and other references mentioned herein are incorporated by reference in their entirety.

Definitions

The term "disease" or "condition" refers to disturbances and/or anomalies that are regarded as being pathological conditions or functions, and that can manifest themselves in the form of particular signs, symptoms, and/or malfunctions. As demonstrated below, compounds of the present disclosure are inhibitors of BCR-ABL and can be used in treating or preventing diseases and conditions wherein inhibition of BCR-ABL provides a benefit.

The terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a compound of the present disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

The terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "BCR-ABL" refers to the fusion gene formed when pieces of chromosomes 9 and 22 break off and trade places. The ABL gene from chromosome 9 joins to the BCR gene on chromosome 22, to form the BCR-ABL fusion gene. The changed chromosome 22 with the fusion gene on it is called the Philadelphia chromosome. The BCR-ABL fusion gene is found in patients having cancer. For example, the BCR-ABL fusion gene is found in most patients with chronic myelogenous leukemia (CML), and in some patients with acute lymphoblastic leukemia (ALL) or acute myelogenous leukemia (AML). This fusion gene encodes the chimeric BCR-ABL protein.

The term "a disease or condition wherein inhibition of BCR-ABL provides a benefit" and the like refers to a disease or condition in which BCR-ABL is important or necessary, e.g., for the onset, progress, expression of that disease or condition, or a disease or a condition which is known to be treated by a BCR-ABL inhibitor. Examples of such conditions include, but are not limited to, a cancer, a neurodegenerative disorder, muscular dystrophy, an autoimmune disease, an inflammatory disease, a viral infection, or a prion disease. One of ordinary skill in the art is readily able to determine whether a compound of the present disclosure treats a disease or condition mediated by a BCR-ABL inhibitor for any particular cell type, for example, by assays which conveniently can be used to assess the activity of particular compounds. See, e.g., Yue and Turkson, *Expert Opinion Invest Drugs* 18:45-56 (2009).

The term "therapeutically effective amount" or "effective dose" refers to an amount of the active ingredient(s) that is(are) sufficient, when administered by a method of the disclosure, to efficaciously deliver the active ingredient(s) for the treatment of a condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The terms "concurrent administration," "administered in combination," "simultaneous administration," and similar phrases refer to that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a compound of the present disclosure can be administered at the same time or sequentially in any order at different points in time as a second therapeutic agent. A compound of the present disclosure and the second therapeutic agent can be administered separately, in any appropriate form and by any suitable route. When a compound of the present disclosure and the second therapeutic agent are not administered concurrently, it is understood that they can be administered in any order to a subject in need thereof. For example, a compound of the present disclosure can be administered prior to (e.g., 5 minutes, 15 minutes, 30 minutes, 45 minutes, 1 hour (h), 2 h, 4 h, 6 h, 12 h, 24 h, 48 h, 72 h, 96 h, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 h, 4 h, 6 h, 12 h, 24 h, 48 h, 72 h, 96 h, 1 week, 2 weeks, 3 weeks, 4 weeks, 5 weeks, 6 weeks, 8 weeks, or 12 weeks after) the administration of a second therapeutic agent treatment modality (e.g., radiotherapy), to a subject in need thereof. In various embodiments, a compound of the present disclosure and the second therapeutic agent are administered 1 minute apart, 10 minutes apart, 30 minutes apart, less than 1 hour apart, 1 hour apart, 1 hour to 2 h apart, 2 h to 3 h apart, 3 h to 4 h apart, 4 h to 5 h apart, 5 h to 6 h apart, 6 h to 7 h apart, 7 h to 8 h apart, 8 h to 9 h apart, 9 h to 10 h apart, 10 h to 11 h apart, 11 h to 12 h apart, no more than 24 h apart or no more than 48 h apart. In one embodiment, the components of the combination therapies are administered at about 1 minute to about 24 h apart.

The terms "a," "an," and "the" are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "halo" refers to —Cl, —F, —Br, or —I.

The term "alkyl" refers to a straight- or branched-chain aliphatic hydrocarbon. The chain may contain an indicated number of carbon atoms. For example, $C_1$-$C_{10}$ or $C_{1-10}$ indicates that the group may have from 1 to 10 (inclusive) carbon atoms in it; $C_1$-$C_6$ or $C_{1-6}$ indicates that the group may have from 1 to 6 (inclusive) carbon atoms in it. If not otherwise indicated, an alkyl group contains from 1 to about 20 carbon atoms. In some aspects, alkyl groups have 1 to about 10 carbon atoms. In some aspects, alkyl groups ("lower alkyl") have 1 to 8, 1 to 6, or 1 to 3 carbon atoms in the chain. Examples may include, but are not limited to methyl, ethyl, propyl, isopropyl, butyl, sec-butyl, iso-butyl, tert-butyl, pentyl, neopentyl, 2-methylbutyl, 1,1-dimethylpropyl, hexyl, heptyl, octyl, nonyl, decyl, and docecyl. An alkyl may be substituted with 0, 1, 2, 3, or 4 substituents selected from the group consisting of halo, —OH, —CN, —NH$_2$, —NO$_2$, —SO$_2$(C$_{1-6}$alkyl), —NH(C$_{1-6}$alkyl), —N(C$_{1-6}$alkyl)$_2$, —C$_{1-6}$alkyl, —C$_{1-6}$alkoxy, -cycloalkyl, -heterocycloalkyl, aryl, and heteroaryl. In some embodiments, the alkyl group is unsubstituted or not optionally substituted. In some embodiments, the alkyl group is substituted with 1, 2, 3, or 4 substituents selected from the group consisting of halo, —OH, —CN, —NH$_2$, —NO$_2$, —SO$_2$(C$_{1-6}$alkyl), —C$_{1-6}$alkoxy, -cycloalkyl, -heterocycloalkyl, aryl, and heteroaryl. In some embodiments, the —C$_{1-6}$alkyl, —C$_{1-6}$alkoxy, -cycloalkyl, -heterocycloalkyl, aryl, and heteroaryl may be further substituted with 0, 1, 2, or 3 substituents selected from the group consisting of halo, —OH, —CN, —NH$_2$, —NO$_2$, —SO$_2$(C$_{1-6}$alkyl), —CO(C$_{1-6}$alkyl), —NH(C$_{1-6}$alkyl), —N(C$_{1-6}$alkyl)$_2$, —C$_{1-6}$alkyl, -cycloalkyl, -heterocycloalkyl, and —C$_{1-6}$alkoxy. In some embodiments, the alkyl group is substituted with 1, 2, or 3 F or Cl. In some embodiments, the alkyl group is substituted with two —F and one Cl such that the alkyl group is difluorochloromethyl.

The term "substituted with 0, 1, 2, 3, or 4 substituents" refers to that a group may be unsubstituted when the group is substituted with 0 substituent, or that the group is substituted with 1, 2, 3, or 4 substituents. The term also means that a group may be optionally substituted with 1, 2, 3, or 4 substituents. The term "optionally substituted" refers to that a group may be unsubstituted, or substituted with one or more of the indicated substituents.

The term "alkoxy" refers to an alkyl group attached to a terminal oxygen atom. Non-limiting exemplary alkoxy groups include methoxy, ethoxy, and tert-butoxy. An alkoxy group can be unsubstituted or substituted with 1, 2, 3, or 4 substituents selected from the group consisting of halo, —OH, —CN, —NH$_2$, —NO$_2$, —SO$_2$(C$_{1-6}$alkyl), —NH(C$_{1-6}$alkyl), —N(C$_{1-6}$alkyl)$_2$, —C$_{1-6}$alkyl, —C$_{1-6}$alkoxy, -cycloalkyl, -heterocycloalkyl, aryl, and heteroaryl. In some embodiments, the —C$_{1-6}$alkyl, —C$_{1-6}$alkoxy, -cycloalkyl, -heterocycloalkyl, aryl, and heteroaryl may be further substituted with 0, 1, 2, or 3 substituents selected from the group consisting of halo, —OH, —CN, —NH$_2$, —NO$_2$, —NH(C$_{1-6}$alkyl), —N(C$_{1-6}$alkyl)$_2$, —C$_{1-6}$alkyl, -cycloalkyl, -heterocycloalkyl, and —C$_{1-6}$alkoxy.

The term "cycloalkyl" refers to saturated and partially unsaturated, e.g., containing one or two double bonds, monocyclic, bicyclic, or tricyclic aliphatic hydrocarbons containing three to twelve carbon atoms, i.e., a $C_{3-12}$ cycloalkyl, or the number of carbons designated, e.g., a $C_3$ cycloalkyl such a cyclopropyl, a $C_4$ cycloalkyl such as cyclobutyl, etc. In one embodiment, the cycloalkyl is bicyclic, i.e., it has two rings. In another embodiment, the cycloalkyl is monocyclic, i.e., it has one ring. A cycloalkyl group may be unsubstituted or substituted with 1, 2, 3, or 4 substituents selected from the group consisting of halo, —OH, —CN, —NH$_2$, —NO$_2$, —SO$_2$(C$_{1-6}$alkyl), —NH(C$_{1-6}$alkyl), —N(C$_{1-6}$alkyl)$_2$, —C$_{1-6}$alkyl, —C$_{1-6}$alkoxy, -cycloalkyl, -heterocycloalkyl, aryl, and heteroaryl. In some embodiments, the —C$_{1-6}$alkyl, —C$_{1-6}$alkoxy, -cycloalkyl, -heterocycloalkyl, aryl, and heteroaryl may be further substituted with 0, 1, 2, or 3 substituents selected from the group consisting of halo, —OH, —CN, —NH$_2$, —NO$_2$, —NH(C$_{1-6}$alkyl), —N(C$_{1-6}$alkyl)$_2$, —C$_{1-6}$alkyl, -cycloalkyl, -heterocycloalkyl, and —C$_{1-6}$alkoxy.

The term "aryl" refers to an aromatic ring system having six to fourteen carbon atoms, i.e., $C_6$-$C_{14}$aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl. An aryl group may be unsubstituted or substituted with 1, 2, 3, or 4 substituents selected from the group consisting of halo, —OH, —CN, —NH$_2$, —NO$_2$, —SO$_2$(C$_{1-6}$alkyl), —NH(C$_{1-6}$alkyl), —N(C$_{1-6}$alkyl)$_2$, —C$_{1-6}$alkyl, —C$_{1-6}$alkoxy, -cycloalkyl, -heterocycloalkyl, aryl, and heteroaryl. In some embodiments, the —C$_{1-6}$alkyl, —C$_{1-6}$alkoxy, -cycloalkyl, -heterocycloalkyl, aryl, and heteroaryl may be further substituted with 0, 1, 2, or 3 substituents selected from the group consisting of halo, —OH, —CN, —NH$_2$, —NO$_2$, —NH(C$_{1-6}$alkyl), —N(C$_{1-6}$alkyl)$_2$, —C$_{1-6}$alkyl, -cycloalkyl, -heterocycloalkyl, and —C$_{1-6}$alkoxy.

The term "heteroaryl" refers to monocyclic and bicyclic aromatic ring systems containing five to fourteen ring atoms including carbon, zero, one, two, three, or four heteroatoms. Each heteroatom is independently oxygen, sulfur, or nitrogen. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl (e.g., thien-2-yl and thien-3-yl), benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrazinyl, pyrimidinyl (e.g., pyrimidin-2-yl, pyrimidin-4-yl, and pyrimidin-5-yl), pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, O-carbolinyl, phenanthridinyl, acridinyl, pyrimidinyl, phenanthrolinyl, phenazinyl, thiazolyl (e.g., thiazol-2-yl, thiazol-4-yl, and thiazol-5-yl), isothiazolyl (e.g., isothiazol-3-yl, isothiazol-4-yl, and isothiazol-5-yl), phenothiazolyl, oxazolyl (e.g., oxazol-2-yl, oxazol-4-yl, and oxazol-5-yl), isoxazolyl (e.g., isoxazol-3-yl, isoxazol-4-yl, and isoxazol-5-yl), furazanyl, phenoxazinyl, triazolyl, triazinyl, and tetrazolyl. The term heteroaryl also includes N-oxides. A non-limiting exemplary N-oxide is pyridyl N-oxide.

A heteroaryl group may be unsubstituted or substituted with 1, 2, 3, or 4 substituents selected from the group consisting of halo, —OH, —CN, —NH$_2$, —NO$_2$, —SO$_2$(C$_{1-6}$alkyl), —CO(C$_{1-6}$alkyl), —NH(C$_{1-6}$alkyl), —N(C$_{1-6}$alkyl)$_2$, —C$_{1-6}$alkyl, —C$_{1-6}$alkoxy, -cycloalkyl, -heterocycloalkyl, aryl, and heteroaryl. In some embodiments, the —C$_{1-6}$alkyl, —C$_{1-6}$alkoxy, -cycloalkyl, -heterocycloalkyl, aryl, and heteroaryl may be further substituted with 0, 1, 2, or 3 substituents selected from the group consisting of halo, —OH, —CN, —NH$_2$, —NO$_2$, —NH(C$_{1-6}$alkyl), —N(C$_{1-6}$alkyl)$_2$, —C$_{1-6}$alkyl, -cycloalkyl, -heterocycloalkyl, and —C$_{1-6}$alkoxy.

The term "heterocycloalkyl" refers to saturated and partially unsaturated, e.g., containing one or two double bonds, monocyclic or bicyclic ring structure containing three to fourteen ring members, in which zero, one, two, or three of the ring atoms is a heteroatom. Each heteroatom is independently oxygen, sulfur, or nitrogen. In one embodiment, the heterocycloalkyl has three heteroatoms. In another embodiment, the heterocycloalkyl has two heteroatoms. In another embodiment, the heterocycloalkyl has one heteroatom. Non-limiting exemplary heterocycloalkyl groups include thiacyclohexanyl, oxiranyl, aziridinyl, azetidinyl, oxetanyl and thietanyl, oxazinyl, oxetanyl, azetidinyl, thietanyl, dihydrofuranyl, tetrahydrofuranyl, tetrahydropyranyl, tetrahydrothiophenyl, dihydrothiophenyl, tetrahydro-2H-pyran, dihydropyranyl, dioxanyl, 1,3-dioxolanyl, 1,4-dithianyl, hexahydropyrimidine, pyrrolidinyl, dihydropyrrolyl, morpholinyl, piperazinyl, piperidinyl, 2H-pyranyl, 4H-pyranyl, pyrazolidinyl, pyrazolinyl, tetrahydropyridinyl, tetrahydrothiopyranyl, thiomorpholinyl, thioxanyl, trithianyl, bicyclo[1.1.1]pentanyl, imidazolidinyl, dioxolanyl, oxathiolanyl and dithiolanyl, triazolinyl, oxadiazolinyl, thiadiazolinyl, dihydropyridinyl, thianyl, dioxanyl, triazinanyl, azepanyl, oxepanyl, thiepanyl, azocanyl, oxecanyl, and thiocanyl.

A heterocycloalkyl group may be unsubstituted or substituted with 1, 2, 3, or 4 substituents selected from the group consisting of halo, —OH, —CN, —NH$_2$, —NO$_2$, —SO$_2$(C$_{1-6}$alkyl), —CO(C$_{1-6}$alkyl), —NH(C$_{1-6}$alkyl), —N(C$_{1-6}$alkyl)$_2$, —C$_{1-6}$alkyl, —C$_{1-6}$alkoxy, -cycloalkyl, -heterocycloalkyl, aryl, and heteroaryl. In some embodiments, the —C$_{1-6}$alkyl, —C$_{1-6}$alkoxy, -cycloalkyl, -heterocycloalkyl, aryl, and heteroaryl may be further substituted with 0, 1, 2, or 3 substituents selected from the group consisting of halo, —OH, —CN, —NH$_2$, —NO$_2$, —NH(C$_{1-6}$alkyl), —N(C$_{1-6}$alkyl)$_2$, —C$_{1-6}$alkyl, -cycloalkyl, -heterocycloalkyl, and —C$_{1-6}$alkoxy.

When any two substituent groups or any two instances of the same substituent group are "independently" selected from a list of alternatives, the groups may be the same or different. For example, if $R^a$ and $R^b$ are each independently alkyl, —F, —NH$_2$, or —OH, then a molecule with two $R^a$ groups and two $R^b$ groups could have all groups be an alkyl group (e.g., four different alkyl groups). Alternatively, the first $R^a$ could be alkyl, the second $R^a$ could be —F, the first $R^b$ could be —OH, and the second $R^b$ could be —NH$_2$ (or any other substituents taken from the group). Alternatively, both $R^a$ and the first $R^b$ could be —F, while the second $R^b$ could be alkyl (i.e., some pairs of substituent groups may be the same, while other pairs may be different).

Compounds of the present disclosure may contain one or more asymmetric centers and may thus give rise to enantiomers, diastereomers, and other stereoisomeric forms. The present disclosure encompasses the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also encompassed by the present disclosure.

The term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer," "enantiomeric," and "enantiomerically" refer to one of two stereoisomers that are mirror images of one another. Furthermore, the molecules are non-superimposable on one another. This means that the molecules cannot be placed on top of one another.

The terms "diastereomer," "diastereomeric," and "diastereomerically" refer to one of stereoisomers that are not mirror images of one another and are non-superimposable on one another.

The term "racemic" refers to a mixture of equal parts of enantiomers and which the mixture is optically inactive. In one embodiment, compounds of the present disclosure are racemic.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

Compounds of the Disclosure

In some embodiments, the present disclosure provides a compound of formula I:

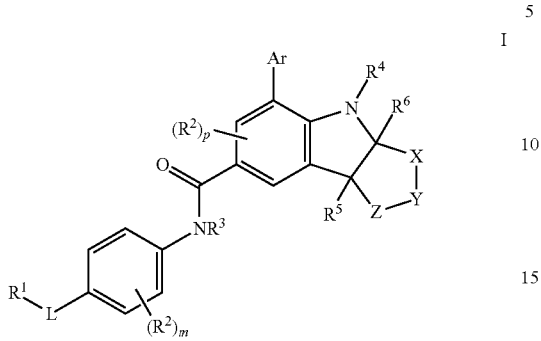

or an enantiomer or diastereomer, or a pharmaceutically acceptable salt thereof, wherein:
$R^1$ is —$C_{1-6}$alkyl, cycloalkyl, or heterocycloalkyl;
each $R^2$ is independently —H, -halo, —OH, —CN, —$NH_2$, —$NO_2$, —$C_{1-6}$alkyl, or —$C_{1-6}$alkoxy;
wherein m is 0, 1, 2, 3, or 4; p is 0, 1 or 2;
$R^3$ is —H or —$C_{1-6}$alkyl; $R^4$ is —H or —$C_{1-6}$alkyl; $R^5$ and $R^6$ are each independently —H or —$C_{1-6}$alkyl;
Ar is aryl or heteroaryl;
X is —$C(R^7R^{7'})$—; Y is —$C(R^8R^{8'})$—, —O—, —$N(R^{10})$—, —$C(=O)$—, —$SO_2$—, or —$SO_2R^{12}$; Z is —$[C(R^9R^{9'})]_n$;
wherein n is 1, 2, 3, or 4;
or X and Y together form —$(R^7)C=C(R^8)$—;
L is —S—, —O—, —$C(=O)R^{11}$—, —$C(=O)OR^{11}$—, —$N(R^{11})$—, —$C(=O)N(R^{11})$—, —$C(=O)N(R^{11})$—$C_{1-4}$alkyl-, —$N(R^{11})C(=O)$—, —$N(R^{11})C(=O)$—$C_{1-4}$alkyl-, —$SO_2N(R^{11})$—, or —$N(R^{11})SO_2$—;
each $R^7$, $R^{7'}$, $R^8$, $R^{8'}$, $R^9$, and $R^{9'}$ is independently selected from —H, —$C_{1-6}$alkyl, -cycloalkyl, -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1-C_6$ alkyl), —$C(=O)N(R^{12})_2$, —$SO_2R^{12}$, —$SO_2N(R^{12})_2$, -aryl, or -heteroaryl;
$R^{10}$ is —H, —$C_{1-6}$alkyl, -cycloalkyl, heterocycloalkyl, —$C(=O)R^{12}$, —$C(=O)OR^{12}$, —$C(=O)N(R^{12})_2$, —$SO_2R^{12}$, —$SO_2N(R^{12})_2$, aryl, or heteroaryl;
each $R^{11}$ is independently —H or —$C_{1-6}$alkyl; and
each $R^{12}$ is independently —H, —$C_{1-6}$alkyl, —$C_{1-6}$alkoxy, -cycloalkyl, heterocycloalkyl, aryl, or heteroaryl;
wherein at each occurrence alkyl is substituted with 0, 1, 2, 3, or 4 substituents selected from the group consisting of halo, -oxo, —OH, —CN, —$NH_2$, —$NO_2$, —$SO_2(C_{1-6}$alkyl), —$C_{1-6}$alkoxy, -cycloalkyl, -heterocycloalkyl, aryl, and heteroaryl;
wherein at each occurrence cycloalkyl and heterocycloalkyl are substituted with 0, 1, 2, 3, or 4 substituents selected from the group consisting of halo, -oxo, —OH, —CN, —$NH_2$, —$NO_2$, —$C_{1-6}$alkyl, —$SO_2(C_{1-6}$alkyl), —$CO(C_{1-6}$alkyl), —$C_{1-6}$alkoxy, aryl, and heteroaryl;
wherein at each occurrence aryl and heteroaryl are substituted with 0, 1, 2, or 3 substituents selected from the group consisting of halo, —OH, —CN, —$NH_2$, $NO_2$, —$NH(C_{1-6}$alkyl), —$N(C_{1-6}$alkyl)$_2$, —$C_{1-6}$alkyl, -cycloalkyl, -heterocycloalkyl, and —$C_{1-6}$alkoxy.

In some embodiments, the present disclosure provides a compound of formula I:

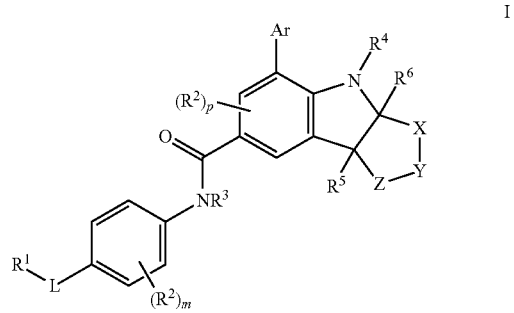

or an enantiomer or diastereomer, or a pharmaceutically acceptable salt thereof, wherein:
$R^1$ is —$C_{1-6}$alkyl, cycloalkyl, or heterocycloalkyl;
each $R^2$ is independently —H, -halo, —OH, —CN, —$NH_2$, —$NO_2$, —$C_{1-6}$alkyl, or —$C_{1-6}$alkoxy;
wherein m is 0, 1, 2, 3, or 4; p is 0, 1 or 2;
$R^3$ is —H or —$C_{1-6}$alkyl; $R^4$ is —H, cycloalkyl, or —$C_{1-6}$alkyl; $R^5$ and $R^6$ are each independently —H or —$C_{1-6}$alkyl;
Ar is aryl or heteroaryl;
X is —$C(R^7R^{7'})$—; Y is —$C(R^8R^8)$—, —O—, —$N(R^{10})$—, —$C(=O)$—, —$SO_2$—, or —$SO_2R^{12}$; Z is —$[C(R^9R^{9'})]_n$;
wherein n is 1, 2, 3, or 4;
or X and Y together form —$(R^7)C=C(R^8)$—;
L is —S—, —O—, —$C(=O)R^{11}$—, —$C(=O)OR^{11}$—, —$N(R^{11})$—, —$C(=O)N(R^{11})$—, —$C(=O)N(R^{11})$—$C_{1-4}$alkyl-, —$N(R^{11})C(=O)$—, —$N(R^{11})C(=O)$—$C_{1-4}$alkyl-, —$SO_2N(R^{11})$—, or —$N(R^{11})SO_2$—;
each $R^7$, $R^{7'}$, $R^8$, $R^{8'}$, $R^9$, and $R^{9'}$ is independently selected from —H, —$C_{1-6}$alkyl, -cycloalkyl, -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1-C_6$ alkyl), —$C(=O)N(R^{12})_2$, —$SO_2R^{12}$, —$SO_2N(R^{12})_2$, -aryl, or -heteroaryl;
$R^{10}$ is —H, —$C_{1-6}$alkyl, -cycloalkyl, heterocycloalkyl, —$C(=O)R^{12}$, —$C(=O)OR^{12}$, —$C(=O)N(R^{12})_2$, —$SO_2R^{12}$, —$SO_2N(R^{12})_2$, aryl, or heteroaryl;
each $R^{11}$ is independently —H or —$C_{1-6}$alkyl; and
each $R^{12}$ is independently —H, —$C_{1-6}$alkyl, —$C_{1-6}$alkoxy, -cycloalkyl, heterocycloalkyl, aryl, or heteroaryl;
wherein at each occurrence alkyl is substituted with 0, 1, 2, 3, or 4 substituents selected from the group consisting of halo, -oxo, —OH, —CN, —$NH_2$, —$NO_2$, —$SO_2(C_{1-6}$alkyl), —$C_{1-6}$alkoxy, -cycloalkyl, -heterocycloalkyl, aryl, and heteroaryl;
wherein at each occurrence cycloalkyl and heterocycloalkyl are substituted with 0, 1, 2, 3, or 4 substituents selected from the group consisting of halo, -oxo, —OH, —CN, —$NH_2$, —$NO_2$, —$C_{1-6}$alkyl, —$SO_2(C_{1-6}$alkyl), —$CO(C_{1-6}$alkyl), —$C_{1-6}$alkoxy, aryl, and heteroaryl;
wherein at each occurrence aryl and heteroaryl are substituted with 0, 1, 2, or 3 substituents selected from the group consisting of halo, —OH, —CN, —$NH_2$, $NO_2$, —$NH(C_{1-6}$alkyl), —$N(C_{1-6}$alkyl)$_2$, —$C_{1-6}$alkyl, -cycloalkyl, -heterocycloalkyl, and —$C_{1-6}$alkoxy.

In some embodiments, the present disclosure provides a compound of formula II:

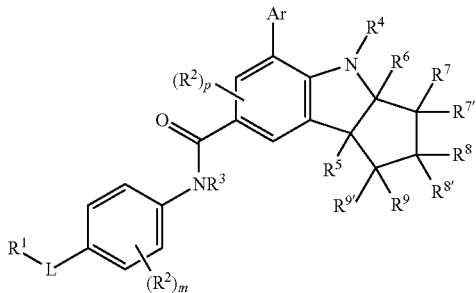

or an enantiomer or diastereomer, or a pharmaceutically acceptable salt thereof, wherein L, Ar, $R^1$, $R^2$, $R^3$ $R^4$, $R^5$, $R^6$, $R^7$, $R^{7'}$, $R^8$, $R^{8'}$, $R^9$, $R^{9'}$, m and p are the same as defined herein.

In some embodiments of formula II, wherein each $R^2$ is independently —H, -halo, —OH, —CN, —$NH_2$, —$NO_2$, —$C_{1-6}$alkyl, or —$C_{1-6}$alkoxy; wherein m is 0, 1, or 2; p is 0, 1 or 2;

$R^3$ is —H or —$C_{1-6}$alkyl; $R^4$ is —H or —$C_{1-6}$alkyl; $R^5$ and $R^6$ are —H;

Ar is aryl or heteroaryl;

L is —S—, —O—, —C(=O)$R^{11}$—, —C(=O)O$R^{11}$—, —N($R^{11}$)—, —C(=O)N($R^{11}$)—, —C(=O)N($R^{11}$)—$C_{1-4}$alkyl-, —N($R^{11}$)C(=O)—, —N($R^{11}$)C(=O)—$C_{1-4}$alkyl-, —$SO_2$N($R^{11}$)—, or —N($R^{11}$)$SO_2$—;

each $R^7$, $R^{7'}$, $R^8$, $R^{8'}$, $R^9$, and $R^{9'}$ is independently selected from —H, —$C_{1-6}$alkyl, -cycloalkyl, -heterocycloalkyl, —O$R^{12}$, —N($R^{12}$)$_2$, —$NR^{11}$C(=O)$R^{12}$, —$NR^{11}$C(=O)O$R^{12}$, —$NR^{11}$C(=O)N($R^{12}$)$_2$, —$NR^{11}SO_2R^{12}$, —$NR^{11}SO_2$N($R^{12}$)$_2$, —C(=O)$R^{12}$, —C(=O)O($C_1$-$C_6$ alkyl), —C(=O)N($R^{12}$)$_2$, —$SO_2R^{12}$, —$SO_2$N($R^{12}$)$_2$, -aryl, or -heteroaryl; or $R^{7'}$ and $R^{8'}$ form a bond;

each $R^{11}$ is independently —H or —$C_{1-6}$alkyl; and each $R^{12}$ is independently —H, —$C_{1-6}$alkyl, —$C_{1-6}$alkoxy, -cycloalkyl, heterocycloalkyl, aryl, or heteroaryl;

wherein at each occurrence alkyl is substituted with 0, 1, 2, 3, or 4 substituents selected from the group consisting of halo, —OH, —CN, —$NH_2$, —$NO_2$, —$SO_2$($C_{1-6}$alkyl), —$C_{1-6}$alkoxy, -cycloalkyl, -heterocycloalkyl, aryl, and heteroaryl;

wherein at each occurrence cycloalkyl and heterocycloalkyl are substituted with 0, 1, 2, 3, or 4 substituents selected from the group consisting of halo, -oxo, —OH, —CN, —$NH_2$, —$NO_2$, —$C_{1-6}$alkyl, —$SO_2$($C_{1-6}$alkyl), —CO($C_{1-6}$alkyl), —$C_{1-6}$alkoxy, aryl, and heteroaryl;

wherein at each occurrence aryl and heteroaryl are substituted with 0, 1, 2, or 3 substituents selected from the group consisting of halo, —OH, —CN, —$NH_2$, —$NO_2$, —NH($C_{1-6}$alkyl), —N($C_{1-6}$alkyl)$_2$, —$C_{1-6}$alkyl, -cycloalkyl, -heterocycloalkyl, and —$C_{1-6}$alkoxy.

In some embodiments of formula II, wherein each $R^2$ is independently —H, -halo, —OH, —CN, —$NH_2$, —$NO_2$, —$C_{1-6}$alkyl, or —$C_{1-6}$alkoxy; wherein m is 0, 1, or 2; p is 0, 1 or 2;

$R^3$ is —H or —$C_{1-6}$alkyl; $R^4$ is —H, cycloalkyl, or —$C_{1-6}$alkyl; $R^5$ and $R^6$ are —H;

Ar is aryl or heteroaryl;

L is —S—, —O—, —C(=O)$R^{11}$—, —C(=O)O$R^{11}$—, —N($R^{11}$)—, —C(=O)N($R^{11}$)—, —C(=O)N($R^{11}$)—$C_{1-4}$alkyl-, —N($R^{11}$)C(=O)—, —N($R^{11}$)C(=O)—$C_{1-4}$alkyl-, —$SO_2$N($R^{11}$)—, or —N($R^{11}$)$SO_2$—;

each $R^7$, $R^{7'}$, $R^8$, $R^{8'}$, $R^9$, and $R^{9'}$ is independently selected from —H, —$C_{1-6}$alkyl, -cycloalkyl, -heterocycloalkyl, —O$R^{12}$, —N($R^{12}$)$_2$, —$NR^{11}$C(=O)$R^{12}$, —$NR^{11}$C(=O)O$R^{12}$, —$NR^{11}$C(=O)N($R^{12}$)$_2$, —$NR^{11}SO_2R^{12}$, —$NR^{11}SO_2$N($R^{12}$)$_2$, —C(=O)$R^{12}$, —C(=O)O($C_1$-$C_6$ alkyl), —C(=O)N($R^{12}$)$_2$, —$SO_2R^{12}$, —$SO_2$N($R^{12}$)$_2$, -aryl, or -heteroaryl; or $R^{7'}$ and $R^{8'}$ form a bond;

each $R^{11}$ is independently —H or —$C_{1-6}$alkyl; and each $R^{12}$ is independently —H, —$C_{1-6}$alkyl, —$C_{1-6}$alkoxy, -cycloalkyl, heterocycloalkyl, aryl, or heteroaryl;

wherein at each occurrence alkyl is substituted with 0, 1, 2, 3, or 4 substituents selected from the group consisting of halo, —OH, —CN, —$NH_2$, —$NO_2$, —$SO_2$($C_{1-6}$alkyl), —$C_{1-6}$alkoxy, -cycloalkyl, -heterocycloalkyl, aryl, and heteroaryl;

wherein at each occurrence cycloalkyl and heterocycloalkyl are substituted with 0, 1, 2, 3, or 4 substituents selected from the group consisting of halo, -oxo, —OH, —CN, —$NH_2$, —$NO_2$, —$C_{1-6}$alkyl, —$SO_2$($C_{1-6}$alkyl), —CO($C_{1-6}$alkyl), —$C_{1-6}$alkoxy, aryl, and heteroaryl;

wherein at each occurrence aryl and heteroaryl are substituted with 0, 1, 2, or 3 substituents selected from the group consisting of halo, —OH, —CN, —$NH_2$, —$NO_2$, —NH($C_{1-6}$alkyl), —N($C_{1-6}$alkyl)$_2$, —$C_{1-6}$alkyl, -cycloalkyl, -heterocycloalkyl, and —$C_{1-6}$alkoxy.

In some embodiments of a compound of formula I or II, $R^1$ is —$C_{1-6}$alkyl. In some embodiments, $R^1$ is —$C_{1-6}$alkyl substituted with 1, 2, or 3 halo. In some embodiments, $R^1$ is —$C_{1-6}$alkyl substituted with 1, 2, or 3 F or Cl.

In some embodiments of a compound of formula I or II, $R^1$ is fluoromethyl, difluoromethyl, difluorochloromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl. In some embodiments of a compound of formula I or II, wherein $R^1$ is difluorochloromethyl.

In some embodiments of a compound of formula I or II, L is a link, selected from alkyl, —S—, —O—, —C(=O)$R^{11}$—, —C(=O)O$R^{11}$—, —N($R^{11}$)—, —C(=O)N($R^{11}$)—, —C(=O)N($R^{11}$)—$C_{1-4}$alkyl, —N($R^{11}$)C(=O)—, —N($R^{11}$)C(=O)—$C_{1-4}$alkyl-, —$SO_2$N($R^{11}$)—, or —N($R^{11}$)$SO_2$—; wherein each $R^{11}$ is independently as defined herein. In some embodiments, L is —S—, —O—, or —N($R^{11}$)—.

In some embodiments of a compound of formula I or II, L is —S— or —O—. In some embodiments, L is —O—.

In some embodiments of a compound of formula I or II, $R^2$ is independently —H, halo, —$C_{1-3}$alkyl, or —$C_{1-3}$alkoxy. In some embodiments, $R^2$ is —H. In some embodiments, $R^2$ is halo.

In some embodiments, $R^2$ is —$C_{1-3}$alkyl.

In some embodiments of a compound of formula I or II, $R^2$ is —H; L is —S— or —O—. In some embodiments, $R^2$ is —H; and L is —O—.

In some embodiments of a compound of formula I or II, $R^1$ is —$C_{1-6}$alkyl substituted with 1, 2, or 3 halo; $R^2$ is —H; and L is —S— or —O—. In some embodiments, $R^1$ is —$C_{1-6}$alkyl substituted with 1, 2, or 3 F or Cl; $R^2$ is —H; and L is —O—.

In some embodiments of a compound of formula I or II, $R^3$ is —H. In some embodiments, $R^3$ is —$C_{1-6}$alkyl. In some embodiments, $R^3$ is methyl, ethyl, propyl, isopropyl, butyl, sec-butyl, iso-butyl or tert-butyl.

In some embodiments of a compound of formula I or II, $R^1$ is —$C_{1-6}$alkyl substituted with 1, 2, or 3 halo; $R^2$ is —H; $R^3$ is —H or —$C_{1-6}$alkyl; and L is —S— or —O—.

In some embodiments of a compound of formula I or II, $R^1$ is —$C_{1-6}$alkyl substituted with 1, 2, or 3 F or Cl; $R^2$ is —H; $R^3$ is —H or methyl; and L is —S— or —O—.

In some embodiments of a compound of formula I or II, $R^1$ is difluorochloromethyl;

$R^2$ is —H; $R^3$ is —H or methyl; and L is —S— or —O—.

In some embodiments of a compound of formula I or II, $R^1$ is difluorochloromethyl; $R^2$ is —H; $R^3$ is —H; and L is —O—.

In some embodiments of a compound of formula I or II, $R^4$ is H or —$C_{1-6}$alkyl.

In some embodiments of a compound of formula I or II, $R^4$ is H, cycloalkyl, or —$C_{1-6}$alkyl. In some embodiments, $R^4$ is —$C_{1-6}$alkyl or -cycloalkyl. In some embodiments, $R^4$ is —$C_{1-6}$alkyl or —$C_{3-8}$cycloalkyl. In some embodiments, $R^4$ is —$C_{1-6}$alkyl or —$C_{3-6}$cycloalkyl. In some embodiments, $R^4$ is —$C_{1-5}$alkyl or —$C_{3-5}$cycloalkyl.

In some embodiments, $R^4$ is —$C_{1-6}$alkyl, —$C_{1-5}$alkyl, —$C_{1-4}$alkyl, or —$C_{1-3}$alkyl. In some embodiments, $R^4$ is —$C_{1-3}$alkyl. In some embodiments $R^4$ is —$C_{1-5}$alkyl. In some embodiments, $R^4$ is $C_{3-8}$cycloalkyl, $C_{3-7}$cycloalkyl, $C_{3-6}$cycloalkyl, $C_{3-5}$cycloalkyl. In some embodiments, $R^4$ is $C_{3-6}$cycloalkyl or $C_{3-5}$cycloalkyl. In some embodiments, $R^4$ is $C_{3-5}$cycloalkyl.

In some embodiments of a compound of formula I or II, $R^4$ is methyl, ethyl, propyl, butyl, pentyl. In some embodiments, $R^4$ is iso-propyl. In some embodiments, $R^4$ is neo-pentyl.

In some embodiments, $R^4$ is cyclopropyl, cyclobutyl, cyclopentyl, or cyclohexyl. In some embodiments, $R^4$ is cyclopropyl or cyclohexyl.

In some embodiments of a compound of formula I or II, $R^4$ is —$C_{1-6}$alkyl substituted with 1 or 2 substituents selected from halo, —OH, —CN, —NH$_2$, —SO$_2$($C_{1-6}$alkyl), —$C_{1-6}$alkoxy, -cycloalkyl, heterocycloalkyl, aryl, and heteroaryl; wherein cycloalkyl and heterocycloalkyl are optionally substituted with halo, -oxo, —OH, —CN, —NH$_2$, —SO$_2$($C_{1-6}$alkyl), —CO($C_{1-6}$alkyl), and —$C_{1-6}$alkyl; wherein cycloalkyl, heterocycloalkyl, aryl, and heteroaryl are the same defined herein.

In some embodiments, $R^4$ is cyclopropyl, cyclobutyl, cyclopentyl, or cyclohexyl, any of which is substituted with 0, 1, 2, 3, or 4 substituents comprising halo, -oxo, —OH, —CN, —NH$_2$, —NO$_2$, —$C_{1-6}$alkyl, —SO$_2$($C_{1-6}$alkyl), —CO($C_{1-6}$alkyl), —$C_{1-6}$alkoxy, aryl, and heteroaryl. In some embodiments, $R^4$ is cyclopropyl or cyclohexyl, either of which is substituted with 0, 1, or 2 substituents comprising halo, -oxo, —OH, —CN, —NH$_2$, —NO$_2$, —$C_{1-6}$alkyl, —SO$_2$($C_{1-6}$alkyl), —CO($C_{1-6}$alkyl), —$C_{1-6}$alkoxy, aryl, and heteroaryl; wherein alkyl, alkoxy, aryl, and heteroaryl are the same defined herein.

In some embodiments of a compound of formula I or II, $R^4$ is any one of the moieties provided in Table 1:

TABLE 1

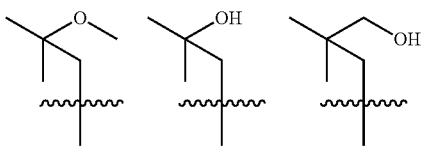

TABLE 1-continued

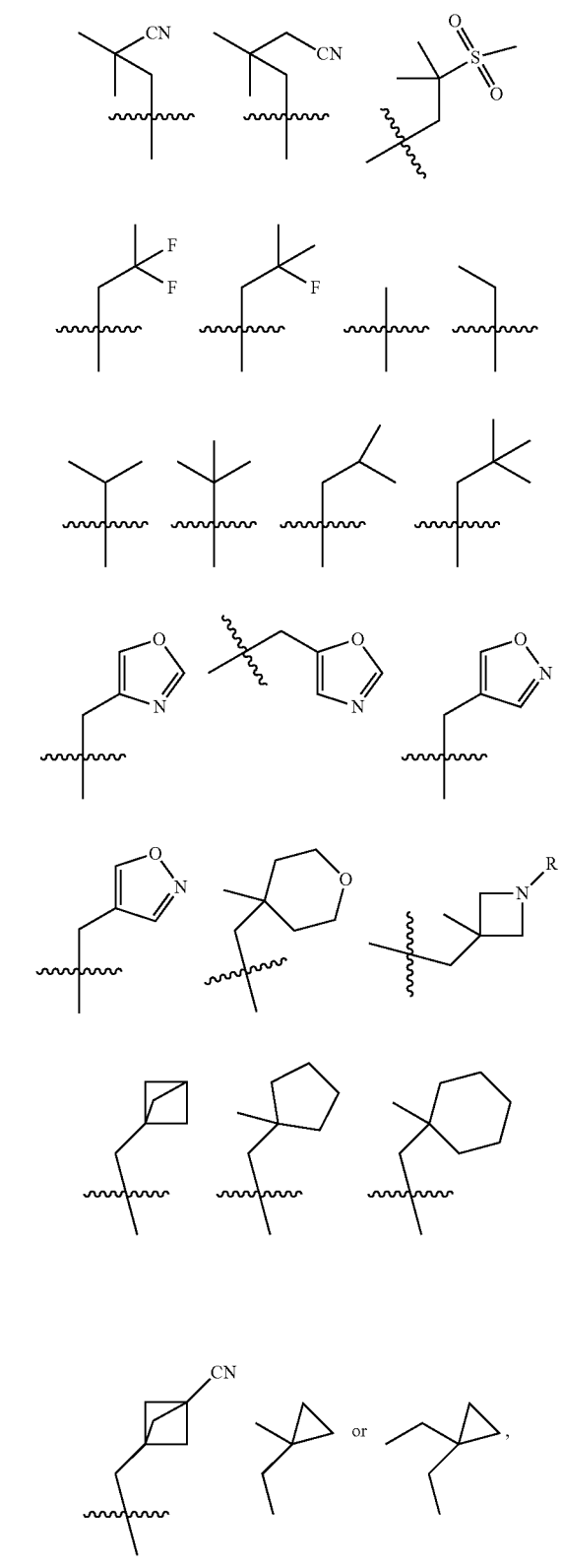

wherein R is H, —$C_{1-6}$alkyl, —SO$_2$($C_{1-6}$alkyl), or —CO($C_{1-6}$alkyl).

In some embodiments of a compound of formula I or II, $R^4$ is any one of the moieties provided in Table 1-A:

TABLE 1-A

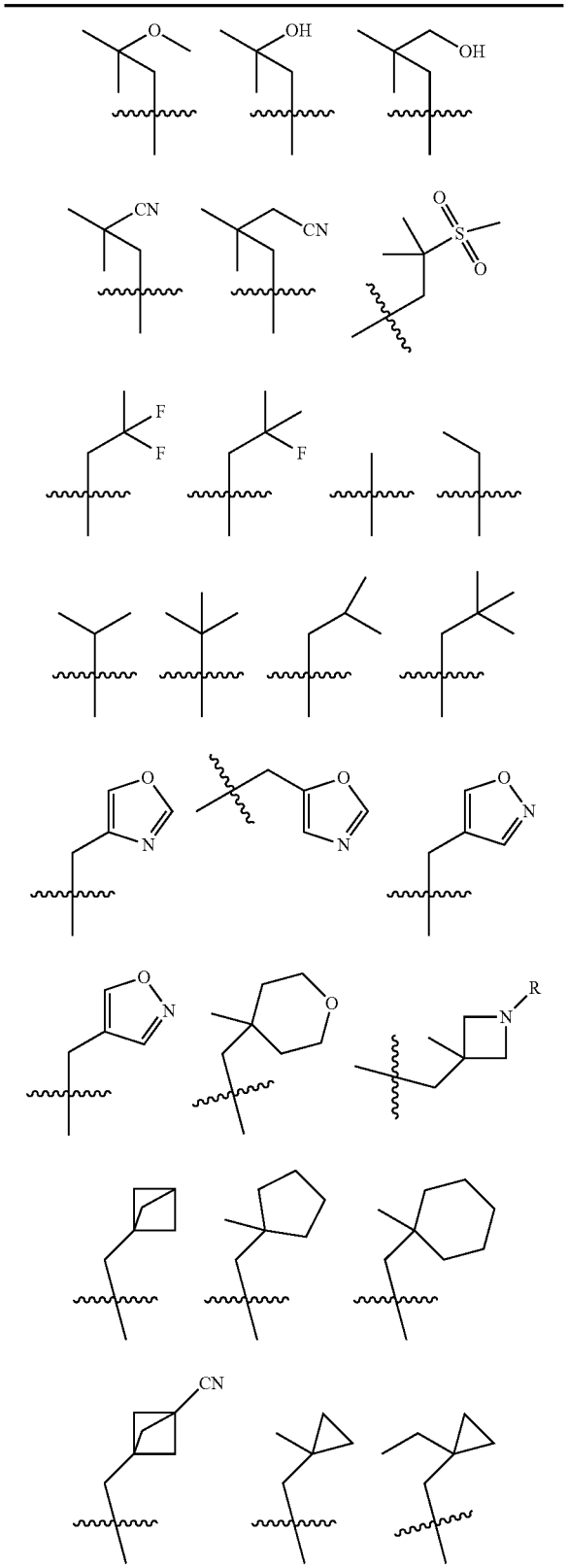

TABLE 1-A-continued

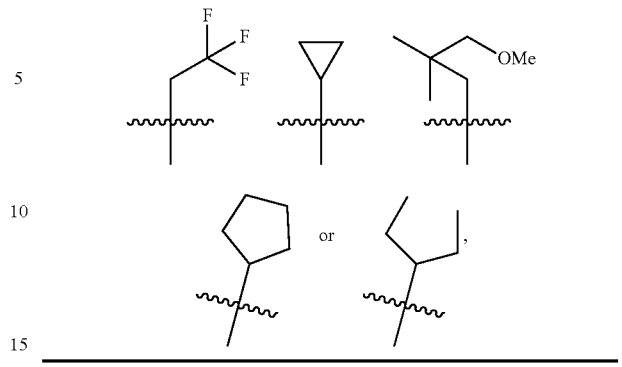

wherein R is H, —$C_{1-6}$alkyl, —$SO_2(C_{1-6}$alkyl), or —CO($C_{1-6}$alkyl).

In some embodiments of a compound of formula I or II, $R^1$ is —$C_{1-6}$alkyl substituted with 1, 2, or 3 halo; $R^2$ is —H; $R^3$ is —H or —$C_{1-6}$alkyl; L is —S— or —O—; and $R^4$ is —$C_{1-6}$alkyl, —$C_{1-5}$alkyl, —$C_{1-4}$alkyl, or —$C_{1-3}$alkyl.

In some embodiments of a compound of formula I or II, $R^1$ is —$C_{1-6}$alkyl substituted with 1, 2, or 3 halo; $R^2$ is —H; $R^3$ is —H or —$C_{1-6}$alkyl; L is —S— or —O—; and $R^4$ is —$C_{1-6}$alkyl, —$C_{1-5}$alkyl, —$C_{1-4}$alkyl, —$C_{1-3}$alkyl, —$C_{3-8}$cycloalkyl, —$C_{3-7}$cycloalkyl, —$C_{3-6}$cycloalkyl, or —$C_{3-8}$cycloalkyl.

In some embodiments of a compound of formula I or II, $R^1$ is —$C_{1-6}$alkyl substituted with 1, 2, or 3 F or Cl; $R^2$ is —H; $R^3$ is —H or methyl; L is —S— or —O—; and $R^4$ is —$C_{1-5}$alkyl or —$C_{1-3}$alkyl.

In some embodiments of a compound of formula I or II, $R^1$ is —$C_{1-6}$alkyl substituted with 1, 2, or 3 F or Cl; $R^2$ is —H; $R^3$ is —H or methyl; L is —S— or —O—; and $R^4$ is —$C_{1-5}$alkyl, —$C_{1-3}$alkyl, $C_{3-6}$cycloalkyl, or —$C_{3-8}$cycloalkyl.

In some embodiments, $R^1$ is difluorochloromethyl; $R^2$ is —H; $R^3$ is —H or methyl; L is —S— or —O—; and $R^4$ is any one of the moieties provided in Table 1.

In some embodiments, $R^1$ is difluorochloromethyl; $R^2$ is —H; $R^3$ is —H or methyl; L is —S— or —O—; and $R^4$ is any one of the moieties provided in Table 1-A.

In some embodiments, $R^1$ is difluorochloromethyl; $R^2$ is —H; $R^3$ is —H; L is —O—; and $R^4$ is iso-propyl, neopentyl, cyclopropyl, or cyclopentyl.

In some embodiments, $R^1$ is difluorochloromethyl; $R^2$ is —H; $R^3$ is —H; L is —O—; and $R^4$ is iso-propyl, or neopentyl.

In some embodiments of a compound of formula I or II, Ar is a 5-14 membered monocyclic and bicyclic aromatic ring systems having 1, 2, 3, or 4 heteroatoms selected from the group consisting of nitrogen, oxygen and sulfur. In some embodiments, Ar is a 5- or 6-membered monocyclic aromatic ring system having 1, 2, or 3 heteroatoms selected from a group consisting of nitrogen, oxygen and sulfur atoms.

In some embodiments of a compound of formula I or II, Ar is a 5-14 membered monocyclic and bicyclic aromatic ring systems having 0, 1, 2, 3, or 4 heteroatoms selected from the group consisting of nitrogen, oxygen and sulfur, wherein Ar is substituted with 0, 1, 2, or 3 substituents comprising halo, —OH, —CN, —$C_{1-6}$alkyl, -cycloalkyl, -heterocycloalkyl, and —$C_{1-6}$alkoxy. In some embodiments, Ar is a 5- or 6-membered monocyclic aromatic ring systems having 0, 1, 2, or 3 heteroatoms selected from a group consisting of nitrogen, oxygen and sulfur atoms, wherein Ar is substituted with 0, 1, 2, or 3 substituents comprising halo, —OH, —CN, —$C_{1-6}$alkyl, -cycloalkyl, -heterocycloalkyl, and —$C_{1-6}$alkoxy. In some embodiments, Ar is a 5- or 6-membered monocyclic aromatic ring systems having 0, 1, or 2 heteroatoms selected from a group consisting of nitrogen, oxygen and sulfur atoms, wherein Ar is substituted with 0, 1, or 2 substituents comprising halo, —CN, —$C_{1-6}$alkyl, and —$C_{1-6}$alkoxy.

In some embodiments of a compound of formula I or II, Ar is thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, O-carbolinyl, phenanthridinyl, acridinyl, pyrimidinyl, phenanthrolinyl, phenazinyl, thiazolyl, isothiazolyl, phenothiazolyl, oxazolyl, isoxazolyl, furazanyl, phenoxazinyl, triazolyl, triazinyl, or tetrazolyl.

In some embodiments of a compound of formula I or II, Ar is phenyl, thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, O-carbolinyl, phenanthridinyl, acridinyl, pyrimidinyl, phenanthrolinyl, phenazinyl, thiazolyl, isothiazolyl, phenothiazolyl, oxazolyl, isoxazolyl, furazanyl, phenoxazinyl, triazolyl, triazinyl, or tetrazolyl, wherein Ar is substituted with 0, 1, 2, or 3 substituents comprising halo, —OH, —CN, —$C_{1-6}$alkyl, -cycloalkyl, -heterocycloalkyl, and —$C_{1-6}$alkoxy.

In some embodiments of a compound of formula I or II, Ar is any one of the moieties provided in Table 2:

TABLE 2

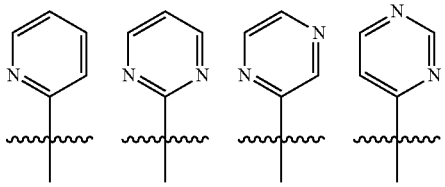

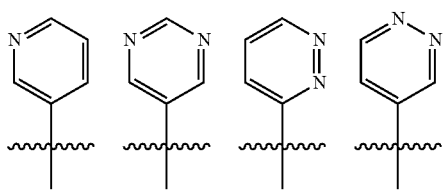

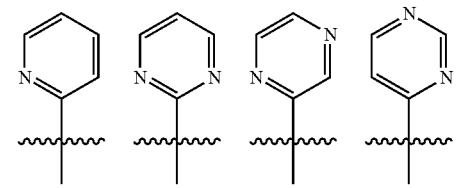

TABLE 2-continued

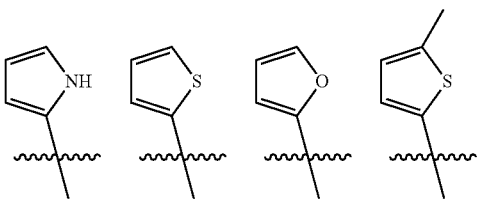

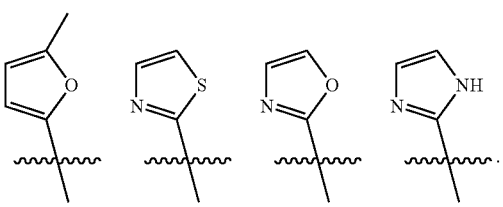

In some embodiments of a compound of formula I or II, Ar is any one of the moieties provided in Table 2-A:

TABLE 2-A

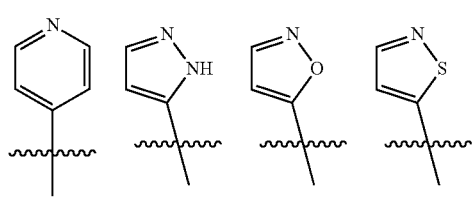

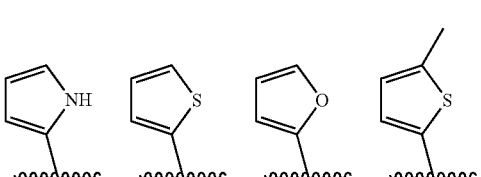

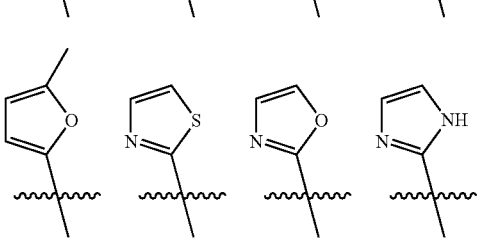

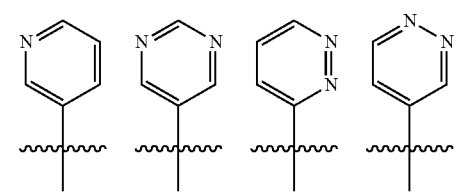

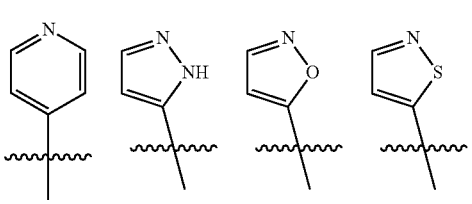

TABLE 2-A-continued

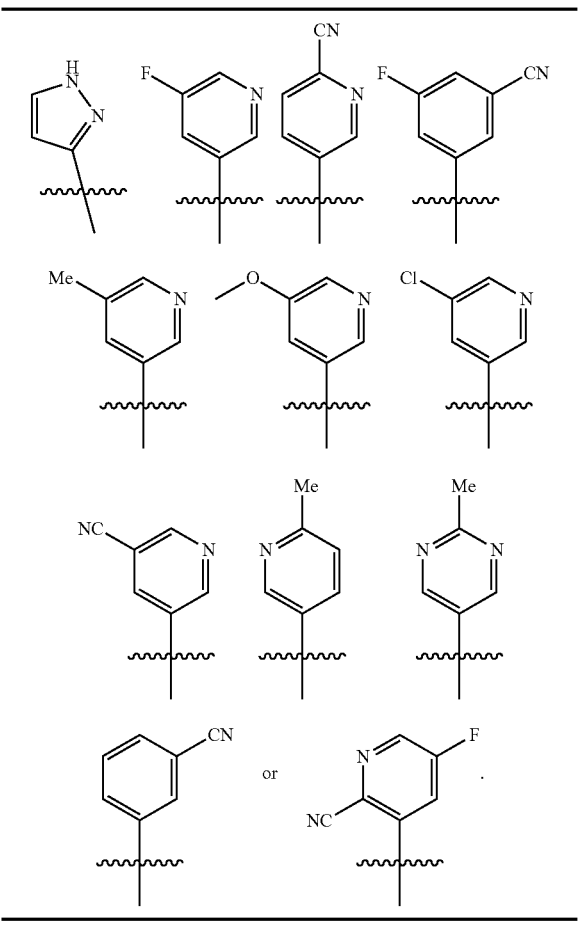

In some embodiment, Ar is phenyl, pyridinyl, pyrimidinyl, pyridazinyl, pyrazinyl, or pyrazolyl, any of which is substituted with 0, 1, 2, or 3 substituents comprising halo, —CN, —$C_{1-6}$alkyl, and —$C_{1-6}$alkoxy.

In some embodiment, Ar is phenyl, pyridinyl, pyrimidinyl, pyridazinyl, pyrazinyl, or pyrazolyl, any of which is substituted with 0, 1, or 2 substituents comprising halo, —CN, —$C_{1-6}$alkyl, and —$C_{1-6}$alkoxy.

In some embodiment, Ar is phenyl, pyridinyl, or pyrazolyl, any of which is substituted with 0, 1, or 2 substituents comprising fluoro, chloro, —CN, methyl, and methoxy.

In some embodiments, Ar is pyridinyl. In some embodiments, Ar is pyrimidinyl or pyrazinyl. In some embodiments, Ar is pyrazolyl. In some embodiments, Ar is 1H-pyrazol-5-yl. In some embodiments, Ar is phenyl. In some embodiments, Ar is pyrimidinyl, pyridazinyl, or pyrazinyl.

In some embodiments of a compound of formula I or II, $R^1$ is —$C_{1-6}$alkyl substituted with 1, 2, or 3 halo; $R^2$ is —H; $R^3$ is —H or —$C_{1-6}$alkyl; L is —S— or —O—; $R^4$ is —$C_{1-6}$alkyl, —$C_{1-5}$alkyl, —$C_{1-4}$alkyl, or —$C_{1-3}$alkyl; and Ar is any one of the moieties provided in Table 2.

In some embodiments of a compound of formula I or II, $R^1$ is —$C_{1-6}$alkyl substituted with 1, 2, or 3 halo; $R^2$ is —H; $R^3$ is —H or —$C_{1-6}$alkyl; L is —S— or —O—; $R^4$ is —$C_{1-6}$alkyl, —$C_{1-5}$alkyl, —$C_{1-4}$alkyl, —$C_{1-3}$alkyl, —$C_{3-8}$cycloalkyl, —$C_{3-7}$cycloalkyl, —$C_{3-6}$cycloalkyl, or —$C_{3-5}$cycloalkyl; and Ar is any one of the moieties provided in Table 2-A.

In some embodiments, $R^1$ is —$C_{1-6}$alkyl substituted with 1, 2, or 3 F or Cl; $R^2$ is —H; $R^3$ is —H or methyl; L is —S— or —O—; and $R^4$ is —$C_{1-5}$alkyl or —$C_{1-3}$alkyl; and Ar is any one of the moieties provided in Table 2.

In some embodiments, $R^1$ is —$C_{1-6}$alkyl substituted with 1, 2, or 3 F or Cl; $R^2$ is —H; $R^3$ is —H or methyl; L is —S— or —O—; and $R^4$ is —$C_{1-5}$alkyl, —$C_{1-3}$alkyl, $C_{3-6}$cycloalkyl, or —$C_{3-5}$cycloalkyl; and Ar is any one of the moieties provided in Table 2-A.

In some embodiments, $R^1$ is difluorochloromethyl; $R^2$ is —H; $R^3$ is —H or methyl; L is —S— or —O—; $R^4$ is any one of the moieties provided in Table 1; and Ar is any one of the moieties provided in Table 2.

In some embodiments, $R^1$ is difluorochloromethyl; $R^2$ is —H; $R^3$ is —H or methyl; L is —S— or —O—; $R^4$ is any one of the moieties provided in Table 1-A; and Ar is any one of the moieties provided in Table 2-A.

In some embodiments, $R^1$ is difluorochloromethyl; $R^2$ is —H; $R^3$ is —H; L is —O—; $R^4$ is iso-propyl, neopentyl, cyclopropyl, or cyclopentyl; and Ar is phenyl, pyridinyl, pyrimidinyl, pyridazinyl, pyrazinyl, or pyrazolyl, any of which is substituted with 0, 1, 2, or 3 substituents comprising halo, —CN, —$C_{1-6}$alkyl, and —$C_{1-6}$alkoxy.

In some embodiments, $R^1$ is difluorochloromethyl; $R^2$ is —H; $R^3$ is —H; L is —O—; $R^4$ is iso-propyl, or neopentyl; and Ar is phenyl, pyridinyl, pyrimidinyl, pyridazinyl, pyrazinyl, or pyrazolyl, any of which is substituted with 0, 1, or 2 substituents comprising halo, —CN, —$C_{1-6}$alkyl, and —$C_{1-6}$alkoxy.

In some embodiments, $R^1$ is difluorochloromethyl; $R^2$ is —H; $R^3$ is —H; L is —O—; $R^4$ is iso-propyl, or neopentyl; and Ar is pyrimidinyl or pyrazinyl.

In some embodiments, $R^1$ is difluorochloromethyl; $R^2$ is —H; $R^3$ is —H; L is —O—; $R^4$ is iso-propyl, or neopentyl; and Ar is pyrazolyl.

In some embodiments of a compound of formula I or II, each $R^5$ and $R^6$ is independently H or —$C_{1-6}$alkyl. In some embodiments, $R^5$ and $R^6$ are H.

In some embodiments, $R^1$ is —$C_{1-6}$alkyl substituted with 1, 2, or 3 halo; $R^2$ is —H; $R^3$ is —H or —$C_{1-6}$alkyl; L is —S— or —O—; $R^4$ is —$C_{1-6}$alkyl, —$C_{1-5}$alkyl, —$C_{1-4}$alkyl, or —$C_{1-3}$alkyl; $R^5$ and $R^6$ is H; and Ar is any one of the moieties provided in Table 2.

In some embodiments, $R^1$ is —$C_{1-6}$alkyl substituted with 1, 2, or 3 halo; $R^2$ is —H; $R^3$ is —H or —$C_{1-6}$alkyl; L is —S— or —O—; $R^4$ is —$C_{1-6}$alkyl, —$C_{1-5}$alkyl, —$C_{1-4}$alkyl, —$C_{1-3}$alkyl, —$C_{3-8}$cycloalkyl, —$C_{3-7}$cycloalkyl, —$C_{3-6}$cycloalkyl, or —$C_{3-8}$cycloalkyl; $R^5$ and $R^6$ is H; and Ar is any one of the moieties provided in Table 2-A.

In some embodiments, $R^1$ is —$C_{1-6}$alkyl substituted with 1, 2, or 3 F or Cl; $R^2$ is —H; $R^3$ is —H or methyl; L is —S— or —O—; and $R^4$ is —$C_{1-5}$alkyl or —$C_{1-3}$alkyl; $R^5$ and $R^6$ are H; and Ar is any one of the moieties provided in Table 2.

In some embodiments, $R^1$ is —$C_{1-6}$alkyl substituted with 1, 2, or 3 F or Cl; $R^2$ is —H; $R^3$ is —H or methyl; L is —S— or —O—; and $R^4$ is —$C_{1-5}$alkyl, —$C_{1-3}$alkyl, $C_{3-6}$cycloalkyl, or —$C_{3-8}$cycloalkyl; $R^5$ and $R^6$ are H; and Ar is any one of the moieties provided in Table 2-A.

In some embodiments, $R^1$ is difluorochloromethyl; $R^2$ is —H; $R^3$ is —H; L is —O—; $R^4$ is any one of the moieties provided in Table 1; $R^5$ and $R^6$ are H; and Ar is any one of the moieties provided in Table 2.

In some embodiments, $R^1$ is difluorochloromethyl; $R^2$ is —H; $R^3$ is —H; L is —O—; $R^4$ is any one of the moieties provided in Table 1-A; $R^5$ and $R^6$ are H; and Ar is any one of the moieties provided in Table 2-A.

In some embodiments, $R^1$ is difluorochloromethyl; $R^2$ is —H; $R^3$ is —H; L is —O—; $R^4$ is iso-propyl or neopentyl; $R^5$ and $R^6$ is H; and Ar is pyrimidinyl or pyrazinyl.

In some embodiments, $R^1$ is difluorochloromethyl; $R^2$ is —H; $R^3$ is —H; L is —O—; $R^4$ is iso-propyl, neopentyl, cyclopropyl, or cyclopentyl; $R^5$ and $R^6$ is H; and Ar is phenyl, pyrimidinyl, pyridazinyl, or pyrazinyl, any of which is substituted with 0, 1, or 2 substituents comprising halo, —CN, —$C_{1-6}$alkyl, and —$C_{1-6}$alkoxy.

In some embodiments, $R^1$ is difluorochloromethyl; $R^2$ is —H; $R^3$ is —H; L is —O—; $R^4$ is iso-propyl, or neopentyl; $R^5$ and $R^6$ is H; and Ar is pyrazolyl.

In some embodiments of a compound of formula I or II, $R^1$ is —$C_{1-3}$alkyl substituted with 1, 2, or 3 halo; each $R^2$ is independently —H, -halo, —$C_{1-3}$alkyl, or —$C_{1-3}$alkoxy; wherein m is 0, 1, or 2; p is 0, 1 or 2; $R^3$ is —H; $R^4$ is —$C_{1-6}$alkyl; $R^5$ and $R^6$ are —H; Ar is a 5- or 6-membered monocyclic aromatic ring systems having 1, 2, or 3 heteroatoms selected from a group consisting of nitrogen, oxygen and sulfur atoms; L is —O— or —S—;
- each $R^7$, $R^{7'}$, $R^8$, $R^{8'}$, $R^9$, and $R^{9'}$ is independently —H, —$C_{1-6}$alkyl, -cycloalkyl, -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1-C_6$ alkyl), —$C(=O)N(R^{12})_2$, —$SO_2R^{12}$, or —$SO_2N(R^{12})_2$;
- each $R^{11}$ is independently —H or —$C_{1-6}$alkyl; and
- each $R^{12}$ is independently —H, —$C_{1-6}$alkyl, —$C_{1-6}$alkoxy, -cycloalkyl, heterocycloalkyl, aryl, or heteroaryl;
- wherein at each occurrence alkyl is substituted with 0, 1, 2, 3, or 4 substituents selected from the group consisting of halo, —OH, —CN, —$NH_2$, —$NO_2$, —$SO_2(C_{1-6}$alkyl), —$C_{1-6}$alkoxy, -cycloalkyl, -heterocycloalkyl, aryl, and heteroaryl;
- wherein at each occurrence cycloalkyl and heterocycloalkyl are substituted with 0, 1, 2, 3, or 4 substituents selected from the group consisting of halo, -oxo, —OH, —CN, —$NH_2$, —$NO_2$, —$C_{1-6}$alkyl, —$SO_2(C_{1-6}$alkyl), —$CO(C_{1-6}$alkyl), —$C_{1-6}$alkoxy, aryl, and heteroaryl;
- wherein at each occurrence aryl and heteroaryl are substituted with 0, 1, 2, or 3 substituents selected from the group consisting of halo, —OH, —CN, —$NH_2$, $NO_2$, —$NH(C_{1-6}$alkyl), —$N(C_{1-6}$alkyl)$_2$, —$C_{1-6}$alkyl, cycloalkyl, heterocycloalkyl, and $C_{1-6}$alkoxy.

In some embodiments of a compound of formula I or II, $R^1$ is —$C_{1-3}$alkyl substituted with 1, 2, or 3 halo; each $R^2$ is independently —H, -halo, —$C_{1-3}$alkyl, or —$C_{1-3}$alkoxy; wherein m is 0, 1, or 2; p is 0, 1 or 2; $R^3$ is —H; $R^4$ is —$C_{1-6}$alkyl or -cycloalkyl; $R^5$ and $R^6$ are —H; Ar is a 5- or 6-membered monocyclic aromatic ring systems having 0, 1, 2, or 3 heteroatoms selected from a group consisting of nitrogen, oxygen and sulfur atoms, wherein Ar is substituted with 0, 1, 2, or 3 substituents comprising halo, —OH, —CN, —$C_{1-6}$alkyl, -cycloalkyl, -heterocycloalkyl, and —$C_{1-6}$alkoxy; L is —O— or —S—;
- each $R^7$, $R^{7'}$, $R^8$, $R^{8'}$, $R^9$, and $R^{9'}$ is independently —H, —$C_{1-6}$alkyl, -cycloalkyl, -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1-C_6$ alkyl), —$C(=O)N(R^{12})_2$, —$SO_2R^{12}$, or —$SO_2N(R^{12})_2$;
- each $R^{11}$ is independently —H or —$C_{1-6}$alkyl; and
- each $R^{12}$ is independently —H, —$C_{1-6}$alkyl, —$C_{1-6}$alkoxy, -cycloalkyl, heterocycloalkyl, aryl, or heteroaryl;
- wherein at each occurrence alkyl is substituted with 0, 1, 2, 3, or 4 substituents selected from the group consisting of halo, —OH, —CN, —$NH_2$, —$NO_2$, —$SO_2(C_{1-6}$alkyl), —$C_{1-6}$alkoxy, -cycloalkyl, -heterocycloalkyl, aryl, and heteroaryl;
- wherein at each occurrence cycloalkyl and heterocycloalkyl are substituted with 0, 1, 2, 3, or 4 substituents selected from the group consisting of halo, -oxo, —OH, —CN, —$NH_2$, —$NO_2$, —$C_{1-6}$alkyl, —$SO_2(C_{1-6}$alkyl), —$CO(C_{1-6}$alkyl), —$C_{1-6}$alkoxy, aryl, and heteroaryl;
- wherein at each occurrence aryl and heteroaryl are substituted with 0, 1, 2, or 3 substituents selected from the group consisting of halo, —OH, —CN, —$NH_2$, $NO_2$, —$NH(C_{1-6}$alkyl), —$N(C_{1-6}$alkyl)$_2$, —$C_{1-6}$alkyl, cycloalkyl, heterocycloalkyl, and $C_{1-6}$alkoxy.

In some embodiments of a compound of formula I or II, $R^7$, $R^{7'}$, $R^8$, $R^{8'}$, $R^9$, and $R^{9'}$ are H.

In some embodiments of a compound of formula I or II, $R^9$ and $R^{9'}$ are H; $R^7$, $R^{7'}$, $R^8$, and $R^{8'}$ are each independently H, —$C_{1-6}$alkyl, -cycloalkyl, -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1-C_6$ alkyl), —$C(=O)N(R^{12})_2$, —$SO_2R^{12}$, or —$SO_2N(R^{12})_2$, each $R^{11}$ is independently —H or —$C_{1-6}$alkyl; and each $R^{12}$ is independently —H, —$C_{1-6}$alkyl, —$C_{1-6}$alkoxy, -cycloalkyl, heterocycloalkyl, aryl, or heteroaryl; wherein at each occurrence alkyl is substituted with 0, 1, 2, 3, or 4 substituents selected from the group consisting of halo, —OH, —CN, —$NH_2$, —$NO_2$, —$SO_2(C_{1-6}$alkyl), —$C_{1-6}$alkoxy, -cycloalkyl, -heterocycloalkyl, aryl, and heteroaryl; wherein at each occurrence cycloalkyl and heterocycloalkyl are substituted with 0, 1, 2, 3, or 4 substituents selected from the group consisting of halo, -oxo, —OH, —CN, —$NH_2$, —$NO_2$, —$C_{1-6}$alkyl, —$SO_2(C_{1-6}$alkyl), —$C_{1-6}$alkoxy, aryl, and heteroaryl; wherein at each occurrence aryl and heteroaryl are substituted with 0, 1, 2, or 3 substituents selected from the group consisting of halo, —OH, —CN, —$NH_2$, $NO_2$, —$NH(C_{1-6}$alkyl), —$N(C_{1-6}$alkyl)$_2$, —$C_{1-6}$alkyl, cycloalkyl, heterocycloalkyl, and $C_{1-6}$alkoxy.

In some embodiments, $R^9$ and $R^{9'}$ are H; $R^7$, $R^{7'}$, $R^8$, and $R^{8'}$ are each independently -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1-C_6$ alkyl), or —$C(=O)N(R^{12})_2$;
- wherein each $R^{12}$ is independently —$C_{1-6}$alkyl, —$C_{1-6}$alkoxy, heterocycloalkyl, or heteroaryl;
- wherein at each occurrence heterocycloalkyl is substituted with 0, 1, or 2, substituents selected from the group consisting of halo, -oxo, —$C_{1-6}$alkyl, —$SO_2(C_{1-6}$alkyl), or —$C_{1-6}$alkoxy.

In some embodiments of a compound of formula I or II, $R^1$ is difluorochloromethyl;
$R^2$ is —H; $R^3$ is —H; $R^4$ is —$C_{1-6}$alkyl; $R^5$ and $R^6$ are —H;
Ar is a 5- or 6-membered monocyclic aromatic ring systems having 1, 2, or 3 heteroatoms selected from a group consisting of nitrogen, oxygen and sulfur atoms;
L is —O—; $R^9$ and $R^{9'}$ are H; $R^7$, $R^{7'}$, $R^8$, and $R^{8'}$ are each independently H, heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1$-$C_6$ alkyl), or —$C(=O)N(R^{12})_2$;
each $R^{11}$ is independently —H or —$C_{1\text{-}6}$alkyl; and
each $R^{12}$ is independently —$C_{1\text{-}6}$alkyl, —$C_{1\text{-}6}$alkoxy, heterocycloalkyl, or heteroaryl;
wherein at each occurrence heterocycloalkyl is substituted with 0, 1, or 2, substituents selected from the group consisting of halo, -oxo, —$C_{1\text{-}6}$alkyl, —$SO_2(C_{1\text{-}6}$alkyl), or —$C_{1\text{-}6}$alkoxy.

In some embodiments of a compound of formula I or II, $R^1$ is difluorochloromethyl;
$R^2$ is —H; $R^3$ is —H; $R^4$ is —$C_{1\text{-}6}$alkyl or -cycloalkyl; $R^5$ and $R^6$ are —H;
Ar is a 5- or 6-membered monocyclic aromatic ring systems having 0, 1, 2, or 3 heteroatoms selected from a group consisting of nitrogen, oxygen and sulfur atoms, wherein Ar is substituted with 0, 1, 2, or 3 substituents comprising halo, —OH, —CN, —$C_{1\text{-}6}$alkyl, -cycloalkyl, -heterocycloalkyl, and —$C_{1\text{-}6}$alkoxy;
L is —O—; $R^9$ and $R^{9'}$ are H; $R^7$, $R^{7'}$, $R^8$, and $R^{8'}$ are each independently H, heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1$-$C_6$ alkyl), or —$C(=O)N(R^{12})_2$;
each $R^{11}$ is independently —H or —$C_{1\text{-}6}$alkyl; and
each $R^{12}$ is independently —$C_{1\text{-}6}$alkyl, —$C_{1\text{-}6}$alkoxy, heterocycloalkyl, or heteroaryl;
wherein at each occurrence heterocycloalkyl is substituted with 0, 1, or 2, substituents selected from the group consisting of halo, -oxo, —$C_{1\text{-}6}$alkyl, —$SO_2(C_{1\text{-}6}$alkyl), or —$C_{1\text{-}6}$alkoxy.

In some embodiments, $R^9$ and $R^{9'}$ are H; $R^7$, $R^{7'}$, $R^8$, and $R^{8'}$ are each independently —H, -heterocycloalkyl, —$OR^{12}$, —$N(R^{12})_2$, —$NR^{11}C(=O)R^{12}$, —$NR^{11}C(=O)N(R^{12})_2$, —$NR^{11}SO_2R^{12}$, —$NR^{11}SO_2N(R^{12})_2$, or —$C(=O)O(C_{1\text{-}6}$alkyl); each $R^{12}$ is independently —$C_{1\text{-}6}$alkyl, —$C_{1\text{-}6}$alkoxy, heterocycloalkyl, or heteroaryl; wherein at each occurrence heterocycloalkyl is substituted with 0, 1, or 2, substituents selected from the group consisting of halo, -oxo, —$C_{1\text{-}6}$alkyl, —$SO_2(C_{1\text{-}6}$alkyl), or —$C_{1\text{-}6}$alkoxy.

In some embodiments, $R^9$ and $R^{9'}$ are H; $R^7$, $R^{7'}$, $R^8$, and $R^{8'}$ are each independently —H or -heterocycloalkyl.

In some embodiments, $R^9$ and $R^{9'}$ are H; $R^7$, $R^{7'}$, $R^8$, and $R^{8'}$ are each independently —H or —$OR^{12}$ or —$N(R^{12})_2$.

In some embodiments, $R^9$ and $R^{9'}$ are H; $R^7$, $R^{7'}$, $R^8$, and $R^{8'}$ are each independently —H or —$NR^{11}C(=O)R^{12}$.

In some embodiments, $R^9$ and $R^{9'}$ are H; $R^7$, $R^{7'}$, $R^8$, and $R^{8'}$ are each independently —H or —$NR^{11}C(=O)N(R^{12})_2$.

In some embodiments, $R^9$ and $R^{9'}$ are H; $R^7$, $R^{7'}$, $R^8$, and $R^{8'}$ are each independently —H or —$NR^{11}SO_2R^{12}$.

In some embodiments, $R^9$ and $R^{9'}$ are H; $R^7$, $R^{7'}$, $R^8$, and $R^{8'}$ are each independently —H or —$NR^{11}SO_2N(R^{12})_2$.

In some embodiments, $R^9$ and $R^{9'}$ are H; $R^7$, $R^{7'}$, $R^8$, and $R^{8'}$ are each independently —H or —$C(=O)O(C_{1\text{-}6}$alkyl).

In some embodiments, each $R^{12}$ is independently —$C_{1\text{-}6}$alkyl, —$C_{1\text{-}6}$alkoxy, heterocycloalkyl, or heteroaryl; wherein at each occurrence heterocycloalkyl is optionally substituted with 0, 1, or 2, substituents selected from the group consisting of halo, -oxo, —$C_{1\text{-}6}$alkyl, —$SO_2(C_{1\text{-}6}$alkyl), or —$C_{1\text{-}6}$alkoxy.

In some embodiments, each $R^{12}$ is independently heterocycloalkyl optionally substituted with oxo. In some embodiments, each $R^{12}$ is independently heterocycloalkyl optionally substituted with oxo.

In some embodiments, $R^{11}$ is H.

In some embodiments, $R^9$ and $R^{9'}$ are H; $R^7$, $R^{7'}$, $R^8$, and $R^{8'}$ are each independently —H, —$OR^{12}$, or —$N(R^{12})_2$, wherein $R^{12}$ is H, $C_{1\text{-}6}$alkyl, heterocycloalkyl, or heteroaryl.

In some embodiments, $R^9$ and $R^{9'}$ are H; $R^7$, $R^{7'}$, $R^8$, and $R^{8'}$ are each independently —H, —$NR^{11}C(=O)R^{12}$ or —$NR^{11}C(=O)N(R^{12})_2$, wherein $R^{11}$ is H, and $R^{12}$ is $C_{1\text{-}6}$alkyl, —$C_{1\text{-}6}$alkoxy, heterocycloalkyl, or heteroaryl.

In some embodiments, $R^9$ and $R^{9'}$ are H; $R^7$, $R^{7'}$, $R^8$, and $R^{8'}$ are each independently —H, —$NR^{11}SO_2R^{12}$ or —$NR^{11}C(=O)N(R^{12})_2$, wherein $R^{11}$ is H, and $R^{12}$ is $C_{1\text{-}6}$alkyl, heterocycloalkyl, or heteroaryl.

In some embodiments of a compound of formula I or II, wherein $R^8$, $R^{8'}$, $R^9$, and $R^{9'}$ are —H, one of $R^7$ and $R^{7'}$ is H, and the other one is -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1$-$C_6$ alkyl), or —$C(=O)N(R^{12})_2$; each $R^{12}$ is independently —$C_{1\text{-}6}$alkyl, —$C_{1\text{-}6}$alkoxy, heterocycloalkyl, or heteroaryl; wherein at each occurrence heterocycloalkyl is substituted with 0, 1, or 2, substituents selected from the group consisting of halo, -oxo, —$C_{1\text{-}6}$alkyl, —$SO_2(C_{1\text{-}6}$alkyl), or —$C_{1\text{-}6}$alkoxy.

In some embodiments of a compound of formula I or II, wherein $R^7$, $R^{7'}$, $R^9$, and $R^{9'}$ are —H, one of $R^8$ and $R^{8'}$ is H, and the other one is -heterocycloalkyl, —$OR^{12}$, —$N(R^{12})_2$, —$NR^{11}C(=O)R^{12}$, —$NR^{11}C(=O)OR^{12}$, —$NR^{11}C(=O)N(R^{12})_2$, —$NR^{11}SO_2R^{12}$, —$NR^{11}SO_2N(R^{12})_2$, —$C(=O)R^{12}$, —$C(=O)O(C_1$-$C_6$ alkyl), or —$C(=O)N(R^{12})_2$; each $R^{12}$ is independently —$C_{1\text{-}6}$alkyl, —$C_{1\text{-}6}$alkoxy, heterocycloalkyl, or heteroaryl; wherein at each occurrence heterocycloalkyl is substituted with 0, 1, or 2, substituents selected from the group consisting of halo, -oxo, —$C_{1\text{-}6}$alkyl, —$SO_2(C_{1\text{-}6}$alkyl), or —$C_{1\text{-}6}$alkoxy.

In some embodiments of a compound of formula I or II, wherein $R^9$ and $R^{9'}$ are H; $R^7$, $R^{7'}$, $R^8$, and $R^{8'}$ are each independently H or -heterocycloalkyl; wherein heterocycloalkyl is 5- or 6-membered monocyclic ring system having 1, 2, or 3 heteroatoms selected from a group consisting of nitrogen, oxygen, and sulfur; or wherein heterocycloalkyl is 5- or 6-membered monocyclic ring system having 1 or 2 heteroatoms selected from a group consisting of nitrogen. In some embodiments, heterocycloalkyl is substituted with 1 or 2 oxo.

In some embodiments of a compound of formula I or II, wherein $R^9$ and $R^{9'}$ are H; $R^7$, $R^{7'}$, $R^8$, and $R^{8'}$ are each independently H or heteroaryl, wherein the heteroaryl is 5- or 6-membered aromatic ring system having 1, 2, or 3 heteroatoms selected from a group consisting of nitrogen, oxygen, and sulfur.

In some embodiments of a compound of formula I or II, wherein $R^9$ and $R^{9'}$ are H; $R^7$, $R^{7'}$, $R^8$, and $R^{8'}$ are each independently H or OH. In some embodiments, $R^{7'}$, $R^{6'}$, $R^9$ and $R^{9'}$ are H; $R^7$ and $R^8$ are each OH.

In some embodiments of a compound of formula I or II, wherein $R^9$ and $R^{9'}$ are H; $R^7$, $R^{7'}$, $R^8$, and $R^{8'}$ are each independently —H or —$C(=O)O(C_1$-$C_6$ alkyl). In some embodiments of a compound of formula I or II, wherein $R^9$ and $R^{9'}$ are H; $R^7$, $R^{7'}$, $R^8$, and $R^{8'}$ are each independently —H or $C_1$-$C_6$ alkyl. In some embodiments of a compound of formula I or II, wherein $R^9$ and $R^{9'}$ are H; $R^7$, $R^{7'}$, $R^1$, and $R^{8'}$ are each independently —H or $C_1$-$C_6$ alkyl substituted with 1, 2, or 3 halo.

In some embodiments of a compound of formula I or II, wherein $R^9$ and $R^{9'}$ are H; $R^7$, $R^{7'}$, $R^8$, and $R^{8'}$ are each independently H or any one of the moieties provided in Table 3. In some embodiments, $R^7$, $R^8$, $R^{8'}$, $R^9$ and $R^{9'}$ are H, $R^7$ is any one of the moieties provided in Table 3. In some embodiments, $R^7$, $R^{7'}$, $R^{8'}$, $R^9$ and $R^{9'}$ are H, $R^8$ is any one of the moieties provided in Table 3:

TABLE 3

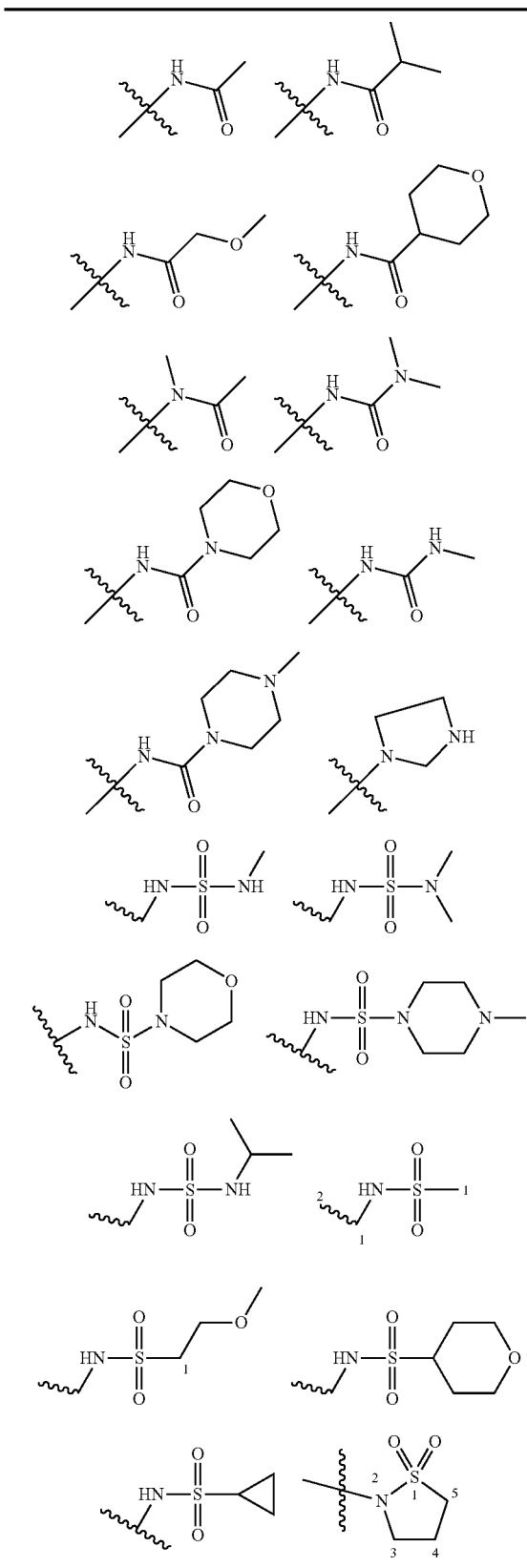

TABLE 3-continued

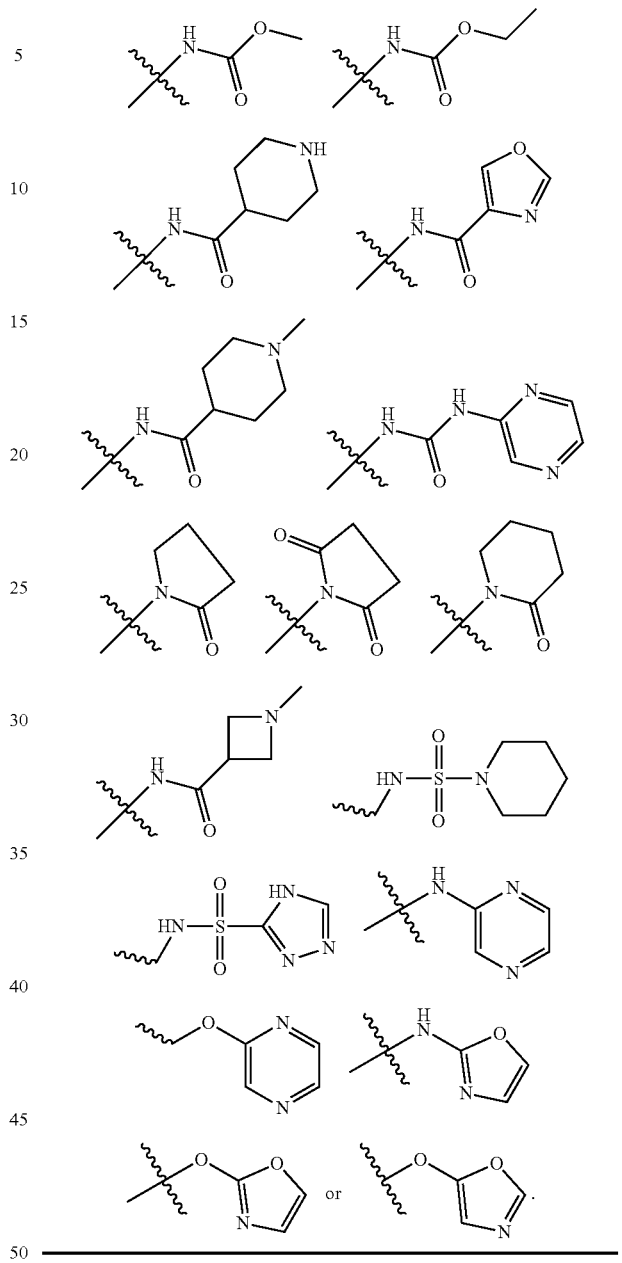

In some embodiments of a compound of formula I or II, $R^7$ and $R^{7'}$ are each independently —H, —OH, or —NHC(=O)($C_{1-3}$alkyl). In some embodiments, $R^{7'}$ is —H. In some embodiments, $R^7$ is —OH. In some embodiments, $R^7$ is —NHC(=O)($R^{12}$), wherein $R^{12}$ is H, $C_{1-3}$alkyl, or heterocycloalkyl. In some embodiment, $R^7$ is —NHC(=O)$C_{1-3}$alkyl.

In some embodiments of a compound of formula I or II, $R^7$ is —$NR^{11}$C(=O)N($R^{12}$)$_2$; wherein each $R^{12}$ is H, $C_{1-3}$alkyl, or heterocycloalkyl. In some embodiment, $R^7$ is —NHC(=O)N$C_{1-3}$alkyl.

In some embodiments of a compound of formula I or II, $R^7$ is —$NR^{11}SO_2R^{12}$; wherein $R^{12}$ is H, $C_{1-3}$alkyl, or heterocycloalkyl. In some embodiment, $R^7$ is —NHSO$_2$$C_{1-3}$alkyl.

In some embodiments of a compound of formula I or II, $R^7$ is $NR^{11}SO_2N(R^{12})_2$; wherein each $R^{12}$ is H, $C_{1-3}$alkyl, or heterocycloalkyl. In some embodiment, $R^7$ is —NHSO$_2$NC$_{1-3}$alkyl.

In some embodiments of a compound of formula I or II, $R^8$ and $R^{8'}$ are each independently —H, —OH, or —NHC(=O)(C$_{1-3}$alkyl). In some embodiments, $R^{8'}$ is —H. In some embodiments, $R^8$ is —OH. In some embodiments, $R^8$ is —NHC(=O)(R$^{12}$), wherein $R^{12}$ is H, C$_{1-3}$alkyl, or heterocycloalkyl. In some embodiment, $R^8$ is —NHC(=O)C$_{1-3}$alkyl.

In some embodiments of a compound of formula I or II, $R^8$ is —NR$^{11}$C(=O)N(R$^{12}$)$_2$; wherein each $R^{12}$ is H, C$_{1-3}$alkyl, or heterocycloalkyl. In some embodiment, $R^8$ is —NHC(=O)NC$_{1-3}$alkyl.

In some embodiments of a compound of formula I or II, $R^8$ is —NR$^{11}$SO$_2$R$^{12}$; wherein $R^{12}$ is H, C$_{1-3}$alkyl, or heterocycloalkyl. In some embodiment, $R^8$ is —NHSO$_2$C$_{1-3}$alkyl.

In some embodiments of a compound of formula I or II, $R^8$ is NR$^{11}$SO$_2$N(R$^{12}$)$_2$; wherein each $R^{12}$ is H, C$_{1-3}$alkyl, or heterocycloalkyl. In some embodiment, $R^8$ is —NHSO$_2$NC$_{1-3}$alkyl.

In some embodiments of a compound of formula I or II, $R^7$, $R^{7'}$, $R^8$, $R^{8'}$, $R^9$ and $R^{9'}$ are H.

In some embodiments of a compound of formula I or II, $R^{7'}$, $R^{8'}$, $R^9$ and $R^{9'}$ are H.

In some embodiments of a compound of formula II, $R^7$ is —NHC(=O)(C$_{1-3}$alkyl), and $R^{7'}$, $R^8$, $R^{8'}$, $R^9$ and $R^{9'}$ are H.

In some embodiments of a compound of formula II, $R^7$ is —NHC(=O)CH$_3$, and $R^{7'}$, $R^8$, $R^{8'}$, $R^9$ and $R^{9'}$ are H.

In some embodiments of a compound of formula I or II, $R^1$ is —C$_{1-6}$alkyl substituted with 1, 2, or 3 halo; $R^2$ is —H; $R^3$ is —H or —C$_{1-6}$alkyl; L is —S— or —O—; $R^4$ is —C$_{1-6}$alkyl, —C$_{1-5}$alkyl, —C$_{1-4}$alkyl, or —C$_{1-3}$alkyl; $R^5$ and $R^6$ is H; Ar is any one of the moieties provided in Table 2; $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is —C$_{1-6}$alkyl substituted with 1, 2, or 3 halo; $R^2$ is —H; $R^3$ is —H or —C$_{1-6}$alkyl; L is —S— or —O—; $R^4$ is —C$_{1-6}$alkyl, —C$_{1-5}$alkyl, —C$_{1-4}$alkyl, —C$_{1-3}$alkyl, —C$_{3-8}$cycloalkyl, —C$_{3-7}$cycloalkyl, —C$_{3-6}$cycloalkyl, or —C$_{3-5}$cycloalkyl; $R^5$ and $R^6$ is H; Ar is any one of the moieties provided in Table 2-A; $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is —C$_{1-6}$alkyl substituted with 1, 2, or 3 F or Cl; $R^2$ is —H; $R^3$ is —H or methyl; L is —S— or —O—; and $R^4$ is —C$_{1-4}$alkyl or —C$_{1-3}$alkyl; $R^5$ and $R^6$ is H; Ar is any one of the moieties provided in Table 2, and $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is —C$_{1-6}$alkyl substituted with 1, 2, or 3 F or Cl; $R^2$ is —H; $R^3$ is —H or methyl; L is —S— or —O—; and $R^4$ is —C$_{1-4}$alkyl, —C$_{1-3}$alkyl, —C$_{3-6}$cycloalkyl, or —C$_{3-5}$cycloalkyl; $R^5$ and $R^6$ is H; Ar is any one of the moieties provided in Table 2-A, and $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is difluorochloromethyl; $R^2$ is —H; $R^3$ is —H or methyl; L is —S— or —O—; $R^4$ is any one of the moieties provided in Table 1; $R^5$ and $R^6$ is H; Ar is any one of the moieties provided in Table 2, $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is difluorochloromethyl; $R^2$ is —H; $R^3$ is —H or methyl; L is —S— or —O—; $R^4$ is any one of the moieties provided in Table 1-A; $R^5$ and $R^6$ is H; Ar is any one of the moieties provided in Table 2-A, $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is difluorochloromethyl; $R^2$ is —H; $R^3$ is —H; L is —O—; $R^4$ is any one of the moieties provided in Table 1; $R^5$ and $R^6$ is H; Ar is any one of the moieties provided in Table 2, $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is difluorochloromethyl; $R^2$ is —H; $R^3$ is —H; L is —O—; $R^4$ is any one of the moieties provided in Table 1-A; $R^5$ and $R^6$ is H; Ar is any one of the moieties provided in Table 2-A, $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is difluorochloromethyl; $R^2$ is —H; $R^3$ is —H; L is —O—; $R^4$ is iso-propyl or neopentyl; $R^5$ and $R^6$ is H; and Ar is pyrimidinyl or pyrazinyl; $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is difluorochloromethyl; $R^2$ is —H; $R^3$ is —H; L is —O—; $R^4$ is iso-propyl, neopentyl, cyclopropyl, or cyclopentyl; $R^5$ and $R^6$ is H; and Ar is phenyl, pyrimidinyl, pyridazinyl, or pyrazinyl, any of which is substituted with 0, 1, or 2 substituents comprising halo, —CN, —C$_{1-6}$alkyl, and —C$_{1-6}$alkoxy; $R^7$, $R^{7'}$, $R^8$, and $R^{8'}$ are each independently H or any one of the moieties provided in Table 3; and $R^9$ and $R^{9'}$ are H.

In some embodiments of a compound of formula I or II, $R^1$ is difluorochloromethyl; $R^2$ is —H; $R^3$ is —H; L is —O—; $R^4$ is iso-propyl, neopentyl, cyclopropyl, or cyclopentyl; $R^5$ and $R^6$ is H; and Ar is phenyl, pyrimidinyl, pyridazinyl, pyrazinyl, or pyrazolyl, any of which is substituted with 0, 1, or 2 substituents comprising halo, —CN, —C$_{1-6}$alkyl, and —C$_{1-6}$alkoxy; $R^7$, $R^{7'}$, $R^8$, and $R^{8'}$ are each independently H or NHC(=O)(R$^{12}$), $R^9$ and $R^{9'}$ are H, and $R^{12}$ is —C$_{1-3}$alkyl, heterocycloalkyl, or heteroaryl.

In some embodiments of a compound of formula I or II, $R^1$ is difluorochloromethyl; $R^2$ is —H; $R^3$ is —H; L is —O—; $R^4$ is iso-propyl, neopentyl, cyclopropyl, or cyclopentyl; $R^5$ and $R^6$ is H; and Ar is phenyl, pyrimidinyl, pyridazinyl, pyrazinyl, or pyrazolyl, any of which is substituted with 0, 1, or 2 substituents comprising fluoro, chloro, —CN, methyl, and methoxy; $R^7$, $R^{7'}$, $R^8$, and $R^{8'}$ are each independently H or NHC(=O)(R$^{12}$), $R^9$ and $R^{9'}$ are H, and $R^{12}$ is —C$_{1-3}$alkyl.

In some embodiments, $R^1$ is difluorochloromethyl; $R^2$ is —H; $R^3$ is —H; L is —O—; $R^4$ is iso-propyl, or pentyl; $R^5$ and $R^6$ is H; and Ar is pyrazolyl; $R^7$, $R^{7'}$, $R^8$, and $R^{8'}$ are each independently H or any one of the moieties provided in Table 3; and $R^9$ and $R^{9'}$ are H.

In some embodiments; $R^1$ is difluorochloromethyl; $R^2$ is —H; $R^3$ is —H; L is —O—; $R^4$ is iso-propyl, or neopentyl; $R^5$ and $R^6$ is H; and Ar is pyrazolyl; $R^7$, $R^{7'}$, $R^8$, and $R^{8'}$ are each independently H or NHC(=O)(R$^{12}$), $R^9$ and $R^{9'}$ are H, and $R^{12}$ is —C$_{1-3}$alkyl, heterocycloalkyl, or heteroaryl.

In some embodiments of a compound of formula I or II, $R^1$ is difluorochloromethyl; $R^2$ is —H; $R^3$ is —H; L is —O—; $R^4$ is iso-propyl, or neopentyl; $R^5$ and $R^6$ is H; and Ar is pyrazolyl; $R^7$, $R^{7'}$, $R^8$, and $R^{8'}$ are each independently H or —NR$^{11}$C(=O)N(R$^{12}$)$_2$, $R^9$ and $R^{9'}$ are H, and $R^{12}$ is —C$_{1-3}$alkyl, heterocycloalkyl, or heteroaryl.

In some embodiments of a compound of formula I or II, $R^1$ is difluorochloromethyl; $R^2$ is —H; $R^3$ is —H; L is —O—; $R^4$ is iso-propyl, or neopentyl; $R^5$ and $R^6$ is H; and Ar is pyrazolyl; $R^7$, $R^{7'}$, $R^8$, and $R^{8'}$ are each independently H or heterocycloalkyl, $R^9$ and $R^{9'}$ are H.

In some embodiments of a compound of formula I or II, $R^1$ is difluorochloromethyl; $R^2$ is —H; $R^3$ is —H; L is —O—; $R^4$ is iso-propyl, or neopentyl; $R^5$ and $R^6$ is H; and Ar is pyrazolyl; $R^7$, $R^{7'}$, $R^8$, and $R^{8'}$ are each independently H or —NR$^{11}$SO$_2$R$^{12}$, $R^9$ and $R^{9'}$ are H, and $R^{12}$ is —C$_{1-6}$alkyl, heterocycloalkyl, cycloalkyl, or heteroaryl.

In some embodiments of a compound of formula I or II, $R^1$ is difluorochloromethyl; $R^2$ is —H; $R^3$ is —H; L is —O—; $R^4$ is iso-propyl, or neopentyl; $R^5$ and $R^6$ is H; and Ar is pyrazolyl; $R^7$, $R^{7'}$, $R^8$, and $R^{8'}$ are each independently H or —NR$^{11}$SO$_2$N(R$^{12}$)$_2$, $R^9$ and $R^{9'}$ are H, and $R^{12}$ is —C$_{1-6}$alkyl, heterocycloalkyl, or heteroaryl.

In some embodiments of a compound of formula I or II, $R^1$ is difluorochloromethyl; $R^2$ is —H; $R^3$ is —H; L is —O—; $R^4$ is iso-propyl, or neopentyl; $R^5$ and $R^6$ is H; and Ar is pyrazolyl; $R^7$, $R^{7'}$, $R^8$, and $R^{8'}$ are each independently H or OR$^{12}$ or NHR$^{12}$, $R^9$ and $R^{9'}$ are H, and $R^{12}$ is alkyl, heterocycloalkyl, or heteroaryl.

In some embodiments of a compound of formula II, which is a compound of formula IIa:

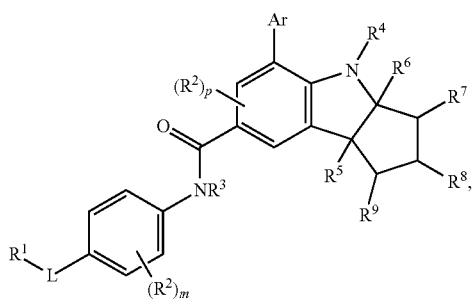

IIa or an enantiomer or diastereomer, or a pharmaceutically acceptable salt thereof, wherein $R^1$, $R^2$, $R^3$, $R^4$, $R^5$, $R^6$, $R^7$, $R^8$, $R^9$, L, Ar, m, and p are the same as defined herein.

In some embodiments of a compound of formula II, which is a compound of formula IIb:

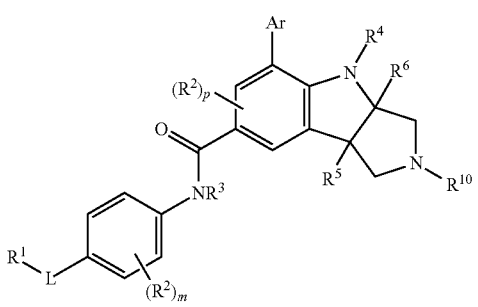

IIb or an enantiomer or diastereomer, or a pharmaceutically acceptable salt thereof, wherein $R^1$, $R^2$, $R^3$, $R^4$, $R^5$, $R^6$, $R^{10}$, L, Ar, m, and p are the same as defined herein.

In some embodiments of a compound of formula IIb, $R^{10}$ is —C$_{1-6}$alkyl, —C(=O)R$^{12}$, —C(=O)N(R$^{12}$)$_2$, —SO$_2$R$^{12}$, —SO$_2$N(R$^{12}$)$_2$, or heteroaryl.

In some embodiments of a compound of formula IIb, $R^1$ is difluorochloromethyl; $R^2$ is —H, $R^3$ is —H; $R^4$ is —C$_{1-6}$alkyl; $R^5$ and $R^6$ are —H; Ar is any one of the moieties provided in Table 2; and L is —O—; wherein $R^{10}$ is any one of the moieties provided in Table 4 below:

TABLE 4

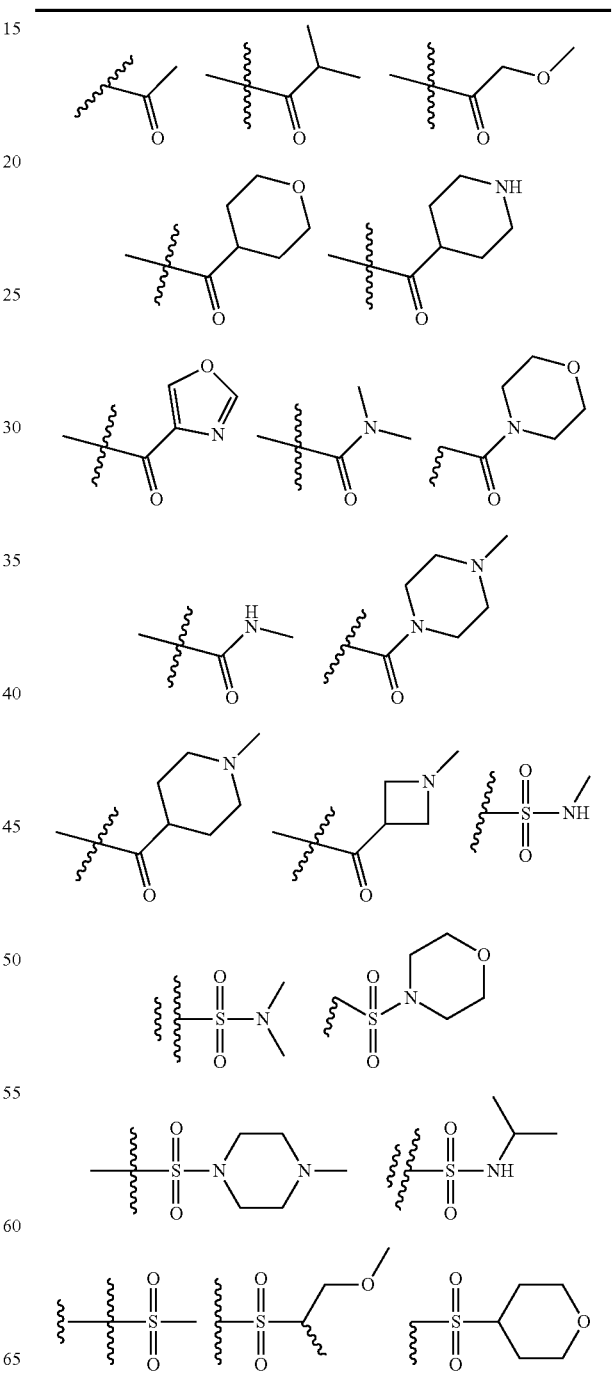

TABLE 4-continued

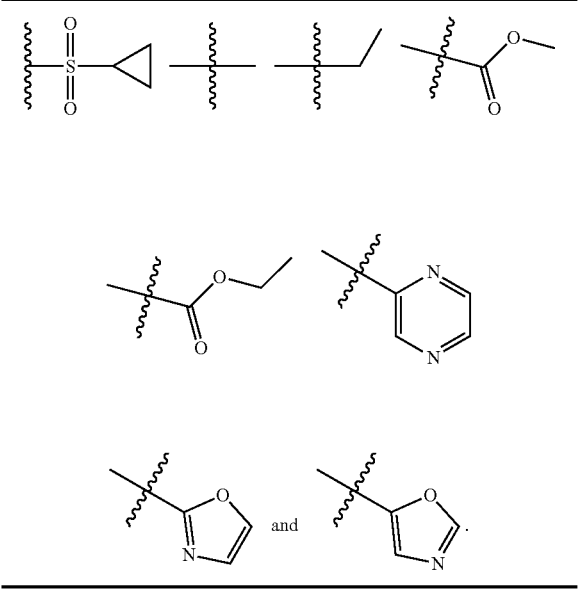

In some embodiments of a compound of formula IIb, R$^1$ is difluorochloromethyl; R$^2$ is —H, R$^3$ is —H; R$^4$ is —C$_{1-6}$alkyl; R$^5$ and R$^6$ are —H; Ar is any one of the moieties provided in Table 2-A; and L is —O—; wherein R$^{10}$ is any one of the moieties provided in Table 4.

In some embodiments of a compound of formula IIb, R$^1$ is difluorochloromethyl; R$^2$ is —H, R$^3$ is —H; R$^4$ is —C$_{1-6}$alkyl; R$^5$ and R$^6$ are —H; Ar is pyrimidinyl, pyrazinyl or pyrazolyl; L is —O; wherein R$^{10}$ is any one of the moieties provided in Table 4 as defined herein.

In some embodiments of a compound of formula IIb, R$^1$ is difluorochloromethyl; R$^2$ is —H, R$^3$ is —H; R$^4$ is —C$_{1-6}$alkyl; R$^5$ and R$^6$ are —H; Ar is pyrimidinyl, pyrazinyl or pyrazolyl, any of which is substituted with 0, 1, or 2 substituents comprising halo, —CN, —C$_{1-6}$alkyl, and —C$_{1-6}$alkoxy; and L is —O—; wherein R$^{10}$ is any one of the moieties provided in Table 4 as defined herein.

In some embodiments of a compound of formula II, which is a compound of formula IIA:

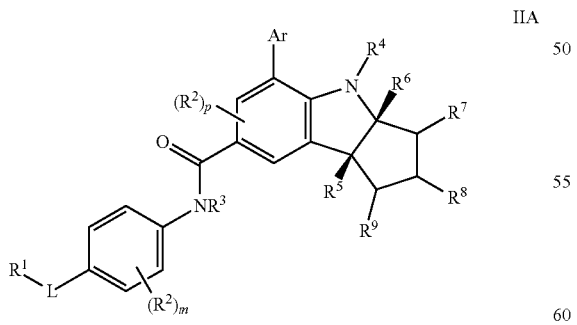

IIA or a pharmaceutically acceptable salt thereof, wherein R$^1$, R$^2$, R$^3$, R$^4$, R$^5$, R$^6$, R$^8$, R$^{8'}$, R$^9$, L, Ar, m, and p are the same as defined herein.

In some embodiments of a compound of formula II, which is a compound of formula IIA-1, IIA-2, IIA-3, IIA-4, IIA-5, IIA-6, IIA-7, or IIA-8:

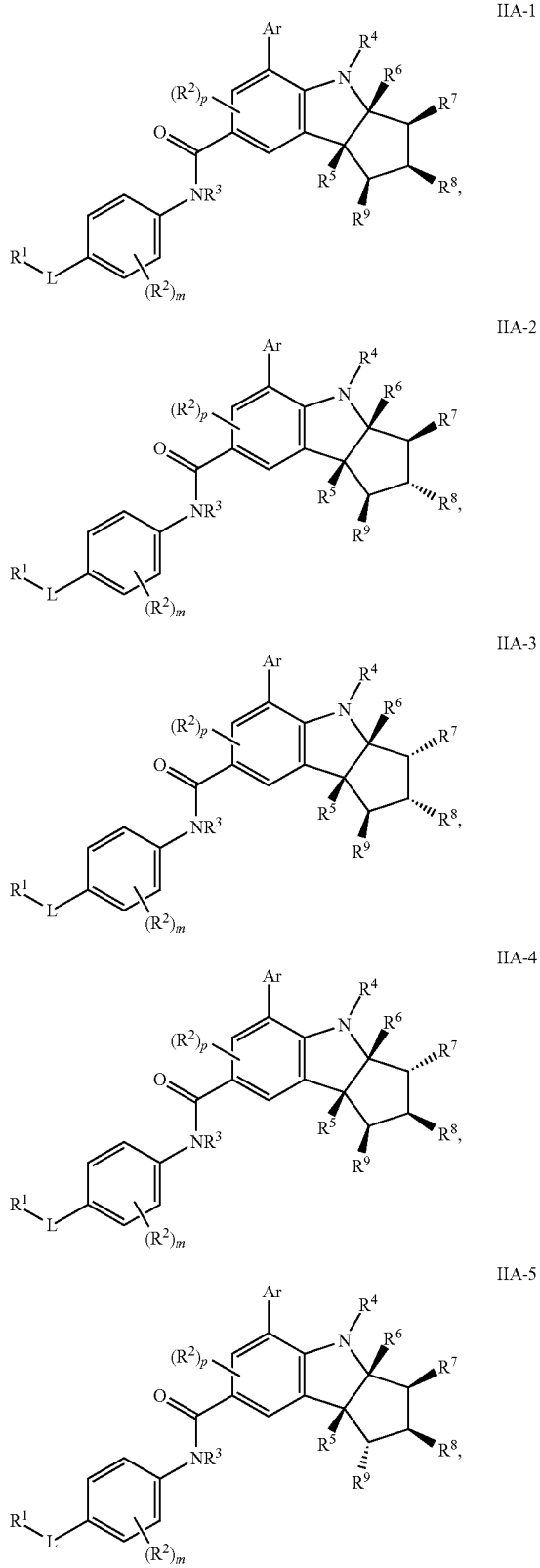

-continued

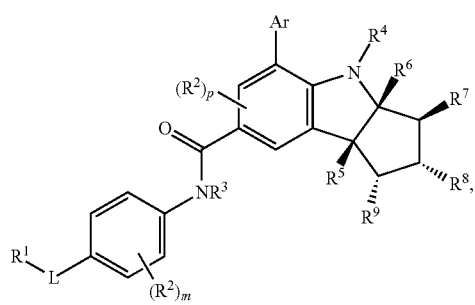
IIA-6

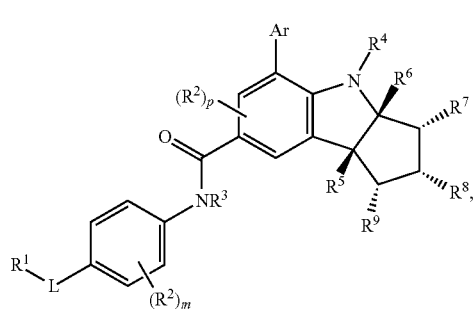
IIA-7

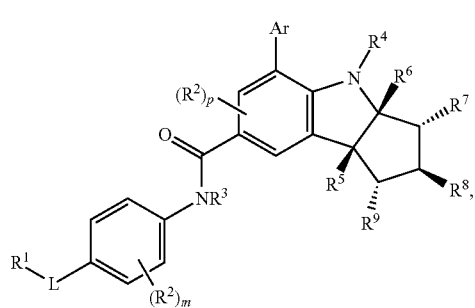
IIA-8 or a pharmaceutically acceptable salt thereof, wherein $R^1$, $R^2$, $R^3$, $R^4$, $R^5$, $R^6$, $R^7$, $R^8$, $R^9$, L, Ar, m, and p are the same as defined herein.

In some embodiments of a compound of formula II, which is a compound of formula IIA-9, IIA-10, IIA-11, IIA-12, IIA-13, or IIA-14:

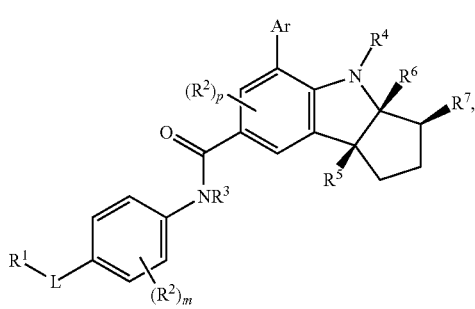
IIA-9

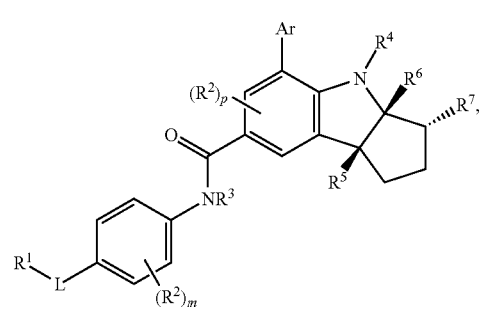
IIA-10

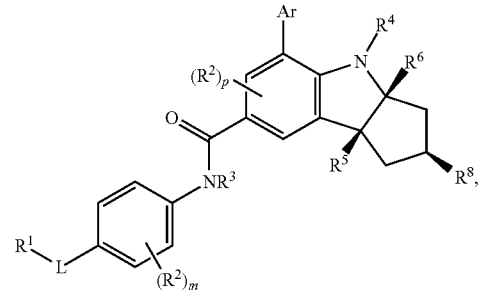
IIA-11

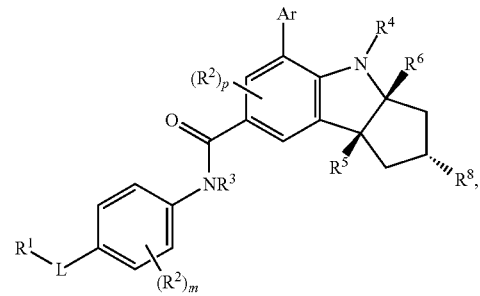
IIA-12

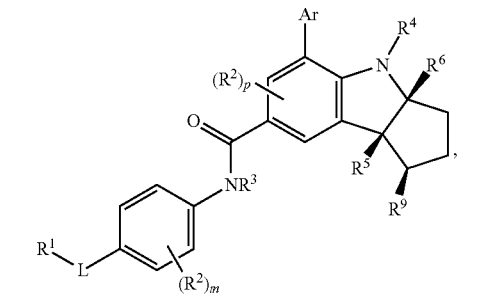
IIA-13

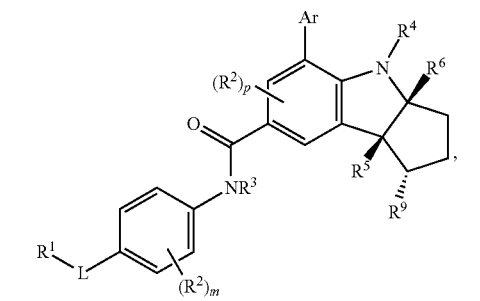
IIA-14 or a pharmaceutically acceptable salt thereof, wherein $R^1$, $R^2$, $R^3$, $R^4$, $R^5$, $R^6$, $R^7$, $R^8$, $R^9$, L, Ar, m, and p are the same as defined herein.

In some embodiments of a compound of formula II, which is a compound of formula IIA-15, IIA-16, IIA-17, or IIA-18:

IIA-15
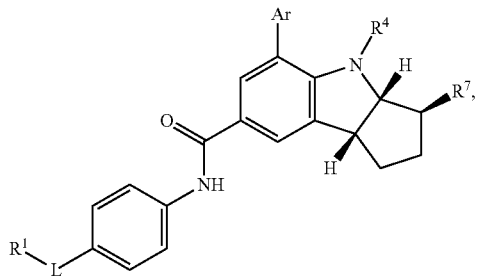
IIA-16
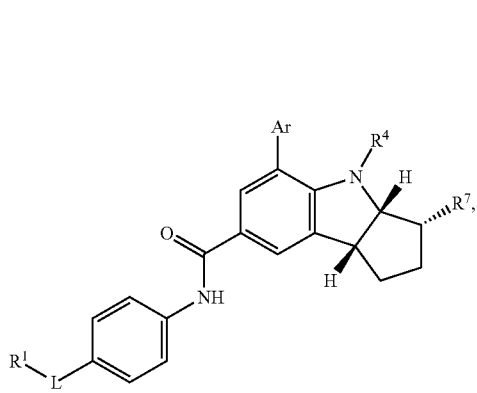
IIA-17
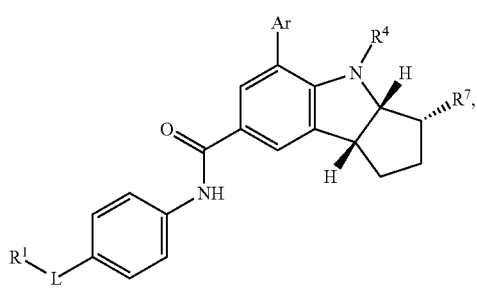
IIA-18
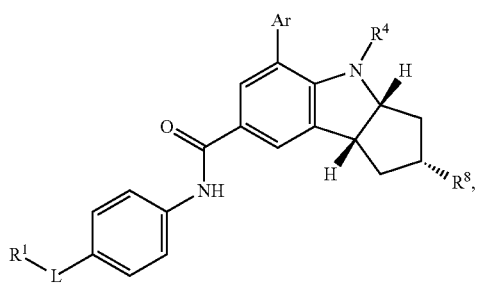
or a pharmaceutically acceptable salt thereof, wherein $R^1$, $R^4$, $R^7$, $R^8$, L, and Ar are the same as defined herein.
In some embodiments of a compound of formula II, which is a compound of formula IIA-19, IIA-20, IIA-21, or IIA-22:
IIA-19
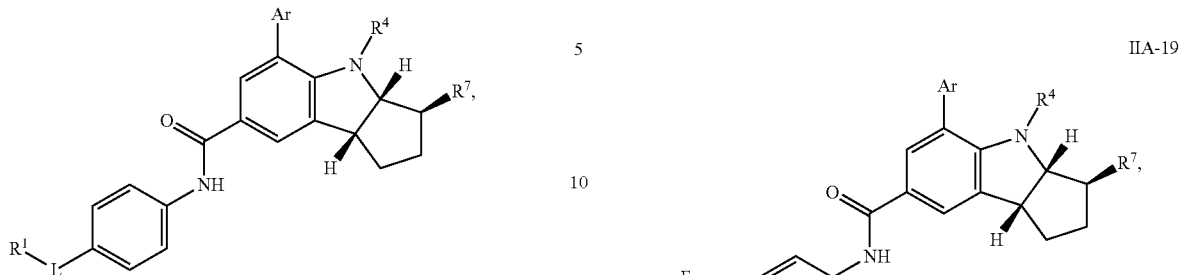
IIA-20
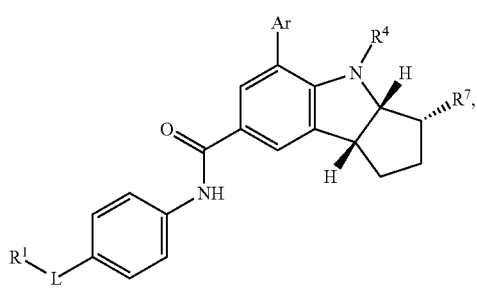
IIA-21
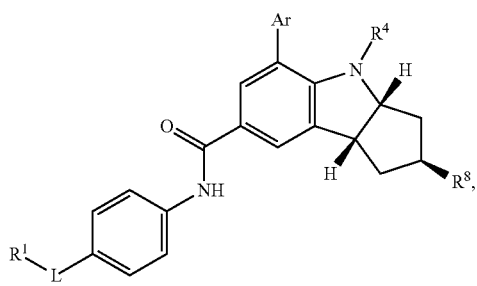
IIA-22
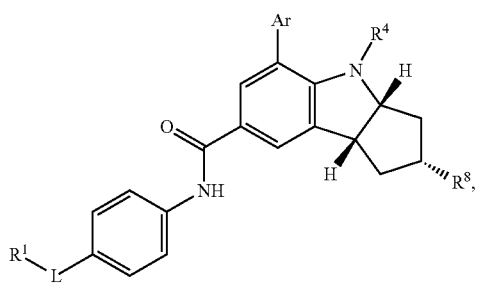
or a pharmaceutically acceptable salt thereof, wherein $R^4$, $R^7$, $R^8$, L, and Ar, are the same as defined herein.

In some embodiments of a compound of formula II, which is a compound of formula IIB:

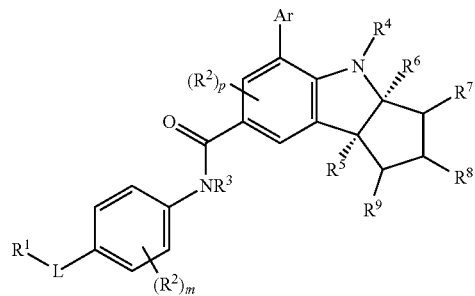

IIB or a pharmaceutically acceptable salt thereof, wherein $R^1$, $R^2$, $R^3$, $R^4$, $R^5$, $R^6$, $R^7$, $R^8$, $R^9$, L, Ar, m, and p are the same as defined herein.

In some embodiments of a compound of formula II, which is a compound of formula IIB-1, IIB-2, IIB-3, IIB-4, IIB-5, IIB-6, IIB-7, or IIB-8:

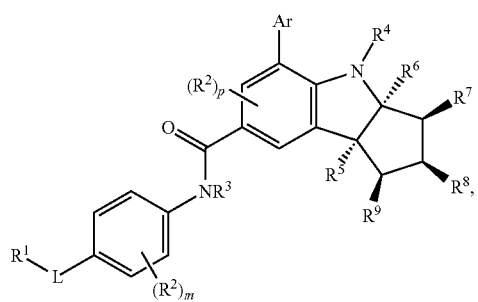

IIB-1

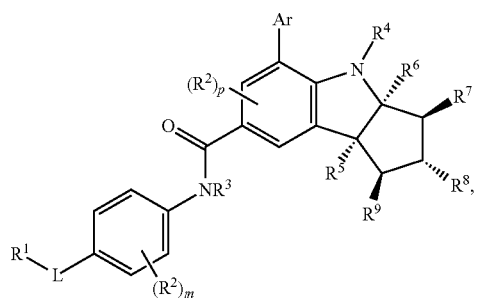

IIB-2

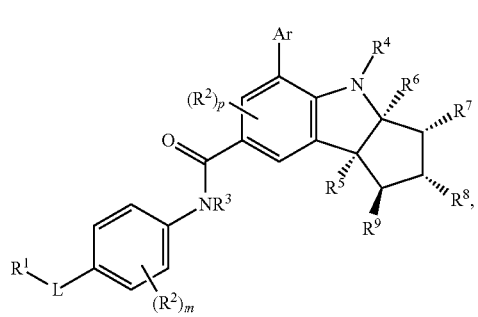

IIB-3

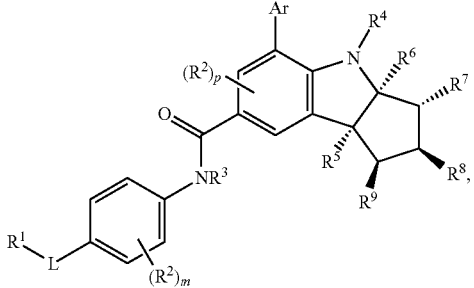

IIB-4

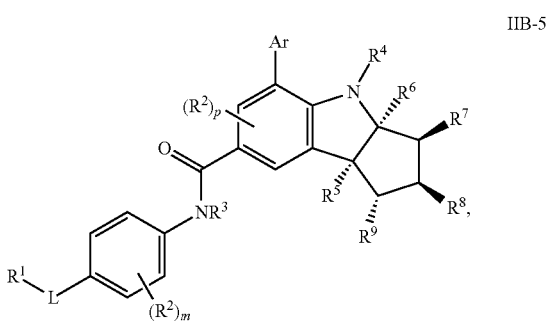

IIB-5

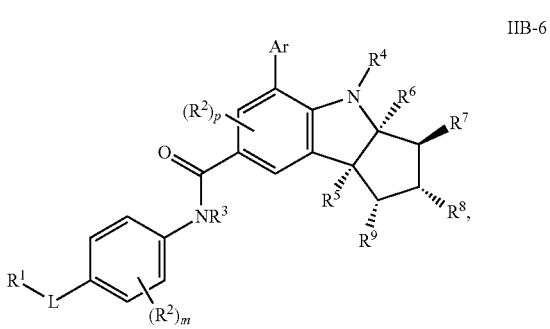

IIB-6

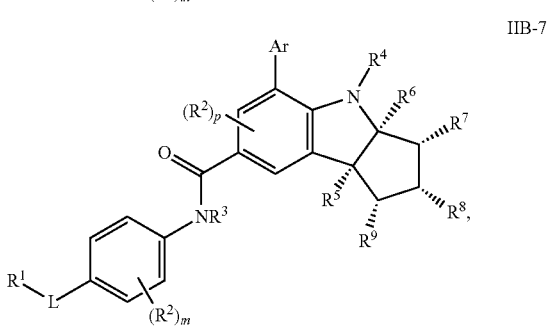

IIB-7

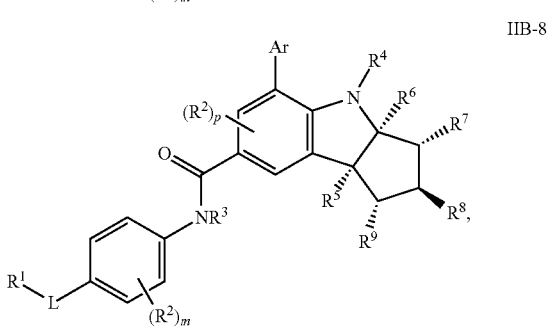

IIB-8 or a pharmaceutically acceptable salt thereof, wherein $R^1$, $R^2$, $R^3$, $R^4$, $R^5$, $R^6$, $R^7$, $R^8$, $R^9$, L, Ar, m, and p are the same as defined herein.

In some embodiments of a compound of formula II, which is a compound of formula IIB-9, IIB-10, IIB-11, IIB-12, IIB-13, IIB-14, or IIB-15:

IIB-9
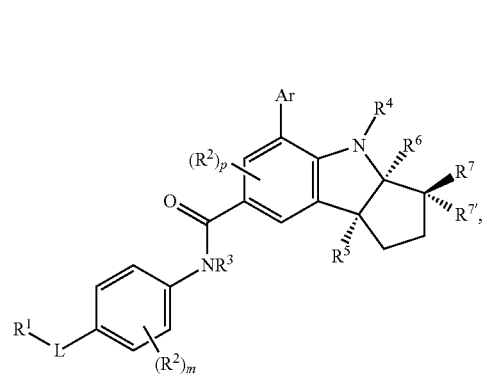

IIB-10
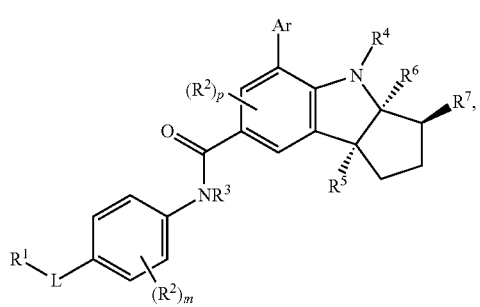

IIB-11
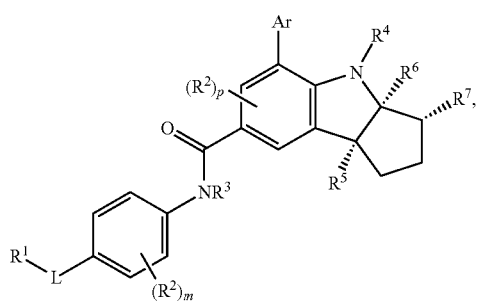

IIB-12
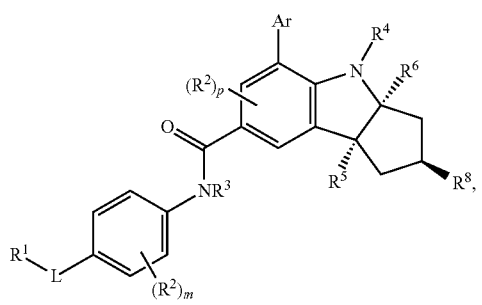

-continued

IIB-13
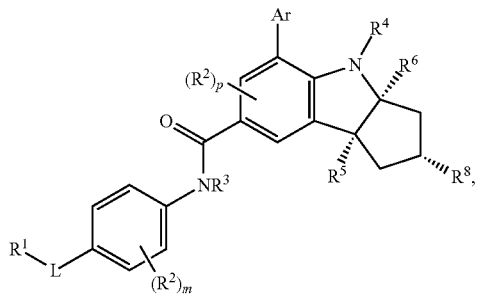

IIB-14
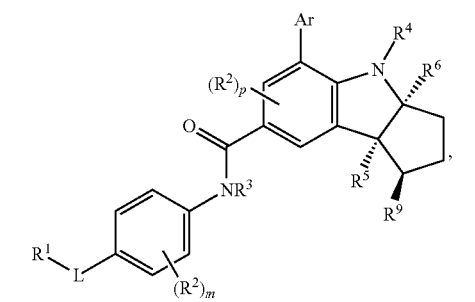

IIB-15
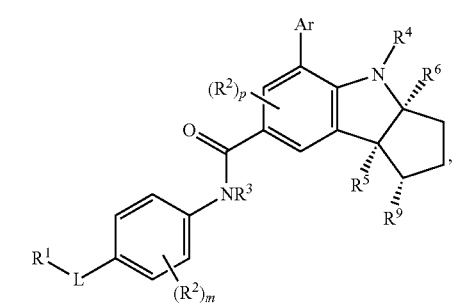

or a pharmaceutically acceptable salt thereof, wherein $R^1$, $R^2$, $R^3$, $R^4$, $R^5$, $R^6$, $R^7$, $R^{7'}$, $R^8$, $R^9$, L, Ar, m, and p are the same as defined herein.

In some embodiments of a compound of formula II, which is a compound of formula IIB-9:

IIB-9
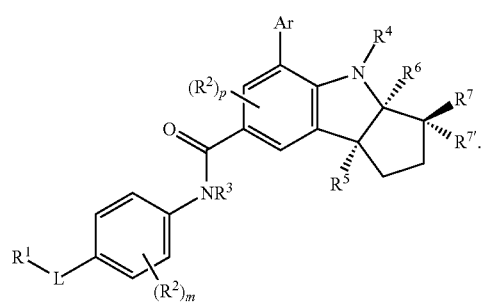

or a pharmaceutically acceptable salt thereof, wherein $R^1$, $R^2$, $R^3$, $R^4$, $R^5$, $R^6$, $R^7$, $R^{7'}$, L, Ar, m, and p are the same as defined herein.

In some embodiments of a compound of formula II, which is a compound of formula IIB-11:

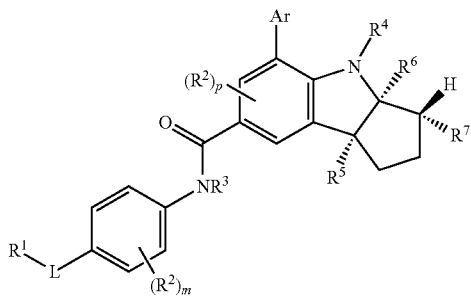
IIB-11 or a pharmaceutically acceptable salt thereof, wherein $R^1$, $R^2$, $R^3$, $R^4$, $R^5$, $R^6$, $R^7$, L, Ar, m, and p are the same as defined herein.

In some embodiments of a compound of formula II, which is a compound of formula IIB-16, IIB-17, IIB-18, or IIB-19:

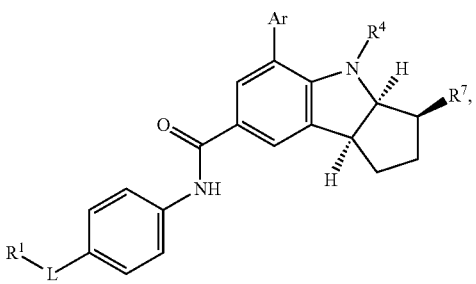
IIB-16

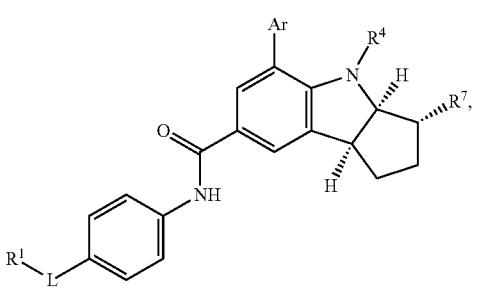
IIB-17

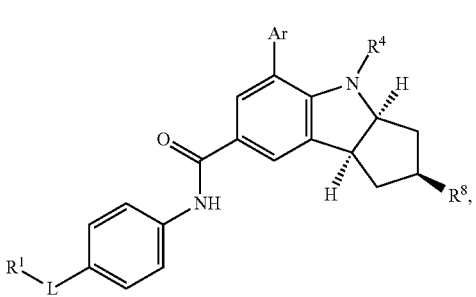
IIB-18

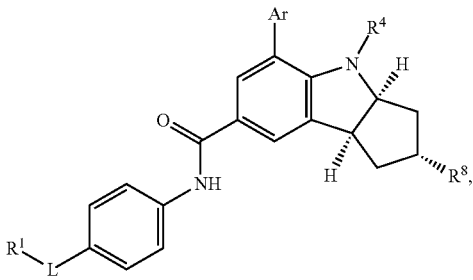
IIB-19 or a pharmaceutically acceptable salt thereof, wherein $R^1$, $R^4$, $R^7$, $R^8$, L, and Ar, are the same as defined herein.

In some embodiments of a compound of formula II, which is a compound of formula IIB-20, IIB-21, IIB-22, or IIB-23:

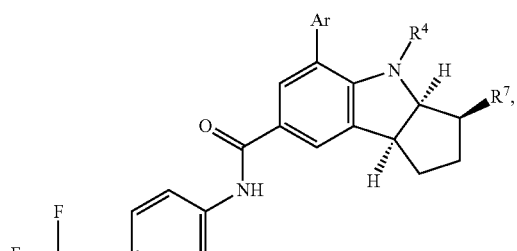
IIB-20

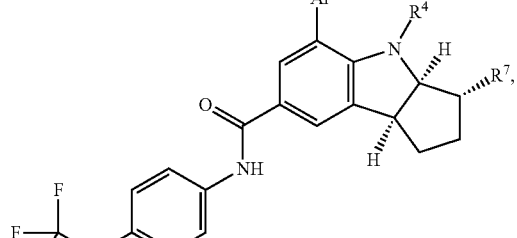
IIB-21

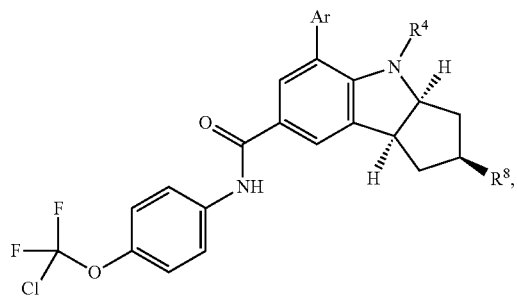
IIB-22

-continued

IIB-23

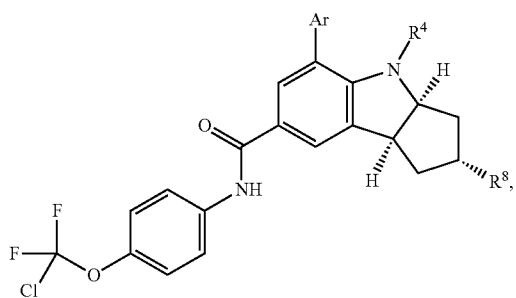

or a pharmaceutically acceptable salt thereof, wherein $R^4$, $R^7$, $R^1$, L, and Ar, are the same as defined herein.

In some embodiments of a compound of formula II, which is a compound of formula IIB-24:

IIB-24

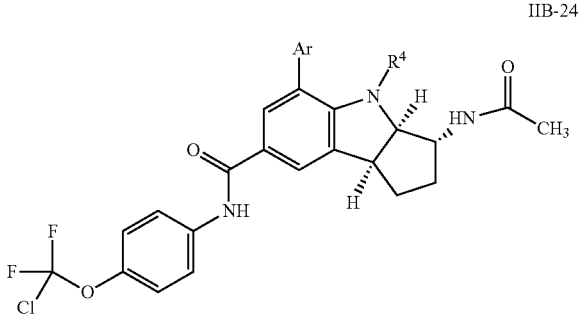

or a pharmaceutically acceptable salt thereof, wherein $R^4$ and Ar are the same as defined herein.

In some embodiments, the present disclosure provides a compound of formula III:

III

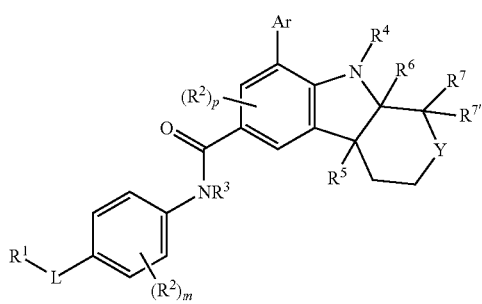

or an enantiomer or diastereomer, or a pharmaceutically acceptable salt thereof.

In some embodiments of a compound of formula III, $R^1$ is —$C_{1-6}$alkyl, cycloalkyl, or heterocycloalkyl;
each $R^2$ is independently —H, -halo, —OH, —CN, —NH$_2$, —NO$_2$, —$C_{1-6}$alkyl, or —$C_{1-6}$alkoxy; wherein m is 0, 1, 2, 3, or 4; p is 0, 1 or 2;
$R^3$ is —H or —$C_{1-6}$alkyl; $R^4$ is H or —$C_{1-6}$alkyl;
$R^5$ and $R^6$ are each independently —H or —$C_{1-6}$alkyl;
Ar is aryl or heteroaryl;
L is —S—, —O—, —C(=O)$R^{11}$—, —C(=O)O$R^{11}$—, —N($R^{11}$)—, —C(=O)N($R^{11}$)—, —C(=O)N($R^{11}$)—$C_{1-4}$alkyl-, —N($R^{11}$)C(=O)—, —N($R^{11}$)C(=O)—$C_{1-4}$alkyl-, —SO$_2$N($R^{11}$)—, or —N($R^{11}$)SO$_2$—;

Y is —C($R^8R^{8'}$)—, —O—, —N($R^{10}$)—, —C(=O)—, —SO$_2$—, or —SO$_2R^{12}$, $R^7$, $R^{7'}$, $R^8$ and $R^{8'}$ are each independently —H, —$C_{1-6}$alkyl, -cycloalkyl, -heterocycloalkyl, —O$R^{12}$, —N($R^{12}$)$_2$, —N$R^{11}$C(=O)$R^{12}$, —N$R^{11}$C(=O)O$R^{12}$, —N$R^{11}$C(=O)N($R^{12}$)$_2$, —N$R^{11}$SO$_2R^{12}$, —N$R^{11}$SO$_2$N($R^{12}$)$_2$, —C(=O)$R^{12}$, —C(=O)O($C_1$-$C_6$ alkyl), —C(=O)N($R^{12}$)$_2$, —SO$_2R^{12}$, —SO$_2$N($R^{12}$)$_2$, -aryl, or -heteroaryl;
$R^{10}$ is —H, —$C_{1-6}$alkyl, -cycloalkyl, heterocycloalkyl, —C(=O)$R^{12}$, —C(=O)O$R^{12}$—, —C(=O)N($R^{12}$)$_2$, —SO$_2R^{12}$, —SO$_2$N($R^{12}$)$_2$, aryl, or heteroaryl;
each $R^{11}$ is independently —H or —$C_{1-6}$alkyl; and
each $R^{12}$ is independently —H, —$C_{1-6}$alkyl, —$C_{1-6}$alkoxy, -cycloalkyl, heterocycloalkyl, aryl, or heteroaryl;
wherein at each occurrence alkyl is substituted with 0, 1, 2, 3, or 4 substituents selected from the group consisting of halo, -oxo, —OH, —CN, —NH$_2$, —NO$_2$, —SO$_2$($C_{1-6}$alkyl), —$C_{1-6}$alkoxy, -cycloalkyl, -heterocycloalkyl, aryl, and heteroaryl;
wherein at each occurrence cycloalkyl and heterocycloalkyl are substituted with 0, 1, 2, 3, or 4 substituents selected from the group consisting of halo, -oxo, —OH, —CN, —NH$_2$, —NO$_2$, —$C_{1-6}$alkyl, —SO$_2$($C_{1-6}$alkyl), —CO($C_{1-6}$alkyl), —$C_{1-6}$alkoxy, aryl, and heteroaryl;
wherein at each occurrence aryl and heteroaryl are substituted with 0, 1, 2, or 3 substituents selected from the group consisting of halo, —OH, —CN, —NH$_2$, NO$_2$, —NH($C_{1-6}$alkyl), —N($C_{1-6}$alkyl)$_2$, —$C_{1-6}$alkyl, -cycloalkyl, -heterocycloalkyl, and —$C_{1-6}$alkoxy.

In some embodiments of a compound of formula III, $R^1$ is —$C_{1-6}$alkyl, cycloalkyl, or heterocycloalkyl;
each $R^2$ is independently —H, -halo, —OH, —CN, —NH$_2$, —NO$_2$, —$C_{1-6}$alkyl, or —$C_{1-6}$alkoxy; wherein m is 0, 1, 2, 3, or 4; p is 0, 1 or 2;
$R^3$ is —H or —$C_{1-6}$alkyl; $R^4$ is —H, cycloalkyl, or —$C_{1-6}$alkyl; $R^5$ and $R^6$ are each independently —H or —$C_{1-6}$alkyl;
Ar is aryl or heteroaryl;
L is —S—, —O—, —C(=O)$R^{11}$—, —C(=O)O$R^{11}$—, —N($R^{11}$)—, —C(=O)N($R^{11}$)—, —C(=O)N($R^{11}$)—$C_{1-4}$alkyl-, —N($R^{11}$)C(=O)—, —N($R^{11}$)C(=O)—$C_{1-4}$alkyl-, —SO$_2$N($R^{11}$)—, or —N($R^{11}$)SO$_2$—;
Y is —C($R^8R^{8'}$)—, —O—, —N($R^{10}$)—, —C(=O)—, —SO$_2$—, or —SO$_2R^{12}$, $R^7$, $R^{7'}$, $R^8$ and $R^{8'}$ are each independently —H, —$C_{1-6}$alkyl, -cycloalkyl, -heterocycloalkyl, —O$R^{12}$, —N($R^{12}$)$_2$, —N$R^{11}$C(=O)$R^{12}$, —N$R^{11}$C(=O)O$R^{12}$, —N$R^{11}$C(=O)N($R^{12}$)$_2$, —N$R^{11}$SO$_2R^{12}$, —N$R^{11}$SO$_2$N($R^{12}$)$_2$, —C(=O)$R^{12}$, —C(=O)O($C_1$-$C_6$ alkyl), —C(=O)N($R^{12}$)$_2$, —SO$_2R^{12}$, —SO$_2$N($R^{12}$)$_2$, -aryl, or -heteroaryl;
$R^{10}$ is —H, —$C_{1-6}$alkyl, -cycloalkyl, heterocycloalkyl, —C(=O)$R^{12}$, —C(=O)O$R^{12}$—, —C(=O)N($R^{12}$)$_2$, —SO$_2R^{12}$, —SO$_2$N($R^{12}$)$_2$, aryl, or heteroaryl;
each $R^{11}$ is independently —H or —$C_{1-6}$alkyl; and
each $R^{12}$ is independently —H, —$C_{1-6}$alkyl, —$C_{1-6}$alkoxy, -cycloalkyl, heterocycloalkyl, aryl, or heteroaryl;
wherein at each occurrence alkyl is substituted with 0, 1, 2, 3, or 4 substituents selected from the group consisting of halo, -oxo, —OH, —CN, —NH$_2$, —NO$_2$, —SO$_2$($C_{1-6}$alkyl), —$C_{1-6}$alkoxy, -cycloalkyl, -heterocycloalkyl, aryl, and heteroaryl;
wherein at each occurrence cycloalkyl and heterocycloalkyl are substituted with 0, 1, 2, 3, or 4 substituents selected from the group consisting of halo, -oxo, —OH, —CN, —NH$_2$, —NO$_2$, —C$_{1-6}$alkyl, —SO$_2$(C$_{1-6}$alkyl), —CO(C$_{1-6}$alkyl), —C$_{1-6}$alkoxy, aryl, and heteroaryl;
wherein at each occurrence aryl and heteroaryl are substituted with 0, 1, 2, or 3 substituents selected from the group consisting of halo, —OH, —CN, —NH$_2$, NO$_2$, —NH(C$_{1-6}$alkyl), —N(C$_{1-6}$alkyl)$_2$, —C$_{1-6}$alkyl, -cycloalkyl, -heterocycloalkyl, and —C$_{1-6}$alkoxy.

In some embodiments of a compound of formula III, R$^1$ is —C$_{1-6}$alkyl; each R$^2$ is independently —H, -halo, —C$_{1-3}$alkyl, or —C$_{1-3}$alkoxy; R$^5$ and R$^6$ are —H; L is —S—, or —O—; and Y is —C(R$^8$R$^{8'}$)—, —O—, —N(R$^{10}$)—, or —SO$_2$—.

In some embodiments of a compound of formula III, Y is —C(R$^8$R$^{8'}$)—.

In some embodiments of a compound of formula III, Y is —N(R$^{10}$)—.

In some embodiments of a compound of formula III, Y is —SO$_2$—.

In some embodiments of a compound of formula III, R$^1$ is —C$_{1-6}$alkyl substituted with 1, 2, or 3 halo.

In some embodiments of a compound of formula III, R$^1$ is —C$_{1-6}$alkyl substituted with 1, 2, or 3 F or Cl.

In some embodiments of a compound of formula III, R$^1$ is fluoromethyl, difluoromethyl, difluorochloromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl.

In some embodiments of a compound of formula III, R$^1$ is difluorochloromethyl.

In some embodiments of a compound of formula III, L is —O—.

In some embodiments of a compound of formula III, R$^3$ is —H.

In some embodiments of a compound of formula III, R$^4$ is C$_{3-8}$cycloalkyl, C$_{3-7}$cycloalkyl, C$_{3-6}$cycloalkyl, C$_{3-5}$cycloalkyl. In some embodiments, R$^4$ is C$_{3-6}$cycloalkyl or C$_{3-6}$cycloalkyl. In some embodiments, R$^4$ is C$_{3-5}$cycloalkyl.

In some embodiments of a compound of formula III, R$^4$ is —C$_{1-6}$alkyl.

In some embodiments of a compound of formula III, R$^4$ is —C$_{1-6}$alkyl substituted with 1 or 2 substituents selected from the group consisting of halo, —OH, —CN, —NH$_2$, —SO$_2$(C$_{1-6}$alkyl), —C$_{1-6}$alkoxy, -cycloalkyl, -heterocycloalkyl, aryl, and heteroaryl; wherein cycloalkyl and heterocycloalkyl are substituted with 0 or 1 substituent selected from the group consisting of halo, -oxo, —OH, —CN, —NH$_2$, or —C$_{1-6}$alkyl.

In some embodiments of a compound of formula III, R$^4$ is any one of the moieties provided in Table 1.

In some embodiments of a compound of formula III, R$^4$ is any one of the moieties provided in Table 1-A.

In some embodiments of a compound of formula III, R$^4$ is C$_{1-4}$alkyl.

In some embodiments of a compound of formula III, R$^1$ is C$_{1-3}$alkyl.

In some embodiments of a compound of formula III, Ar is a 5-14 membered monocyclic and bicyclic aromatic ring systems having 1, 2, 3, or 4 heteroatoms selected from nitrogen, oxygen and sulfur.

In some embodiments of a compound of formula III, Ar is a 5-14 membered monocyclic and bicyclic aromatic ring systems having 0, 1, 2, 3, or 4 heteroatoms selected from nitrogen, oxygen and sulfur.

In some embodiments of a compound of formula III, Ar is a 5- or 6-membered monocyclic aromatic ring system having 1, 2, or 3 heteroatoms selected from nitrogen, oxygen and sulfur atoms.

In some embodiments of a compound of formula III, Ar is a 5- or 6-membered monocyclic aromatic ring system having 0, 1, 2, or 3 heteroatoms selected from nitrogen, oxygen and sulfur atoms.

In some embodiments of a compound of formula III, Ar is thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, O-carbolinyl, phenanthridinyl, acridinyl, pyrimidinyl, phenanthrolinyl, phenazinyl, thiazolyl, isothiazolyl, phenothiazolyl, oxazolyl, isoxazolyl, furazanyl, phenoxazinyl, triazolyl, triazinyl, and tetrazolyl.

In some embodiments of a compound of formula III, Ar is phenyl, thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, O-carbolinyl, phenanthridinyl, acridinyl, pyrimidinyl, phenanthrolinyl, phenazinyl, thiazolyl, isothiazolyl, phenothiazolyl, oxazolyl, isoxazolyl, furazanyl, phenoxazinyl, triazolyl, triazinyl, and tetrazolyl.

In some embodiments of a compound of formula III, Ar is any one of the moieties provided in Table 2.

In some embodiments of a compound of formula III, Ar is any one of the moieties provided in Table 2-A.

In some embodiments of a compound of formula III, R$^1$ is —C$_{1-6}$alkyl substituted with 1, 2, or 3 halo; each R$^2$ is independently —H, -halo, —C$_{1-3}$alkyl, or —C$_{1-3}$alkoxy;
wherein m is 0, 1, or 2; p is 0, 1 or 2; R$^3$ is —H; R$^4$ is —C$_{1-6}$alkyl; R$^5$ and R$^6$ are —H;
Ar is a 5- or 6-membered monocyclic aromatic ring system having 1, 2, or 3 heteroatoms selected from nitrogen, oxygen and sulfur atoms;
L is —O—, or —S—; and Y is —C(R$^8$R$^{8'}$)— or —N(R$^{10}$)—.

In some embodiments of a compound of formula III, R$^1$ is —C$_{1-6}$alkyl substituted with 1, 2, or 3 halo; each R$^2$ is independently —H, -halo, —C$_{1-3}$alkyl, or —C$_{1-3}$alkoxy;
wherein m is 0, 1, or 2; p is 0, 1 or 2; R$^3$ is —H; R$^4$ is —C$_{1-6}$alkyl; R$^5$ and R$^6$ are —H;
Ar is a 5- or 6-membered monocyclic aromatic ring system having 0, 1, 2, or 3 heteroatoms selected from nitrogen, oxygen and sulfur atoms;
L is —O—, or —S—; and Y is —C(R$^8$R$^{8'}$)—, —N(R$^{10}$)—, or —SO$_2$—.

In some embodiments of a compound of formula III, R$^1$ is —C$_{1-6}$alkyl substituted with 1, 2, or 3 halo; each R$^2$ is independently —H, -halo, —C$_{1-3}$alkyl, or —C$_{1-3}$alkoxy; wherein m is 0, 1, or 2; p is 0, 1 or 2; R$^3$ is —H; R$^4$ is —C$_{1-6}$alkyl; R$^5$ and R$^6$ are —H; Ar is a 5- or 6-membered monocyclic aromatic ring systems having 1, 2, or 3 heteroatoms selected from nitrogen, oxygen and sulfur atoms; L is —O—; and Y is —C(R$^8$R$^8$)—.

In some embodiments of a compound of formula III, R$^1$ is —C$_{1-6}$alkyl substituted with 1, 2, or 3 halo; each R$^2$ is independently —H, -halo, —C$_{1-3}$alkyl, or —C$_{1-3}$alkoxy; wherein m is 0, 1, or 2; p is 0, 1 or 2; R$^3$ is —H; R$^4$ is —C$_{1-6}$alkyl; R$^5$ and R$^6$ are —H; Ar is a 5- or 6-membered monocyclic aromatic ring systems having 1, 2, or 3 heteroatoms selected from nitrogen, oxygen and sulfur atoms; L is —O—; and Y —N($R^{10}$)—.

In some embodiments of a compound of formula III, $R^1$ is —$C_{1-6}$alkyl substituted with 1, 2, or 3 halo; each $R^2$ is independently —H, -halo, —$C_{1-3}$alkyl, or —$C_{1-3}$alkoxy; wherein m is 0, 1, or 2; p is 0, 1 or 2; $R^3$ is —H; $R^4$ is —$C_{1-6}$alkyl; $R^5$ and $R^6$ are —H; Ar is a 5- or 6-membered monocyclic aromatic ring systems having 0, 1, 2, or 3 heteroatoms selected from nitrogen, oxygen and sulfur atoms; L is —O—; and Y —N($R^{10}$)—.

In some embodiments of a compound of formula III, $R^1$ is —$C_{1-6}$alkyl substituted with 1, 2, or 3 halo; each $R^2$ is independently —H, -halo, —$C_{1-3}$alkyl, or —$C_{1-3}$alkoxy; wherein m is 0, 1, or 2; p is 0, 1 or 2; $R^3$ is —H; $R^4$ is —$C_{1-6}$alkyl; $R^5$ and $R^6$ are —H; Ar is a 5- or 6-membered monocyclic aromatic ring systems having 0, 1, 2, or 3 heteroatoms selected from nitrogen, oxygen and sulfur atoms; L is —O—; and Y is —$SO_2$—.

In some embodiments of a compound of formula III, $R^1$ is difluorochloromethyl; $R^2$ is H; $R^3$ is —H; $R^4$ is —$C_{1-6}$alkyl; $R^5$ and $R^6$ are —H; Ar is any one of the moieties provided in Table 2; L is —O—; and Y is —C($R^8R^{8'}$)—; $R^7$, $R^{7'}$, $R^8$, and $R^{8'}$ are each independently H, heterocycloalkyl, —$OR^{12}$, —N($R^{12}$)$_2$, —$NR^{11}$C(=O)$R^{12}$, —$NR^{11}$C(=O)O$R^{12}$, —$NR^{11}$C(=O)N($R^{12}$)$_2$, —$NR^{11}SO_2R^{12}$, —$NR^{11}SO_2N(R^{12})_2$, —C(=O)$R^{12}$, —C(=O)O($C_1$-$C_6$ alkyl), or —C(=O)N($R^{12}$)$_2$, wherein $R^{12}$ is —$C_{1-6}$alkyl, O$C_{1-4}$alkyl, heterocycloalkyl, or heteroaryl.

In some embodiments of a compound of formula III, $R^1$ is difluorochloromethyl; $R^2$ is H; $R^3$ is —H; $R^4$ is —$C_{1-6}$alkyl; $R^5$ and $R^6$ are —H; Ar is any one of the moieties provided in Table 2-A; L is —O—; and Y is —C($R^8R^{8'}$)—; $R^7$, $R^{7'}$, $R^8$, and $R^{8'}$ are each independently H, heterocycloalkyl, —$OR^{12}$, —N($R^{12}$)$_2$, —$NR^{11}$C(=O)$R^{12}$, —$NR^{11}$C(=O)O$R^{12}$, —$NR^{11}$C(=O)N($R^{12}$)$_2$, —$NR^{11}SO_2R^{12}$, —$NR^{11}SO_2N(R^{12})_2$, —C(=O)$R^{12}$, —C(=O)O($C_1$-$C_6$ alkyl), or —C(=O)N($R^{12}$)$_2$, wherein $R^{12}$ is —$C_{1-6}$alkyl, O$C_{1-4}$alkyl, heterocycloalkyl, or heteroaryl.

In some embodiments of a compound of formula III, $R^1$ is difluorochloromethyl; $R^2$ is H; $R^3$ is —H; $R^4$ is —$C_{1-6}$alkyl; $R^5$ and $R^6$ are —H; Ar is any one of the moieties provided in Table 2 or Table 2-A; L is —O—; Y is —$SO_2$—; and $R^7$ and $R^{7'}$ are each independently H, heterocycloalkyl, —$OR^{12}$, —N($R^{12}$)$_2$, —$NR^{11}$C(=O)$R^{12}$, —$NR^{11}$C(=O)O$R^{12}$, —$NR^{11}$C(=O)N($R^{12}$)$_2$, —$NR^{11}SO_2R^{12}$, —$NR^{11}SO_2N(R^{12})_2$, —C(=O)$R^{12}$, —C(=O)O($C_1$-$C_6$ alkyl), or —C(=O)N($R^{12}$)$_2$, wherein $R^{12}$ is —$C_{1-6}$alkyl, O$C_{1-4}$alkyl, heterocycloalkyl, or heteroaryl.

In some embodiments of a compound of formula III, $R^1$ is difluorochloromethyl; $R^2$ is H; $R^3$ is —H; $R^4$ is —$C_{1-6}$alkyl; $R^5$ and $R^6$ are —H; Ar is any one of the moieties provided in Table 2 or Table 2-A; L is —O—; Y is —$SO_2$—; and $R^7$ and $R^{7'}$ are each independently H or —$NR^{11}$C(=O)$R^{12}$, wherein $R^{12}$ is —$C_{1-6}$alkyl.

In some embodiments of a compound of formula III, $R^1$ is difluorochloromethyl; $R^2$ is H; $R^3$ is —H; $R^4$ is —$C_{1-6}$alkyl; $R^5$ and $R^6$ are —H; Ar is any one of the moieties provided in Table 2 or Table 2-A; L is —O—; Y is —N($R^{10}$)—; and $R^7$ and $R^{7'}$ are each independently H, heterocycloalkyl, —$OR^{12}$, —N($R^{12}$)$_2$, —$NR^{11}$C(=O)$R^{12}$, —$NR^{11}$C(=O)O$R^{12}$, —$NR^{11}$C(=O)N($R^{12}$)$_2$, —$NR^{11}SO_2R^{12}$, —$NR^{11}SO_2N(R^{12})_2$, —C(=O)$R^{12}$, —C(=O)O($C_1$-$C_6$ alkyl), or —C(=O)N($R^{12}$)$_2$, wherein $R^{12}$ is —$C_{1-6}$alkyl, O$C_{1-4}$alkyl, heterocycloalkyl, or heteroaryl.

In some embodiments of a compound of formula III, $R^1$ is difluorochloromethyl; $R^2$ is —H, $R^3$ is —H; $R^4$ is —$C_{1-6}$alkyl; $R^5$ and $R^6$ are —H; Ar is any one of the moieties provided in Table 2; L is —O—; and Y is —N($R^{10}$)—; $R^{10}$ is —$C_{1-6}$alkyl, —C(=O)$R^{12}$, —C(=O)N($R^{12}$)$_2$, —$SO_2R^{12}$, —$SO_2N(R^{12})_2$, or heteroaryl.

In some embodiments of a compound of formula III, $R^1$ is difluorochloromethyl; $R^2$ is —H, $R^3$ is —H; $R^4$ is —$C_{1-6}$alkyl; $R^5$ and $R^6$ are —H; Ar is any one of the moieties provided in Table 2-A; L is —O—; and Y is —N($R^{10}$)—; $R^{10}$ is —$C_{1-6}$alkyl, —C(=O)$R^{12}$, —C(=O)N($R^{12}$)$_2$, —$SO_2R^{12}$, —$SO_2N(R^{12})_2$, or heteroaryl.

In some embodiments, $R^{10}$ is —$C_{1-6}$alkyl, optionally substitute with 1, 2, or 3 halo.

In some embodiments, $R^{10}$ is —C(=O)$R^{12}$; $R^{12}$ is $C_{1-3}$alkyl, heterocycloalkyl, or heteroaryl.

In some embodiments, $R^{10}$ is —C(=O)N($R^{12}$)$_2$, each $R^{12}$ is independently H, $C_{1-3}$alkyl, heterocycloalkyl, or heteroaryl.

In some embodiments, $R^{10}$ is —$SO_2R^{12}$, $R^{12}$ is $C_{1-3}$alkyl, heterocycloalkyl, or heteroaryl.

In some embodiments, $R^{10}$ is —$SO_2N(R^{12})_2$, each $R^{12}$ is independently H, $C_{1-3}$alkyl, heterocycloalkyl, or heteroaryl.

In some embodiments of a compound of formula III, $R^1$ is difluorochloromethyl; $R^2$ is —H, $R^3$ is —H; $R^4$ is —$C_{1-6}$alkyl; $R^5$ and $R^6$ are —H; Ar is any one of the moieties provided in Table 2; L is —O—; and Y is —N($R_{10}$)—; wherein $R^{10}$ is any one of the moieties provided in Table 4.

In some embodiments of a compound of formula III, $R^1$ is difluorochloromethyl; $R^2$ is —H, $R^3$ is —H; $R^4$ is —$C_{1-6}$alkyl; $R^5$ and $R^6$ are —H; $R^7$ and $R^{7'}$ are each independently H; Ar is any one of the moieties provided in Table 2-A; L is —O—; and Y is —N($R^{10}$)—; wherein $R^{10}$ is any one of the moieties provided in Table 4.

In some embodiments of a compound of formula III, which is a compound of formula IIIA:

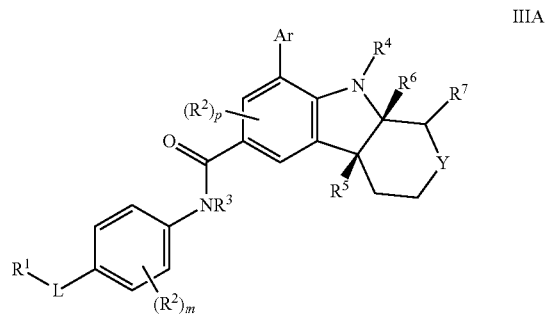

IIIA or a pharmaceutically acceptable salt thereof, wherein $R^1$, $R^2$, $R^3$, $R^4$, $R^5$, $R^6$, $R^7$, Y, L, Ar, m, and p are the same as defined herein.

In some embodiments of a compound of formula III, which is a compound of formula IIIA-1, IIIA-2, IIIA-3 or IIIA-4:

In some embodiments of a compound of formula III, which is a compound of formula IIIB-1, IIIB-2, IIIB-3, or IIIB-4:

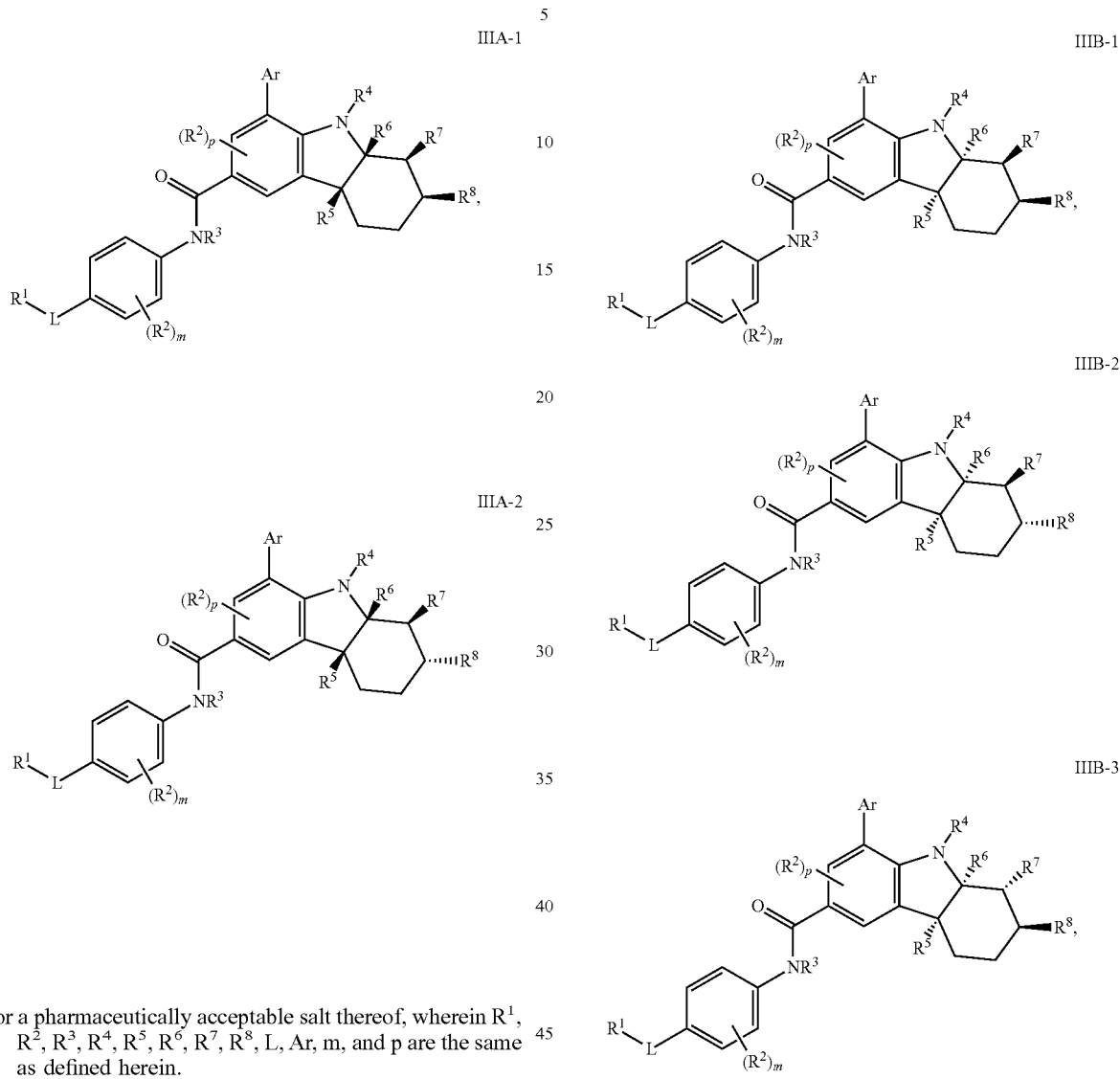

or a pharmaceutically acceptable salt thereof, wherein $R^1$, $R^2$, $R^3$, $R^4$, $R^5$, $R^6$, $R^7$, $R^8$, L, Ar, m, and p are the same as defined herein.

In some embodiments of a compound of formula III, which is a compound of formula IIIB:

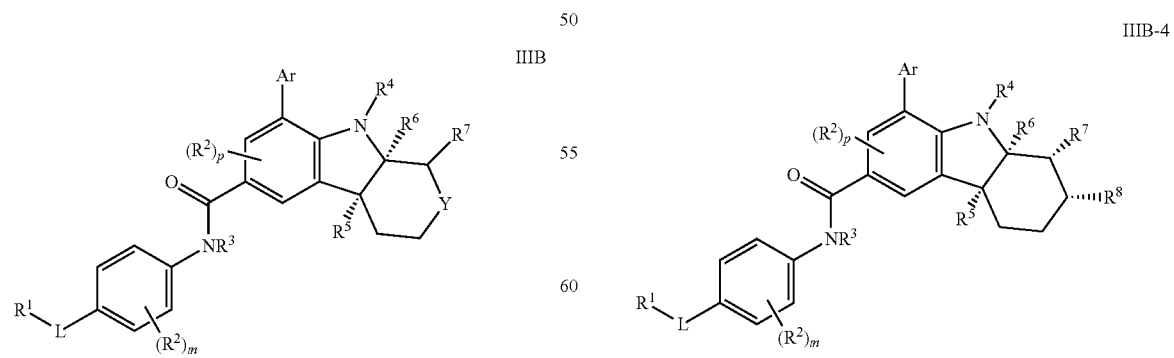

or a pharmaceutically acceptable salt thereof, wherein $R^1$, $R^2$, $R^3$, $R^4$, $R^5$, $R^6$, $R^7$, Y, L, Ar, m, and p are the same as defined herein.

or a pharmaceutically acceptable salt thereof, wherein $R^1$, $R^2$, $R^3$, $R^4$, $R^5$, $R^6$, $R^7$, $R^8$, L, Ar, m, and p are the same as defined herein.

In some embodiments of a compound of formula III, which is a compound of formula IIIA-5 or IIIB-5:

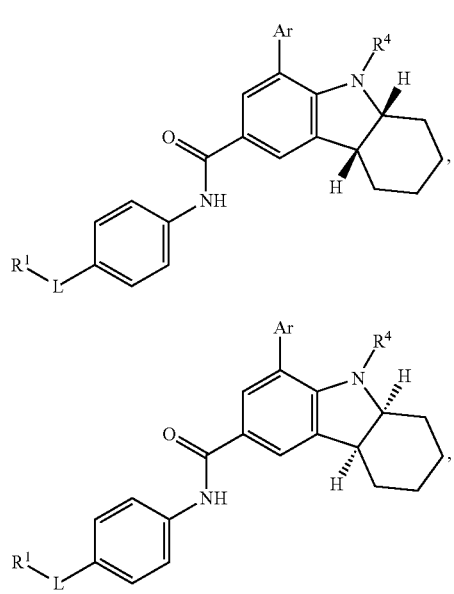

In some embodiments of a compound of formula III, which is a compound of formula IIIA-7 or IIIB-7:

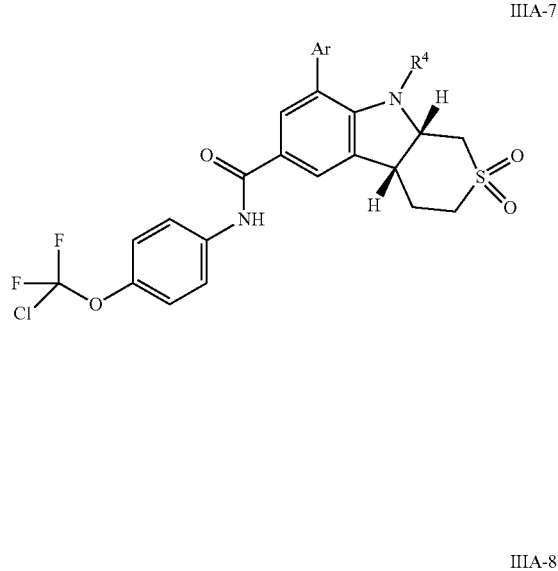

or a pharmaceutically acceptable salt thereof, wherein $R^1$, $R^4$, L, and Ar are the same as defined herein.

In some embodiments of a compound of formula III, which is a compound of formula IIIA-6 or IIIB-6:

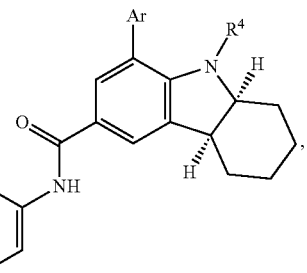

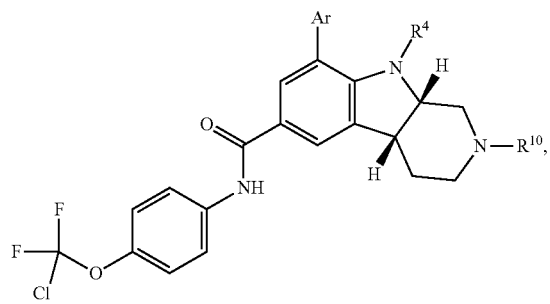

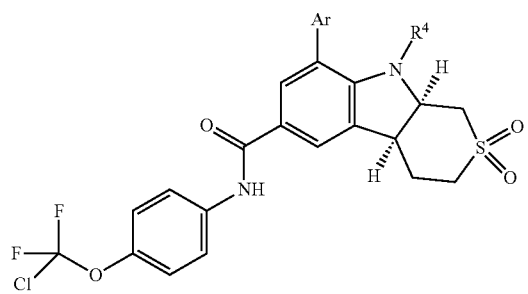

or a pharmaceutically acceptable salt thereof, wherein $R^4$ and Ar are the same as defined herein.

In some embodiments of a compound of formula III, which a compound of formula IIIC:

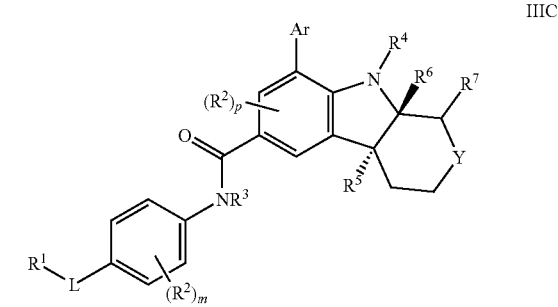

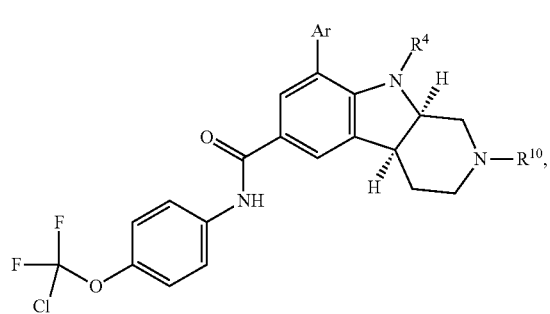

or a pharmaceutically acceptable salt thereof, wherein $R^4$, $R^{10}$, and Ar are the same as defined herein.

or a pharmaceutically acceptable salt thereof, wherein $R^1$, $R^2$, $R^3$, $R^4$, $R^5$, $R^6$, $R^7$, Y, L, Ar, m, and p are the same as defined herein.

In some embodiments of a compound of formula III, which a compound of formula IIIC-1, IIIC-2, IIIC-3, or IIIC-4:

In some embodiments of a compound of formula III, which a compound of formula IIID:

In some embodiments of a compound of formula III, which is a compound of formula IID-1, IIID-2, IIID-3, or IIID-4:

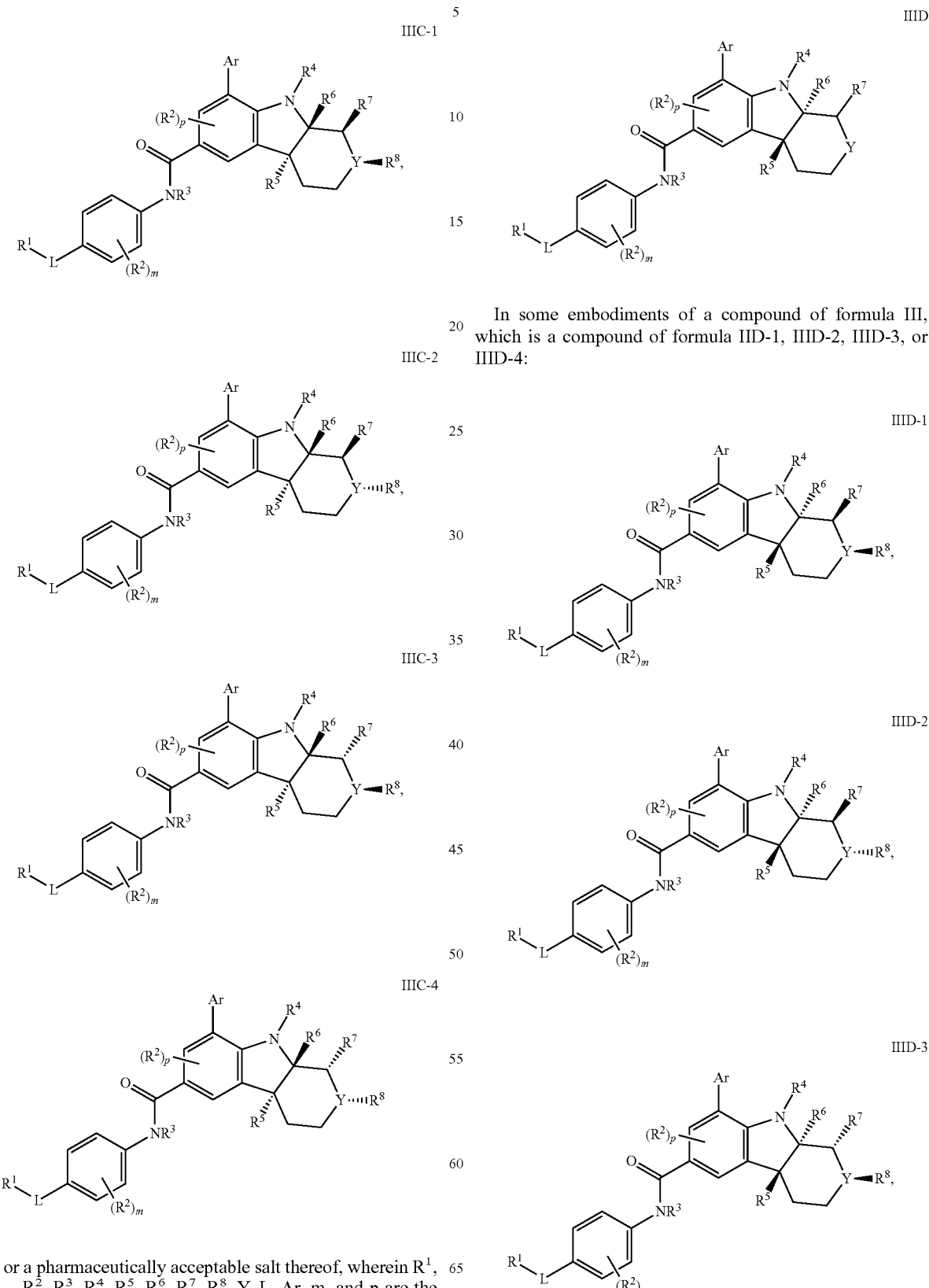

or a pharmaceutically acceptable salt thereof, wherein $R^1$, $R^2$, $R^3$, $R^4$, $R^5$, $R^6$, $R^7$, $R^8$, Y, L, Ar, m, and p are the same as defined herein.

-continued

IIID-4

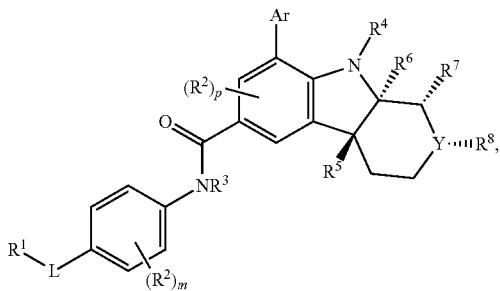

or a pharmaceutically acceptable salt thereof, wherein $R^1$, $R^2$, $R^3$, $R^4$, $R^5$, $R^6$, $R^7$, $R^8$, Y, L, Ar, m, and p are the same as defined herein.

In some embodiments of a compound of formula III, which a compound of formula IIIC-5 or IIID-5:

IIIC-5

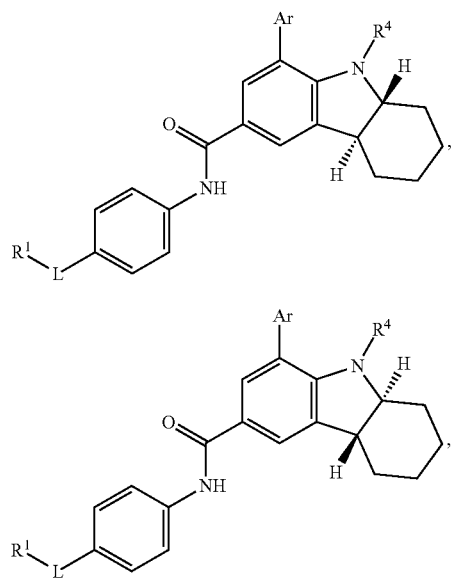

IIID-5

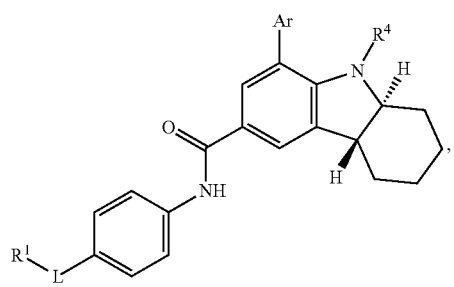

or a pharmaceutically acceptable salt thereof, wherein $R^1$, $R^4$, L, and Ar are the same as defined herein.

In some embodiments of a compound of formula III, which a compound of formula IIIC-6 or IIID-6:

IIIC-6

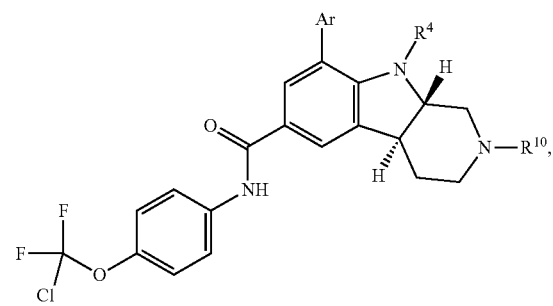

IIID-6

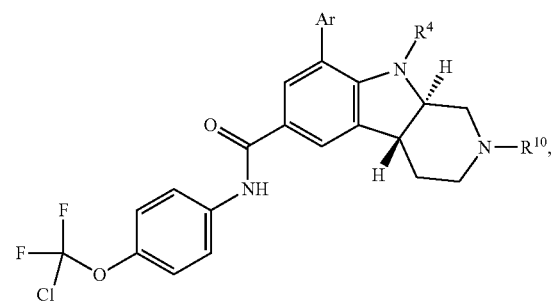

or a pharmaceutically acceptable salt thereof, wherein $R^4$, $R^{10}$, and Ar are the same as defined herein.

In some embodiments, the present disclosure provides a compound in Table 5,

TABLE 5

| Compound No. | Compound Structure |
| --- | --- |
| 1 | 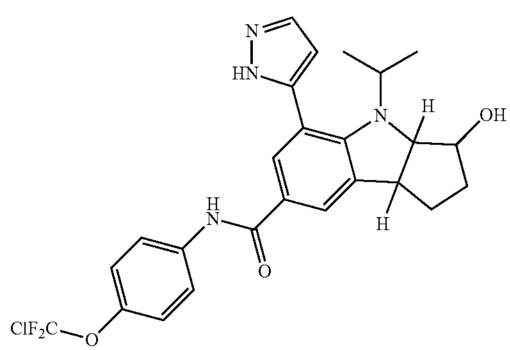 |

TABLE 5-continued
| Compound No. | Compound Structure |
|---|---|
| 2 | 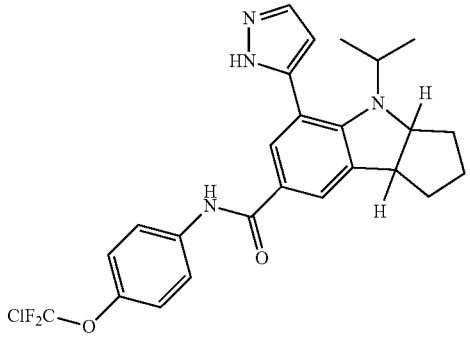 |
| 3 | 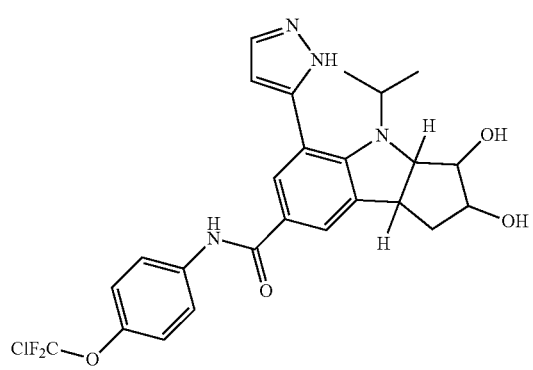 |
| 4 | 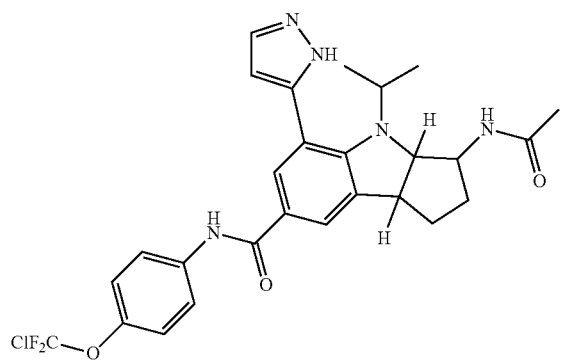 |
| 5 | 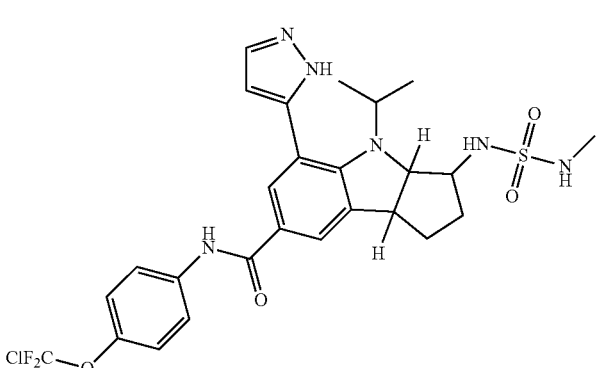 |

TABLE 5-continued
| Compound No. | Compound Structure |
|---|---|
| 6 | 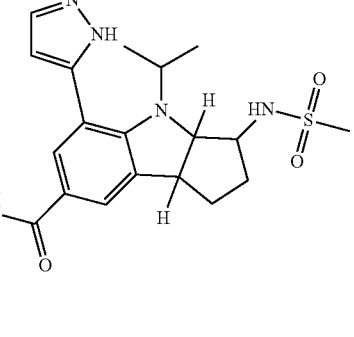 |
| 7 | 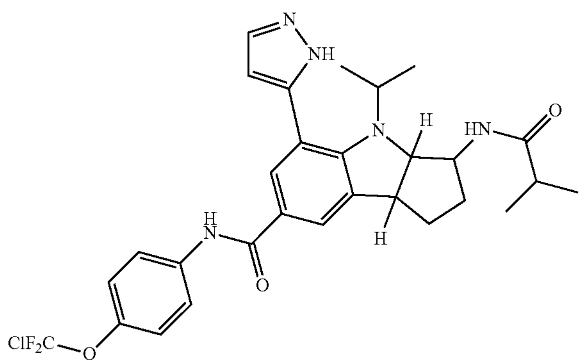 |
| 8 | 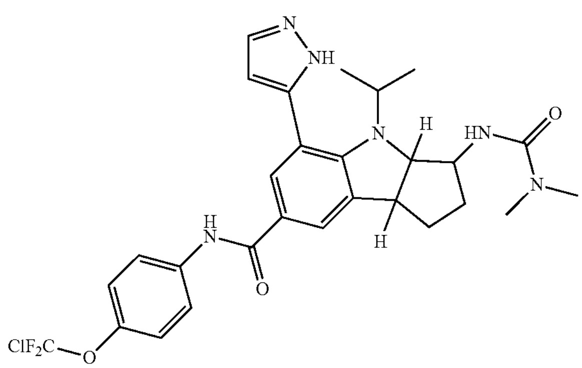 |
| 9 | 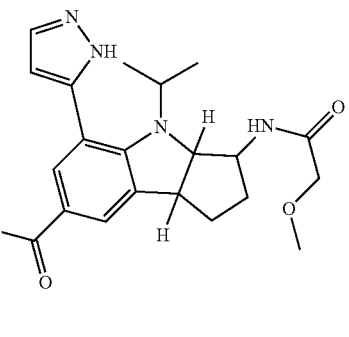 |

TABLE 5-continued
| Compound No. | Compound Structure |
|---|---|
| 10 | 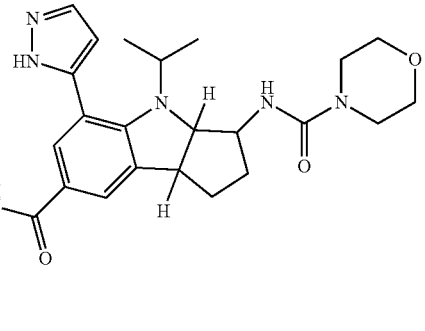 |
| 11 | 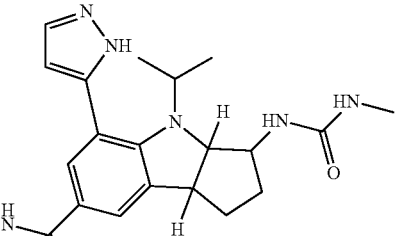 |
| 12 | 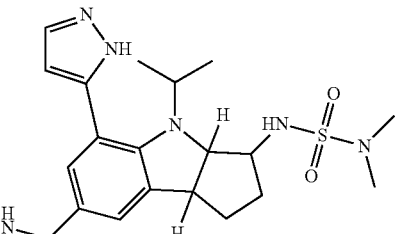 |
| 13 | 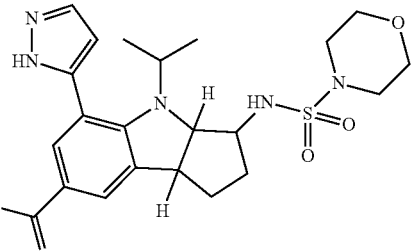 |

TABLE 5-continued
| Compound No. | Compound Structure |
| --- | --- |
| 14 | 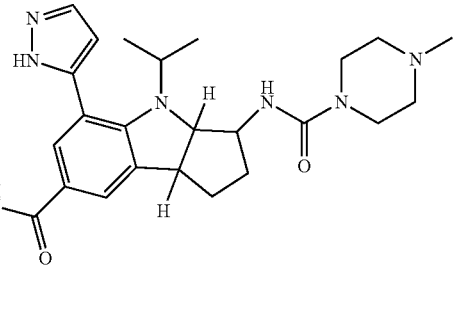 |
| 15 | 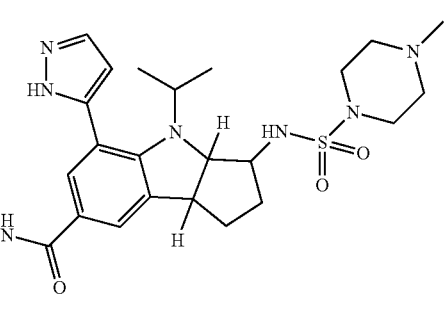 |
| 16 | 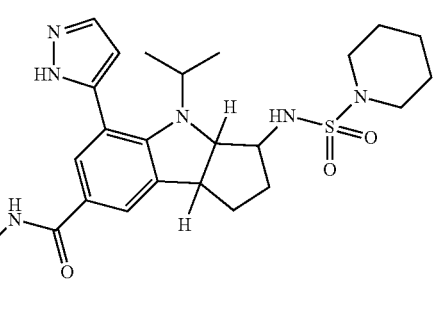 |
| 17 | 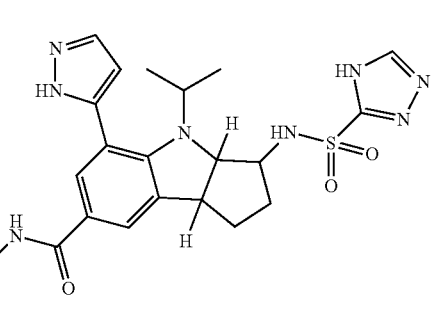 |

TABLE 5-continued
| Compound No. | Compound Structure |
|---|---|
| 18 | 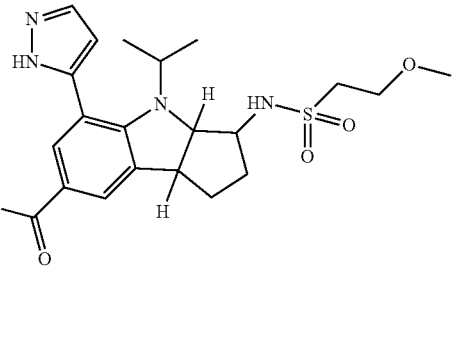 |
| 19 | 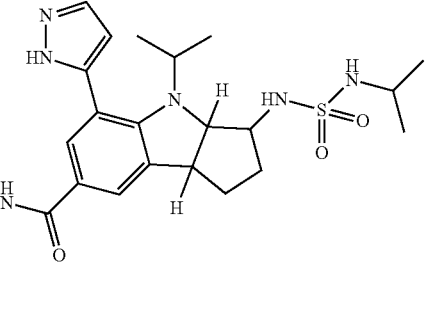 |
| 20 | 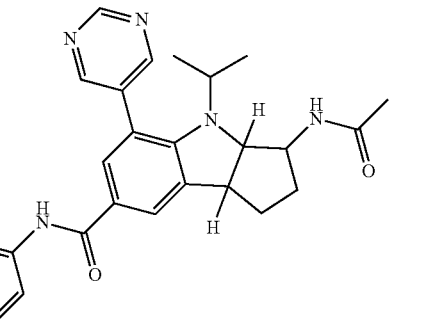 |
| 21 | 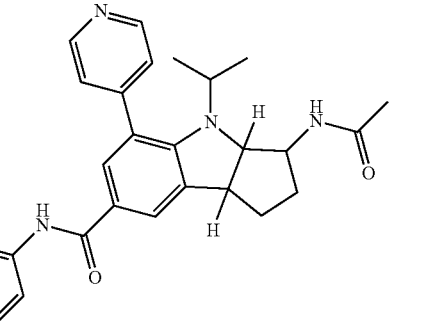 |

TABLE 5-continued
| Compound No. | Compound Structure |
|---|---|
| 22 | 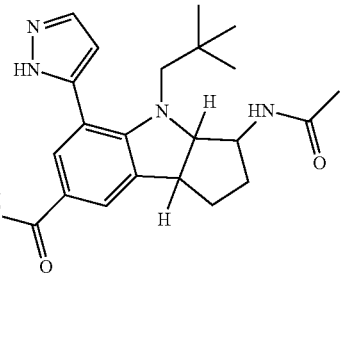 |
| 23 | 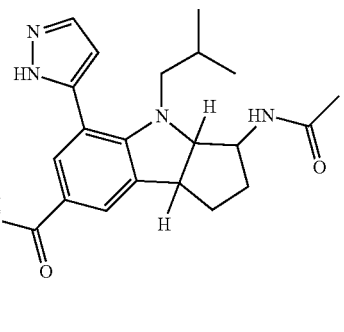 |
| 24 | 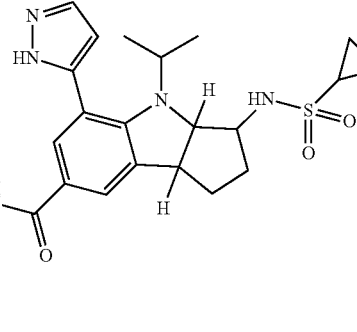 |
| 25 | 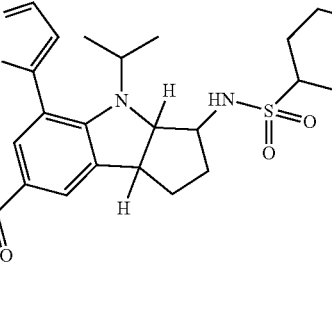 |

TABLE 5-continued
| Compound No. | Compound Structure |
|---|---|
| 26 | 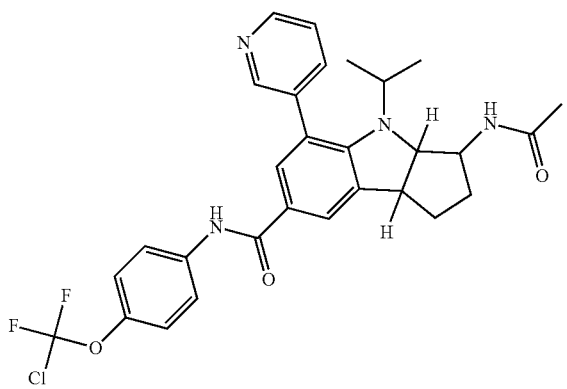 [SMILES: CC(=O)NC1CCC2c3cc(C(=O)Nc4ccc(OC(F)(F)Cl)cc4)cc(-c4cccnc4)c3N(C(C)C)C12] |
| 27 | 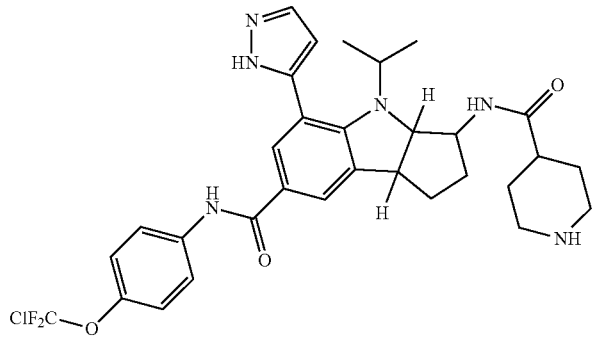 |
| 28 | 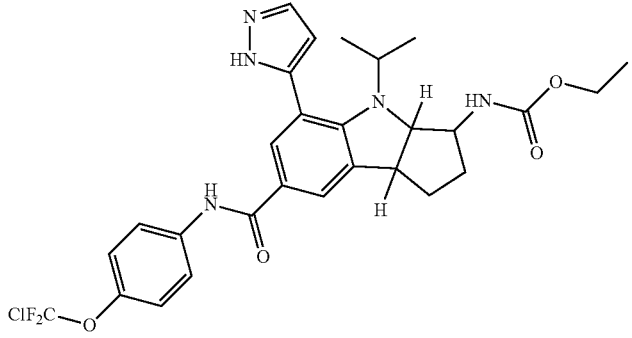 |
| 29 | 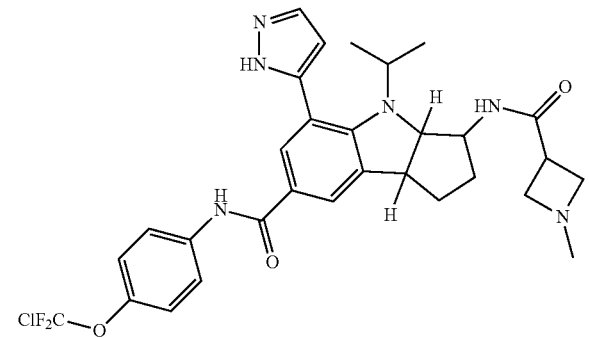 |

TABLE 5-continued

| Compound No. | Compound Structure |
| --- | --- |
| 30 | 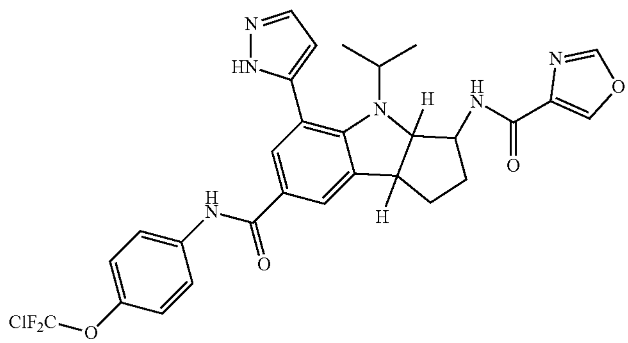 |
| 31 | 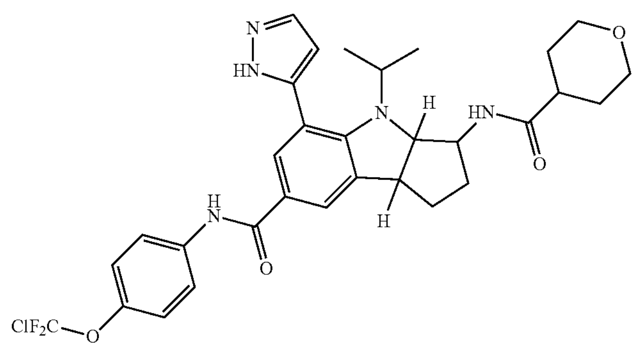 |
| 32 | 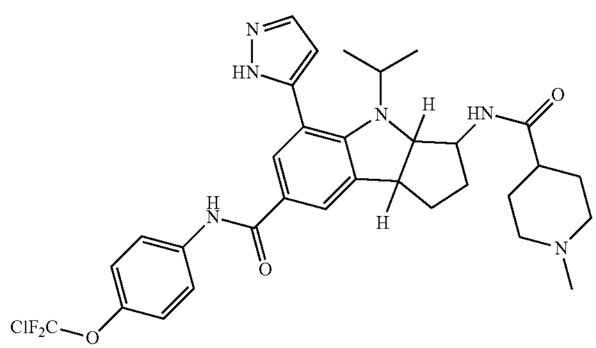 |
| 33 | 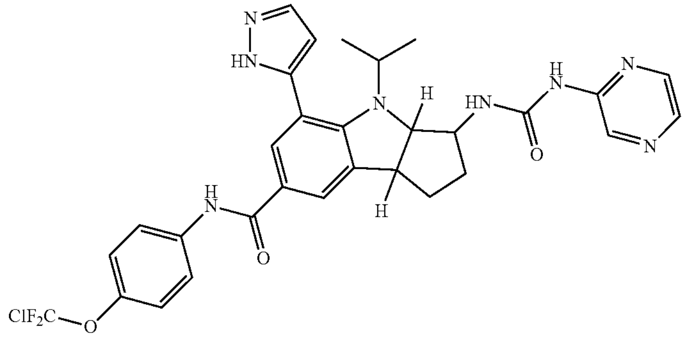 |

TABLE 5-continued
| Compound No. | Compound Structure |
|---|---|
| 34 | 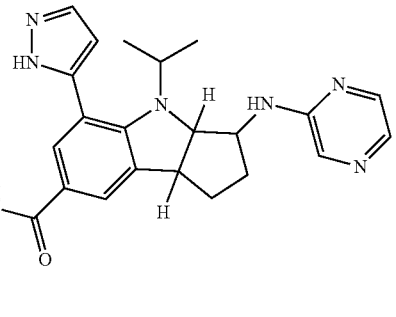 |
| 35 | 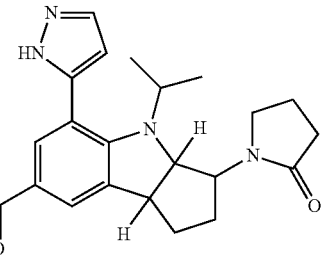 |
| 36 | 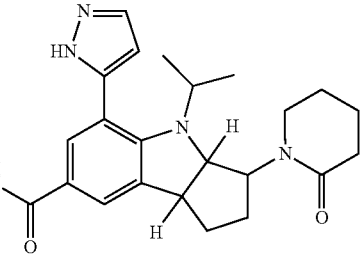 |
| 37 | 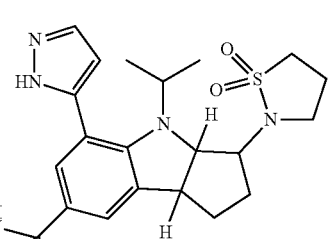 |
| 38 | 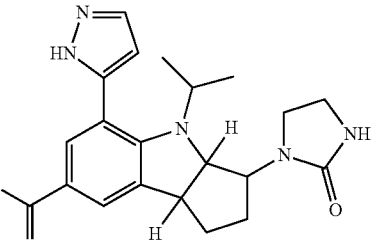 |

TABLE 5-continued

| Compound No. | Compound Structure |
|---|---|
| 39 | 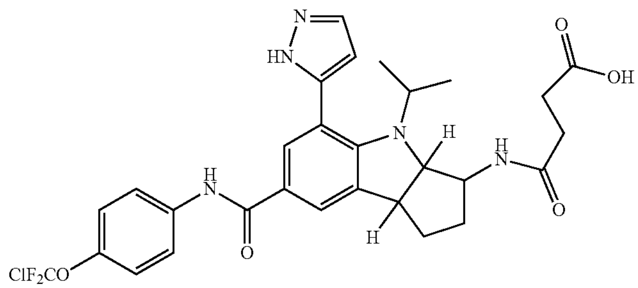 |
| 40 | 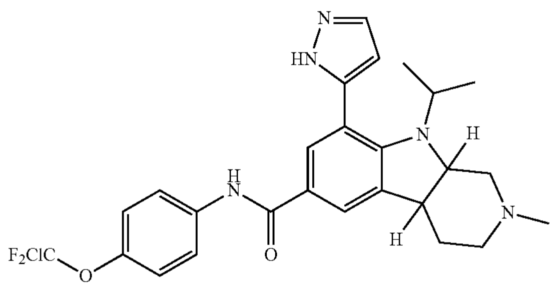 |
| 41 | 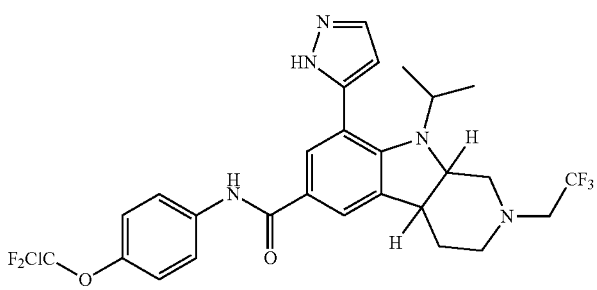 |
| 42 | 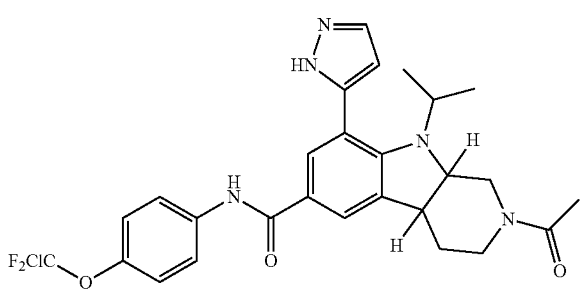 |
| 43 | 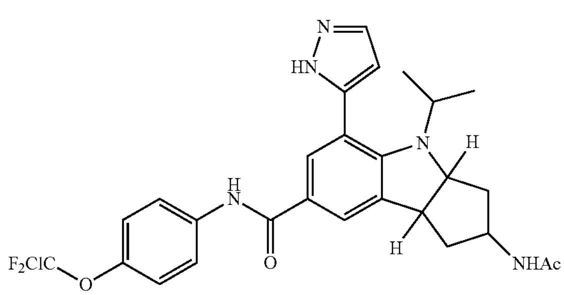 |

TABLE 5-continued
| Compound No. | Compound Structure |
| --- | --- |
| 44 | 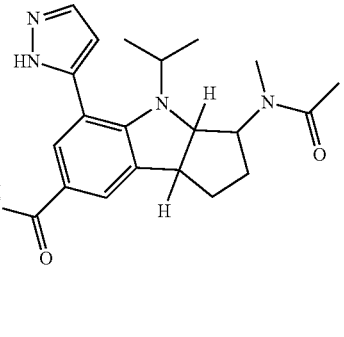 |
| 45 | 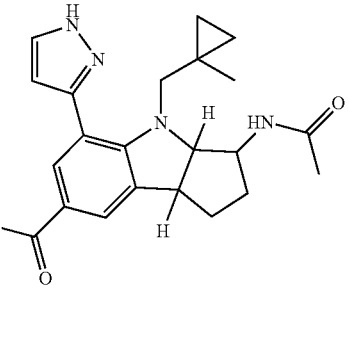 |
| 46 | 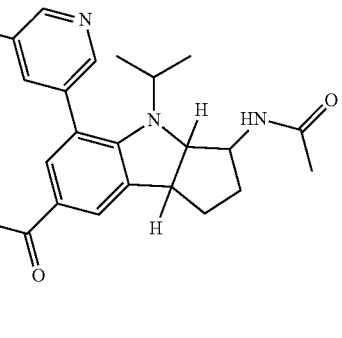 |
| 47 | 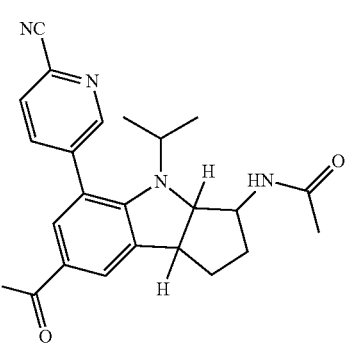 |

TABLE 5-continued

| Compound No. | Compound Structure |
|---|---|
| 48 | 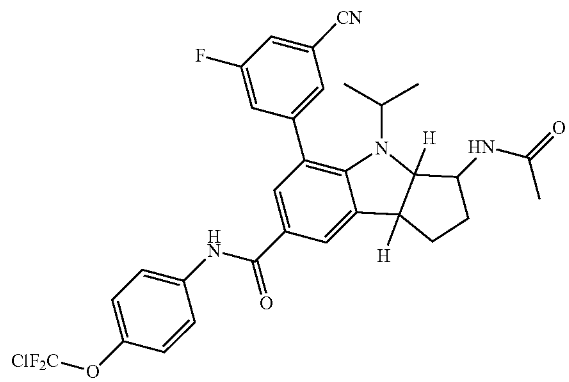 |
| 49 | 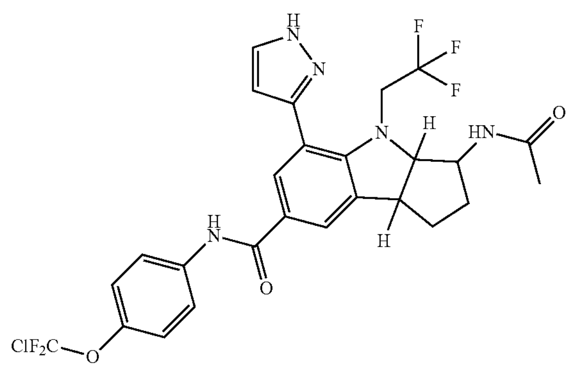 |
| 50 | 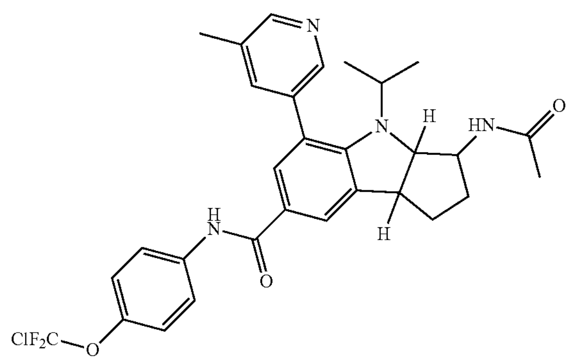 |
| 51 | 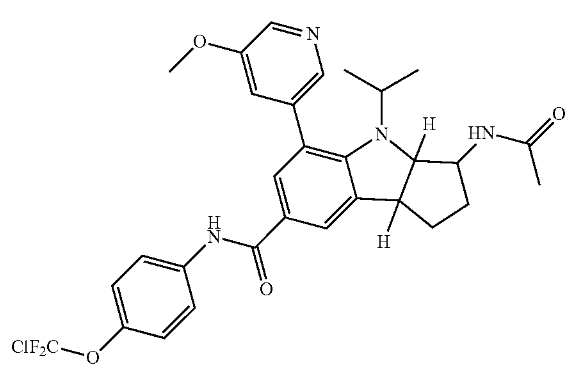 |

TABLE 5-continued
| Compound No. | Compound Structure |
|---|---|
| 52 | 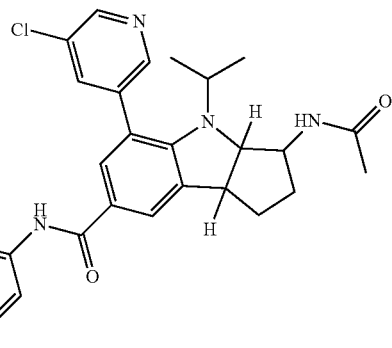 |
| 53 | 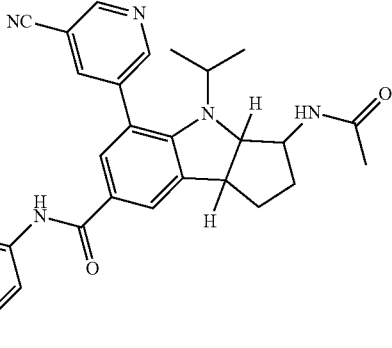 |
| 54 | 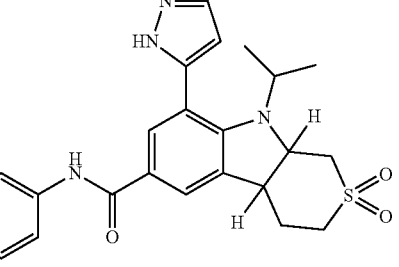 |
| 55 | 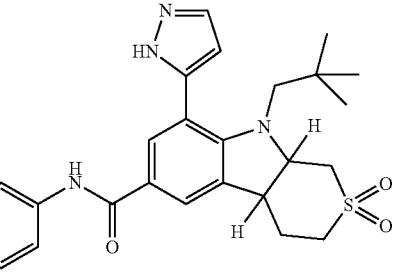 |
| 56 | 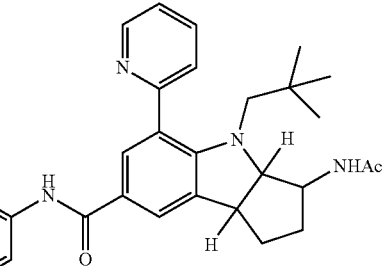 |

TABLE 5-continued

| Compound No. | Compound Structure |
|---|---|
| 57 | 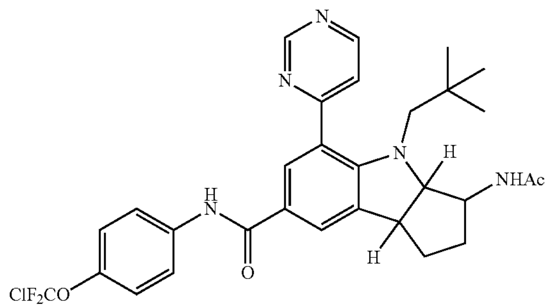 |
| 58 | 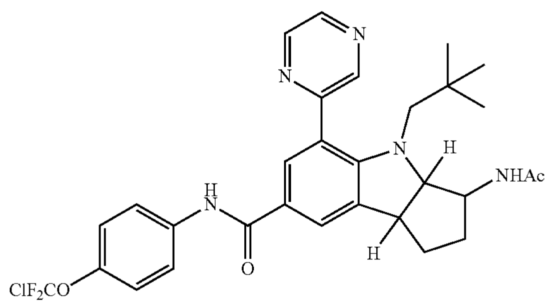 |
| 59 | 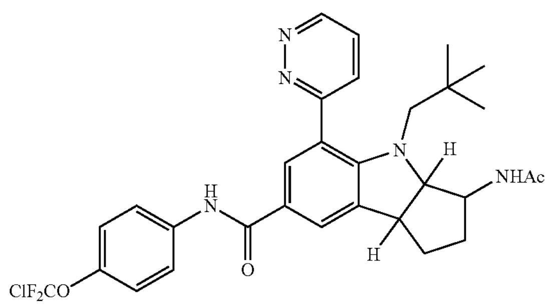 |
| 60 | 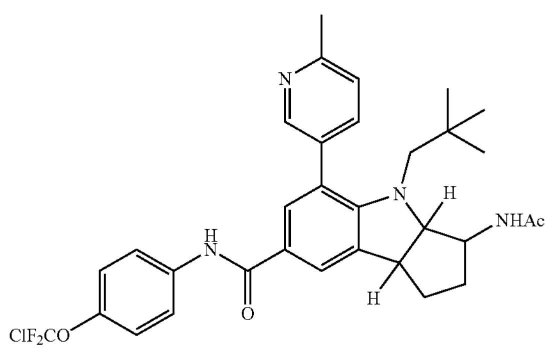 |
| 61 | 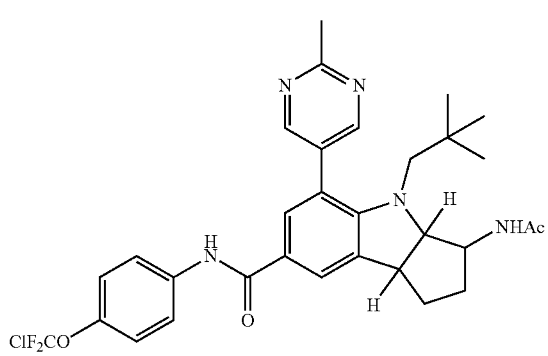 |

TABLE 5-continued
| Compound No. | Compound Structure |
|---|---|
| 62 | 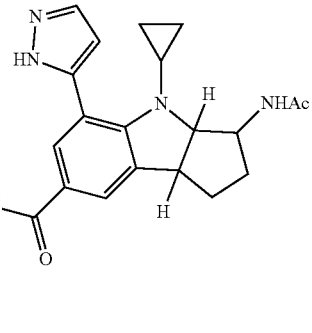 |
| 63 | 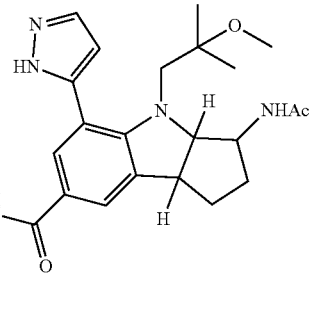 |
| 64 | 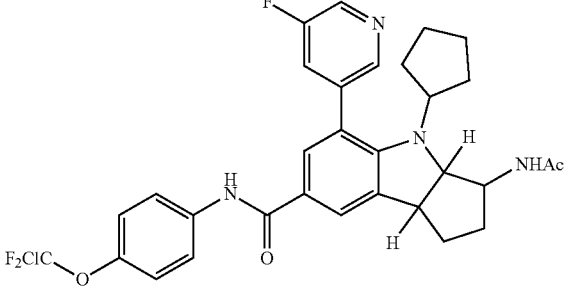 |
| 65 | 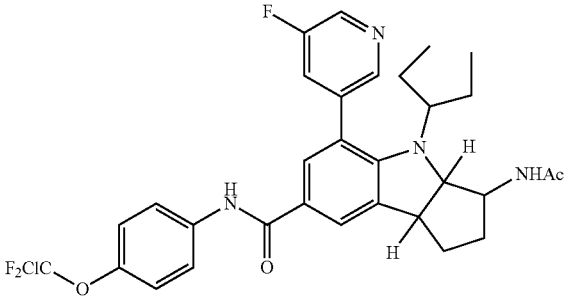 |

TABLE 5-continued

| Compound No. | Compound Structure |
|---|---|
| 66 | 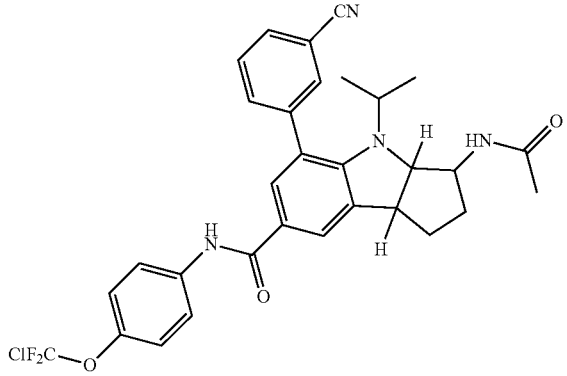 |
| 67 | 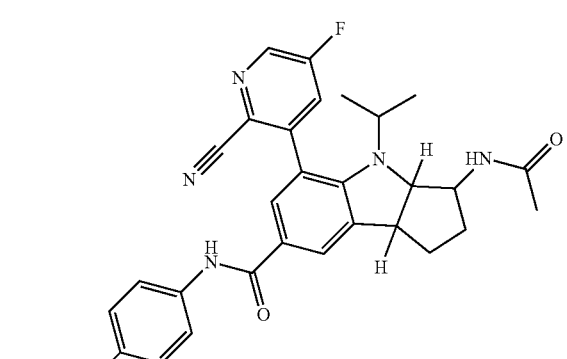 | or an enantiomer or diastereomer, or a pharmaceutically acceptable salt thereof.

In some embodiments, compounds of the present disclosure are enantiomerically or diastereomerically enriched. The excess of a stereoisomer can be measured by chiral HPLC. The excess of one specific stereoisomer is about 5%, 10%, 20%, 30%, 40%, 50%, 60%, 70%, 80%, 85%, or 90%. In some embodiments, the excess of one specific stereoisomer is about 91%, 92%, 93%, 94%, 95%, 96%, 97%, 98%, 99%, 99.5%, or 99.9%.

In some embodiments, the present disclosure provides a compound in Table 6,

TABLE 6

| Compound No. | Compound Structure |
|---|---|
| 4-A | 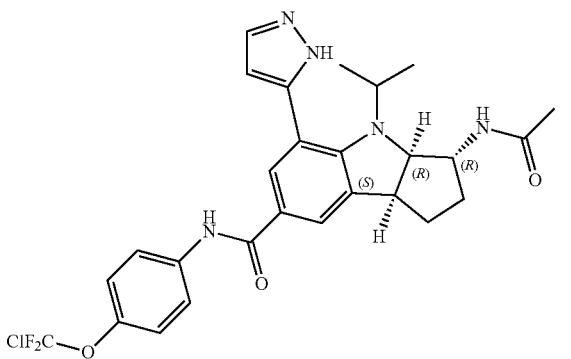 |

TABLE 6-continued
| Compound No. | Compound Structure |
|---|---|
| 20-A | 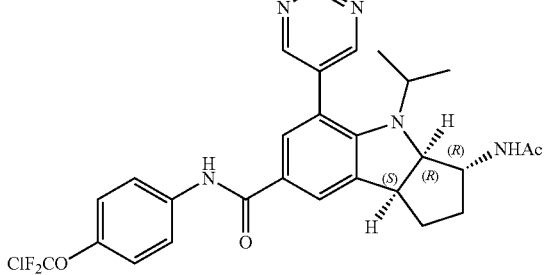 |
| 22-A | 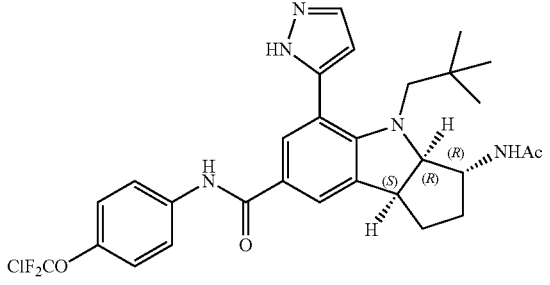 |
| 26-A | 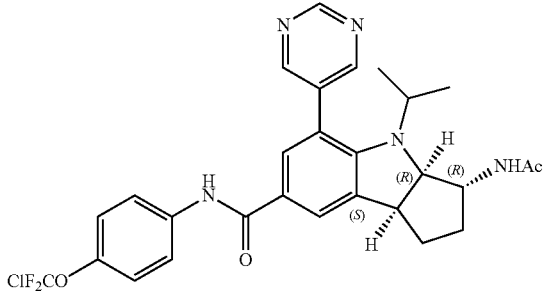 |
| 46-A | 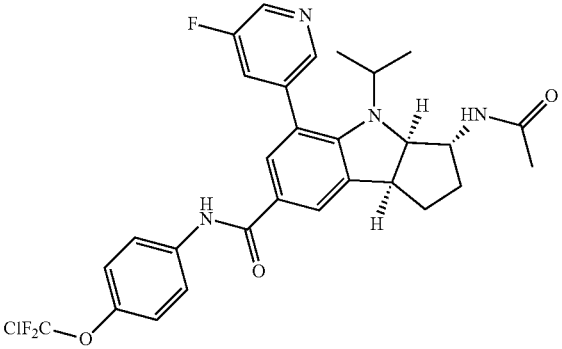 |

TABLE 6-continued
| Compound No. | Compound Structure |
|---|---|
| 47-A | 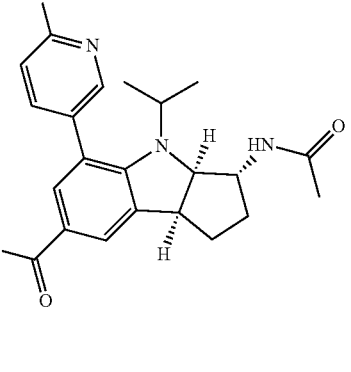 |
| 48-A | 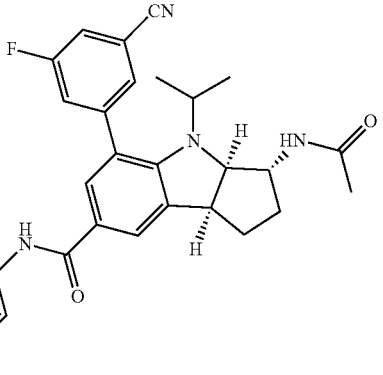 |
| 50-A | 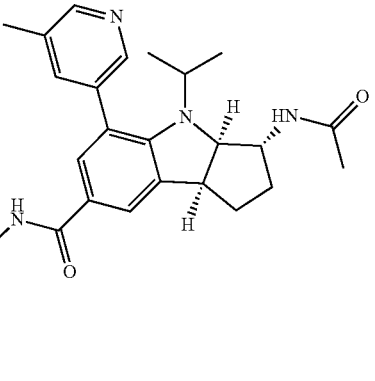 |
| 51-A | 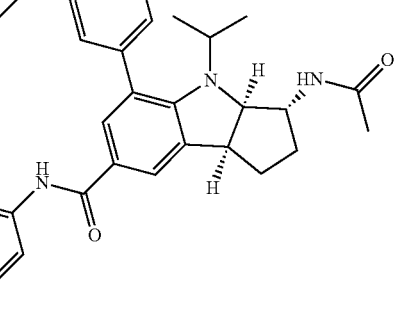 |

TABLE 6-continued

| Compound No. | Compound Structure |
|---|---|
| 52-A | 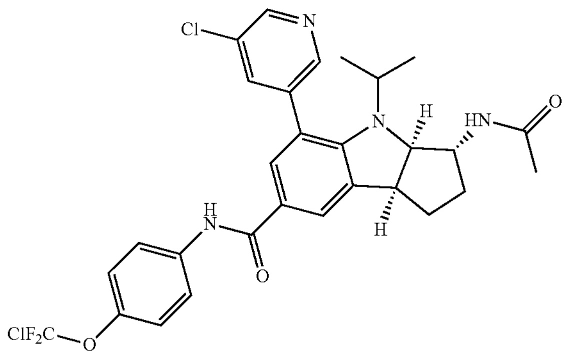 |
| 53-A | 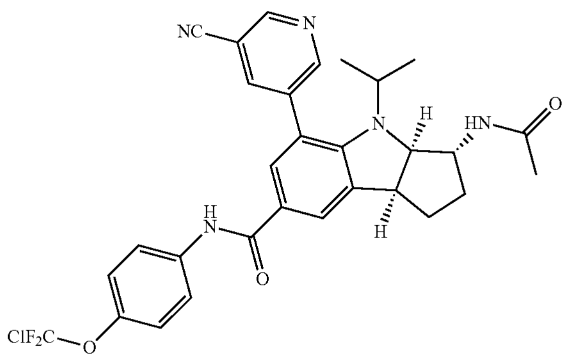 |
| 54-A | 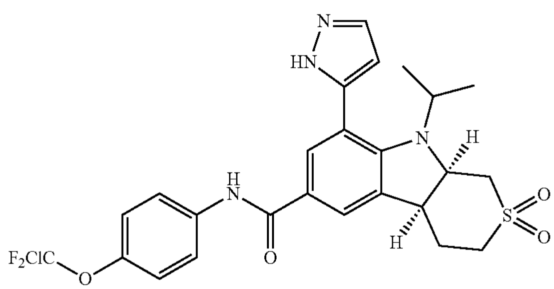 |
| 56-A | 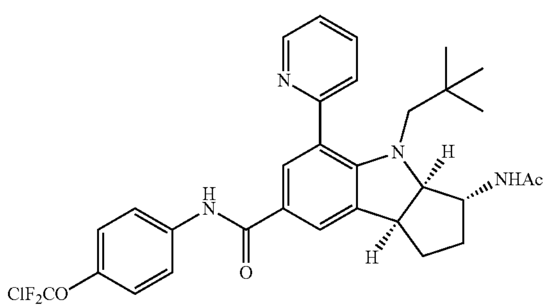 |
| 57-A | 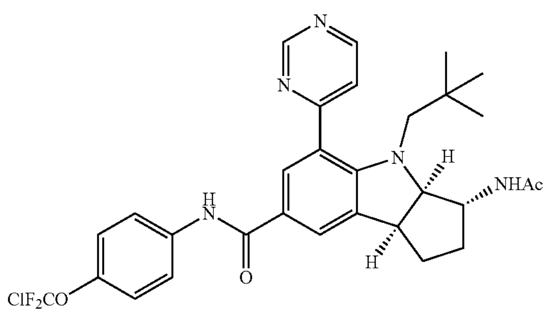 |

TABLE 6-continued
| Compound No. | Compound Structure |
|---|---|
| 58-A | 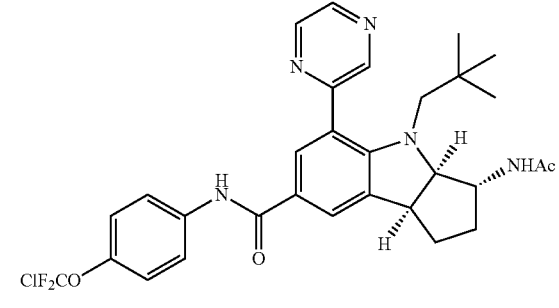 |
| 59-A | 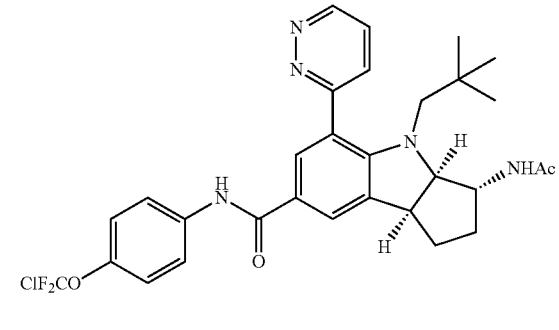 |
| 60-A | 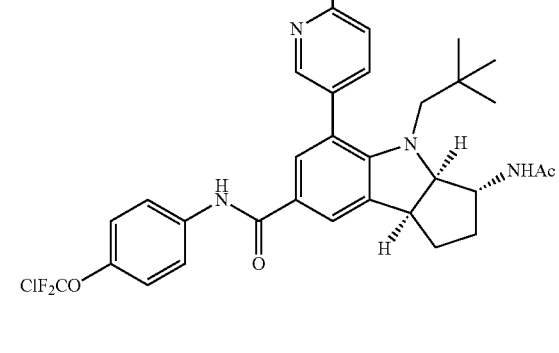 |
| 61-A | 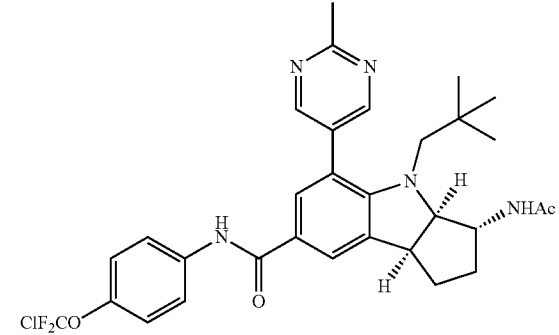 |

TABLE 6-continued

| Compound No. | Compound Structure |
| --- | --- |
| 66-A | *(chemical structure)* |
| 67-A | *(chemical structure)* | or a pharmaceutically acceptable salt thereof.
In some embodiments, the present disclosure provides a compound in Table 7,

TABLE 7

| Compound No. | Compound Structure |
| --- | --- |
| 4-B | *(chemical structure)* |

TABLE 7-continued

| Compound No. | Compound Structure |
|---|---|
| 20-B | 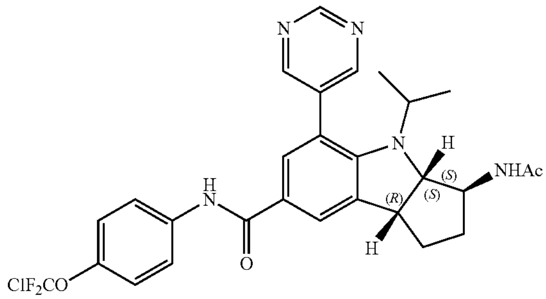 |
| 22-B | 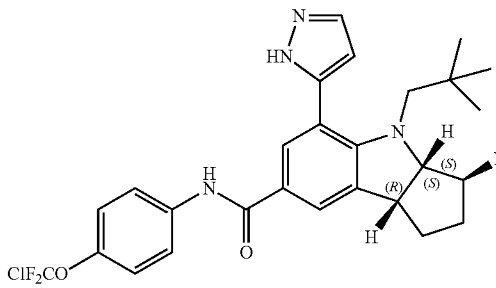 |
| 26-B | | or a pharmaceutically acceptable salt thereof.

The present disclosure encompasses the preparation and use of salts of compounds of the present disclosure. As used herein, the pharmaceutical "pharmaceutically acceptable salt" refers to salts or zwitterionic forms of compounds of the present disclosure. Salts of compounds of the present disclosure can be prepared during the final isolation and purification of the compounds or separately by reacting the compound with a suitable acid. The pharmaceutically acceptable salts can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the present disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the present disclosure can be quaternized with methyl, ethyl, propyl, and butyl chlorides, bromides, and iodides; dimethyl, diethyl, dibutyl, and diamyl sulfates; decyl, lauryl, myristyl, steryl chlorides, bromides, and iodides; and benzyl and phenethyl bromides. In light of the foregoing, any reference compounds of the present disclosure appearing herein is intended to include compounds of the present disclosure as well as pharmaceutically acceptable salts, hydrates, or solvates thereof.

The present disclosure encompasses the preparation and use of solvates of compounds of the present disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the present disclosure can be present as solvated forms with a pharmaceutically acceptable solvent, such as water, methanol, and ethanol, and it is intended that the disclosure includes both solvated and unsolvated forms of compounds of the present disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a compound of the present disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvate in a crystal of the solvate.

Medical Treatments or Uses

Compounds of the present disclosure inhibit BCR-ABL and are thus useful in the treatment or prevention of a variety of diseases and conditions. In particular, compounds of the present disclosure are useful in methods of treating or preventing a disease or condition wherein inhibition of BCR-ABL provides a benefit. These diseases and conditions include cancers, e.g., metastatic invasive carcinomas, proliferative diseases, viral infections, e.g., pox and Ebola viruses. These diseases and conditions also include diseases or disorders associated with abnormally activated kinase activity of wild-type ABL1, including non-malignant diseases or disorders include CNS diseases, e.g., neurodegenerative diseases, e.g., Alzheimer's disease and Parkinson's diseases, muscular dystrophies, autoimmune diseases, inflammatory diseases, viral infections, and prion diseases.

In one embodiment, the cancer is referred to as a "BCR-ABL driven cancer." BCR-ABL driven cancers are known in the art. The therapeutic methods of this disclosure comprise administering a therapeutically effective amount of a compound of the present disclosure to a subject, e.g., human, in need thereof. The present methods also encompass optionally administering a second therapeutic agent to the subject in addition to the compound of the present disclosure. The second therapeutic agent is selected from drugs known as useful in treating the disease or condition afflicting the subject in need thereof, e.g., a chemotherapeutic agent, e.g., an ATP-competitive BCR-ABL inhibitor, and/or radiation known as useful in treating a particular cancer.

The present disclosure provides compounds of the present disclosure as BCR-ABL inhibitors for the treatment of diseases and conditions wherein inhibition of BCR-ABL has a beneficial effect. Compounds of the present disclosure typically have a half maximal inhibitory concentration ($IC_{50}$) for inhibiting BCR-ABL of less than 100 µM. In other embodiments, the $IC_{50}$ for inhibiting BCR-ABL is less than 50 µM, less than 25 µM, and less than 5 µM, less than about 1 µM, less than about 0.5 µM, less than about 0.1 µM, less than about 0.05 µM, or less than about 0.01 µM.

In some embodiments, the present disclosure relates to a method of treating an individual suffering from a disease or condition wherein inhibition of BCR-ABL provides a benefit comprising administering a therapeutically effective amount of a compound of the present disclosure to an individual in need thereof.

In some embodiments, the present disclosure relates to a method of treating an individual suffering from a disease or condition wherein inhibition of BCR-ABL provides a benefit, the method comprising administering a therapeutically effective amount of a compound of the present disclosure.

Compounds of the present disclosure are inhibitors of BCR-ABL protein. Accordingly, diseases and conditions mediated by BCR-ABL can be treated by employing these compounds. The present disclosure is thus directed generally to a method for treating a condition or disorder responsive to BCR-ABL inhibition in a subject, e.g., a human subject, suffering from, or at risk of suffering from, the condition or disorder, the method comprising administering to the subject an effective amount of one or more compounds of the present disclosure.

In some embodiments, the present disclosure is directed to a method of inhibiting BCR-ABL in a subject in need thereof, said method comprising administering to the subject an effective amount of at least one compound of the present disclosure.

The methods of the present disclosure can be accomplished by administering a compound of the present disclosure as the neat compound or as a pharmaceutical composition.

Administration of a pharmaceutical composition, or neat compound of a compound of the present disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of the present disclosure and, optionally, a second therapeutic agent, packaged separately or together, and an insert having instructions for using these active agents.

Diseases and conditions treatable by the compounds of the present disclosure and methods of the present disclosure include, but are not limited to, cancer and other proliferative disorders, neurogenerative disorders, muscular dystrophies, autoimmune diseases, inflammatory diseases, viral infections, and prion diseases.

In some embodiments, a human subject is treated with a compound of the present disclosure, or a pharmaceutical composition comprising a compound of the present disclosure, wherein the compound is administered in an amount sufficient to inhibit BCR-ABL protein in the subject.

In some embodiments, the present disclosure provides a method of treating cancer in a subject comprising administering a therapeutically effective amount of a compound of the present disclosure. While not being limited to a specific mechanism, in some embodiments, compounds of the present disclosure treat cancer by inhibiting BCR-ABL. Examples of treatable cancers include, but are not limited to, any one or more of the cancers of Table 8,

TABLE 8

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |

TABLE 8-continued

| | | | |
|---|---|---|---|
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |
| vulvar cancer | vaginal cancer | Waldenstrom's macroglobulinemia | Warthin's tumor |
| Wilms' tumor | | | |

In some embodiments, the cancer is a solid tumor. In another embodiment, the cancer is a hematological cancer. Exemplary hematological cancers include, but are not limited to, the cancers listed in Table 9. In another embodiment, the hematological cancer is acute lymphocytic leukemia, chronic lymphocytic leukemia (including B-cell chronic lymphocytic leukemia), or acute myeloid leukemia. In another embodiment, the hematological cancer is chronic myeloid leukemia

TABLE 9

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | chronic myeloid leukemia |

In some embodiments, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment, the cancer is a NUT-midline carcinoma. In another embodiment, the cancer is multiple myeloma. In another embodiment, the cancer is a lung cancer such as small cell lung cancer (SCLC). In another embodiment, the cancer is a neuroblastoma. In another embodiment, the cancer is Burkitt's lymphoma. In another embodiment, the cancer is cervical cancer. In another embodiment, the cancer is esophageal cancer. In another embodiment, the cancer is ovarian cancer. In another embodiment, the cancer is colorectal cancer. In another embodiment, the cancer is prostate cancer. In another embodiment, the cancer is breast cancer.

In some embodiments, the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

In some embodiments, the present disclosure provides methods of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome. In another embodiment, the present disclosure provides methods of treating neurodegenerative diseases comprising administration of an effective amount of a compound of the present disclosure to a subject in need of such treatment. Exemplary non-limiting neurodegenerative diseases include Alzheimer's disease, multiple sclerosis, Parkinson's disease, amyotrophic lateral sclerosis, and certain lysosomal storage disorders.

In some embodiments, the present disclosure provides methods of treating muscular dystrophies comprising administration of an effective amount of a compound of the present disclosure to a subject in need of such treatment. Exemplary non-limiting muscular dystrophies include Myotonic, Duchenne, Becker, Limb-girdle, Facioscapulohumeral, Congenital, Oculopharyngeal, Distal, and Emery-Dreifuss muscular dystrophies.

In some embodiments, the present disclosure provides methods of treating infectious and non-infectious inflammatory events, and autoimmune and other inflammatory diseases comprising administration of an effective amount of a compound of the present disclosure to a subject in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystutus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In some embodiments, the present disclosure provides a method of treating systemic inflammatory response syndromes, such as LPS-induced endotoxic shock and/or bacteria-induced sepsis by administration of an effective amount of a compound of the present disclosure to a mammal, in particular a human in need of such treatment.

In some embodiments, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In some embodiments, prion diseases or disorders comprising administration of an effective amount of a compound of the present disclosure to a subject in need of such treatment. Exemplary non-limiting prion diseases or disorders include Creutzfeldt-Jakob disease, Gerstmann-Straussler-Scheinker syndrome, fatal familial insomnia, and kuru.

In another embodiments, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a compound of the present disclosure to a subject in need of such therapy.

In some embodiments, the present disclosure provides a method of regulating endogenous or heterologous promoter activity by contacting a cell with a compound of the present disclosure.

In some embodiments, the present disclosure provides a therapeutically effective amount of a compound of the present disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

Combination Therapy

In some embodiments, a compound of the present disclosure is administered in conjunction with a second therapeutic agent useful in the treatment of a disease or condition wherein inhibition of BCR-ABL provides a benefit. The second therapeutic agent is different from the compound of the present disclosure. A compound of the present disclosure and the second therapeutic agent can be administered simultaneously or sequentially to achieve the desired effect. In addition, the compound of the present disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of the present disclosure and the second therapeutic agent can be administered together as a single-unit dose or separately as multi-unit doses, wherein the compound of the present disclosure is administered before the second therapeutic agent or vice versa. One or more doses of the compound of the present disclosure and/or one or more dose of the second therapeutic agent can be administered. The compound of the present disclosure therefore can be used in conjunction with one or more second therapeutic agents, for example, but not limited to, anticancer agents.

Administrations and Dosage

A compound of the present disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of the present disclosure is administered in an effective amount to achieve its intended purpose. The exact formulation, route of administration, and dosage is determined by an individual physician in view of the diagnosed condition or disease. Dosage amount and interval can be adjusted individually to provide levels of a compound of the present disclosure that is sufficient to maintain therapeutic effects.

Toxicity and therapeutic efficacy of the compounds of the present disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of the present disclosure required for use in therapy varies with the nature of the condition being treated, the length of time that activity is desired, and the age and the condition of the subject, and is ultimately determined by the attendant physician. Dosage amounts and intervals can be adjusted individually to provide plasma levels of the compound of the present disclosure that are sufficient to maintain the desired therapeutic effects. The desired dose can be administered in a single dose, or as multiple doses administered at appropriate intervals, for example as one, two, three, four or more subdoses per day. Multiple doses often are desired, or required. For example, a compound of the present disclosure can be administered at a frequency of: four doses delivered as one dose per day at four-day intervals (q4d×4); four doses delivered as one dose per day at three-day intervals (q3d×4);

one dose delivered per day at five-day intervals (qd×5); one dose per week for three weeks (qwk3); five daily doses, with two-day rest, and another five daily doses (5/2/5); or, any dose regimen determined to be appropriate for the circumstance.

A compound of the present disclosure used in a method of the present disclosure can be administered in an amount of about 0.005 to about 500 milligrams per dose, about 0.05 to about 250 milligrams per dose, or about 0.5 to about 100 milligrams per dose. For example, a compound of the present disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a compound of the present disclosure, or a composition containing the same, can be from about 1 µg/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, about 10 µg/kg, about 25 µg/kg, about 50 µg/kg, about 75 µg/kg, about 100 µg/kg, about 125 µg/kg, about 150 µg/kg, about 175 µg/kg, about 200 µg/kg, about 225 µg/kg, about 250 µg/kg, about 275 µg/kg, about 300 µg/kg, about 325 µg/kg, about 350 µg/kg, about 375 µg/kg, about 400 µg/kg, about 425 µg/kg, about 450 µg/kg, about 475 µg/kg, about 500 µg/kg, about 525 µg/kg, about 550 µg/kg, about 575 µg/kg, about 600 µg/kg, about 625 µg/kg, about 650 µg/kg, about 675 µg/kg, about 700 µg/kg, about 725 µg/kg, about 750 µg/kg, about 775 µg/kg, about 800 µg/kg, about 825 µg/kg, about 850 µg/kg, about 875 µg/kg, about 900 µg/kg, about 925 µg/kg, about 950 µg/kg, about 975 µg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more.

The above dosages are exemplary of the average case, but there can be individual instances in which higher or lower dosages are merited, and such are within the scope of this disclosure. In practice, the physician determines the actual dosing regimen that is most suitable for an individual subject, which can vary with the age, weight, and response of the particular subject.

Pharmaceutical Compositions

In some embodiments, compounds of the present disclosure typically are administered in admixture with a pharmaceutical carrier to give a pharmaceutical composition selected with regard to the intended route of administration and standard pharmaceutical practice.

Pharmaceutical compositions for use in accordance with the present disclosure are formulated in a conventional manner using one or more physiologically acceptable carriers comprising excipients and/or auxiliaries that facilitate processing of compound of the present disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of the present disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of the present disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of the present disclosure.

When a therapeutically effective amount of a compound of the present disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the present disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a subject to be treated.

Pharmaceutical preparations for oral use can be obtained by adding the compound of the present disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the present disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of the present disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions.

Alternatively, a present composition can be in powder form for constitution with a suitable vehicle, e.g., sterile pyrogen-free water, before use.

Compounds of the present disclosure also can be formulated in rectal compositions, such as suppositories or retention enemas, e.g., containing conventional suppository bases. In addition to the formulations described previously, the compound of the present disclosure also can be formulated as a depot preparation. Such long-acting formulations can be administered by implantation (for example, subcutaneously or intramuscularly) or by intramuscular injection. Thus, for example, the compound of the present disclosure can be formulated with suitable polymeric or hydrophobic materials (for example, as an emulsion in an acceptable oil) or ion exchange resins.

In particular, the compounds of the present disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the present disclosure also can be injected parenterally, for example, intravenously, intramuscularly, subcutaneously, or intracoronarily.

For parenteral administration, the compound of the present disclosure are typically used in the form of a sterile aqueous solution which can contain other substances, for example, salts or monosaccharides, such as mannitol or glucose, to make the solution isotonic with blood.

Medical Kits

In some embodiments, the present disclosure provides kits which comprise a compound of the present disclosure (or a composition comprising a compound of the present disclosure) packaged in a manner that facilitates their use to practice methods of the present disclosure. In one embodiment, the kit includes a compound of the present disclosure (or a composition comprising a compound of the present disclosure) packaged in a container, such as a sealed bottle or vessel, with a label affixed to the container or included in the kit that describes use of the compound or composition to practice the method of the present disclosure.

In some embodiments, the kit further can include a device suitable for administering the composition according to the intended route of administration.

General Synthetic Methods

In some embodiments, the compounds of the present disclosure and intermediates can be prepared according to Schemes 1-3 below. In the general schemes, variables such as $R^1$, $R^4$, $R^7$, $R^8$, L and Ar are as the same defined herein. Each expression "Lv" refers to a leaving group including but not limited to halo, mesylates, tosylates and the like. The expression "P" refers to H or a protecting group such as alkyl ester. The expression "T" refers to halogen such as —Cl, —Br, or —I. In some embodiment, $R^1$ is —$C_{1-6}$alkyl substituted with 1, 2, or 3 halo. In some embodiments, $R^1$ is difluorochloromethyl. In some embodiment, $R^4$ is any one of the moieties provided in Table 1. In some embodiment, $R^4$ is any one of the moieties provided in Table 1-A. In some embodiments, $R^4$ is iso-propyl or neopentyl. In some embodiment, $R^7$ is any one of the moieties provided in Table 3. In some embodiments, $R^7$ is H, —OH, or —NHC(=O)CH$_3$. In some embodiment, $R^8$ is any one of the moieties provided in Table 3. In some embodiments, $R^8$ is H, —OH or —NHC(=O)CH$_3$. In some embodiment, L is —O— or —S—. In some embodiment, Ar is any one of the moieties provided in Table 2. In some embodiment, Ar is any one of the moieties provided in Table 2-A. In some embodiments, Ar is pyridinyl, pyrimidinyl, or pyrazinyl. In some embodiments, Ar is pyrazolyl. In some embodiments, Ar is 1H-pyrazol-5-yl.

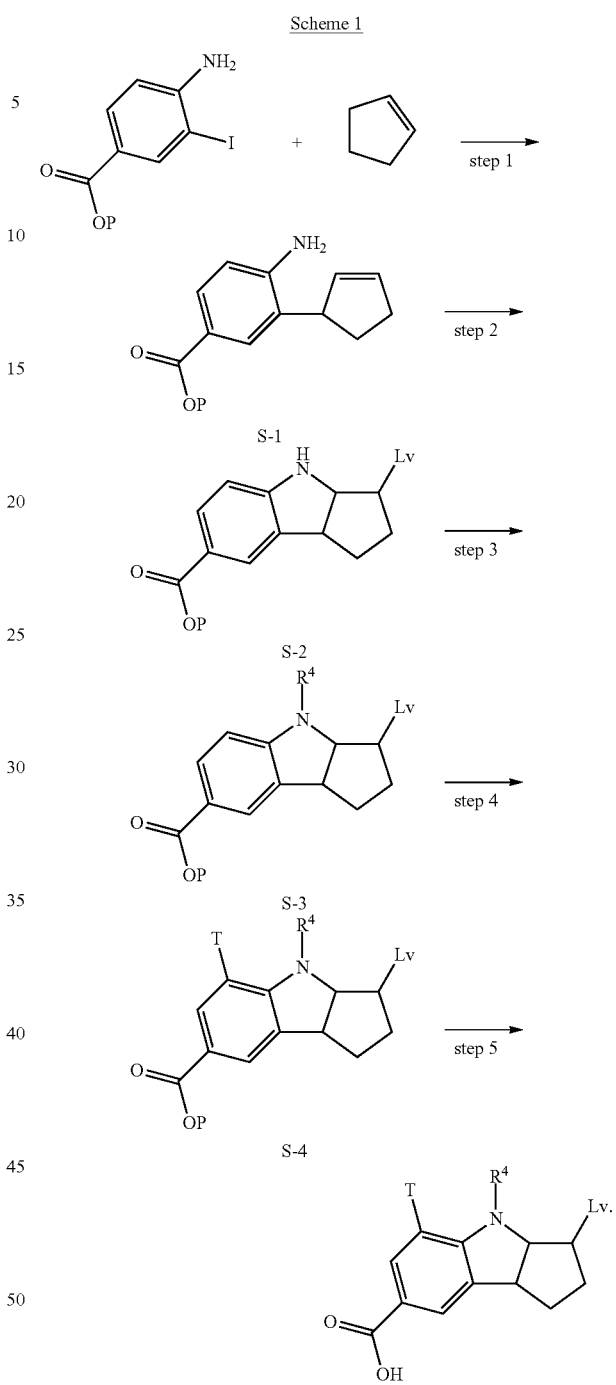

Scheme 1

In step 1 of Scheme 1, intermediate S-1 can be prepared in the presence of a suitable base and a solvent. The base may be an inorganic base or an organic base. Non-limiting examples of the inorganic base may include bicarbonates, carbonates, phosphates, and acetates. The organic base may include but is not limited to amines, e.g., tertiary amines. The suitable solvent includes but is not limited to DMF, THF, EA, DMSO, acetonitrile, ether, ketone, 1,4-dioxane, and the like. In some embodiment, the reaction may be carried out in the presence of a catalyst. The catalyst may include but is not limited to palladium compounds, platinum compounds, and phosphorus compounds, Non-limiting examples are palladium acetate and triphenyl phosphine.

Intermediate S-2 can be prepared from S-1 with an addition reagent in the presence of a suitable base and a solvent. The addition reagent includes but is not limited to hydrogen halides, $Cl_2$, $Br_2$, and $I_2$. The base may be an inorganic base or an organic base. Non-limiting examples of the inorganic base may include bicarbonates, carbonates, phosphates, and acetates. The organic base may include but is not limited to amines, e.g., tertiary amines. The suitable solvent includes but is not limited to DMF, DCM, EA, THF, DMSO, ether, ketone, 1,4-dioxane, and the like.

Intermediate S-3 can be prepared from S-2 with a ketone in the presence of a suitable acid, a silane, and a solvent. The acid may be an inorganic acid or an organic acid. Non-limiting examples of the inorganic acid may include hydrogen sulfate ion, hydrochloride acid and phosphoric acid. The organic acid may include but is not limited to oxalic acid, acetic acid, benzoic acid, and TFA. The suitable solvent includes but is not limited to DMF, DCM, THF, DMSO, ether, ketone, 1,4-dioxane, and the like. The silane may be an organosilane such as phenylsilane and triethylsilane. Alternatively, S-3 can be prepared with an alkylating reagent such as alkyl halide in presence of a suitable base and a solvent.

Intermediate S-4 can be prepared from S-3 with a halogenating reagent in the presence of a suitable solvent. The halogenating reagent may include but is not limited to $Cl_2$, $Br_2$, $I_2$, and NBS. The suitable solvent includes but is not limited to DMF, DCM, EA, THF, DMSO, ether, ketone, 1,4-dioxane, and the like.

The free acid S-5 can be prepared from S-4 by hydrolysis in the presence of a base and a solvent. The base may be an inorganic base or an organic base. Non-limiting examples of the inorganic base may include hydroxides, bicarbonates, carbonates, phosphates, and acetates. The organic base may include but is not limited to amines, e.g., tertiary amines. The suitable solvent includes protic and aprotic solvents such as water, methanol, ethanol, DMF, DCM, EA, THF, DMSO, ether, ketone, 1,4-dioxane, and the like. The suitable solvent may also be a combination of two or three solvents. The hydrolysis product may be acidified to afford the free acid.

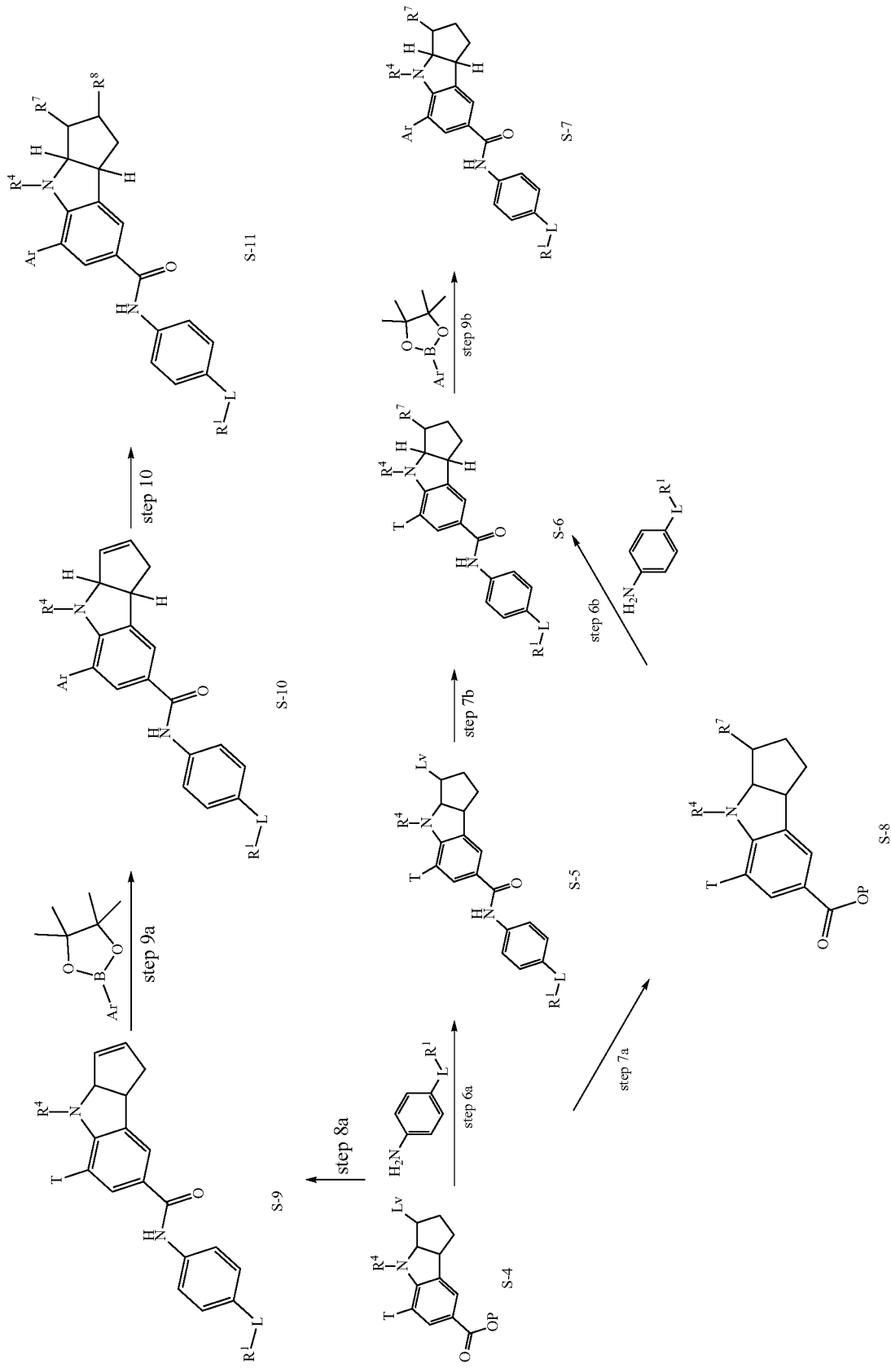

Scheme 3
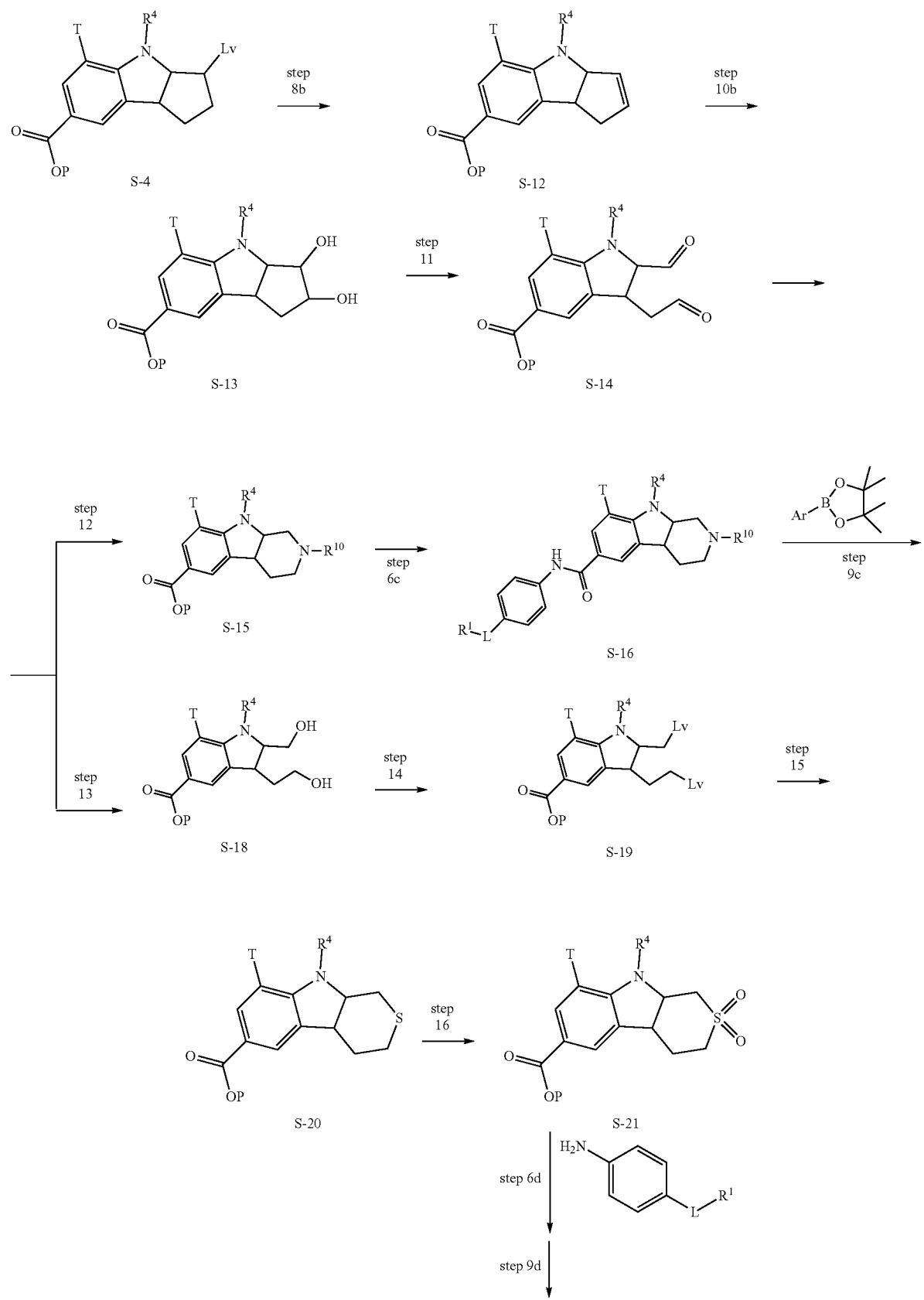

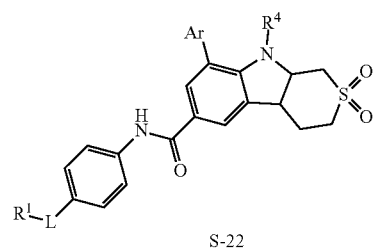

S-22

In Schemes 2 and 3, Steps 6a-6d: Steps 6a-6d can be performed in the presence of a suitable base, a coupling reagent, and a solvent. The coupling reaction can be conducted by prior conversion of the carboxylate moiety of S-4, S-8, S-15, and S-21 to a carboxylic acid as described in Step 5. The suitable base in Steps 6a-6d may be an inorganic base or an organic base. Non-limiting examples of the inorganic base may include bicarbonates, carbonates, phosphates, and acetates. The organic base may include but is not limited to amines, e.g., tertiary amines. The coupling reagent can be a suitable peptide coupling agent including, without limitation, HUTA, dicyclohexylcarbodiimide (DCC) or 1-(3-dimethylaminopropyl)-3-ethylcarbodiimide (EDC), benzotriazol-1-yloxytris(dimethylamino)phosphonium hexafluorophosphate (BOP), and O-(1H-benzotriazol-1-yl)-N,N,N',N'-tetramthyluronium tetrafluoroborate (TBTU). The suitable solvent includes but is not limited to DMF, THF, DMSO, acetonitrile, ethers, 1,4-dioxane, and the like.

Steps 7a & 7b: Steps 7a and 7b can be carried out with a substituting reagent in the presence of a suitable solvent. The substituting reagent can include but is not limited to hydroxide, oxygen containing reagent, sulfur containing reagent, or nitrogen containing reagent. The suitable solvent includes but is not limited to protic and aprotic solvents such as water, methanol, ethanol, DMF, DCM, EA, THF, DMSO, ether, ketone, 1,4-dioxane, and the like. The suitable solvent may also be a combination of two or three solvents.

Steps 8a & 8b: Steps 8a and 8b can be carried out in the presence of a suitable base and solvent. The base may be an inorganic base or an organic base. Non-limiting examples of the inorganic base may include hydroxides, bicarbonates, carbonates, phosphates, and acetates. The organic base may include but is not limited to amines, e.g., tertiary amines; pyridine, and piperidine. The suitable solvent includes but is not limited to protic and aprotic solvents such as water, methanol, ethanol, DMF, DCM, EA, THF, DMSO, ether, ketone, 1,4-dioxane, and the like. The suitable solvent may also be a combination of two or three solvents.

Steps 9a-9d: Steps 9a-9d can be carried out in the presence of a suitable base, catalyst, and solvent. The base may be an inorganic base or an organic base. Non-limiting examples of the inorganic base may include bicarbonates, carbonates, phosphates, and acetates. The organic base may include amines, e.g., tertiary amines; pyridine, and piperidine. The catalyst is any catalyst suitable for the Suzuki-coupling, and includes but is not limited to nickel, palladium, and platinum catalysts. Non-limiting examples are $NiCl_2(dppf)$, $PdCl_2(PPh_3)_4$, $PdCl_2(dppf)-CH_2Cl_2$ adduct. The suitable solvent includes but is not limited to protic and aprotic solvents such as water, methanol, ethanol, DMF, DME, DCM, THF, DMSO, ether, ketone, 1,4-dioxane, and the like. The suitable solvent may also be a combination of two or three solvents.

Steps 10 and 10b: Step 10 can be carried out under the standard addition reaction of an alkene. When $R^7$ and $R^8$ are hydrogen, S-11 can be obtained under the standard hydrogenation reaction with a catalyst including but not limited to platinum, palladium, rhodium and ruthenium catalysts. Step 10b can be carried out with an oxidizing reagent in the presence of a suitable solvent. The oxidizing reagent includes but is not limited to hydrogen peroxide, potassium permanganate, 4-methylmorpholine 4-oxide, and osmium tetroxide. The suitable solvent includes but is not limited to protic and aprotic solvents such as water, DMF, DME, DCM, EA, THF, DMSO, ether, ketone, 1,4-dioxane, and the like. The suitable solvent may also be a combination of two or three solvents.

Step 11: Step 11 can be carried out with an oxidizing reagent in the presence of a suitable solvent. The oxidizing reagent includes but is not limited to NBS, potassium permanganate, TEMPO (2,2,6,6-Tetramethylpiperidinyloxy or 2,2,6,6-Tetramethylpiperidine 1-oxyl), and sodium periodate. The suitable solvent includes but is not limited to protic and aprotic solvents such as water, DMF, DME, DCM, THF, DMSO, ether, ketone, 1,4-dioxane, and the like. The suitable solvent may also be a combination of two or three solvents.

Step 12: S-16 can be prepared by reductive amination with $R^{10}NH_2$ in the presence of a reducing reagent and a suitable solvent. The reducing reagent includes but is not limited to a borohydride reagent or a metal hydride reagent. Non-limiting examples are lithium borohydride, sodium borohydride, sodium cyanoborohydride. The suitable solvent includes but is not limited to protic and aprotic solvents such as water, methanol, ethanol, DME, DCM, EA, THF, DMSO, ether, 1,4-dioxane, and the like. The suitable solvent may also be a combination of two or three solvents.

Step 13: S-18 can be prepared by reducing S-14 in the presence of a reducing reagent and a suitable solvent. The reducing reagent includes but is not limited to a borohydride reagent and a metal hydride reagent. Non-limiting examples are lithium borohydride, sodium borohydride, sodium cyanoborohydride. The suitable solvent includes but is not limited to protic and aprotic solvents such as water, methanol, ethanol, DME, DCM, EA, THF, DMSO, ether, 1,4-dioxane, and the like. The suitable solvent may also be a combination of two or three solvents.

Step 14: S-19 can be prepared by replacing the hydroxyl groups in S-18 with a leaving group in the presence of a replacing reagent and a suitable solvent. The replacing reagent may include but is not limited to a halogenating reagent such as $Cl_2$, $Br_2$, $I_2$, $CBr_4$, $Cl_4$, NBS, and HBr, and other reagents such as methansulfonoyl chloride and p-toluenesulfonyl chloride. The reaction can be carried out in the presence of a phosphine reagent such as triphenylphosphine. The suitable solvent includes but is not limited to DMF, DCM, EA, THF, DMSO, ether, ketone, 1,4-dioxane, and the like.

Step 15: S-20 can be prepared by replacing the leaving groups in S-19 with a thiolating reagent such as Na₂S in the presence of a suitable solvent. The suitable solvent includes but is not limited to DMF, DCM, EA, THF, DMSO, ether, ketone, 1,4-dioxane, and the like.

Step 16: S-21 can be prepared from S-20 with an oxidizing reagent in the presence of a suitable solvent. The oxidizing reagent includes but is not limited to oxone, hydrogen peroxide, potassium permanganate, TEMPO (2,2,6,6-Tetramethylpiperidinyloxy or 2,2,6,6-Tetramethylpiperidine 1-oxyl), and m-chloroperoxybenzoic acid. The suitable solvent includes but is not limited to DMF, DME, DCM, THF, DMSO, ether, ketone, 1,4-dioxane, and the like.

EXAMPLES

TABLE 10

| Abbreviations/Acronyms | Full Name/Description |
| --- | --- |
| AcOH | Acetic acid |
| AcOK | Potassium acetate |
| AcCl | Acetyl chloride |
| t-BuOK | potassium tertbutoxide/ potassium2-methylpropan-2-olate |
| CDI | 1,1'-Carbonyldiimidazole |
| DCM | Dichloromethane |
| DIEA/DIPEA | MA-Diisopropylethylamine |
| DME | Dimethyl ether |
| DMF | Dimethylformamide |
| DMSO | Dimethylsulfoxide |
| EA | Ethyl acetate |
| EtOH | Ethanol |
| HATU | 1-[Bis(dimethylamino)methylene]-1H-1,2,3-triazolo[4,5-b]pyridinium 3-oxid hexafluorophosphate |
| MeOH | Methanol |
| MsCl | Methanesulfonyl chloride |
| NMO | 4-Methylmorpholine N-oxide |
| NBS | N-Bromosuccinimide |
| PdCl₂(dppf)-CH₂Cl₂adduct | [1,1'-Bis(diphenylphosphino)ferrocene]dichloropalladium(II), complex with dichloromethane |
| TEA | Triethylamine |
| TFA | Trifluoroacetic acid |
| TFE | 2,2,2-Trifluoroethanol |
| THF | Tetrahydrofuran |

Example 1

Synthesis of N-(4-(chlorodifluoromethoxy)phenyl)-3-hydroxy-4-isopropyl-5-(1H-pyrazol-5-yl)-1,2,3,3a,4,8b-hexahydrocyclopenta[b]indole-7-carboxamide (Compound No. 1)

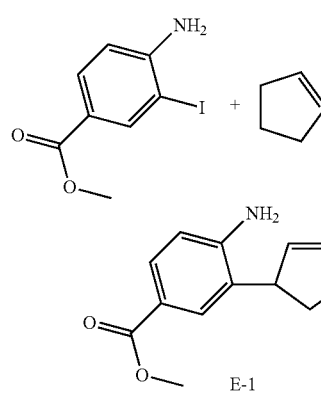

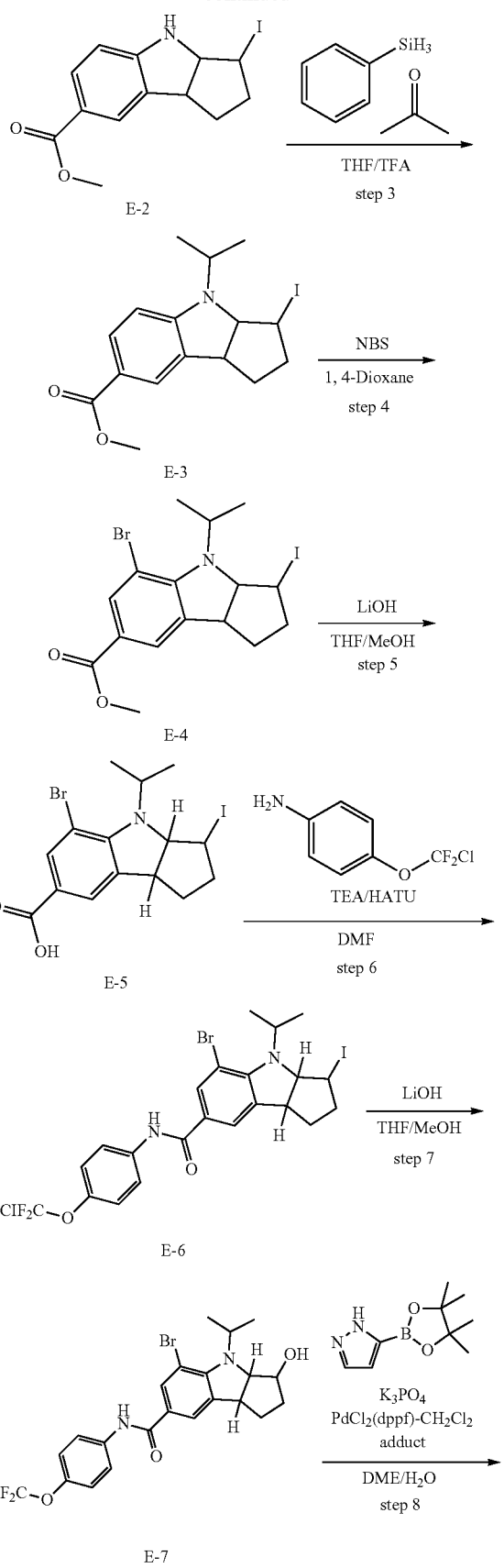

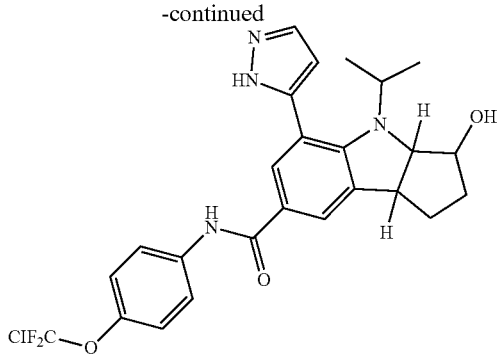

1

Step 1: Synthesis of Methyl 4-amino-3-(cyclopent-2-en-1-yl)benzoate (E-1)

Under Ar, the mixture of methyl 4-amino-3-iodobenzoate (5.0 g, 18.05 mmol), cyclopentene (6.15 g, 90 mmol), potassium acetate (4.43 g, 45.1 mmol), Pd(OAc)$_2$ (0.608 g, 2.71 mmol) and Ph$_3$P (1.420 g, 5.41 mmol) in N,N'-dimethylformamide (30 ml) was stirred at 80° C. for 12 h. After being cooled to room temperature, the mixture was quenched with water (100 mL), followed by extraction with ethyl acetate (50 mL×3). The combined organic layers were washed with brine, dried over Na$_2$SO$_4$, filtrated and concentrated in vacuo to give a yellow oil, which was purified by silica gel column chromatography (ethyl acetate/hexane from 0% to 20%) to give methyl 4-amino-3-(cyclopent-2-en-1-yl)benzoate (2.9 g, 74.0%) as a yellow solid.

Step 2: Synthesis of Methyl 3-iodo-1,2,3,3a,4,8b-hexahydrocyclopenta[b]indole-7-carboxylate (E-2)

Under Ar, to a solution of methyl 4-amino-3-(cyclopent-2-en-1-yl)benzoate (2.4 g, 11.05 mmol) and NaHCO$_3$ (9.28 g, 110 mmol) in dichloromethane (100 ml), was added iodine (2.80 g, 11.05 mmol) at room temperature. The mixture was stirred at room temperature for overnight, then quenched with Na$_2$S$_2$O$_3$ aqueous solution, followed by extraction with ethyl acetate (50 mL×3). The combined organic layers were washed with brine, dried over Na$_2$SO$_4$, filtrated and concentrated in vacuum to give a residue, which was purified by silica column gel chromatography (ethyl acetate/hexane from 0% to 20%) to give methyl 3-iodo-1,2,3,3a,4,8b-hexahydrocyclopenta[b]indole-7-carboxylate (2.5 g, 66.0%) as a light yellow solid. $^1$H NMR (400 MHz, CDCl$_3$) δ 7.77-7.69 (m, 2H), 6.43 (d, J=8.2 Hz, 1H), 4.82 (d, J=8.8 Hz, 1H), 4.57 (s, 1H), 4.27-4.11 (m, 1H), 3.92 (t, J=8.7 Hz, 1H), 3.84 (s, 3H), 2.68-2.46 (m, 1H), 2.15-1.99 (m, 1H), 1.97-1.78 (m, 2H). MS: 343.9 (M+H)$^+$.

Step 3: Synthesis of Methyl 3-iodo-4-isopropyl-1,2,3,3a,4,8b-hexahydrocyclopenta[b]indole-7-carboxylate (E-3)

To a solution of methyl 3-iodo-1,2,3,3a,4,8b-hexahydrocyclopenta[b]indole-7-carboxylate (2.5 g, 7.29 mmol) in tetrahydrofuran (12 ml) and acetone (4 ml), were added trifluoroacetic acid (1.6 ml) and phenylsilane (2.365 g, 21.86 mmol) at room temperature. The mixture was stirred at room temperature for overnight, then quenched with NaHCO$_3$ aqueous solution, followed by extraction with ethyl acetate (60 mL×3). The combined organic layers were washed with brine, dried over Na$_2$SO$_4$, filtrated and concentrated in vacuum to give a residue, which was purified by silica column gel chromatography (ethyl acetate/hexane acetate from 0% to 20%) to give methyl 3-iodo-4-isopropyl-1,2,3,3a,4,8b-hexahydrocyclopenta[b]indole-7-carboxylate (2.5 g, 89%) as a colorless oil. $^1$H NMR (400 MHz, MeOD) δ 7.73 (dd, J=8.4, 1.6 Hz, 1H), 7.64-7.61 (m, 1H), 6.43 (d, J=8.5 Hz, 1H), 4.75 (d, J=8.9 Hz, 1H), 4.44 (d, J=4.8 Hz, 1H), 3.95-3.83 (m, 2H), 3.81 (s, 3H), 2.69-2.52 (m, 1H), 2.05 (dd, J=14.4, 5.8 Hz, 1H), 1.91 (dd, J=12.8, 5.9 Hz, 1H) 1.76-1.60 (m, 1H), 1.31 (d, J=6.8 Hz, 3H), 1.19 (d, J=6.7 Hz, 3H). MS: 385.95 (M+H)$^+$.

Step 4: Synthesis of Methyl 5-bromo-3-iodo-4-isopropyl-1,2,3,3a,4,8b-hexahydrocyclopenta[b]indole-7-carboxylate (E-4)

Under Ar, to a solution of methyl 3-iodo-4-isopropyl-1,2,3,3a,4,8b-hexahydrocyclopenta[b]indole-7-carboxylate (2 g, 5.19 mmol) in 1,4-Dioxane (30 mL) was added N-Bromosuccinimide (0.970 g, 5.45 mmol) at room temperature. The mixture was stirred for 2 h at room temperature, then quenched with Na$_2$SO$_3$ aqueous solution, followed by extraction with ethyl acetate (50 mL×3). The combined organic layers were washed with brine, dried over Na$_2$SO$_4$, filtrated and concentrated in vacuum to give a residue, which was purified by silica column gel chromatography (ethyl acetate/hexane from 0% to 20%) to give methyl 5-bromo-3-iodo-4-isopropyl-1,2,3,3a,4,8b-hexahydrocyclopenta[b]indole-7-carboxylate (2 g, 83%). $^1$H NMR (400 MHz, CDCl$_3$) δ 7.94 (d, J=1.5 Hz, 1H), 7.62-7.57 (m, 1H), 5.00-4.85 (m, 1H), 4.62 (d, J=9.0 Hz, 1H), 4.28 (d, J=4.9 Hz, 1H), 3.95 (t, J=8.5 Hz, 1H), 3.85 (s, 3H), 2.69-2.53 (m, 1H), 2.12-1.87 (m, 2H), 1.70-1.57 (m, 1H), 1.32 (d, J=6.9 Hz, 3H), 0.97 (d, J=6.5 Hz, 3H). MS: 465.8 (M+H)$^+$.

Step 5: Synthesis of 5-bromo-3-iodo-4-isopropyl-1,2,3,3a,4,8b-hexahydrocyclopenta[b]indole-7-carboxylic Acid (E-5)

The mixture of methyl 5-bromo-3-iodo-4-isopropyl-1,2,3,3a,4,8b-hexahydrocyclopenta[b]indole-7-carboxylate (2 g, 4.31 mmol) and LiOH (8.62 mmol) in tetrahydrofuran (15 ml) was stirred at 40° C. for overnight. The mixture was acidified with TN HCl to pH=4, followed by extraction with ethyl acetate (50 mL×3). The combined organic layers were washed with brine, dried over Na$_2$SO$_4$, filtrated and concentrated in vacuum to give the crude 5-bromo-3-iodo-4-isopropyl-1,2,3,3a,4,8b-hexahydrocyclopenta[b]indole-7-carboxylic acid (2 g), which was used in the next step without purification. $^1$H NMR (400 MHz, CDCl$_3$) δ 8.01 (d, J=0.8 Hz, 1H), 7.63 (s, 1H), 5.08-4.93 (m, 1H), 4.20-4.14 (m, 1H), 4.05 (d, J=9.2 Hz, 1H), 3.94 (t, J=8.5 Hz, 1H), 2.42-2.27 (m, 1H), 1.89-1.77 (m, 1H), 1.73-1.62 (m, 1H), 1.59-1.46 (m, 1H), 1.38 (d, J=6.8 Hz, 3H), 1.04 (d, J=6.5 Hz, 3H).

Step 6: Synthesis of 5-bromo-N-(4-(chlorodifluoromethoxy)phenyl)-3-iodo-4-isopropyl-1,2,3,3a,4,8b-hexahydrocyclopenta[b]indole-7-carboxamide (E-6)

Under Ar, the mixture of 5-bromo-3-iodo-4-isopropyl-1,2,3,3a,4,8b-hexahydrocyclopenta[b]indole-7-carboxylic acid (2.3 g, 5.11 mmol), 4-(chlorodifluoromethoxy)aniline (1.484 g, 7.66 mmol), triethylamine (1.551 g, 15.33 mmol)

and HATU (3.11 g, 8.18 mmol) in N,N'-dimethylformamide (20 mL) was stirred at room temperature for overnight, then quenched with water, followed by extraction with ethyl acetate (50 mL×3). The combined organic layers were washed with brine, dried over $Na_2SO_4$, filtrated and concentrated in vacuum to give a residue, which was purified by silica column gel chromatography (ethyl acetate/hexane from 0% to 20%) to give 5-bromo-N-(4-(chlorodifluoromethoxy)phenyl)-3-iodo-4-isopropyl-1,2,3,3a,4,8b-hexahydrocyclopenta[b]indole-7-carboxamide (1.9 g, 59.4%) as a light yellow solid.

Step 7: Synthesis of 5-bromo-N-(4-(chlorodifluoromethoxy)phenyl)-3-hydroxy-4-isopropyl-1,2,3,3a,4,8b-hexahydrocyclopenta[b]indole-7-carboxamide (E-7)

The a solution of 5-bromo-N-(4-(chlorodifluoromethoxy)phenyl)-3-iodo-4-isopropyl-1,2,3,3a,4,8b-hexahydrocyclopenta[b]indole-7-carboxamide (500 mg, 0.799 mml) in tetrahydrofuran (5.00 ml) and methanol (5 ml), was added LiOH (38.3 mg, 1.598 mmol) at room temperature, the mixture was stirred at room temperature for overnight, then diluted with water (10 mL), followed by extraction with ethyl acetate (20 mL×3). The combined organic layers were washed with brine, dried over $Na_2SO_4$, filtrated and concentrated in vacuum to give a residue, which was purified by silica column gel chromatography (ethyl acetate/hexane from 0% to 20%) to give 5-bromo-N-(4-(chlorodifluoromethoxy)phenyl)-3-hydroxy-4-isopropyl-1,2,3,3a,4,8b-hexahydrocyclopenta[b]indole-7-carboxamide (150 mg, 36.4%).

Step 8: Synthesis of N-(4-(chlorodifluoromethoxy)phenyl)-3-hydroxy-4-isopropyl-5-(1H-pyrazol-5-yl)-1,2,3,3a,4,8b-hexahydrocyclopenta[b]indole-7-carboxamide (1)

Under Ar, the mixture of 5-bromo-N-(4-(chlorodifluoromethoxy)phenyl)-3-hydroxy-4-isopropyl-1,2,3,3a,4,8b-hexahydrocyclopenta[b]indole-7-carboxamide (150 mg, 0.291 mmol), 5-(4,4,5,5-tetramethyl-1,3,2-dioxaborolan-2-yl)-1H-pyrazole (226 mg, 1.163 mmol), $PdCl_2$(dppf)-$CH_2Cl_2$ adduct (23.75 mg, 0.029 mmol), $K_3PO_4$ (309 mg, 1.454 mmol) in the 1,4-dioxane (8 ml)/water (2 mL) was stirred at 100° C. for 3 h under microwave irradiation. After cooled to room temperature, the mixture was diluted with water (20 mL), then extracted with ethyl acetate (20 mL×3). The combined organic layers were washed with brine, dried over $Na_2SO_4$, filtrated and concentrated in vacuum to give a residue, which was purified by Prep-HPLC to give N-(4-(chlorodifluoromethoxy)phenyl)-3-hydroxy-4-isopropyl-5-(1H-pyrazol-5-yl)-1,2,3,3a,4,8b-hexahydrocyclopenta[b]indole-7-carboxamide (20 mg, 13.67%). $^1$H NMR (400 MHz, DMSO) δ 13.09-12.80 (m, 1H), 10.21-10.05 (m, 1H), 7.94-7.50 (m, 5H), 7.32 (d, J=8.8 Hz, 2H), 6.51-6.34 (m, 1H), 4.79 (d, J=3.1 Hz, 1H), 3.97 (d, J=13.3 Hz, 1H), 3.93-3.85 (m, 2H), 3.76-3.35 (m, 1H), 2.38-2.22 (m, 1H) 1.77-1.53 (m, 2H), 1.47-1.27 (m, 1H), 1.13 (d, J=6.7 Hz, 3H), 0.75 (d, J=6.4 Hz, 3H).

Example 2

Synthesis of N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (Compound No. 2)

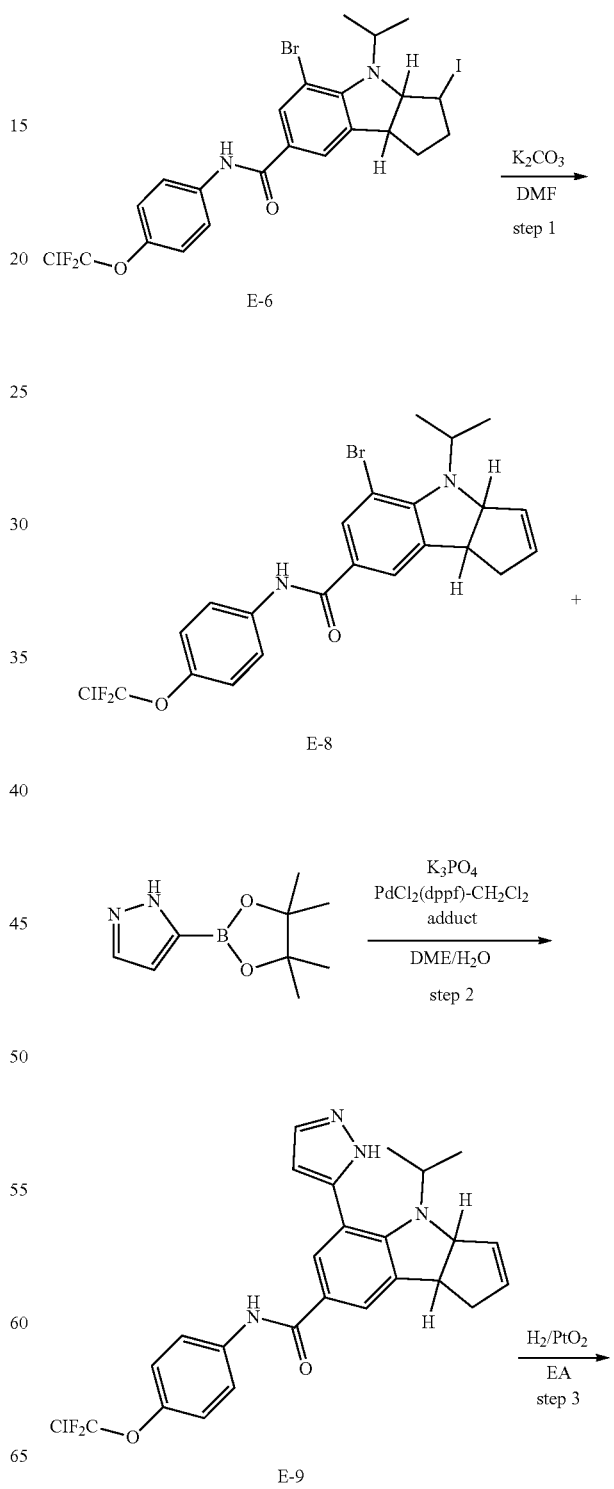

-continued

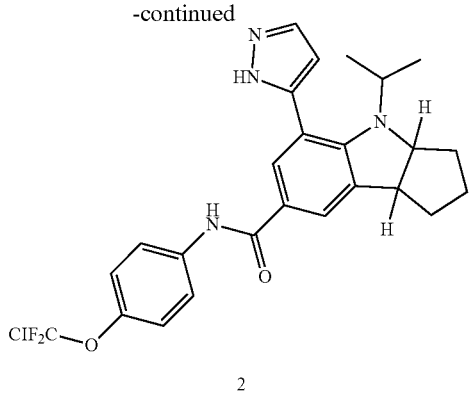

2

Step 1: Synthesis of 5-bromo-N-(4-(chlorodifluoromethoxy)phenyl)-4-isopropyl-1,3a,4,8b-tetrahydrocyclopenta[b]indole-7-carboxamide (E-8)

Under Ar, the mixture of 5-bromo-N-(4-(chlorodifluoromethoxy)phenyl)-3-iodo-4-isopropyl-1,2,3,3a,4,8b-hexahydrocyclopenta[b]indole-7-carboxamide (800 mg, 1.279 mmol) and K$_2$CO$_3$ (530 mg, 3.84 mmol) in N,N'-dimethylformamide (6 ml) was stirred at 80° C. for 2 h. After being cooled to room temperature, the mixture was diluted with water (30 mL), followed by extraction with ethyl acetate (50 mL×3). The combined organic layers were washed with brine, dried over Na$_2$SO$_4$, filtrated and concentrated in vacuum to give the yellow oil, which was purified by silica gel column chromatography (ethyl acetate/hexane from 0% to 20%) to give 5-bromo-N-(4-(chlorodifluoromethoxy)phenyl)-4-isopropyl-1,3a,4,8b-tetrahydrocyclopenta[b]indole-7-carboxamide (430 mg, 67.6%). $^1$H NMR (400 MHz, CDCl$_3$) δ 7.86 (s, 1H), 7.76 (s, 1H), 7.67 (d, J=8.8 Hz, 2H), 7.53 (s, 1H), 7.22 (d, J=8.7 Hz, 2H), 5.91-5.81 (m, 1H), 5.76-5.66 (m, 1H), 4.98-4.79 (m, 2H), 4.04 (t, J=8.3 Hz, 1H), 3.04-2.85 (m, 1H), 2.65-2.54 (m, 1H), 1.39 (d, J=6.8 Hz, 3H), 1.09 (d, J=6.6 Hz, 3H).

Step 2: Synthesis of N-(4-(chlorodifluoromethoxy)phenyl)-4-isopropyl-5-(1H-pyrazol-5-yl)-1,3a,4,8b-tetrahydrocyclopenta[b]indole-7-carboxamide (E-9)

The mixture of 5-bromo-N-(4-(chlorodifluoromethoxy)phenyl)-4-isopropyl-1,3a,4,8b-tetrahydrocyclopenta[b]indole-7-carboxamide (600 mg, 1.205 mmol), 5-(4,4,5,5-tetramethyl-1,3,2-dioxaborolan-2-yl)-1H-pyrazole (936 mg, 4.82 mmol), K$_3$PO$_4$ (256 mg, 1.205 mmol) and PdCl$_2$(dppf)-CH$_2$Cl$_2$ adduct (984 mg, 1.205 mmol) in DME (10 ml)/water (2 ml) was stirred at 110° C. under microwave irradiation for 2.5 h. After being cooled to room temperature, the mixture was diluted with water, followed by extraction with ethyl acetate (50 mL×3). The combined organic layers were washed with brine, dried over Na$_2$SO$_4$, filtrated and concentrated in vacuum to give the yellow oil, which was purified by silica gel column chromatography (ethyl acetate/hexane from 0% to 50%) to give the crude N-(4-(chlorodifluoromethoxy)phenyl)-4-isopropyl-5-(1H-pyrazol-5-yl)-1,3a,4,8b-tetrahydrocyclopenta[b]indole-7-carboxamide (700 mg) as a yellow solid. $^1$H NMR (400 MHz, CDCl$_3$) δ 7.86 (s, 1H), 7.76 (s, 1H), 7.67 (d, J=8.8 Hz, 2H), 7.53 (s, 1H), 7.22 (d, J=8.7 Hz, 2H), 5.91-5.81 (m, 1H), 5.76-5.66 (m, 1H), 4.98-4.79 (m, 2H), 4.04 (t, J=8.3 Hz, 1H), 3.04-2.85 (m, 1H), 2.65-2.54 (m, 1H), 1.39 (d, J=6.8 Hz, 3H), 1.09 (d, J=6.6 Hz, 3H).

Step 3: Synthesis of N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (2)

The mixture of N-(4-(chlorodifluoromethoxy)phenyl)-4-isopropyl-5-(1H-pyrazol-5-yl)-1,3a,4,8b-tetrahydrocyclopenta[b]indole-7-carboxamide (60 mg, 0.124 mmol) and platinum(IV) oxide (8.43 mg, 0.037 mmol) in ethyl acetate (5 ml) was hydrogenated under atmosphere pressure for overnight at room temperature. The mixture was filtrated, and concentrated in vacuum to give a residue, which was purified using Prep-HPLC to give N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (7 mg, 11.62%) as a white solid. $^1$H NMR (400 MHz, DMSO) δ 13.11-12.76 (m, 1H), 10.20-10.03 (m, 1H), 7.86 (d, J=9.0 Hz, 2H), 7.83-7.50 (m, 3H), 7.32 (d, J=8.7 Hz, 2H), 6.51-6.33 (m, 1H), 4.32-4.17 (m, 1H), 3.89-3.78 (m, 1H)), 3.75-3.38 (m, 1H), 2.10-1.96 (m, 1H), 1.94-1.80 (m, 1H), 1.79-1.62 (m, 2H), 1.61-1.53 (m, 1H), 1.49-1.33 (m, 1H), 1.06 (d, J=6.5 Hz, 3H), 0.75 (d, J=6.0 Hz, 3H).

Example 3

Synthesis of N-(4-(chlorodifluoromethoxy)phenyl)-2,3-dihydroxy-4-isopropyl-5-(1H-pyrazol-5-yl)-1,2,3,3a,4,8b-hexahydrocyclopenta[b]indole-7-carboxamide (Compound No. 3)

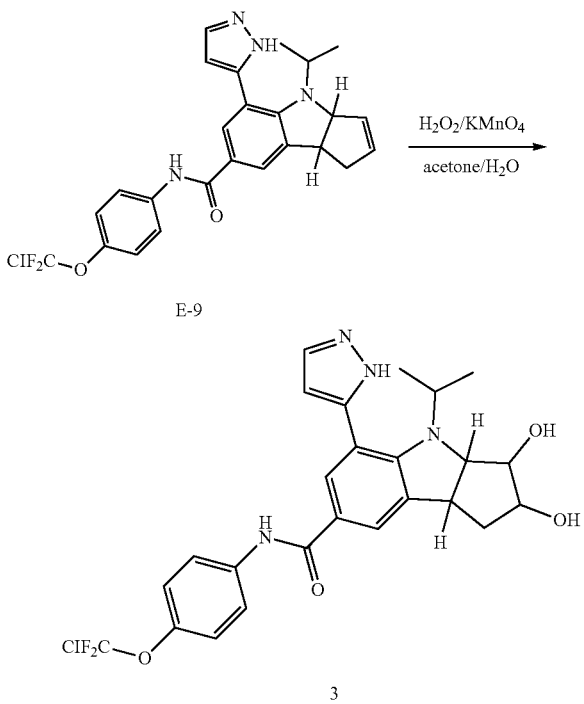

To a solution of N-(4-(chlorodifluoromethoxy)phenyl)-4-isopropyl-5-(1H-pyrazol-5-yl)-1,3a,4,8b-tetrahydrocyclopenta[b]indole-7-carboxamide (150 mg, 0.309 mmol) in acetone (6 ml)/water (3 ml), were added potassium permanganate (24.44 mg, 0.155 mmol) and hydrogen peroxide (31.6 mg, 0.928 mmol) under ice-water bath. After being stirred at room temperature for 1 h, the mixture was cooled under ice-water bath and were added another portion of potassium permanganate (24.44 mg, 0.155 mmol) and hydrogen peroxide (31.6 mg, 0.928 mmol), then stirred at room temperature for 1 h. The reaction was quenched with Na$_2$SO$_3$ aqueous solution, followed by filtration, and the filtrate was extracted with ethyl acetate (50 mL×3). The combined organic layers were washed with brine, dried over Na$_2$SO$_4$, filtrated and concentrated in vacuo to give crude product, which was purified using prep-HPLC to give N-(4-(chlorodifluoromethoxy)phenyl)-2,3-dihydroxy-4-isopropyl-5-(1H-pyrazol-5-yl)-1,2,3,3a,4,8b-hexahydrocyclopenta[b]indole-7-carboxamide (9 mg, 5.61%) as a white solid. $^1$H NMR (400 MHz, DMSO) δ 13.14-12.75 (m, 1H), 10.20-10.04 (m, 1H), 7.91-7.52 (m, 5H), 7.32 (d, J=8.6 Hz, 2H), 6.54-6.38 (m, 1H), 4.77-4.68 (m, 1H), 4.63-4.54 (m, 1H), 3.95-3.36 (m, 5H), 2.30-2.17 (m, 1H), 1.83-1.71 (m, 1H), 1.12 (d, J=6.6 Hz, 3H), 0.73 (d, J=6.2 Hz, 3H).

Example 4

Synthesis of 3-acetamido-N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (Compound No. 4)

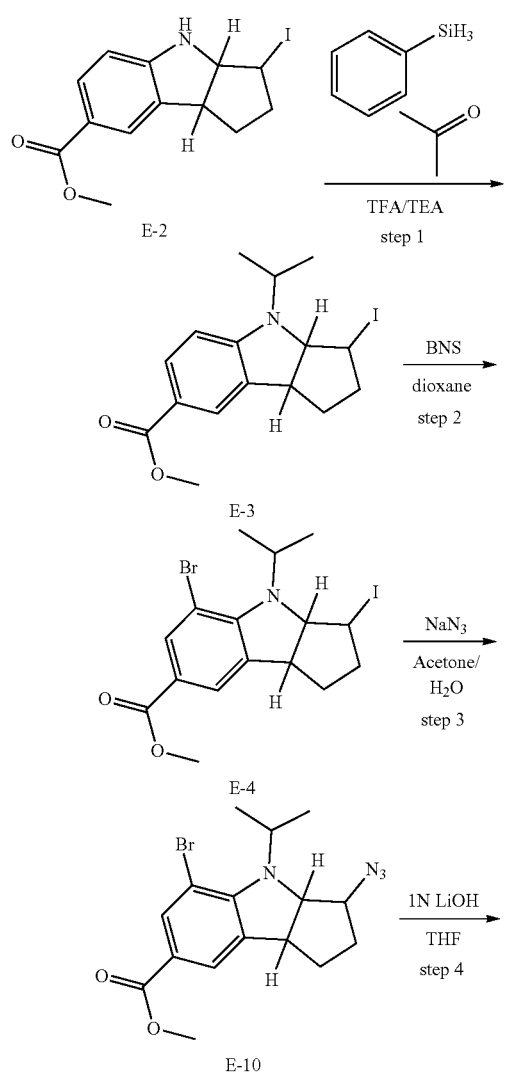

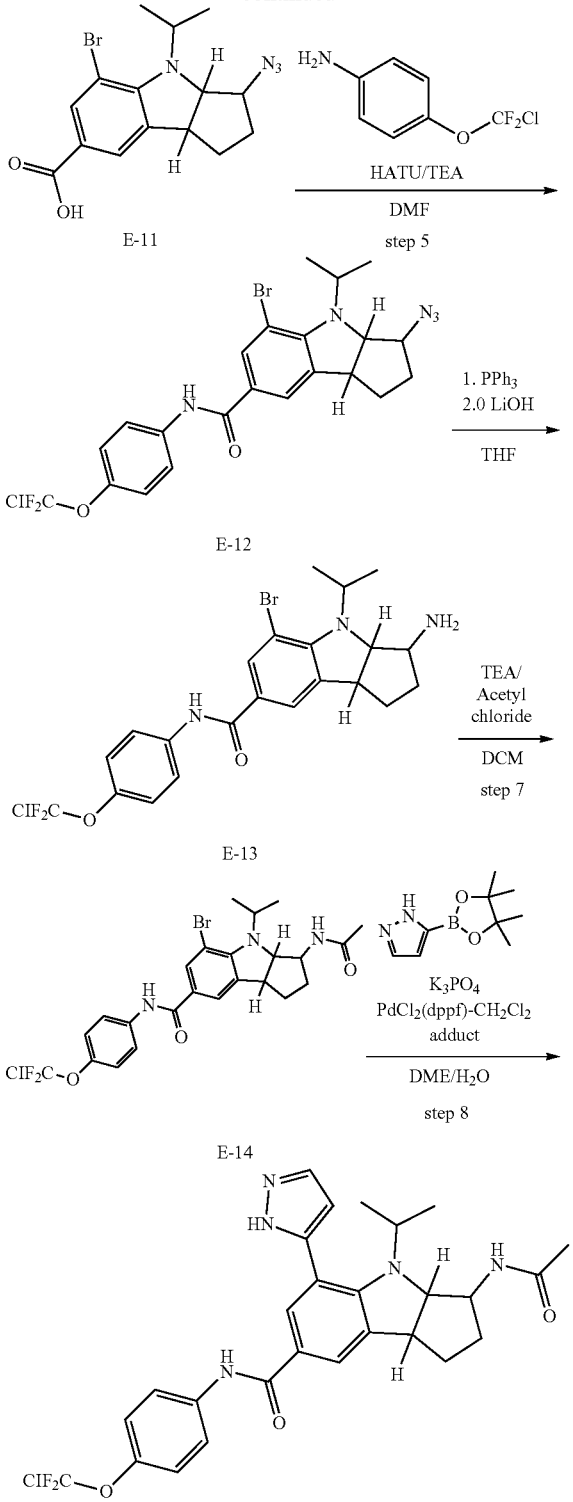

Step 1: Synthesis of Methyl 3-iodo-4-isopropyl-1,2,3,3a,4,8b-hexahydrocyclopenta[b]indole-7-carboxylate (E-3)

Under Ar, to a solution of methyl 3-iodo-1,2,3,3a,4,8b-hexahydrocyclopenta[b]indole-7-carboxylate (11 g, 32.1 mmol) in tetrahydrofuran (12 ml) were added acetone (20 ml), trifluoroacetic acid (3 ml) and phenylsilane (10.41 g, 96 mmol) at room temperature. The mixture was stirred for overnight at room temperature, then quenched with NaHCO$_3$ aqueous solution, followed by extraction with ethyl acetate (60 mL×3). The combined organic layers were washed with brine, dried over Na$_2$SO$_4$, filtrated and concentrated to give a residue, which was purified by silica gel column chromatography (ethyl acetate/hexane 0% to 15%) to give methyl 3-iodo-4-isopropyl-1,2,3,3a,4,8b-hexahydrocyclopenta[b]indole-7-carboxylate (11.8 g, 96%) as a yellow oil. $^1$H NMR (400 MHz, MeOD) δ 7.73 (dd, J=8.4, 1.6 Hz, 1H), 7.64-7.61 (m, 1H), 6.43 (d, J=8.5 Hz, 1H), 4.75 (d, J=8.9 Hz, 1H), 4.44 (d, J=4.8 Hz, 1H), 3.95-3.83 (m, 2H), 3.81 (s, 3H), 2.69-2.52 (m, 1H), 2.05 (dd, J=14.4, 5.8 Hz, 1H), 1.91 (dd, J=12.8, 5.9 Hz, 1H) 1.76-1.60 (m, 1H), 1.31 (d, J=6.8 Hz, 3H), 1.19 (d, J=6.7 Hz, 3H). MS: 385.95 (M+H)$^+$.

Step 2: Synthesis of Methyl 5-bromo-3-iodo-4-isopropyl-1,2,3,3a,4,8b-hexahydrocyclopenta[b]indole-7-carboxylate (E-4)

Under Ar, to a solution of methyl 3-iodo-4-isopropyl-1,2,3,3a,4,8b-hexahydrocyclopenta[b]indole-7-carboxylate (11.8 g, 30.6 mmol) in 1,4-Dioxane was added N-bromosuccinimide (5.45 g, 30.65 mmol) at room temperature in an oven-dried 250 mL round-bottomed flask. The mixture was stirred at room temperature for 2 h, then quenched with NaHCO$_3$ aqueous solution, followed by extraction with ethyl acetate (50 mL×3). The combined organic layers were washed with brine, dried over Na$_2$SO$_4$, filtrated and concentrated to give a residue, which was purified by silica gel column chromatography (ethyl acetate/hexane 0% to 15%) to give methyl 5-bromo-3-iodo-4-isopropyl-1,2,3,3a,4,8b-hexahydrocyclopenta[b]indole-7-carboxylate (11.8 g, 83%) as a white solid. $^1$H NMR (400 MHz, CDCl$_3$) δ 7.94 (d, J=1.5 Hz, 1H), 7.62-7.57 (m, 1H), 5.00-4.85 (m, 1H), 4.62 (d, J=9.0 Hz, 1H), 4.28 (d, J=4.9 Hz, 1H), 3.95 (t, J=8.5 Hz, 1H), 3.85 (s, 3H), 2.69-2.53 (m, 1H), 2.12-1.87 (m, 2H), 1.70-1.57 (m, 1H), 1.32 (d, J=6.9 Hz, 3H), 0.97 (d, J=6.5 Hz, 3H). MS: 465.8 (M+H)$^+$.

Step 3: Synthesis of Methyl 3-azido-5-bromo-4-isopropyl-1,2,3,3a,4,8b-hexahydrocyclopenta[b]indole-7-carboxylate (E-10)

Under Ar, the mixture of methyl 5-bromo-3-iodo-4-isopropyl-1,2,3,3a,4,8b-hexahydrocyclopenta[b]indole-7-carboxylate (1.5 g, 3.23 mmol) and sodium azide (1.051 g, 16.16 mmol) in acetone (50 ml)/water (5 ml) was stirred at 80° C. for 60 h. Most of the acetone was removed in vacuum to give residue, which was partitioned between ethyl acetate/water. The separated organic layer was concentrated in vacuum to give a residue, which was purified by silica gel column chromatography (ethyl acetate/hexane from 0% to 20%) to give methyl 3-azido-5-bromo-4-isopropyl-1,2,3,3a,4,8b-hexahydrocyclopenta[b]indole-7-carboxylate (1.05 g, 86%).

Step 4: Synthesis of 3-azido-5-bromo-4-isopropyl-1,2,3,3a,4,8b-hexahydrocyclopenta[b]indole-7-carboxylic Acid (E-11)

To a solution of methyl 3-azido-5-bromo-4-isopropyl-1,2,3,3a,4,8b-hexahydrocyclopenta[b]indole-7-carboxylate (1.05 g, 2.77 mmol) in tetrahydrofuran (10 ml) was added LiOH (1N, 5.54 mmol) at room temperature. The mixture was stirred at 50° C. for overnight, then acidified with 1N HCl to pH=4-5, followed by extraction with ethyl acetate (50 mL×3). The combined organic layers were washed with brine, dried over Na$_2$SO$_4$, filtrated and concentrated in vacuum to give crude 3-azido-5-bromo-4-isopropyl-1,2,3,3a,4,8b-hexahydrocyclopenta[b]indole-7-carboxylic acid (1 g, 99%), which was used in the next step without purification.

Step 5: Synthesis of 3-azido-5-bromo-N-(4-(chlorodifluoromethoxy)phenyl)-4-isopropyl-1,2,3,3a,4,8b-hexahydro cyclopenta[b]indole-7-carboxamide (E-12)

Under Ar, to a solution of 3-azido-5-bromo-4-isopropyl-1,2,3,3a,4,8b-hexahydrocyclopenta[b]indole-7-carboxylic acid (1 g, 2.74 mmol), 4-(chlorodifluoromethoxy)aniline (0.795 g, 4.11 mmol), triethylamine (0.554 g, 5.48 mmol) in N,N'-dimethylformamide (10 ml), was added HATU (2.082 g, 5.48 mmol) under ice-water bath. The mixture was stirred at room temperature for overnight, then quenched with water (30 mL), followed by extraction with ethyl acetate (50 mL×3). The combined organic layers were washed with brine, dried over Na$_2$SO$_4$, filtrated and concentrated in vacuo to give a residue, which was purified by silica column gel chromatography (ethyl acetate/hexane from 0% to 50%) to give 3-azido-5-bromo-N-(4-(chlorodifluoromethoxy)phenyl)-4-isopropyl-1,2,3,3a,4,8b-hexahydro cyclopenta[b]indole-7-carboxamide (1.4 g, 95%).

Step 6: Synthesis of 3-amino-5-bromo-N-(4-(chlorodifluoromethoxy)phenyl)-4-isopropyl-1,2,3,3a,4,8b-hexahydrocyclopenta[b]indole-7-carboxamide (E-13)

Under Ar, the mixture of 3-azido-5-bromo-N-(4-(chlorodifluoromethoxy)phenyl)-4-isopropyl-1,2,3,3a,4,8b-hexahydro cyclopenta[b]indole-7-carboxamide (1.4 g, 2.59 mmol) and Ph$_3$P (0.883 g, 3.37 mmol) in tetrahydrofuran (20 ml) was stirred at 50° C. for 2 h. LiOH (0.094 g, 3.93 mmol) was added to the mixture, then the mixture was stirred at 50° C. for overnight. After being cooled to room temperature, the mixture was diluted with water (20 mL), followed by extraction with ethyl acetate (50 mL×3). The combined organic layers were washed with brine, dried over Na$_2$SO$_4$, filtrated and concentrated in vacuum to give a residue, which was purified by silica column gel chromatography (methanol/dichloromethane from 0% to 6%) to give 3-amino-5-bromo-N-(4-(chlorodifluoromethoxy)phenyl)-4-isopropyl-1,2,3,3a,4,8b-hexahydrocyclopenta[b]indole-7-carboxamide (1.2 g, 90%). $^1$H NMR (400 MHz, MeOD) δ 7.90 (d, J=1.5 Hz, 1H), 7.77 (d, J=9.1 Hz, 2H), 7.65-7.59 (m, 1H), 7.26 (d, J=9.0 Hz, 2H), 4.95-4.85 (m, 1H), 3.98 (t, J=8.7 Hz, 1H), 3.90 (dd, J=9.1, 2.0 Hz, 1H), 3.23-3.14 (m, 1H), 2.48-2.32 (m, 1H), 1.87-1.76 (m, 1H), 1.62-1.49 (m, 2H), 1.39 (d, J=6.9 Hz, 3H), 1.00 (d, J=6.5 Hz, 3H).

Step 7: Synthesis of 3-acetamido-5-bromo-N-(4-(chlorodifluoromethoxy)phenyl)-4-isopropyl-1,2,3,3a,4,8b-hexahydrocyclopenta[b]indole-7-carboxamide (E-14)

Under Ar, to a solution of 3-amino-5-bromo-N-(4-(chlorodifluoromethoxy)phenyl)-4-isopropyl-1,2,3,3a,4,8b-hexahydrocyclopenta[b]indole-7-carboxamide (300 mg, 0.583 mmol) and triethylamine (118 mg, 1.166 mmol) in dichloromethane (20 ml) was added acetyl chloride (91 mg, 1.166 mmol) under ice-water bath. The mixture was stirred for 2 h at room temperature, then quenched with water (30 mL), followed by extraction with dichloromethane (30 mL×3). The combined organic layers were washed with brine, dried over $Na_2SO_4$, filtrated and concentrated in vacuum to give the crude 3-acetamido-5-bromo-N-(4-(chlorodifluoromethoxy)phenyl)-4-isopropyl-1,2,3,3a,4,8b-hexahydrocyclopenta[b]indole-7-carboxamide (320 mg, 99%) as a light yellow solid, which was used in next step directly.

Step 8: Synthesis of 3-acetamido-N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (4)

Under Ar, the mixture of 3-acetamido-5-bromo-N-(4-(chlorodifluoromethoxy)phenyl)-4-isopropyl-1,3a,4,8b-tetrahydrocyclopenta[b]indole-7-carboxamide (600 mg, 1.205 mmol), 5-(4,4,5,5-tetramethyl-1,3,2-dioxaborolan-2-yl)-1H-pyrazole (936 mg, 4.82 mmol), $K_3PO_4$ (256 mg, 1.205 mmol) and $PdCl_2$(dppf)-$CH_2Cl_2$ adduct (984 mg, 1.205 mmol) in DME (10 ml)/water (2 ml) was stirred at 110° C. under microwave irradiation for 2.5 h. After being cooled to room temperature, the mixture was poured into water (30 mL), followed by extraction with ethyl acetate (30 mL×3). The combined organic layers were washed with brine, dried over $Na_2SO_4$, filtrated and concentrated in vacuum to give a residue, which was purified by silica column gel chromatography (ethyl acetate/hexane from 00 to 50%) to give the crude 3-acetamido 5-bromo-N-(4-(chlorodifluoromethoxy)phenyl)-4-isopropyl-5-(1H-pyrazol-5-yl)-1,2,3,3a,4,8b-tetrahydrocyclopenta[b]indole-7-carboxamide (700 mg, 120 O) as a yellow solid. $^1$H NMR (400 MHz, dimethylsulfoxide-$d_6$+$D_2O$) δ 13.10-12.77 (m, 1H), 10.24-10.10 (m, 1H), 7.97-7.51 (m, 6H), 7.33 (d, J=8.5 Hz, 2H), 6.59-6.39 (m, 1H), 4.08 d 3.83 (i, 3H), 3.71-3.36 (i, 1H), 2.42-2.23 (m, 1H), 1.85 (s, 3H), 1.78-1.68 (m, 1H), 1.63-1.46 (m, 2H), 1.12 (d, J=6.7 Hz, 3H), 0.73 (d, J 6.6.4 Hz, 3H).

Following the procedure described in Example 4 and making non-critical changes, Compounds 5-28, 45, 49, and 62-65 in Table 11 were prepared.

TABLE 11

| Compound No. | Compound Structure | $^1$H NMR & MS |
|---|---|---|
| 5 | 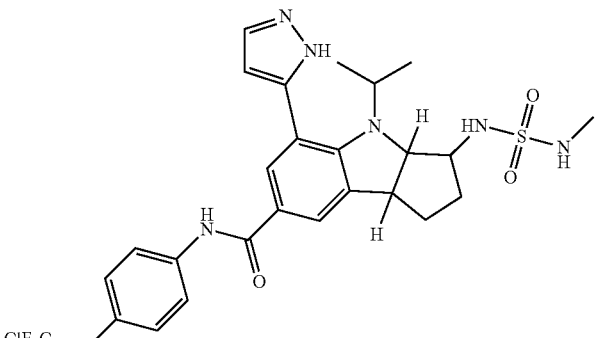 | $^1$H NMR (400 MHz, DMSO-$d_6$) δ 13.11-12.79 (m, 1H), 10.28-10.06 (m, 1H), 7.97-7.51 (m, 5H), 7.32 (d, J = 8.6 Hz, 2H), 7.02 (d, J = 6.1 Hz, 1H), 6.73-6.68 (m, 1H), 6.60-6.39 (m, 1H), 4.13-4.01 (m, 1H), 3.90-3.80 (m, 1H), 3.70-3.41 (m, 2H), 2.51-2.50 (m, 3H), 2.40-2.24 (m, 1H), 1.84-1.64 (m, 2H), 1.55-1.40 (m, 1H), 1.16 (d, J = 6.6 Hz, 3H), 0.72 (d, J = 6.3 Hz, 3H). |
| 6 | 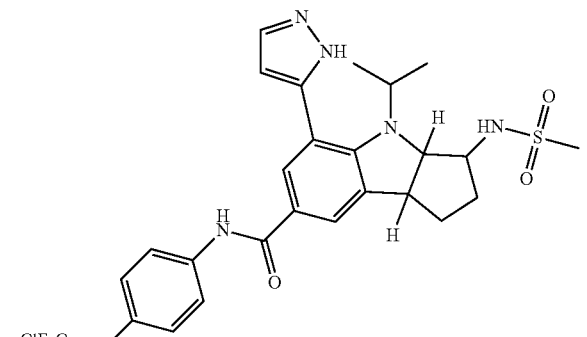 | $^1$H NMR (400 MHz, DMSO-$d_6$) δ 13.13-12.76 (m, 1H), 10.28-10.07 (m, 1H), 8.01-7.48 (m, 5H), 7.33 (d, J = 8.6 Hz, 2H), 7.21 (d, J = 6.3 Hz, 1H), 6.67-6.45 (m, 1H), 4.09-3.97 (m, 1H), 3.95-3.82 (m, 1H), 3.71-3.50 (m, 2H), 2.96 (s, 3H), 2.41-2.23 (m, 1H), 1.79-1.66 (m, 2H), 1.65-1.51 (m, 1H), 1.16 (d, J = 6.6 Hz, 3H), 0.72 (d, J = 5.5 Hz, 3H). |

TABLE 11-continued
| Compound No. | Compound Structure | ¹H NMR & MS |
|---|---|---|
| 7 | 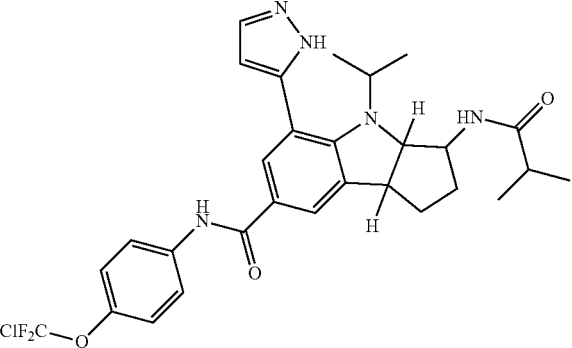 | ¹H NMR (400 MHz, DMSO-d$_6$) δ 13.08-12.78 (m, 1H), 10.21-10.08 (m, 1H), 7.93-7.50 (m, 6H), 7.32 (d, J = 8.5 Hz, 2H), 6.59-6.39 (m, 1H), 4.07-3.81 (m, 3H), 3.71-3.35 (m, 1H), 2.45-2.35 (m, 1H), 2.35-2.25 (m,1H), 1.78-1.67 (m, 1H), 1.62-1.49 (m, 2H), 1.10 (d, J = 6.5 Hz, 3H), 1.06-0.99 (m, 6H), 0.73 (d, J = 6.6 Hz, 3H). |
| 8 | 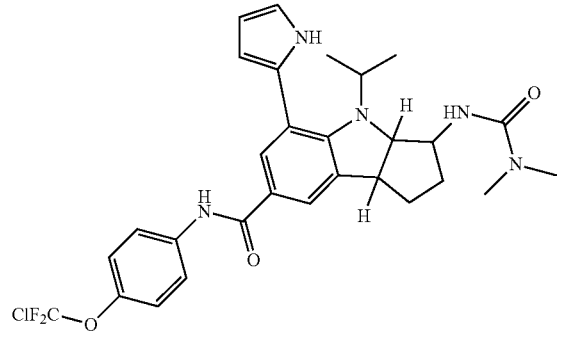 | ¹H NMR (400 MHz, DMSO-d$_6$) δ 13.08-12.78 (m, 1H), 10.25-10.06 (m, 1H), 7.96-7.49 (m, 5H), 7.32 (d, J = 8.4 Hz, 2H), 6.60-6.41 (m, 1H), 6.19-6.05 (m, 1H), 4.11-3.96 (m, 1H), 3.96-3.79 (m, 2H), 3.69-3.39 (m, 1H), 2.81 (s, 6H), 2.39-2.22 (m, 1H), 1.79-1.38 (m, 3H), 1.15-1.02 (m, 3H), 0.80-0.67 (m, 3H). |
| 9 | 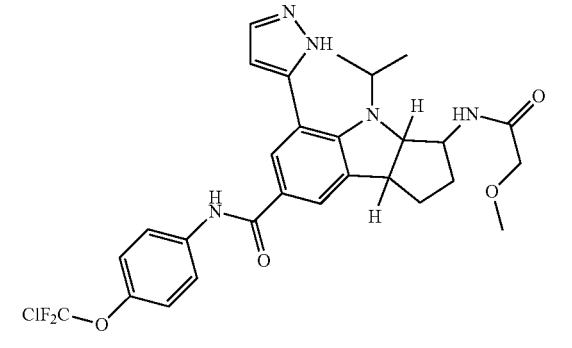 | ¹H NMR (400 MHz, DMSO-d$_6$) δ 13.20-12.63 (m, 1H), 10.17 (s, 1H), 8.06-7.47 (m, 6H), 7.32 (d, J = 8.9 Hz, 2H), 6.53 (s, 1H), 4.17-3.98 (m, 2H), 3.95-3.79 (m, 3H), 3.69-3.48 (m, 1H), 3.33 (s, 3H), 2.41-2.22 (m, 1H), 1.82-1.49 (m, 3H), 1.08 (d, J = 6.8 Hz, 3H), 0.72 (d, J = 6.3 Hz, 3H). |
| 10 | 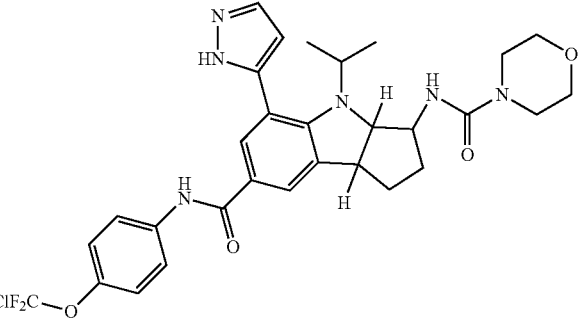 | ¹H NMR (400 MHz, DMSO-d$_6$) δ 13.22-12.41 (m, 1H), 10.15 (s, 1H), 8.01-7.77 (m, 3H), 7.77-7.55 (m, 2H), 7.32 (d, J = 8.8 Hz, 2H), 6.57-6.45 (m, 1H), 6.44-6.33 (m, 1H), 4.08-3.98 (m, 1H), 3.97-3.88 (m, 1H), 3.88-3.80 (m, 1H), 3.62-3.51 (m, 5H), 3.33-3.23 (m, 4H), 2.38-2.23 (m, 1H), 1.75-1.46 (m, 3H), 1.09 (d, J = 6.8 Hz, 3H), 0.74 (d, J = 6.4 Hz, 3H). MS: 616.6 (M + H)⁺. |

TABLE 11-continued
| Compound No. | Compound Structure | ¹H NMR & MS |
|---|---|---|
| 11 | 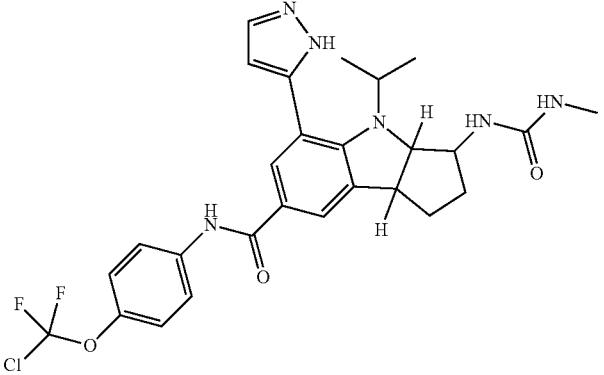 [SMILES: CNC(=O)NC1CCC2c3cc(C(=O)Nc4ccc(OC(F)(F)Cl)cc4)cc(-c4ccn[nH]4)c3N(C(C)C)C12] | ¹H NMR (400 MHz, DMSO-d$_6$) δ 10.13 (s, 1H), 7.87 (d, J = 9.0 Hz, 2H), 7.85-7.79 (m, 1H), 7.65 (s, 1H), 7.32 (d, J = 9.0 Hz, 2H), 6.49 (s, 1H), 6.04-6.02 (m, 1H), 5.64-5.61 (m, 1H), 3.94-3.83 (m, 3H), 3.38-3.34 (m, 1H), 2.58-2.57 (m, 3H), 2.27-2.21 (m, 1H), 1.77-1.65 (m, 1H), 1.54-1.52 (m, 2H), 1.16-1.14 (m, 3H), 0.75-0.73 (m, 3H). |
| 12 | 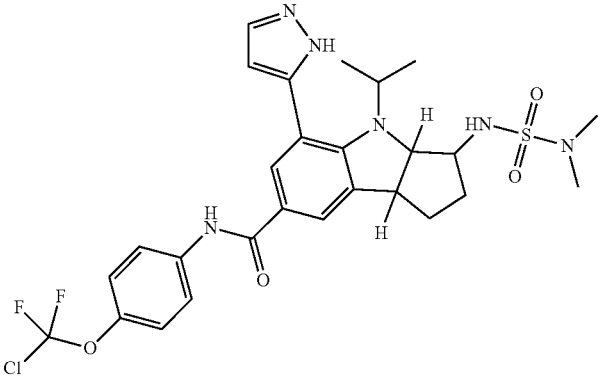 [SMILES: CC(C)N1c2c(-c3ccn[nH]3)cc(C(=O)Nc3ccc(OC(F)(F)Cl)cc3)cc2C2CCC(NS(=O)(=O)N(C)C)C21] | ¹H NMR (400 MHz, DMSO-d$_6$) δ 12.86 (s, 1H), 10.15 (s, 1H), 7.87-7.65 (m, 4H), 7.33-7.30 (m, 3H), 6.55-6.51 (m, 1H), 4.08-4.06 (m, 1H), 3.89-3.85 (m, 1H), 3.58-3.40 (m, 2H), 2.73-2.62 (m, 6H), 2.36-2.28 (m, 1H), 2.08-1.89 (m, 1H), 1.76-1.69 (m, 2H), 1.17-1.15 (m, 3H), 0.74-0.72 (m, 3H). |
| 13 | 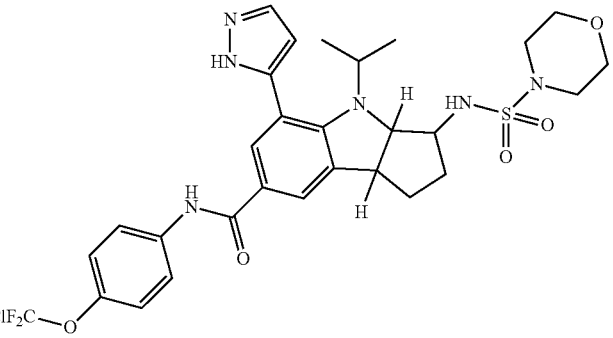 | ¹H NMR (400 MHz, DMSO-d$_6$) δ 10.15 (s, 1H), 7.93-7.80 (m, 3H), 7.77-7.61 (m, 2H), 7.54-7.45 (m, 1H), 7.32 (d, J = 8.7 Hz, 2H), 6.59-6.50 (m, 1H), 4.12-4.03 (m, 1H), 3.94-3.81 (m, 1H), 3.71-3.60 (m, 4H), 3.60-3.52 (m, 2H), 3.09-2.98 (m, 4H), 2.38-2.26 (m, 1H), 1.80-1.65 (m, 2H), 1.61-1.50 (m, 1H), 1.17 (d, J = 6.8 Hz, 3H), 0.73 (d, J = 6.4 Hz, 3H). MS: 652.5 (M + H)⁺. |
| 14 | 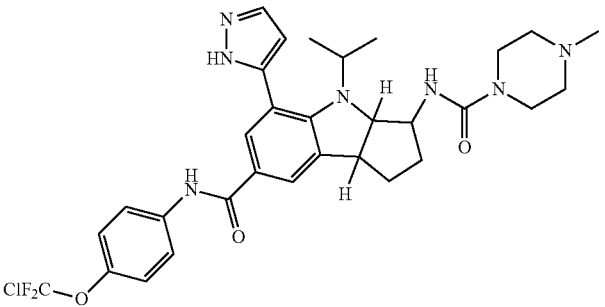 | ¹NMR (400 MHz, DMSO-d$_6$) δ 10.19 (s, 1H), 9.86-9.61 (m, 1H), 7.98-7.85 (m, 3H), 7.78-7.71 (m, 1H), 7.69 (s, 1H), 7.36 (d, J = 8.7 Hz, 2H), 6.72-6.61 (m, 1H), 6.57-6.51 (m, 1H), 4.25-4.10 (m, 2H), 4.10-4.01 (m, 1H), 4.00-3.86 (m, 4H), 3.13-2.91 (m, 5H), 2.86 (s, 3H), 2.40-2.27 (m, 1H), 1.82-1.52 (m, 3H), 1.14 (d, J = 6.8 Hz, 3H), 0.78 (d, J = 6.4 Hz, 3H). MS: 629.5 (M + H)⁺. |

TABLE 11-continued

| Compound No. | Compound Structure | ¹H NMR & MS |
|---|---|---|
| 15 | 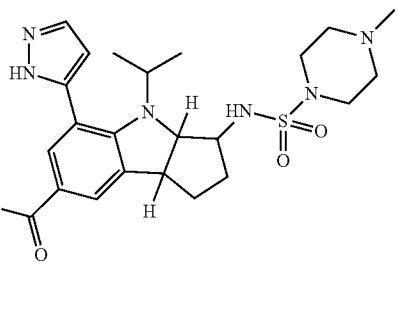 | ¹NMR (400 MHz, DMSO-d₆) δ 10.16 (s, 1H), 9.93-9.62 (m, 1H), 7.96-7.81 (m, 3H), 7.79-7.69 (m, 2H), 7.66 (s, 1H), 7.32 (d, J = 8.8 Hz, 2H), 6.60-6.52 (m, 1H), 4.07-3.99 (m, 1H), 3.94-3.85 (m, 1H), 3.79-3.57 (m, 5H), 3.19-2.91 (m, 5H), 2.85 (s, 3H), 2.41-2.28 (m, 1H), 1.79-1.66 (m, 2H), 1.64-1.50 (m, 1H), 1.16 (d, J = 6.8 Hz, 3H), 0.73 (d, J = 6.4 Hz, 3H). MS: 664.6 (M + H)⁺. |
| 16 | 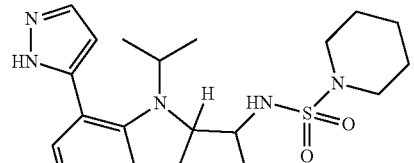 | ¹H NMR (400 MHz, DMSO-d₆) δ 13.16-12.70 (m, 1H), 10.15 (s, 1H), 7.98-7.50 (m, 5H), 7.40-7.25 (m, 3H), 6.65-6.44 (m, 1H), 4.18-4.05 (m, 1H), 3.93-3.82 (m, 1H), 3.71-3.46 (m, 2H), 3.14-2.98 (m, 4H), 2.41-2.26 (m, 1H), 1.83-1.66 (m, 2H), 1.63-1.42 (m, 7H), 1.17 (d, J = 6.9 Hz, 3H), 0.74 (d, J = 6.4 Hz, 3H). MS: 650.7 (M + H)⁺. |
| 17 | 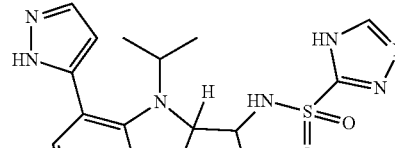 | ¹H NMR (400 MHz, DMSO-d₆) δ 13.14-12.68 (m, 1H), 10.13 (s, 1H), 8.70 (s, 1H), 8.20-8.06 (m, 1H), 7.95-7.56 (m, 6H), 7.32 (d, J = 8.8 Hz, 2H), 6.53-6.39 (m, 1H), 4.12-4.02 (m, 1H), 3.90-3.80 (m, 1H), 3.67-3.56 (m, 1H), 3.53-3.49 (m, 1H), 2.32-2.23 (m, 1H), 1.73-1.58 (m, 2H), 1.53-1.36 (m, 1H), 0.91 (d, J = 6.5 Hz, 3H), 0.68 (d, J = 6.4 Hz, 3H). MS: 634.6 (M + H)⁺. |
| 18 | 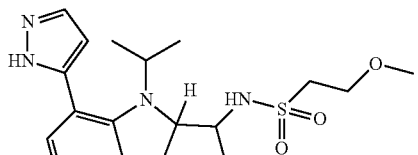 | ¹H NMR (400 MHz, DMSO-d₆) δ 13.19-12.50 (m, 1H), 10.16 (s, 1H), 7.99-7.80 (m, 3H), 7.79-7.56 (m, 2H), 7.32 (d, J = 8.6 Hz, 2H), 7.26 (d, J = 6.5 Hz, 1H), 6.66-6.49 (m, 1H), 4.08-3.96 (m, 1H), 3.92-3.82 (m, 1H), 3.76-3.64 (m, 2H), 3.64-3.52 (m, 2H), 3.33-3.29 (m, 2H), 3.27 (s, 3H), 2.42-2.25 (m, 1H), 1.79-1.65 (m, 2H), 1.64-1.49 (m, 1H), 1.16 (d, J = 6.6 Hz, 3H), 0.72 (d, J = 6.3 Hz, 3H). MS: 625.5 (M + H)⁺. |

TABLE 11-continued

| Compound No. | Compound Structure | ¹H NMR & MS |
|---|---|---|
| 19 | 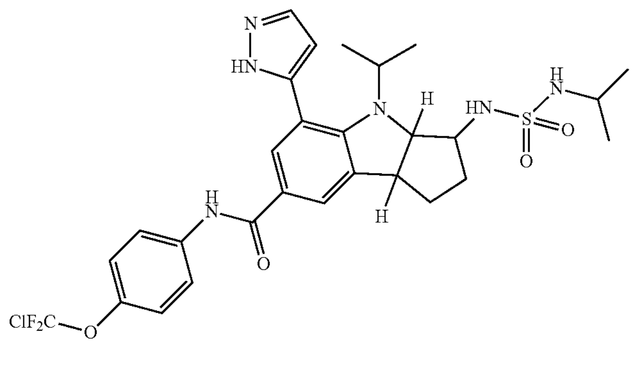 | ¹H NMR (400 MHz, DMSO-d₆) δ 13.10-12.76 (m, 1H), 10.17 (s, 1H), 7.98-7.50 (m, 5H), 7.35 (d, J = 8.6 Hz, 2H), 6.90 (d, J = 5.7 Hz, 1H), 6.71 (d, J = 7.3 Hz, 1H), 6.62-6.42 (d, 1H), 4.22-4.03 (m, 1H), 3.96-3.81 (m, 1H), 3.77-3.61 (m, 1H), 3.61-3.48 (m, 1H), 3.43-3.26 (m, 1H), 2.41-2.27 (m, 1H), 1.92-1.79 (m, 1H), 1.78-1.65 (m, 1H), 1.63-1.43 (m, 1H), 1.25-1.08 (m, 9H), 0.76 (d, J = 4.9 Hz, 3H). MS: 624.7 (M + H)⁺. |
| 20 | 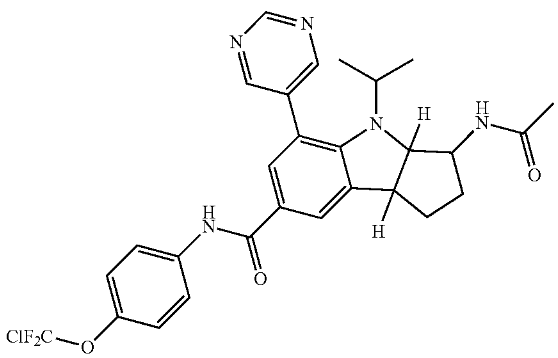 | ¹NMR (400 MHz, DMSO-d₆) δ 10.14 (s, 1H), 9.18 (s, 1H), 9.05 (s, 2H), 7.91 (d, J = 7.6 Hz, 1H), 7.89-7.83 (m, 2H), 7.80-7.73 (m, 2H), 7.35 (d, J = 8.6 Hz, 2H), 4.04 (m, 1H), 3.93 (m, 2H), 3.25 (m, 1H), 2.36 (dd, J = 12.8, 7.5 Hz, 1H), 1.86 (s, 3H), 1.80-1.71 (m, 1H), 1.59 (m, 2H), 1.07 (d, J = 6.8 Hz, 3H), 0.76 (d, J = 6.3 Hz, 3H). MS: 556.1 (M + H)⁺ |
| 21 | 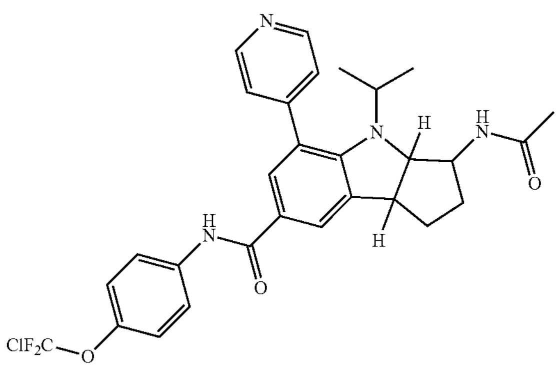 | ¹H NMR (400 MHz, DMSO-d₆) δ 10.21 (s, 1H), 8.81 (d, J = 5.7 Hz, 2H), 8.01 (d, J = 4.8 Hz, 2H), 7.94 (d, J = 7.4 Hz, 1H), 7.86 (d, J = 9.1 Hz, 2H), 7.81 (s, 1H), 7.80 (s, 1H), 7.35 (d, J = 8.9 Hz, 2H), 4.12-4.03 (m, 1H), 4.02-3.97 (m, 1H), 3.97-3.90 (m, 1H), 3.36-3.23 (m, 1H), 2.39-2.31 (m, 1H), 1.83-1.71 (m, 1H), 1.67-1.51 (m, 2H), 1.14 (d, J = 6.8 Hz, 3H), 0.76 (d, J = 6.4 Hz, 3H). |
| 22 | 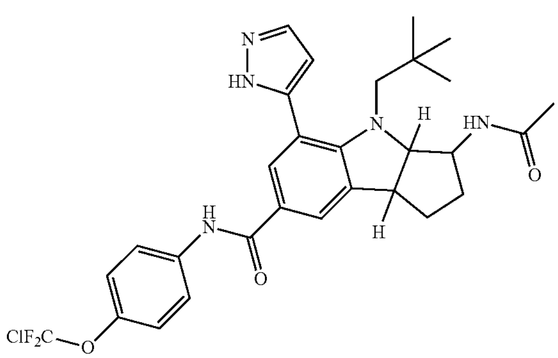 | ¹H NMR (400 MHz, DMSO-d₆) δ 9.98 (s, 1H), 7.94 (d, J = 6.8 Hz, 1H), 7.85 (d, J = 9.1 Hz, 2H), 7.71 (s, 1H), 7.61-7.55 (m, 2H), 7.30 (d, J = 9.1 Hz, 2H), 6.34 (d, J = 1.6 Hz, 1H), 4.17 (d, J = 9.3 Hz, 1H), 3.94-3.87 (m, 1H), 3.94-3.87 (m, 2H), 3.13 (d, J = 15.0 Hz, 1H), 2.40-2.24 (m, 1H), 1.83 (s, 3H), 1.82-1.75 (m, 1H), 1.65-1.45 (m, 2H), 0.62 (s, 9H). MS: 572.1 (M + H)⁺ |

TABLE 11-continued

| Compound No. | Compound Structure | ¹H NMR & MS |
|---|---|---|
| 23 | 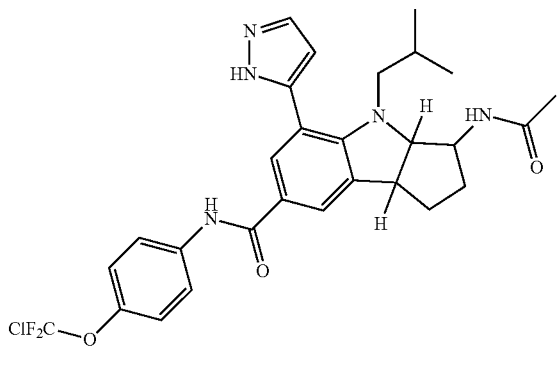 | ¹H NMR (400 MHz, DMSO-$d_6$-D2O) δ 10.00 (s, 1H), 7.92 (d, J = 6.5 Hz, 1H), 7.85 (d, J = 8.9 Hz, 2H), 7.70 (s, 1H), 7.67-7.59 (m, 2H) 7.30 (d, J = 8.9 Hz, 2H), 6.33 (d, J = 1.7 Hz, 1H), 4.08-3.95 (m, 2H), 3.89 (t, J = 8.6 Hz, 1H), 3.05-2.84 (m, 2H), 2.42-2.25 (m, 1H), 1.83 (s, 3H), 1.81-1.71 (m, 1H), 1.67-1.52 (m, 3H), 0.64 (d, J = 6.5 Hz, 3H), 0.41 (d, J = 6.6 Hz, 3H). MS: 558.0 (M + H)⁺ |
| 24 | 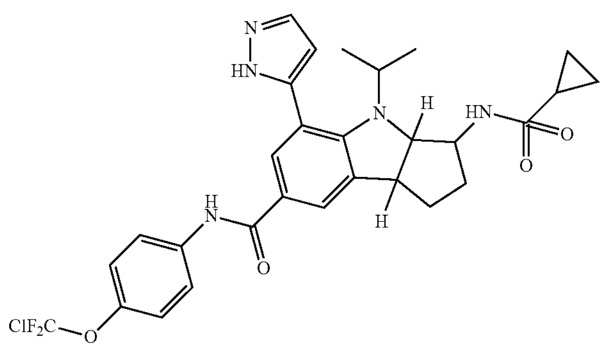 | ¹H NMR (400 MHz, DMSO-$d_6$) δ 13.10-12.72 (m, 1H), 10.16 (s, 1H), 7.86 (d, J = 9.1 Hz, 2H), 7.82-7.69 (m, 2H), 7.65 (s, 1H), 7.32 (d, J = 9.1 Hz, 2H), 7.22 (d, J = 6.7 Hz, 1H), 6.72-6.36 (m, 1H), 4.07-3.97 (m, 1H), 3.91-3.82 (m, 1H), 3.78-3.55 (m, 2H), 2.69-2.57 (m, 1H), 2.41-2.27 (m, 1H), 1.83-1.68 (m, 2H), 1.65-1.52 (m, 1H), 1.16 (d, J = 6.8 Hz, 3H), 1.01-0.89 (m, 4H), 0.73 (d, J = 6.4 Hz, 3H). MS: 607.5 (M + H)⁺. |
| 25 | 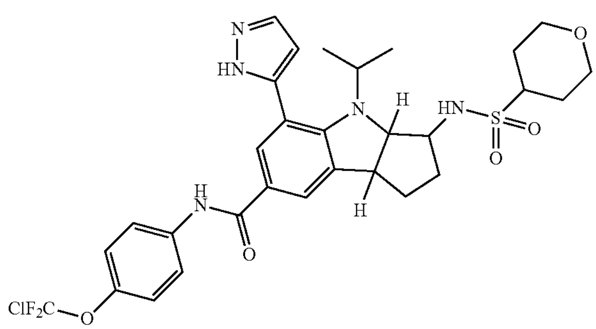 | ¹H NMR (400 MHz, DMSO-$d_6$) δ 13.10-12.72 (m, 1H), 10.18 (s, 1H), 8.06-7.91 (m, 1H), 7.87 (d, J = 9.0 Hz, 2H), 7.80 (s, 1H), 7.72-7.48 (m, 1H), 7.40-7.23 (m, 3H), 6.74-6.44 (m, 1H), 4.06-3.91 (m, 3H), 3.91-3.80 (m, 1H), 3.72-3.47 (m, 2H), 3.33-3.17 (m, 3H), 2.42-2.26 (m, 1H), 1.97-1.83 (m, 2H), 1.79-1.53 (m, 5H), 1.17 (d, J = 6.7 Hz, 3H), 0.72 (d, J = 6.7 Hz, 3H). MS: 651.6 (M + H)⁺. |
| 26 | 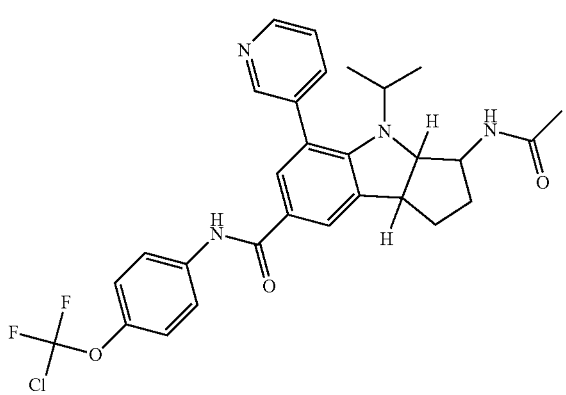 [SMILES: CC(=O)NC1CCC2c3cc(C(=O)Nc4ccc(OC(F)(F)Cl)cc4)cc(-c4cccnc4)c3N(C(C)C)C12] | ¹H NMR (400 MHz, DMSO-$d_6$-D2O) δ 10.16 (s, 1H), 8.90 (s, 1H), 8.65 (d, J = 4.4 Hz, 1H), 8.23 (d, J = 7.9 Hz, 1H), 7.91 (d, J = 7.6 Hz, 1H), 7.86 (d, J = 8.9 Hz, 2H), 7.76-7.71 (m, 2H), 7.70-7.64 (m, 1H), 7.34 (d, J = 8.9 Hz, 2H), 4.06-3.99 (m, 1H), 3.97-3.89 (m, 1H), 3.33-3.19 (m, 1H), 2.41-2.29 (m, 1H), 2.05-1.93 (m, 1H), 1.85 (s, 3H), 1.81-1.71 (m, 1H), 1.64-1.52 (m, 2H), 1.05 (d, J = 6.8 Hz, 3H), 0.74 (d, J = 6.4 Hz, 3H). |

TABLE 11-continued

| Compound No. | Compound Structure | ¹H NMR & MS |
|---|---|---|
| 27 | 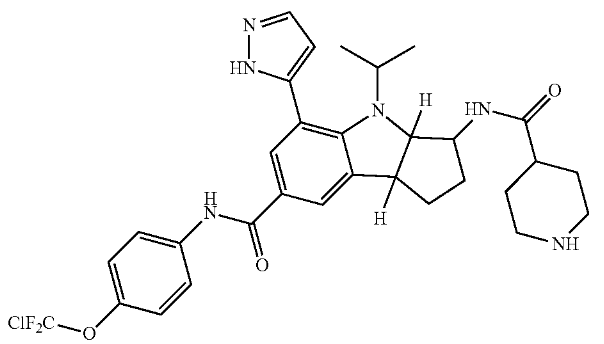 | ¹H NMR (400 MHz, dimethylsulfoxide-$d_6$ + $D_2O$) δ 7.80 (s, 1H), 7.78 (d, J = 8.9 Hz, 2H), 7.67 (d, J = 1.9 Hz, 1H), 7.62 (s, 1H), 7.30 (d, J = 8.9 Hz, 2H), 6.50 (d, J = 2.0 Hz, 1H), 4.03-3.91 (m, 3H), 3.54-3.40 (m, 1H), 3.34-3.21 (m, 2H), 2.93-2.80 (m, 2H), 2.47-2.38 (m, 1H), 2.34-2.17 (m, 1H), 1.91-1.80 (m, 2H), 1.78-1.65 (m, 3H), 1.60-1.48 (m, 2H), 1.04 (d, J = 6.8 Hz, 3H), 0.70 (d, J = 6.4 Hz, 3H). MS: 613.3 (M + H)⁺. |
| 28 | 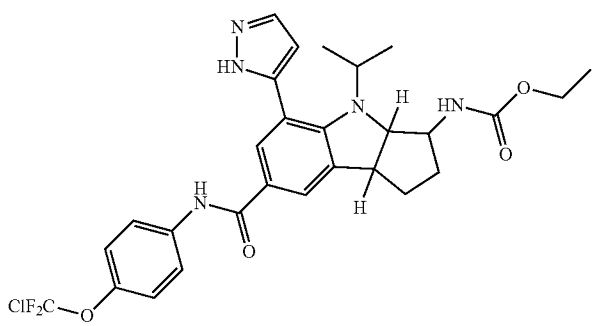 | ¹H NMR (400 MHz, DMSO-$d_6$) δ 13.07-12.72 (m, 1H) 10.26-10.01 (m, 1H), 7.98-7.51 (m, 5H), 7.32 (d, J = 8.7 Hz, 2H), 7.24 (s, 1H), 6.64-6.38 (m, 1H), 4.08-3.92 (m, 3H), 3.90-3.71 (m, 2H), 3.70-3.34 (m, 1H), 2.41-2.22 (m, 1H), 1.76-1.43 (m, 3H), 1.18 (t, J = 7.1 Hz, 3H), 1.12 (d, J = 6.7 Hz, 3H), 0.73 (d, J = 6.7 Hz, 3H). MS: 574.2 (M + H)⁺. |
| 45 | 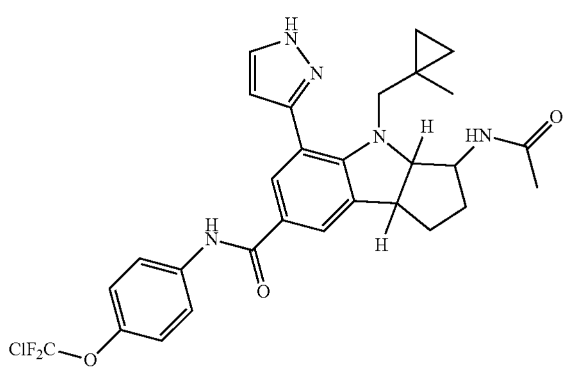 | ¹H NMR (400 MHz, DMSO-$d_6$) 12.89 (s, 1H), 10.01 (s, 1H), 7.95-7.94 (m, 1H), 7.85 (d, J = 9.0 Hz, 2H), 7.71-7.65 (m, 3H), 7.30 (d, J = 9.0 Hz, 2H), 6.35-6.34 (m, 1H), 4.22-4.20 (m, 1H), 4.10-4.05 (m, 1H), 3.96-3.91 (m, 1H), 2.70-2.66 (m, 1H), 2.37-2.27 (m, 1H), 1.84 (s, 3H), 1.78-1.76 (m, 1H), 1.60-1.53 (m, 2H), 1.26-1.21 (m, 1H), 0.71 (s, 3H), 0.46-0.37 (m, 1H), 0.22-0.12 (m, 1H), 0.02--0.10 (m, 2H). |
| 49 | 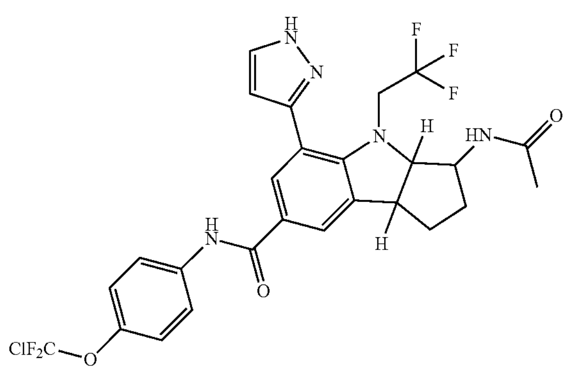 | ¹H NMR (400 MHz, DMSO-$d_6$) δ 13.28-12.88 (m, 1H), 10.12 (s, 1H), 8.08-8.06 (m, 1H), 7.87-7.84 (m, 3H), 7.72-7.69 (m, 2H), 7.32 (d, J = 9.0 Hz, 2H), 6.54-6.31 (m, 1H), 4.55-4.49 (m, 1H), 4.33-4.16 (m, 1H), 4.13-4.11 (m, 1H), 4.02-3.86 (m, 2H), 2.43-2.20 (m, 1H), 2.07-1.92 (m, 1H), 1.85 (s, 3H), 1.72-1.53 (m, 2H). |

TABLE 11-continued

| Compound No. | Compound Structure | ¹H NMR & MS |
|---|---|---|
| 62 | 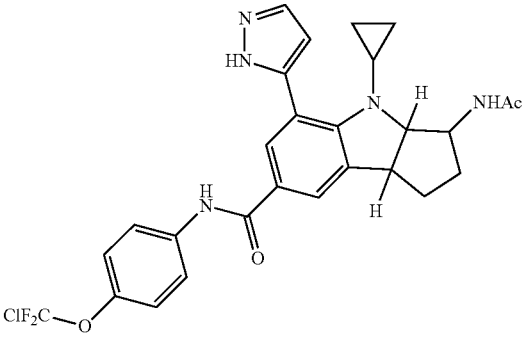 | ¹H NMR (400 MHz, DMSO-d$_6$) δ 12.93 (s, 1H), 10.04 (s, 1H), 7.97 (d, J = 7.5 Hz, 1H), 7.93-7.84 (m, 2H), 7.72 (s, 1H), 7.66 (s, 1H), 7.33 (d, J = 8.8 Hz, 2H), 6.36 (s, 1H), 4.32-4.18 (m, 1H), 3.92 (d, J = 8.7 Hz, 1H), 3.79 (t, J = 8.5 Hz, 1H), 3.44-3.31 (m, 1H), 2.37-2.26 (m, 1H), 1.86 (s, 3H), 1.78-1.69 (m, 1H), 1.68-1.56 (m, 2H), 0.62-0.43 (m, 4H) |
| 63 | 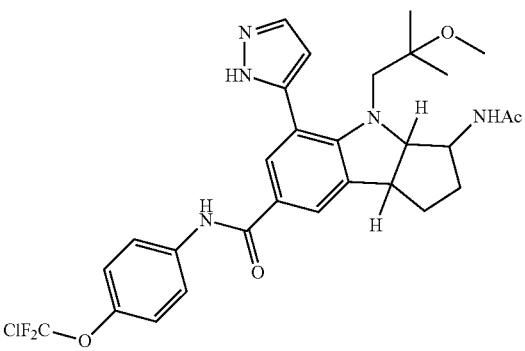 | ¹H NMR (400 MHz, DMSO-d$_6$) δ 10.06 (s, 1H), 7.91-7.82 (m, 2H), 7.77-7.70 (m, 2H), 7.69-7.63 (m, 2H), 7.32 (d, J = 8.7 Hz, 2H), 6.51 (d, J = 2.0 Hz, 1H), 4.57 (dd, J = 9.0, 6.9 Hz, 1H), 4.25-4.14 (m, 1H), 3.94 (t, J = 8.3 Hz, 1H), 3.03-2.83 (m, 2H), 2.97 (s, 3H), 2.08-1.94 (m, 1H), 1.90 (s, 3H), 1.79-1.71 (m, 2H), 1.40-1.28 (m, 1H), 0.74 (s, 3H), 0.62 (s, 3H) |
| 64 | 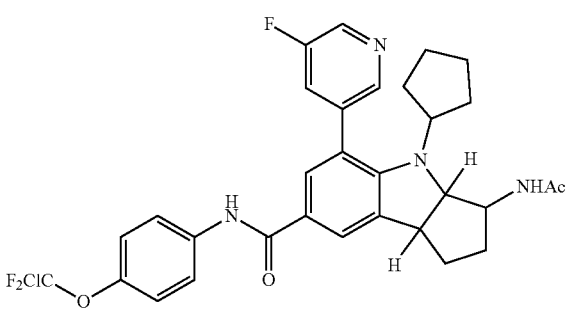 | ¹H NMR (400 MHz, DMSO-d$_6$) δ 10.12 (s, 1H), 8.68 (s, 1H), 8.58 (d, J = 2.7 Hz, 1H), 8.01-7.90 (m, 2H), 7.86 (d, J = 8.7 Hz, 2H), 7.73 (s, 2H), 7.34 (d, J = 8.7 Hz, 2H), 4.08-4.00 (m, 1H), 4.00-3.86 (m, 2H), 3.47-3.36 (m, 1H), 2.34-2.27 (m, 1H), 1.85 (s, 3H), 1.82-1.69 (m, 3H), 1.64-1.49 (m, 3H), 1.28-1.22 (m, 4H), 1.18-1.06 (m, 1H) |
| 65 | 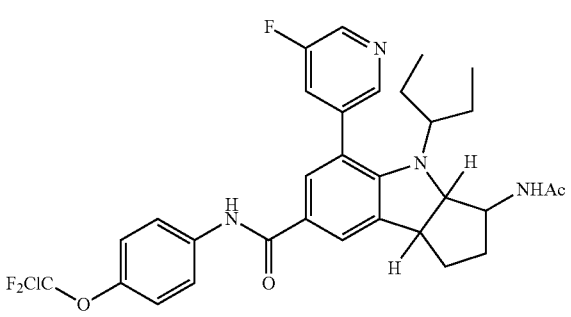 | ¹H NMR (400 MHz, DMSO-d$_6$) δ 10.10 (s, 1H), 8.63-8.55 (m, 2H), 7.91-7.81 (m, 4H), 7.74 (d, J = 1.9 Hz, 1H), 7.67 (d, J = 1.9 Hz, 1H), 7.33 (d, J = 8.7 Hz, 2H), 4.06-4.00 (m, 1H), 3.98-3.92 (m, 2H), 2.78-2.67 (m, 1H), 2.42-2.25 (m, 2H), 1.84 (s, 3H), 1.82-1.74 (m, 1H), 1.64-1.52 (m, 2H), 1.51-1.40 (m, 1H), 1.36-1.21 (m, 2H), 0.62 (t, J = 7.3 Hz, 3H), 0.46 (t, J = 7.4 Hz, 3H) |

Following the procedure of Example 4 by replacing intermediate E-10 with methyl (3R,3aR,8bS)-3-azido-5-bromo-4-isopropyl-1,2,3,3a,4,8b-hexahydrocyclopenta[b]indole-7-carboxylate (E-10-A), and making no other critical changes, optically pure Compounds 46-A, 47-A, 48-A, 50-A, 51-A, 52-A, 53-A, 66-A, and 67-A were prepared. Intermediate E-10-A is prepared as follows:

Synthesis of Methyl (3R,3aR,8bS)-3-azido-5-bromo-4-isopropyl-1,2,3,3a,4,8b-hexahydrocyclopenta[b]indole-7-carboxylate (E-10-A)

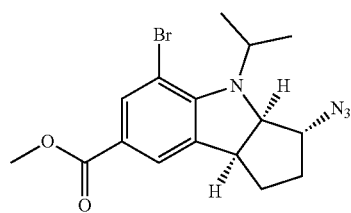

E-10-A

Optically pure intermediate E-10-A was separated from intermediate E-10 through Prep-Chiral HPLC by the following separation condition:

Column: Lux Cellulose-2

Column Size: 0.46×10 cm; 3 um

Mobile phase: Hex:IPA=99:1

Flow rate: 1.0 mL/min

Pressure: MPa

Instrument: LC-79

Detector: 220 nm

Temperature: 25° C.

Retention time: 5.718 min

Compound 46-A, 47-A, 48-A, 50-A, 51-A, 52-A, 53-A, 66-A, and 67-A prepared by following the procedure of Example 4 from intermediate E-10-A are listed in Table 12.

TABLE 12

| Compound No. | Compound Structure | $^1$H NMR |
|---|---|---|
| 46-A | 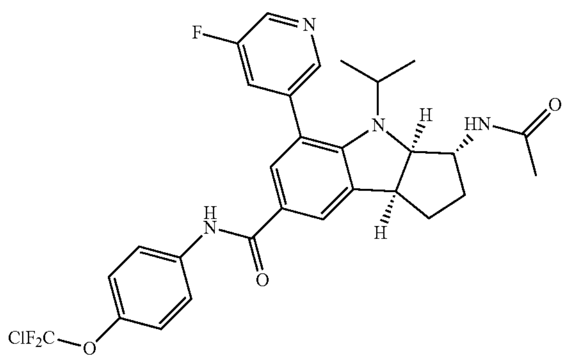 | $^1$H NMR (400 MHz, DMSO-$d_6$) δ 10.13 (s, 1H), 8.70 (s, 1H), 8.57-8.56 (m, 1H), 7.99-7.96 (m, 1H), 7.90-7.88 (m, 1H), 7.86-7.84 (m, 2H), 7.74 (d, J = 8.8 Hz, 2H), 7.34 (d, J = 8.8 Hz, 2H), 4.03-4.02 (m, 1H), 3.97-3.85 (m, 2H), 3.30-3.21 (m, 1H), 2.37-2.32 (m, 1H), 1.85 (s, 3H), 1.80-1.69 (m, 1H), 1.65-1.50 (m, 2H), 1.07-1.06 (m, 3H), 0.76-0.74 (m, 3H). |
| 47-A | 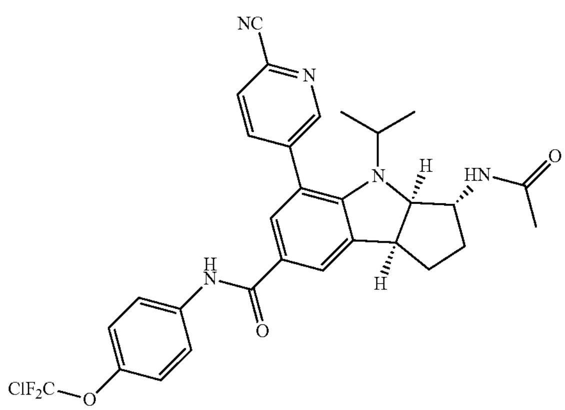 | $^1$H NMR (400 MHz, DMSO-$d_6$) δ 10.18 (s, 1H), 9.05-9.03 (m, 1H), 8.32-8.29 (m, 1H), 8.18-8.16 (m, 1H), 7.94-7.92 (m, 1H), 7.88 (d, J = 9.0 Hz, 2H), 7.80-7.78 (m, 2H), 7.37 (d, J = 9.0 Hz, 2H), 4.07-4.06 (m, 1H), 4.00-3.90 (m, 2H), 3.27-3.20 (m, 1H), 2.40-2.35 (m, 1H), 1.89 (s, 3H), 1.83-1.72 (m, 1H), 1.65-1.53 (m, 2H), 1.11 (d, J = 6.8 Hz, 3H), 0.78 (d, J = 6.8 Hz, 3H). |

TABLE 12-continued
| Compound No. | Compound Structure | ¹H NMR |
|---|---|---|
| 48-A | 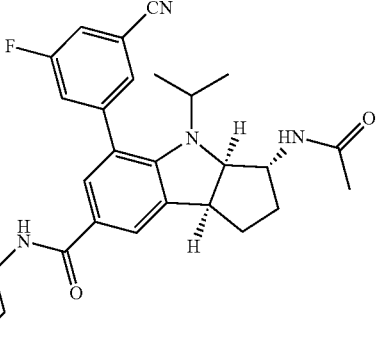 | ¹H NMR (400 MHz, DMSO-d$_6$) δ 10.13 (s, 1H), 7.99 (s, 1H), 7.93-7.80 (m, 5H), 7.78-7.70 (m, 2H), 7.34 (d, J = 9.0 Hz, 2H), 4.09-3.99 (m, 1H), 3.95-3.82 (m, 2H), 3.26-3.17 (m, 1H), 2.36-2.31 (m, 1H), 1.85 (s, 3H), 1.81-1.68 (m, 1H), 1.64-1.51 (m, 2H), 1.07 (d, J = 6.8 Hz, 3H), 0.75 (d, J = 6.8 Hz, 3H). |
| 50-A | 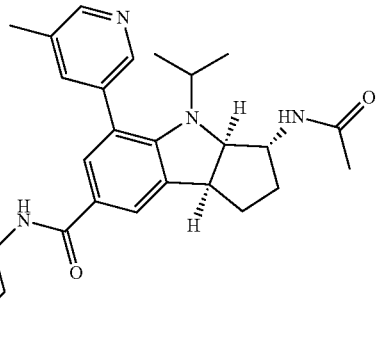 | ¹H NMR (400 MHz, DMSO-d$_6$) δ 10.12 (s, 1H), 8.60-8.59 (m, 1H), 8.40-8.39 (m, 1H), 7.92-7.82 (m, 4H), 7.71-7.69 (m, 2H), 7.33 (d, J = 9.0 Hz, 2H), 4.14-3.99 (m, 1H), 3.95-3.83 (m, 2H), 3.18-3.16 (m, 1H), 2.36 (s, 3H), 2.35-2.27 (m, 1H), 1.85 (s, 3H), 1.80-1.70 (m, 1H), 1.62-1.53 (m, 2H), 1.04 (d, J = 6.4 Hz, 3H), 0.73 (d, J = 6.4 Hz, 3H) |
| 51-A | 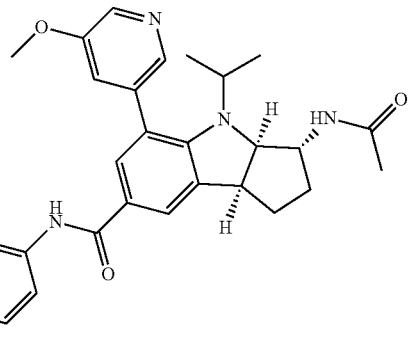 | ¹H NMR (400 MHz, DMSO-d$_6$) δ 10.14 (s, 1H), 8.44 (s, 1H), 8.32-8.31 (m, 1H), 7.97-7.82 (m, 3H), 7.79-7.64 (m, 3H), 7.33 (d, J = 8.8 Hz, 2H), 4.04-4.03 (m, 1H), 3.91-3.89 (m, 5H), 3.36-3.23 (m, 1H), 2.38-2.33 (m, 1H), 1.85 (s, 3H), 1.79-1.71 (m, 1H), 1.60-1.58 (m, 2H), 1.05 (d, J = 6.2 Hz, 3H), 0.74 (d, J = 6.2 Hz, 3H). |
| 52-A | 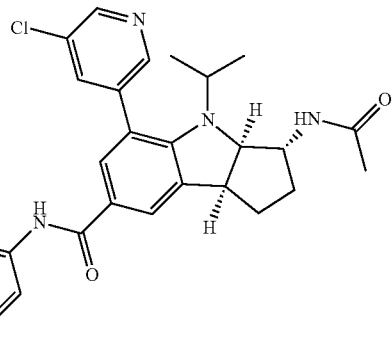 | ¹H NMR (400 MHz, DMSO-d$_6$) δ 10.13 (s, 1H), 8.78-8.77 (m, 1H), 8.61-8.59 (m, 1H), 8.18-8.17 (m, 1H), 7.94-7.81 (m, 3H), 7.74 (d, J = 9.0 Hz, 2H), 7.34 (d, J = 9.0 Hz, 2H), 4.03-4.01 (m, 1H), 3.96-3.84 (m, 2H), 3.30-3.22 (m, 1H), 2.41-2.28 (m, 1H), 1.85 (s, 3H), 1.81-1.69 (m, 1H), 1.65-1.52 (m, 2H), 1.07 (d, J = 6.8 Hz, 3H), 0.76 (d, J = 6.8 Hz, 3H) |

TABLE 12-continued
| Compound No. | Compound Structure | ¹H NMR |
|---|---|---|
| 53-A | 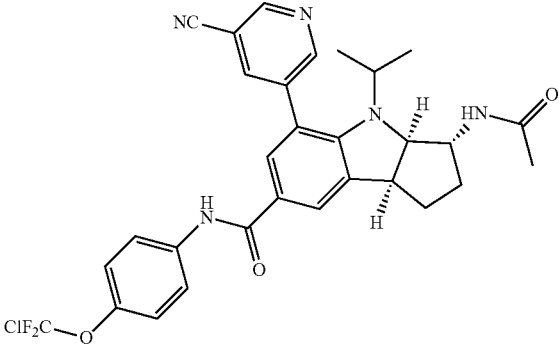 | ¹H NMR (400 MHz, DMSO-d₆) δ 10.13 (s, 1H), 9.10-9.09 (m, 1H), 9.00-8.99 (m, 1H), 8.59-8.57 (m, 1H), 7.94-7.82 (m, 3H), 7.76 (d, J = 9.0 Hz, 2H), 7.34 (d J = 9.0 Hz, 2H), 4.06-4.04 (m, 1H), 3.96-3.86 (m, 2H), 3.21-3.15 (m, 1H), 2.41-2.29 (m, 1H), 1.86 (s, 3H), 1.81-1.70 (m, 1H), 1.66-1.51 (m, 2H), 1.06 (d, J = 6.8 Hz, 3H), 0.75 (d, J = 6.8 Hz, 3H). |
| 66-A | 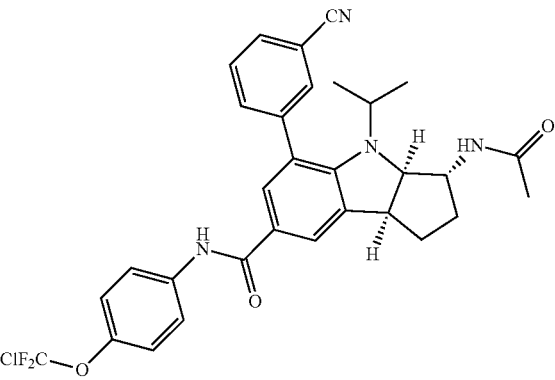 | ¹H NMR (400 MHz, dimethylsulfoxide-d6) δ 10.15 (s, 1H), 8.05-8.11 (m, 1H), 7.99-7.89 (m, 2H), 7.85 (d, J = 9.1 Hz, 2H), 7.83-7.78 (m, 1H), 7.74-7.70 (m, 2H), 7.70-7.64 (m, 1H), 7.33 (d, J = 8.9 Hz, 2H), 4.08-3.99 (m, 1H), 3.97-3.85 (m, 2H), 3.27-3.17 (m, 1H), 2.39-2.27 (m, 1H), 1.85 (s, 3H), 1.81-1.70 (m, 1H), 1.65-1.52 (m, 2H), 1.05 (d, J = 6.8 Hz, 3H), 0.72 (d, J = 6.4 Hz, 3H). |
| 67-A | 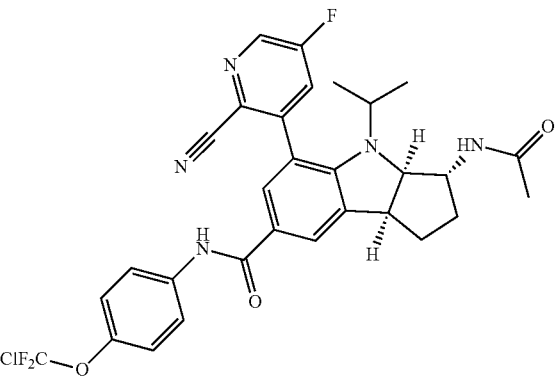 | ¹H NMR (400 MHz, dimethylsulfoxide-d6) δ 10.12 (s, 1H), 8.89-8.83 (m, 1H), 8.39-8.14 (m, 1H), 7.99-7.89 (m, 1H), 7.85 (d, J = 9.1 Hz, 2H), 7.82-7.79 (m, 1H), 7.76-7.59 (m, 1H), 7.34 (d, J = 9.0 Hz, 2H), 4.16-4.00 (m, 2H), 3.99-3.90 (m, 1H), 3.09-2.84 (m, 1H), 2.40-2.23 (m, 1H), 1.88-1.76 (m, 4H), 1.76-1.61 (m, 1H), 1.51-1.60 (m, 1H), 1.08 (d, J = 6.0 Hz, 3H), 0.80 (d, J = 6.1 Hz, 3H). |

Following the procedure of Example 4 by replacing intermediate E-10 with methyl (3R,3aR,8bS)-3-azido-5-bromo-4-neopentyl-1,2,3,3a,4,8b-hexahydrocyclopenta[b]indole-7-carboxylate (E-10'-A), and making no other critical changes, optically pure Compounds 56-A, 57-A, 58-A, 59-A, 60-A, 61-A were prepared. Intermediate E-10'-A was prepared as follows:

Synthesis of Methyl (3R,3aR,8bS)-3-azido-5-bromo-4-neopentyl-1,2,3,3a,4,8b-hexahydrocyclopenta[b]indole-7-carboxylate (E-10'-A)

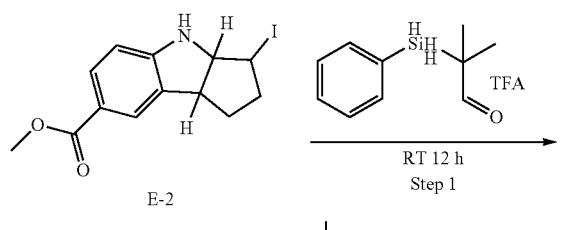

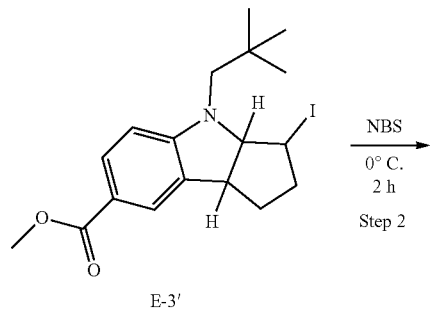

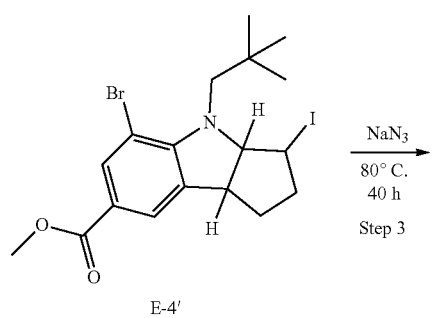

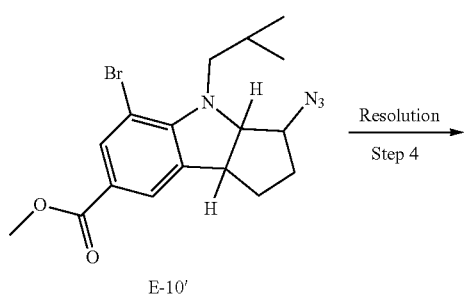

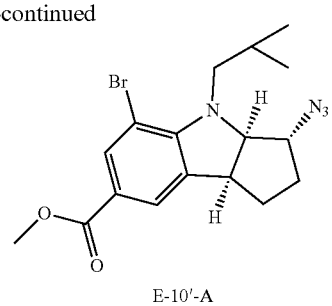

E-10'-A

Step 1: Methyl 3-iodo-4-neopentyl-1,2,3,3a,4,8b-hexahydrocyclopenta[b]indole-7-carboxylate (E-3'

In an oven-dried 25 mL round-bottomed flask methyl 3-iodo-1,2,3,3a,4,8b-hexahydrocyclopenta[b]indole-7-carboxylate (2.2 g, 6.41 mmol) was dissolved in THF (15 ml) under nitrogen to give a yellow solution. To the mixture were added Phenylsilane (2.081 g, 19.23 mmol), pivalaldehyde (1.104 g, 12.82 mmol) and 2,2,2-trifluoroacetaldehyde (0.628 g, 6.41 mmol), then the mixture was stirred at room temperature for overnight. After LC-MS showed the reaction was complete, the reaction was quenched by water, followed by extraction with ethyl acetate. The combined organic layers were dried over $Na_2SO_4$, filtered and concentrated. The resulting crude product was eluted with ethyl acetate/hexane (0 to 100%) to give methyl 3-iodo-4-neopentyl-1,2,3,3a,4,8b-hexahydrocyclopenta[b]indole-7-carboxylate (2.5 g, 940%) as a white solid.

Step 2: Methyl 5-bromo-3-iodo-4-neopentyl-1,2,3,3a,4,8b-hexahydrocyclopenta[b]indole-7-carboxylate (E-4')

In an oven-dried 50 mL round-bottomed flask methyl 3-iodo-4-neopentyl-1,2,3,3a,4,8b-hexahydrocyclopenta[b]indole-7-carboxylate (2.5 g, 6.05 mmol) was dissolved in 1,4-Dioxane (30 ml) under nitrogen to give a yellow solution. To the solution was added NBS (1.077 g, 6.05 mmol) in one portion and the mixture was stirred at 0° C. for 2 h. After LC MS showed the reaction was complete, saturated $NaHCO_3$ was added to the reaction mixture, followed by extraction with ethyl acetate. The combined organic layers were dried over $Na_2SO_4$, filtrated and concentrated. The resulting crude product was eluted with ethyl acetate/hexane to give methyl 5-bromo-3-iodo-4-neopentyl-1,2,3,3a,4,8b-hexahydrocyclopenta[b]indole-7-carboxylate (2.9 g, 97%) as a white solid. MS: 493.8 (M+H+). 1H NMR (400 MHz, Chloroform-d) δ 7.92 (d, J=1.7 Hz, 1H), 7.59 (d, J=1.7 Hz, 1H), 4.86 (d, J=9.0 Hz, 1H), 4.44 (d, J=5.2 Hz, 1H), 4.35 (d, J=15.2 Hz, 1H), 3.95 (t, J=8.5 Hz, 1H), 3.86 (s, 3H), 3.10 (d, J=15.1 Hz, 1H), 2.59 (s, 1H), 2.07 (dd, J=14.4, 6.0 Hz, 1H), 1.94 (dd, J=13.2, 6.0 Hz, 1H), 1.75-1.61 (m, 1H), 1.04 (s, 9H).

Step 3: Methyl 3-azido-5-bromo-4-neopentyl-1,2,3,3a,4,8b-hexahydrocyclopenta[b]indole-7-carboxylate (E-10')

The mixture of methyl 5-bromo-3-iodo-4-neopentyl-1,2,3,3a,4,8b-hexahydrocyclopenta[b]indole-7-carboxylate (3 g, 6.10 mmol) and sodium azide (1.981 g, 30.5 mmol) was stirred at 80° C. for 40 hours. After the reaction was completed, most of the acetone was removed in vacuo and the residual was partitioned between EA/Water, the organic layer was concentrated in vacuo to give the residual which was eluted with ethyl acetate/hexane to give methyl 3-azido-5-bromo-4-neopentyl-1,2,3,3a,4,8b-hexahydrocyclopenta[b]indole-7-carboxylate (2 g, 81%). MS: 408.0 (M+H+).

Step 4: Methyl (3R,3aR,8bS)-3-azido-5-bromo-4-neopentyl-1,2,3,3a,4,8b-hexahydrocyclopenta[b]indole-7-carboxylate (E-10'-A)

Intermediate E-10'-A was isolated from methyl 3-azido-5-bromo-4-neopentyl-1,2,3,3a,4,8b-hexahydrocyclopenta[b]indole-7-carboxylate (E-10') by the following elution condition:

Column: LuxCellulose-2
Size: 0.46×5 cm; 3 um
Mobile phase: He:IPA=99:1
Flow: 1.0 mL/min
Pressure: MPa
Detector: 220 nm
Instrument: LC-38
Temperature: 25° C.
Retention time: 3.024 min Compound 56-A, 57-A, 58-A, 59-A, 60-A, 61-A prepared by following the procedure of Example 4 from intermediate E-10'-A are listed in Table 13.

TABLE 13

| Compound No. | Compound Structure | $^1$H NMR |
|---|---|---|
| 56-A | 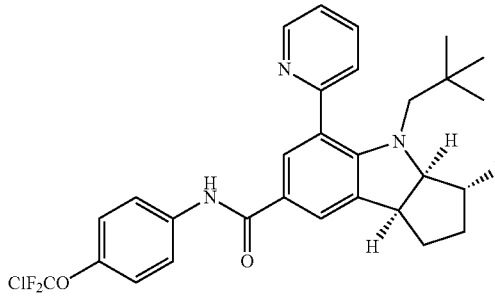 | $^1$H NMR (400 MHz, DMSO-$d_6$) δ 10.03 (s, 1H), 8.70 (d, J = 4.9 Hz, 1H), 7.96 (d, J = 6.6 Hz, 1H), 7.88-7.82 (m, 2H), 7.71-7.64 (m, 2H), 7.51 (d, J = 7.8 Hz, 1H), 7.38 (dd, J = 7.4, 5.1 Hz, 1H), 7.31 (d, J = 8.6 Hz, 2H), 4.19 (d, J = 9.1 Hz, 1H), 4.05-3.92 (m, 2H), 3.21 (d, J = 15.1 Hz, 1H), 3.09 (d, J = 15.1 Hz, 1H), 2.06-1.95 (m, 2H), 1.85 (s, 3H), 1.70-1.38 (m, 2H), 0.56 (s, 9H). |
| 57-A | 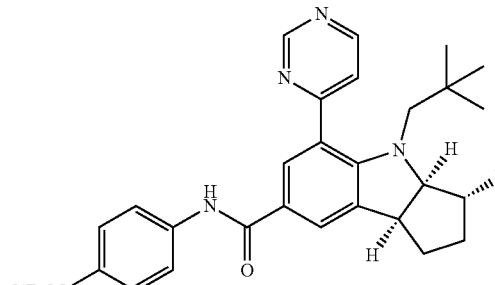 | $^1$H NMR (400 MHz, DMSO-$d_6$) δ 10.08 (s, 1H), 9.29 (d, J = 1.3 Hz, 1H), 8.86 (d, J = 5.3 Hz, 1H), 7.98 (d, J = 6.4 Hz, 1H), 7.90-7.81 (m, 2H), 7.79 (d, J = 1.9 Hz, 1H), 7.71 (t, J = 1.6 Hz, 1H), 7.66 (dd, J = 5.3, 1.4 Hz, 1H), 7.32 (d, J = 8.7 Hz, 2H), 4.23 (d, J = 8.9 Hz, 1H), 4.04-3.93 (m, 2H), 3.37 (d, J = 15.2 Hz, 1H), 3.22 (d, J = 15.2 Hz, 1H), 2.39-2.28 (m, 1H), 1.86 (s, 3H), 1.69-1.61 (m, 2H), 1.58-1.47 (m, 1H), 0.58 (s, 9H) |
| 58-A | 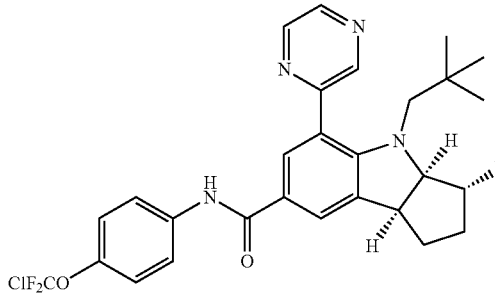 | $^1$H NMR (400 MHz, DMSO-$d_6$) δ 10.04 (s, 1H), 8.84-8.76 (m, 2H), 8.61 (d, J = 2.6 Hz, (1H), 7.98 (d, J = 6.5 Hz, 1H), 7.85 (d, J = 9.1 Hz, 2H), 7.74 (d, J = 1.9 Hz, 1H), 7.73-7.69 (m, 1H), 7.32 (d, J = 8.7 Hz, 2H), 4.20 (d, J = 9.2 Hz, 1H), 4.04-3.95 (m, 2H), 3.31 (d, J = 15.2 Hz, 1H), 3.03 (d, J = 15.2 Hz, 1H), 2.40-2.29 (m, 1H), 1.85 (s, 3H), 1.65-1.49 (m, 3H), 0.56 (s, 9H) |

TABLE 13-continued
| Compound No. | Compound Structure | ¹H NMR |
|---|---|---|
| 59-A | 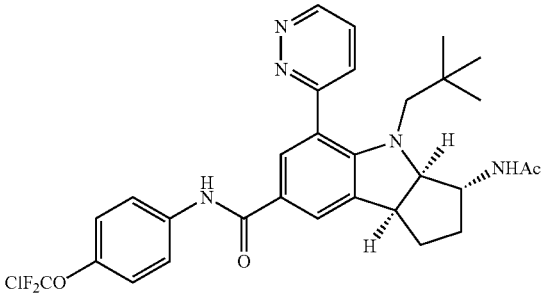 | ¹H NMR (400 MHz, DMSO-d$_6$) δ 10.05 (s, 1H), 9.32 (d, J = 5.1 Hz, 2H), 7.98 (d, J = 6.5 Hz, 1H), 7.87-7.80 (m, 2H), 7.78-7.69 (m, 2H), 7.66 (d, J = 1.9 Hz, 1H), 7.33 (d, J = 8.8 Hz, 2H), 4.17 (dd, J = 8.9, 2.0 Hz, 1H), 4.09-3.94 (m, 2H), 3.30 (d, J = 15.2 Hz, 1H), 2.81 (d, J = 15.1 Hz, 1H), 2.41-2.30 (m, 1H), 1.86 (s, 3H), 1.70-1.55 (m, 2H), 1.38-1.28 (m, 1H), 0.59 (s, 9H) |
| 60-A | 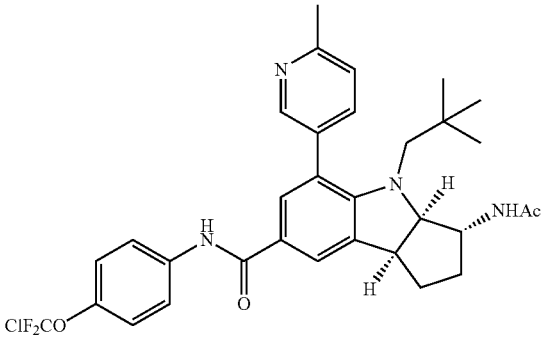 | ¹H NMR (400 MHz, DMSO-d$_6$) δ 10.04 (s, 1H), 8.68 (s, 1H), 8.05 (d, J = 8.2 Hz, 1H), 7.99 (d, J = 6.7 Hz, 1H), 7.88-7.81 (m, 2H), 7.71 (t, J = 1.5 Hz, 1H), 7.68 (d, J = 8.3 Hz, 1H), 7.57 (d, J = 1.9 Hz, 1H), 7.33 (d, J = 8.7 Hz, 2H), 4.13 (dd, J = 8.8, 2.1 Hz, 1H), 4.09-3.92 (m, 2H), 3.19 (d, J = 15.1 Hz, 1H), 2.82 (d, J = 15.1 Hz, 1H), 2.66 (s, 3H), 2.39-2.28 (m, 1H), 1.85 (s, 3H), 1.68-1.50 (m, 3H), 0.61 (s, 9H). |
| 61-A | 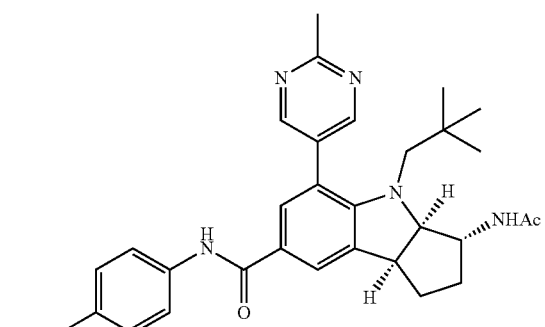 | ¹H NMR (400 MHz, DMSO-d$_6$) δ 10.00 (s, 1H), 8.73 (s, 2H), 7.97 (d, J = 6.8 Hz, 1H), 7.88-7.80 (m, 2H), 7.69 (d, J = 1.5 Hz, 1H), 7.58 (d, J = 1.9 Hz, 1H), 7.33 (d, J = 8.8 Hz, 2H), 4.12 (dd, J = 9.0, 2.1 Hz, 1H), 4.05-3.95 (m, 2H), 3.22 (d, J = 15.0 Hz, 1H), 2.82 (d, J = 15.0 Hz, 1H), 2.70 (s, 3H), 2.39-2.26 (m, 1H), 1.85 (s, 3H), 1.64-1.50 (m, 3H), 0.61 (s, 9H) |

Example 29

Synthesis of —N-(4-(chlorodifluoromethoxy)phenyl)-4-isopropyl-3-(1-methylazetidine-3-carboxamido)-5-(1H-pyrazol-5-yl)-1,2,3,3a,4,8b-hexahydrocyclopenta[b]indole-7-carboxamide (Compound No. 29)

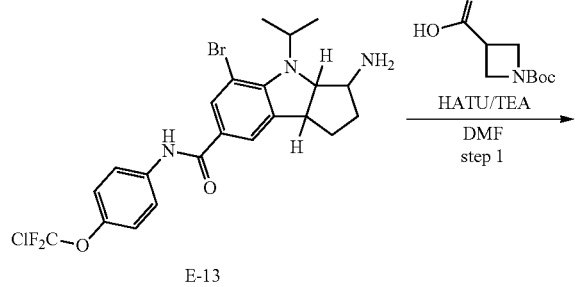

Step 1: Synthesis of Tert-butyl 3-((-5-bromo-7-((4-(chlorodifluoromethoxy)phenyl)carbamoyl)-4-isopropyl-1,2,3,3a,4,8b-hexahydrocyclopenta[b]indol-3-yl)carbamoyl)azetidine-1-carboxylate (E-15)

Under Ar, to a solution of -3-amino-5-bromo-N-(4-(chlorodifluoromethoxy)phenyl)-4-isopropyl-1,2,3,3a,4,8b-hexahydrocyclopenta[b]indole-7-carboxamide (150 mg, 0.291 mmol) in DMF (2.9 mL) was added 1-(tert-butoxycarbonyl)azetidine-3-carboxylic acid (70.4 mg, 0.350 mmol), triethylamine (59.0 mg, 0.583 mmol) and HATU (133 mg, 0.350 mmol) at room temperature, and it was stirred for 2 h at room temperature. Water (20 mL) was added to the mixture, followed by extraction with ethyl acetate (30 mL×3). The combined organic layers were washed with brine, dried over $Na_2SO_4$, filtrated and concentrated to give a residue, which was purified by silica gel column chromatography (ethyl acetate/hexane from 0% to 70%) to give tert-butyl 3-((-5-bromo-7-((4-(chlorodifluoromethoxy)phenyl)carbamoyl)-4-isopropyl-1,2,3,3a,4,8b-hexahydrocyclopenta[b]indol-3-yl)carbamoyl)azetidine-1-carboxylate (190 mg, 93%) as a white solid. MS: 699.2 $(M+H)^+$.

Step 2: Synthesis of -3-(azetidine-3-carboxamido)-5-bromo-N-(4-(chlorodifluoromethoxy)phenyl)-4-isopropyl-1,2,3,3a,4,8b-hexahydrocyclopenta[b]indole-7-carboxamide (E-15a)

Under Ar, to a solution of tert-butyl 3-((-5-bromo-7-((4-(chlorodifluoromethoxy)phenyl)carbamoyl)-4-isopropyl-1,2,3,3a,4,8b-hexahydrocyclopenta[b]indol-3-yl)carbamoyl)azetidine-1-carboxylate (100 mg, 0.143 mmol) in dichloromethane (2.0 mL) was added TFA (0.5 mL) at room temperature, and it was stirred at room temperature for 2 h. The mixture was concentrated to give a crude product (80 mg), which was used for the next step without purification.

Step 3: Synthesis of -5-bromo-N-(4-(chlorodifluoromethoxy)phenyl)-4-isopropyl-3-(1-methylazetidine-3-carboxamido)-1,2,3,3a,4,8b-hexahydrocyclopenta[b]indole-7-carboxamide (E-16)

Under Ar, to a solution of -3-(azetidine-3-carboxamido)-5-bromo-N-(4-(chlorodifluoromethoxy)phenyl)-4-isopropyl-1,2,3,3a,4,8b-hexahydrocyclopenta[b]indole-7-carboxamide (80 mg, 0.134 mmol) in 1,2-Dichloroethane (1.2 mL) was added HCHO (60.9 mg, 0.669 mmol) and $NaBH_3CN$ (16.82 mg, 0.268 mmol) at room temperature, it was stirred at room temperature for 12 h. Water (30 mL) was added to the mixture, followed by extraction with ethyl acetate (30 mL×3). The combined organic layers were washed with brine, dried over Na$_2$SO$_4$, filtrated and concentrated to give a residue, which was purified by silica gel column chromatography (ethyl acetate/hexane from 0% to 70%) to give -5-bromo-N-(4-(chlorodifluoromethoxy)phenyl)-4-isopropyl-3-(1-methylazetidine-3-carboxamido)-1,2,3,3a,4,8b-hexahydrocyclopenta[b]indole-7-carboxamide (70 mg, 85%) as a white solid.

Step 4: Synthesis of —N-(4-(chlorodifluoromethoxy)phenyl)-4-isopropyl-3-(1-methylazetidine-3-carboxamido)-5-(1H-pyrazol-5-yl)-1,2,3,3a,4,8b-hexahydrocyclopenta[b]indole-7-carboxamide (29)

The mixture of -5-bromo-N-(4-(chlorodifluoromethoxy)phenyl)-4-isopropyl-3-(1-methylazetidine-3-carboxamido)-1,2,3,3a,4,8b-hexahydrocyclopenta[b]indole-7-carboxamide (70 mg, 0.114 mmol), 5-(4,4,5,5-tetramethyl-1,3,2-dioxaborolan-2-yl)-1H-pyrazole (44.4 mg, 0.229 mmol) and Pd(dppf)Cl$_2$·CH$_2$Cl$_2$ (18.68 mg, 0.023 mmol) in DME (1.5 mL)/2N Na$_2$CO$_3$ (0.5 mL) was stirred under microwave for 0.5 h at 100° C. After being cooled to room temperature, the mixture was poured into water (30 mL), followed by extraction with ethyl acetate (20 mL×3). The combined organic layers were washed with brine, dried over Na$_2$SO$_4$, filtrated and concentrated to give a residue, which was purified using Prep-HPLC to give —N-(4-(chlorodifluoromethoxy)phenyl)-4-isopropyl-3-(1-methylazetidine-3-carboxamido)-5-(1H-pyrazol-5-yl)-1,2,3,3a,4,8b-hexahydrocyclopenta[b]indole-7-carboxamide (15.9 mg, 23.20%) as a white solid. $^1$H NMR (400 MHz, DMSO-d$_6$) δ 7.84-7.49 (m, 3H), 7.70 (s, 1H), 7.64 (s, 1H), 7.31 (d, J=8.9 Hz, 2H), 6.50 (d, J=1.9 Hz, 1H), 4.39-4.27 (m, 1H), 4.27, 4.18 (m, 1H), 4.10-3.99 (m, 2H), 3.99-3.83 (i, 3H), 3.57-3.43 (m, 2H), 2.81 (d, J 8.9 Hz, 3H), 2.37-2.20 (m, 1H), 1.79-1.67 (m, 1H), 1.65-1.50 (i, 2H), 1.09 (dd, J=6.6, 3.3 Hz, 3H), 0.72 (d, J=6.4 Hz, 3H). Following the procedure of Example 29 and making non-critical changes, compound 30-32 in Table 14 were prepared.

TABLE 14

| Compound No. | Structure | $^1$H NMR & MS |
| --- | --- | --- |
| 30 | 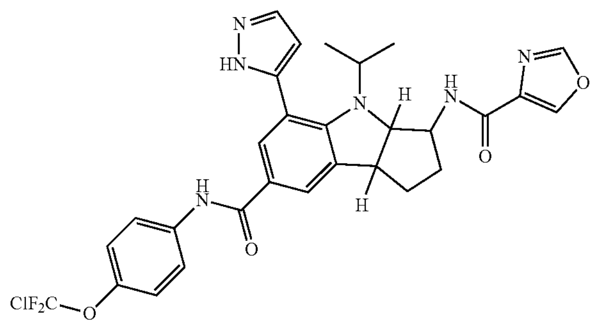 | $^1$H NMR (400 MHz, DMSO-d$_6$) δ 13.20-12.62 (m, 1H), 10.18 (s, 1H), 8.65 (s, 1H), 8.53 (s, 1H), 8.37 (d, J = 7.5 Hz, 1H), 8.02-7.45 (m, 5H), 7.32 (d, J = 8.7 Hz, 2H), 6.72-6.37 (m, 1H), 4.31-4.06 (m, 2H), 3.90-3.87 (m, 1H), 3.68-3.50 (m, 1H), 2.44-2.24 (m, 1H), 1.83-1.48 (m, 3H), 1.04 (d, J = 6.7 Hz, 3H), 0.73 (d, J = 6.0 Hz, 3H). |
| 31 | 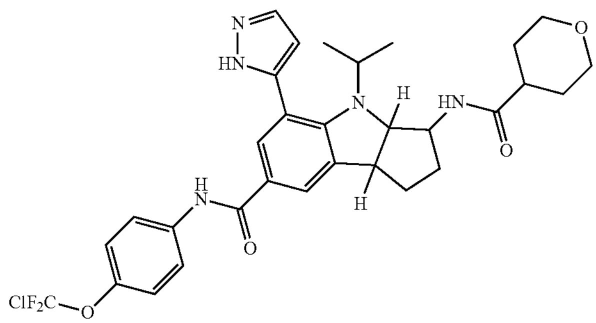 | $^1$H NMR (400 MHz, DMSO-d$_6$) δ 10.15 (s, 1H), 7.90-7.80 (m, 4H), 7.70 (s, 1H), 7.65 (s, 1H), 7.32 (d, J = 8.8 Hz, 2H), 6.50 (d, J = 1.8 Hz, 1H), 4.03-4.83 (m, 6H), 3.56-3.51 (m, 2H), 2.44-2.34 (m, 1H), 2.34-2.24 (m, 1H), 1.79-1.68 (m, 1H), 1.65-1.49 (m, 6H), 1.09 (d, J = 6.8 Hz, 3H), 0.73 (d, J = 6.4 Hz, 3H). |
| 32 | 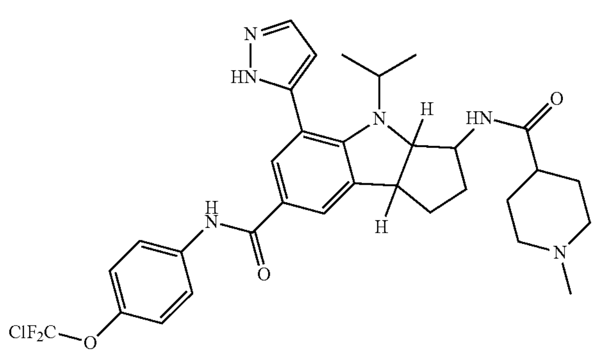 | $^1$H NMR (400 MHz, DMSO-d$_6$ + D$_2$O) δ 7.82 (d, J = 1.6 Hz, 1H), 7.80 (d, J = 8.8 Hz, 2H), 7.69 (d, J = 2.0 Hz, 1H), 7.64 (s, 1H), 7.30 (d, J = 8.8 Hz, 2H), 6.51 (d, J = 1.9 Hz, 1H), 4.04-3.85 (m, 3H), 3.56-3.47 (m, 1H), 3.46-3.38 (m, 2H), 2.98-2.83 (m, 2H), 2.73 (s, 3H), 2.45-2.20 (m, 2H), 1.96-1.84 (m, 2H), 1.84-1.65 (m, 3H), 1.61-1.48 (m, 2H), 1.05 (d, J = 6.7 Hz, 3H), 0.71 (d, J = 6.4 Hz, 3H). |

Example 33
Synthesis of —N-(4-(chlorodifluoromethoxy)phenyl)-4-isopropyl-3-(3-(pyrazin-2-yl)ureido)-5-(1H-pyrazol-5-yl)-1,2,3,3a,4,8b-hexahydrocyclopenta[b]indole-7-carboxamide (Compound No. 33)
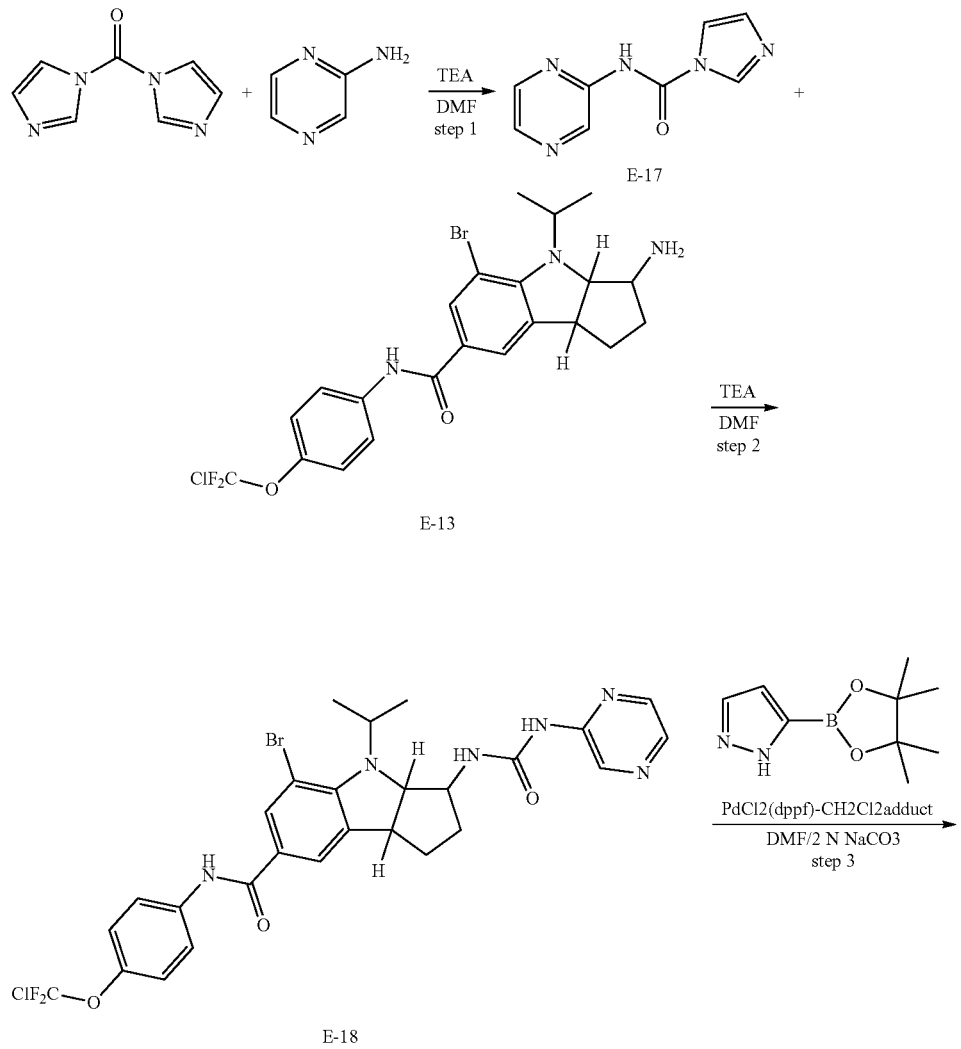

Step 1: Synthesis of N-(pyrazin-2-yl)-1H-imidazole-1-carboxamide (E-17)

Under Ar, to a solution of pyrazin-2-amine (216 mg, 2.271 mmol) and triethylamine (1213 mg, 11.99 mmol) in anhydrous DMF (6 mL) was added CDI (605 mg, 3.73 mmol) in portions at 0° C., it was stirred at room temperature for 18 h. Without any workup, the solution was used directly for the next step.

Step 2: Synthesis of 5-bromo-N-(4-(chlorodifluoromethoxy)phenyl)-4-isopropyl-3-(3-(pyrazin-2-yl)ureido)-1,2,3,3a,4,8b-hexahydrocyclopenta[b]indole-7-carboxamide (E-18)

Under Ar, to a solution of 3-amino-5-bromo-N-(4-(chlorodifluoromethoxy)phenyl)-4-isopropyl-1,2,3,3a,4,8b-hexahydrocyclopenta[b]indole-7-carboxamide (41.1 mg, 0.080 mmol) in anhydrous DMF (2 mL) was added triethylamine (100 mg, 0.988 mmol) and N-(pyrazin-2-yl)-1H-imidazole-1-carboxamide (60.4 mg, 0.319 mmol) at room temperature, it was stirred at 70° C. for 3 h. After being cooled to room temperature, the mixture was poured into water (20 mL), followed by extraction with acetate ethyl (20 mL×3). The combined organic layers were washed with brine, dried over $Na_2SO_4$, filtrated and concentrated to give a crude product (70 mg, 138%), which was used for the next step without purification.

Step 3: Synthesis of —N-(4-(chlorodifluoromethoxy)phenyl)-4-isopropyl-3-(3-(pyrazin-2-yl)ureido)-5-(1H-pyrazol-5-yl)-1,2,3,3a,4,8b-hexahydrocyclopenta[b]indole-7-carboxamide (33)

Under Ar, the mixture of 5-bromo-N-(4-(chlorodifluoromethoxy)phenyl)-4-isopropyl-3-(3-(pyrazin-2-yl)ureido)-1,2,3,3a,4,8b-hexahydrocyclopenta[b]indole-7-carboxamide (70 mg, 0.110 mmol), 5-(4,4,5,5-tetramethyl-1,3,2-dioxaborolan-2-yl)-1H-pyrazole (18.7 mg, 0.096 mmol) and $PdCl_2$(dppf)-$CH_2Cl_2$ adduct (9 mg, 0.011 mmol, 0.100) in DME (6 mL) and 2N $Na_2CO_3$ (1.5 mL) was stirred at 90° C. under microwave for 25 minute. After being cooled to room temperature, the mixture was poured into water (20 mL), followed by extraction with acetate ethyl (20 mL×3). The combined organic layers were washed with brine, dried over $Na_2SO_4$, filtrated and concentrated to give the crude product, which was purified using prep-HPLC to give —N-(4-(chlorodifluoromethoxy)phenyl)-4-isopropyl-3-(3-(pyrazin-2-yl)ureido)-5-(1H-pyrazol-5-yl)-1,2,3,3a,4,8b-hexahydrocyclopenta[b]indole-7-carboxamide (11.6 mg, 16.91%). $^1$H NMR (400 MHz, DMSO-$d_6$) δ 13.29-12.50 (m, 1H), 10.17 (s, 1H), 9.33 (s, 1H), 8.93 (s, 1H), 8.24-8.21 (m, 1H), 8.18 (d, J=2.5 Hz, 1H), 7.98-7.49 (m, 6H), 7.32 (d, J=8.7 Hz, 2H), 6.67-6.33 (m, 1H), 4.18-4.02 (m, 2H), 3.94 (t, J=8.3 Hz, 1H), 3.73-3.54 (m, 1H), 2.38-2.20 (m, 1H), 1.88-1.76 (m, 1H), 1.75-1.53 (m, 2H), 1.18 (d, J=6.8 Hz, 3H), 0.75 (d, J=6.2 Hz, 3H).

Example 34

Synthesis of N-(4-(chlorodifluoromethoxy)phenyl)-4-isopropyl-3-(pyrazin-2-ylamino)-5-(1H-pyrazol-5-yl)-1,2,3,3a,4,8b-hexahydrocyclopenta[b]indole-7-carboxamide (Compound No. 34)

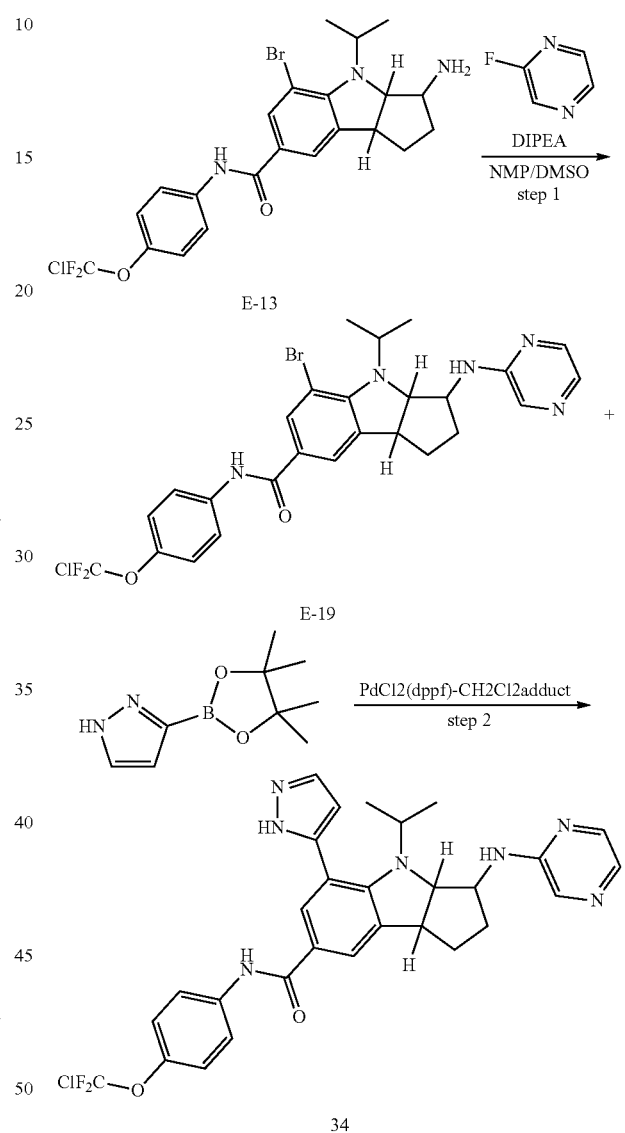

Step 1: Synthesis of -5-bromo-N-(4-(chlorodifluoromethoxy)phenyl)-4-isopropyl-3-(pyrazin-2-ylamino)-1,2,3,3a,4,8b-hexahydrocyclopenta[b]indole-7-carboxamide (E-19)

The mixture of 3-amino-5-bromo-N-(4-(chlorodifluoromethoxy)phenyl)-4-isopropyl-1,2,3,3a,4,8b-hexahydrocyclopenta[b]indole-7-carboxamide (40 mg, 0.078 mmol), 2-fluoropyrazine (22.86 mg, 0.233 mmol) and DIPEA (50.2 mg, 0.389 mmol) in DMSO (0.6 mL)/NMP (0.5 mL) was stirred under sealed tube at 90° C. for 15 h. After being cooled to temperature, the mixture was purified by silica gel column chromatography (ethyl acetate/hexane from 10% to 50%) to give -5-bromo-N-(4-(chlorodifluoromethoxy)phenyl)-4-isopropyl-3-(pyrazin-2-ylamino)-1,2,3,3a,4,8b-hexahydrocyclopenta[b]indole-7-carboxamide (200 mg contained residual solvent) that was used directly for the next step.

Step 2 Synthesis of N-(4-(chlorodifluoromethoxy)phenyl)-4-isopropyl-3-(pyrazin-2-ylamino)-5-(1H-pyrazol-5-yl)-1,2,3,3a,4,8b-hexahydrocyclopenta[b]indole-7-carboxamide (34)

Under Ar, the mixture of -5-bromo-N-(4-(chlorodifluoromethoxy)phenyl)-4-isopropyl-3-(pyrazin-2-ylamino)-1,2,3,3a,4,8b-hexahydrocyclopenta[b]indole-7-carboxamide (100 mg, 0.169 mmol), 5-(4,4,5,5-tetramethyl-1,3,2-dioxaborolan-2-yl)-1H-pyrazole (203 mg, 1.046 mmol) and PdCl$_2$(dppf)-CH$_2$Cl$_2$ adduct (128 mg, 0.157 mmol) in DME (7.5 mL) and 2N Na$_2$CO$_3$ (2.5 mL) was stirred under microwave for 25 minutes at 95° C. After being cooled to room temperature, the mixture was poured into water (10 ml), followed by extraction with ethyl acetate (20 mL×3). The combined organic layers were dried over anhydrous Na$_2$SO$_4$, filtered and concentrated to give a residue, which was purified using prep-HPLC to give —N-(4-(chlorodifluoromethoxy)phenyl)-4-isopropyl-3-(pyrazin-2-ylamino)-5-(1H-pyrazol-5-yl)-1,2,3,3a,4,8b-hexahydrocyclopenta[b]indole-7-carboxamide (8.5 mg, 8.69%). $^1$H NMR (400 MHz, DMSO-d$_6$) δ 10.15 (s, 1H), 8.03-7.79 (m, 5H), 7.79-7.59 (m, 3H), 7.32 (d, J=8.6 Hz, 2H), 7.18 (d, J=7.1 Hz, 1H), 6.49 (s, 1H), 4.25-4.13 (m, 1H), 4.13-4.02 (m, 1H), 3.95 (t, J=8.4 Hz, 1H), 3.58-3.46 (m, 1H), 2.42-2.27 (m, 1H), 1.83-1.73 (m, 1H), 1.73-1.55 (m, 2H), 1.09 (d, J=6.7 Hz, 3H), 0.75 (d, J=6.3 Hz, 3H).

Example 35

Synthesis of N-(4-(chlorodifluoromethoxy)phenyl)-4-isopropyl-3-(2-oxopyrrolidin-1-yl)-5-(1H-pyrazol-5-yl)-1,2,3,3a,4,8b-hexahydrocyclopenta[b]indole-7-carboxamide (Compound No. 35)

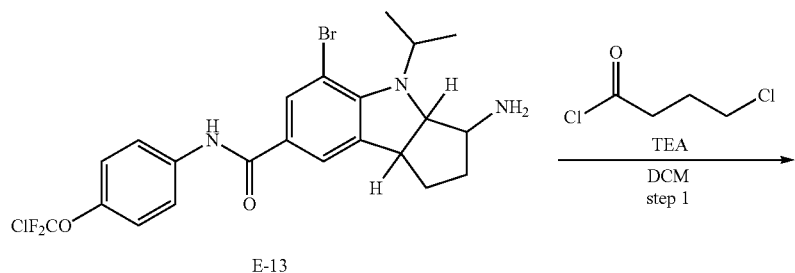

E-13

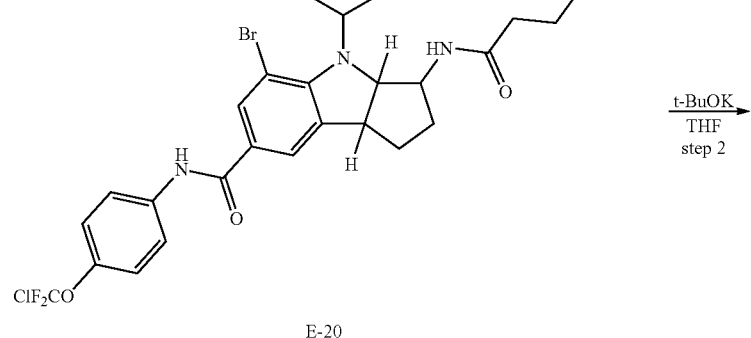

E-20

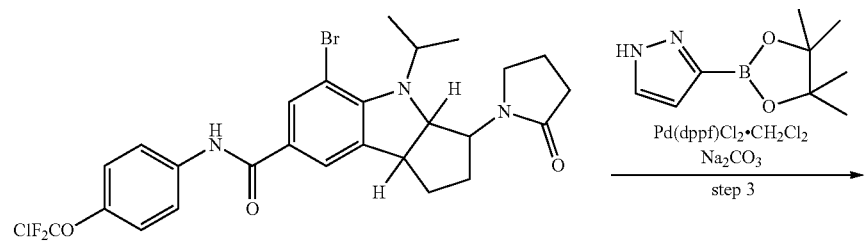

E-21

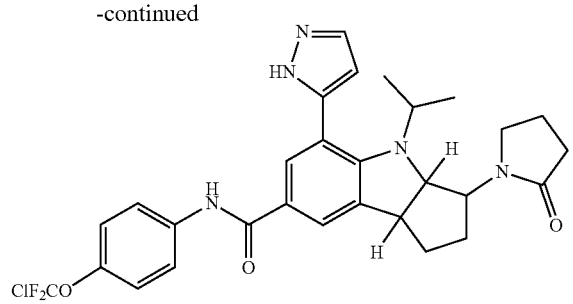

35

Step 1: 5-bromo-3-(4-chlorobutanamido)-N-(4-(chlorodifluoromethoxy)phenyl)-4-isopropyl-1,2,3,3a,4,8b-hexahydrocyclopenta[b]indole-7-carboxamide (E-20)

Under nitrogen, to a solution of 3-amino-5-bromo-N-(4-((difluoro-13-chloranyl)oxy)phenyl)-4-isobutyl-1,2,3,3a,4,8b-hexahydrocyclopenta[b]indole-7-carboxamide (150 mg, 0.290 mmol) and triethylamine (44.1 mg, 0.435 mmol, 1.5) in dichloromethane (8 mL) was added 4-chlorobutanoyl chloride (49.1 mg, 0.348 mmol) at 0° C. in a 25 mL round-bottomed flask, it was stirred for 2 h at room temperature. Water (20 mL) was added to the mixture, followed by extraction with dichloromethane (20 mL×3). The combined organic layers were washed with brine, dried over $Na_2SO_4$, filtrated and concentrated to give a crude product (180 mg, yield as 100%), which was used for the next step without purification.

Step 2: 5-bromo-N-(4-(chlorodifluoromethoxy)phenyl)-4-isopropyl-3-(2-oxopyrrolidin-1-yl)-1,2,3,3a,4,8b-hexahydrocyclopenta[b]indole-7-carboxamide (E-21)

Under nitrogen, to a solution of 5-bromo-3-(4-chlorobutanamido)-N-(4-(chlorodifluoromethoxy)phenyl)-4-isopropyl-1,2,3,3a,4,8b-hexahydrocyclopenta[b]indole-7-carboxamide (180 mg 0.290 mmol) in THF (6 mL) was added potassium 2-methylpropan-2-olate (65 mg, 0.58 mmol) at 0° C., it was stirred for 2 h at room temperature. Water (20 mL) was added to the mixture, followed by extraction with ethyl acetate (30 mL×3). The combined organic layers were concentrated to give a residue, which was purified by silica gel column chromatography (ethyl acetate/hexane from 50% to 70%) to give 5-bromo-N-(4-(chlorodifluoromethoxy)phenyl)-4-isopropyl-3-(2-oxopyrrolidin-1-yl)-1,2,3,3a,4,8b-hexahydrocyclopenta[b]indole-7-carboxamide (130 mg, 72.7%) as a white solid. MS: 581.9 (M+H)$^+$.

Step 3: N-(4-(chlorodifluoromethoxy)phenyl)-4-isopropyl-3-(2-oxopyrrolidin-1-yl)-5-(1H-pyrazol-5-yl)-1,2,3,3a,4,8b-hexahydrocyclopenta[b]indole-7-carboxamide (35)

The mixture of 5-bromo-N-(4-(chlorodifluoromethoxy)phenyl)-4-isopropyl-3-(2-oxopyrrolidin-1-yl)-1,2,3,3a,4,8b-hexahydrocyclopenta[b]indole-7-carboxamide (80 mg, 0.137 mmol), 5-(4,4,5,5-tetramethyl-1,3,2-dioxaborolan-2-yl)-1H-pyrazole (39.9 mg, 0.206 mmol), Pd(dppf)Cl$_2$·CH$_2$Cl$_2$ (11.21 mg, 0.014 mmol) and Na$_2$CO$_3$ (43.6 mg, 0.412 mmol) in DME (2 mL)/water (0.6 mL) was stirred under microwave at 110° C. for 3 h. After being cooled to room temperature, the mixture was concentrated to give a residue, which was purified by silica gel column chromatography (ethyl acetate/hexane from 50% to 90%) to give N-(4-(chlorodifluoromethoxy)phenyl)-4-isopropyl-3-(2-oxopyrrolidin-1-yl)-5-(1H-pyrazol-5-yl)-1,2,3,3a,4,8b-hexahydrocyclopenta[b]indole-7-carboxamide (29 mg, 37.1%) as a yellow solid. $^1$H NMR (400 MHz, DMSO-d$_6$) δ 10.22 (s, 1H), 7.96 (s, 1H), 7.88 (d, J=9.1 Hz, 2H), 7.71 (s, 1H), 7.67 (s, 1H), 7.33 (d, J=8.9 Hz, 2H), 6.64 (s, 1H), 4.23-4.13 (m, 1H), 4.13-4.05 (m, 1H), 3.90-3.79 (m, 1H), 3.59-3.49 (m, 1H), 3.45-3.30 (m, 2H), 2.48-2.37 (m, 1H), 2.33-2.23 (m, 2H), 2.05-1.90 (m, 2H), 1.86-1.66 (m, 2H), 1.55 (d, J=10.6 Hz, 1H), 0.97 (d, J=6.7 Hz, 3H), 0.71 (d, J=6.7 Hz, 3H), MS: 570.1 (M+H)$^+$.

Example 36

Synthesis of N-(4-(chlorodifluoromethoxy)phenyl)-4-isopropyl-3-(2-oxopiperidin-1-yl)-5-(1H-pyrazol-5-yl)-1,2,3,3a,4,8b-hexahydrocyclopenta[b]indole-7-carboxamide (Compound No. 36)

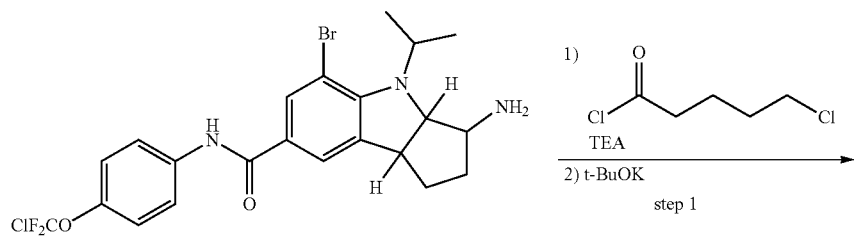

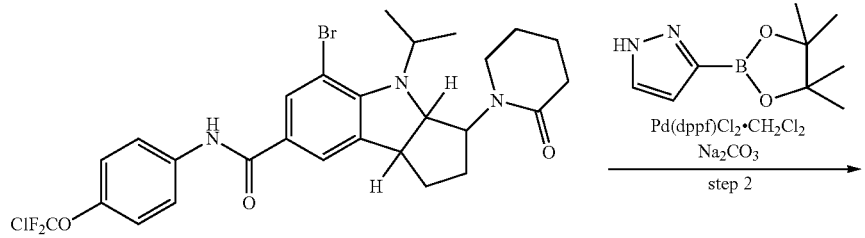
E-22
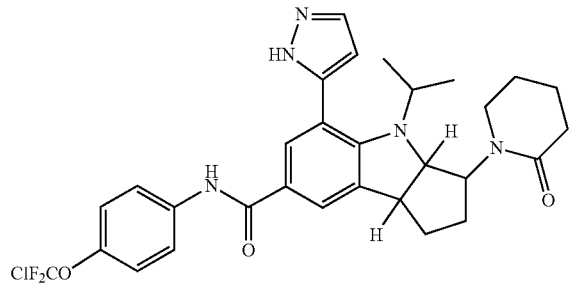
36
Example 36 (Compound No. 36) was prepared in a similar fashion as Compound 35 to afford a white solid. $^1$H NMR (400 MHz, DMSO-$d_6$)) δ 10.23 (s, 1H), 7.96 (s, 1H), 7.88 (d, J=9.1 Hz, 2H), 7.70 (s, 1H), 7.67 (s, 1H), 7.33 (d, J=9.1 Hz, 2H), 6.63 (s, 1H), 4.59-4.45 (m, 1H), 4.19 (t, J=8.8 Hz, 1H), 3.85-3.76 (m, 1H), 3.46-3.35 (m, 1H), 3.32-3.22 (m, 1H), 2.46-1.37 (m, 1H), 2.29-2.30 (m, 2H), 2.03-1.47 (m, 8H), 0.98 (d, J=6.7 Hz, 3H), 0.71 (d, J=6.7 Hz, 3H).
Example 37
Synthesis of —N-(4-(chlorodifluoromethoxy)phenyl)-3-(1,1-dioxidoisothiazolidin-2-yl)-4-isopropyl-5-(1H-pyrazol-5-yl)-1,2,3,3a,4,8b-hexahydrocyclopenta[b]indole-7-carboxamide (Compound No. 37)
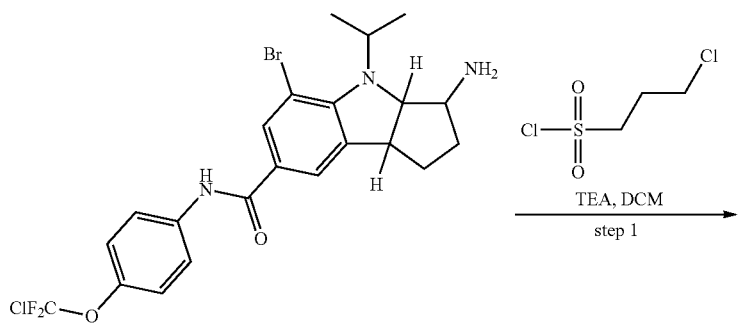
E-13
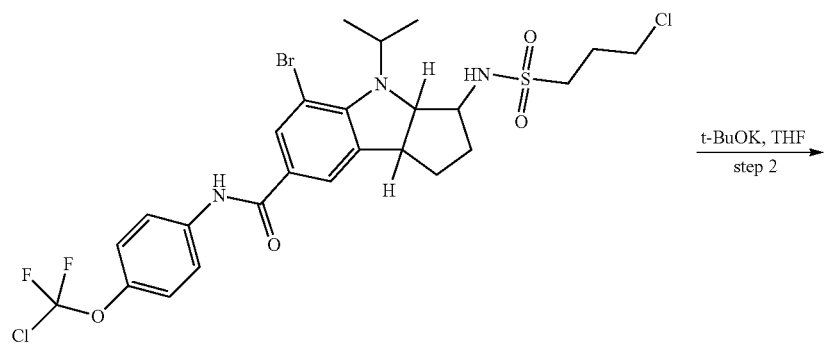
E-23

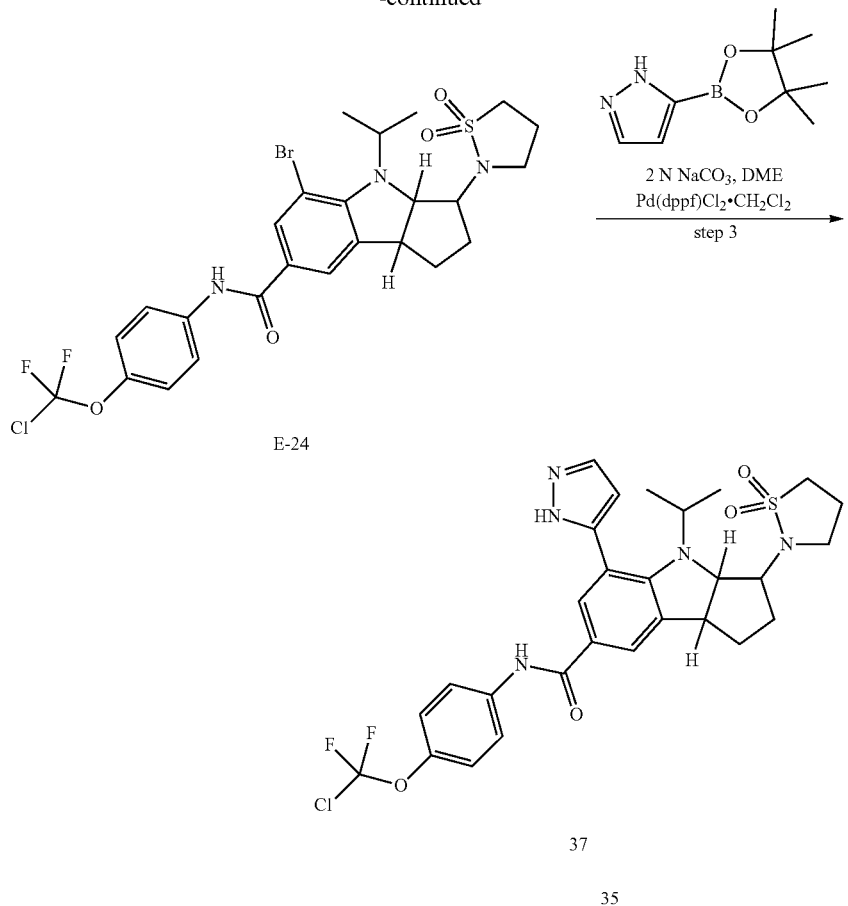
E-24
37
Example 37 (Compound No. 37) was prepared in a similar fashion as Compound 35 to afford a white solid. $^1$H NMR (400 MHz, DMSO-$d_6$)) δ 13.13-12.67 (m, 1H), 10.20 (s, 1H), 8.12-7.47 (m, 5H), 7.33 (d, J=8.5 Hz, 2H), 6.84-6.47 (m, 1H), 4.31-4.05 (m, 1H), 3.96-3.79 (m, 1H), 3.71-3.47 (m, 2H), 3.47-3.36 (m, 1H), 3.29-3.12 (m, 3H), 2.45-2.33 (m, 1H), 2.32-2.19 (m, 2H), 1.95-1.80 (m, 1H), 1.79-1.49 (m, 2H), 1.13 (d, J=6.7 Hz, 3H), 0.74 (d, J=6.7 Hz, 3H).
Example 38
Synthesis of N-(4-(chlorodifluoromethoxy)phenyl)-4-isopropyl-3-(2-oxoimidazolidin-1-yl)-5-(1H-pyrazol-5-yl)-1,2,3,3a,4,8b-hexahydrocyclopenta[b]indole-7-carboxamide (Compound No. 38)
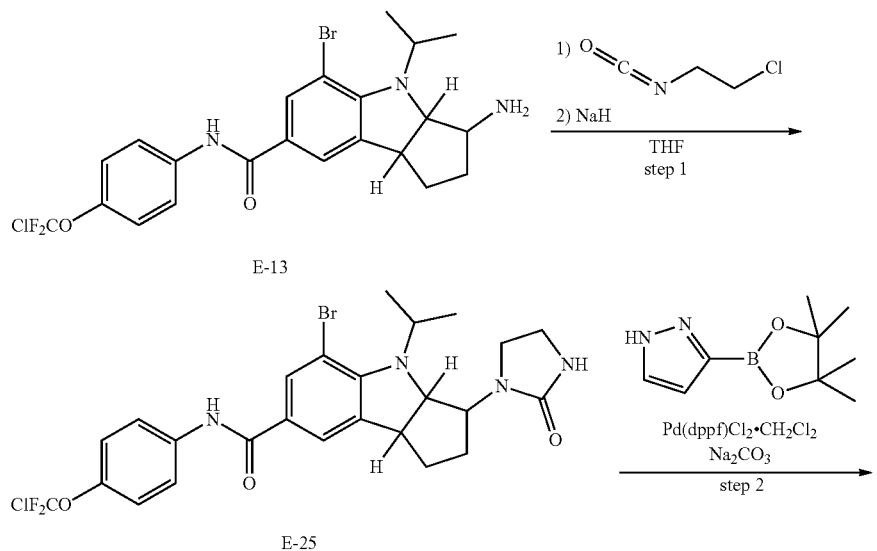

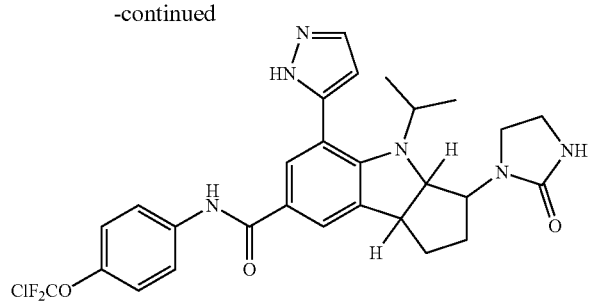

38

Step 1: 5-bromo-N-(4-(chlorodifluoromethoxy)phenyl)-4-isopropyl-3-(2-oxoimidazolidin-1-yl)-1,2,3,3a,4,8b-hexahydrocyclopenta[b]indole-7-carboxamide (E-25)

Under nitrogen, to a solution of 3-amino-5-bromo-N-(4-(chlorodifluoromethoxy)phenyl)-4-isopropyl-1,2,3,3a,4,8b-hexahydrocyclopenta[b]indole-7-carboxamide (150 mg, 0.291 mmol) in THF (6 mL) was added 1-chloro-2-isocyanatoethane (30.7 mg, 0.291 mmol) at room temperature, it was stirred for 2 h at room temperature. After being cooled to 0° C., sodium hydride (8.39 mg, 0.350 mmol) was added to the mixture at 0° C., it was stirred for 2 h at room temperature, quenched with water (20 mL), followed by extraction with ethyl acetate (20 mL×3). The combined organic layers were washed with brine, dried over $Na_2SO_4$, filtrated and concentrated to give a residue, which was purified by silica gel column chromatography (ethyl acetate/hexane from 50% to 80%) to give 5-bromo-N-(4-(chlorodifluoromethoxy)phenyl)-4-isopropyl-3-(2-oxoimidazolidin-1-yl)-1,2,3,3a,4,8b-hexahydrocyclopenta[b]indole-7-carboxamide (40 mg, 23.5%) as a solid. MS: 582.9 $(M+H)^+$.

Step 2: N-(4-(chlorodifluoromethoxy)phenyl)-4-isopropyl-3-(2-oxoimidazolidin-1-yl)-5-(1H-pyrazol-5-yl)-1,2,3,3a,4,8b-hexahydrocyclopenta[b]indole-7-carboxamide (38)

The mixture of 5-bromo-N-(4-(chlorodifluoromethoxy)phenyl)-4-isopropyl-3-(2-oxoimidazolidin-1-yl)-1,2,3,3a,4,8b-hexahydrocyclopenta[b]indole-7-carboxamide (40 mg, 0.069 mmol), 5-(4,4,5,5-tetramethyl-1,3,2-dioxaborolan-2-yl)-1H-pyrazole (19.94 mg, 0.103 mmol), Pd(dppf)Cl₂·CH₂Cl₂ (5.59 mg, 6.85 µmol) and $Na_2CO_3$ (21.78 mg, 0.206 mmol) in DME (2 mL)/water (0.6 mL) was stirred under microwave at 110° C. for 3 h. After being cooled to room temperature, the mixture was concentrated to give a residue, which was purified by silica gel chromatography (methanol/ethyl acetate from 0% to 10%) to give N-(4-(chlorodifluoromethoxy)phenyl)-4-isopropyl-3-(2-oxoimidazolidin-1-yl)-5-(1H-pyrazol-5-yl)-1,2,3,3a,4,8b-hexahydrocyclopenta[b]indole-7-carboxamide (19 mg, 48.6%) as a yellow oil. ¹H NMR (400 MHz, DMSO-d₆) δ 10.22 (s, 1H), 7.94 (s, 1H), 7.88 (d, J=9.1 Hz, 2H), 7.70-7.65 (m, 2H), 7.33 (d, J=8.9 Hz, 2H), 6.67 (s, 1H), 4.12-4.03 (m, 1H), 3.97-3.89 (m, 1H), 3.86-3.77 (m, 1H), 3.59-3.21 (m, 4H), 2.45-2.35 (m, 1H), 2.05-1.93 (m, 1H), 1.81-1.65 (m, 2H), 1.57-1.48 (m, 1H), 1.04 (d, J=6.7 Hz, 3H), 0.73 (d, J=6.4 Hz, 3H), MS: 571.2 $(M+H)^+$.

Example 39

Synthesis of 4-((7-((4-(chlorodifluoromethoxy)phenyl)carbamoyl)-4-isopropyl-5-(1H-pyrazol-5-yl)-1,2,3,3a,4,8b-hexahydrocyclopenta[b]indol-3-yl)amino)-4-oxobutanoic acid (Compound No. 39)

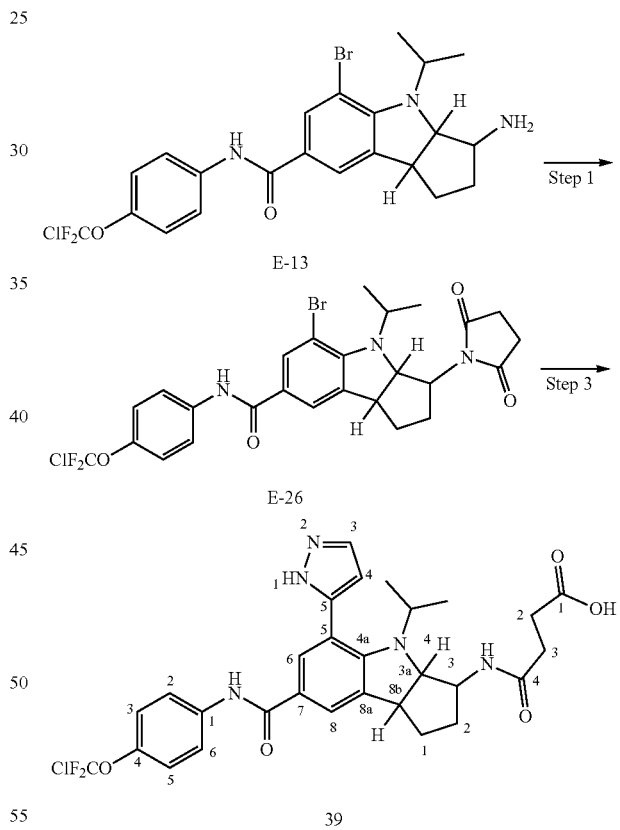

Step 1: 5-bromo-N-(4-(chlorodifluoromethoxy)phenyl)-3-(2,5-dioxopyrrolidin-1-yl)-4-isopropyl-1,2,3,3a,4,8b-hexahydrocyclopenta[b]indole-7-carboxamide (E-26)

Under nitrogen, to a solution of -3-amino-5-bromo-N-(4-(chlorodifluoromethoxy)phenyl)-4-isopropyl-1,2,3,3a,4,8b-hexahydrocyclopenta[b]indole-7-carboxamide (150 mg, 0.291 mmol) in AcOH (9 mL) was added dihydrofuran-2, 5-dione (29.2 mg, 0.291 mmol) and sodium acetate (71.7 mg, 0.874 mmol) at room temperature in a 25 mL round-bottomed flask, it was stirred at refluxing temperature for overnight. After being cooled to room temperature, it was concentrated to give a residue, which was purified by silica gel chromatography (ethyl acetate/hexane from 20% to 50%) to give 5-bromo-N-(4-(chlorodifluoromethoxy)phenyl)-3-(2,5-dioxopyrrolidin-1-yl)-4-isopropyl-1,2,3,3a,4,8b-hexahydrocyclopenta[b]indole-7-carboxamide (80 mg, 46.0%) as a solid. MS: 595.9 (M+H)+.

Step 2: 4-((7-((4-(chlorodifluoromethoxy)phenyl)carbamoyl)-4-isopropyl-5-(1H-pyrazol-5-yl)-1,2,3,3a,4,8b-hexahydrocyclopenta[b]indol-3-yl)amino)-4-oxobutanoic acid (39)

The mixture of 5-bromo-N-(4-(chlorodifluoromethoxy)phenyl)-3-(2,5-dioxopyrrolidin-1-yl)-4-isopropyl-1,2,3,3a,4,8b-hexahydrocyclopenta[b]indole-7-carboxamide (80 mg, 0.134 mmol), 5-(4,4,5,5-tetramethyl-1,3,2-dioxaborolan-2-yl)-1H-pyrazole (39.0 mg, 0.201 mmol), Pd(dppf)Cl₂·CH₂Cl₂ (10.95 mg, 0.013 mmol) and Na₂CO₃ (42.6 mg, 0.402 mmol) in DME (2 mL)/water (0.6 mL) was stirred under microwave at 110° C. for 3 h. After being cooled to room temperature, the mixture was concentrated to give a residue, which was purified by silica column chromatography (methanol/dichloromethane from 0% to 10%) to give N-(4-(chlorodifluoromethoxy)phenyl)-3-(2,5-dioxopyrrolidin-1-yl)-4-isopropyl-5-(1H-pyrazol-5-yl)-1,2,3,3a,4,8b-hexahydrocyclopenta[b]indole-7-carboxamide (80 mg, 100%) as a yellow oil. MS: 584.1 (M+H)+. ¹H NMR (400 MHz, DMSO-d₆) δ 10.15 (s, 1H), 7.91 (d, J=7.5 Hz, 1H), 7.87 (d, J=9.1 Hz, 2H), 7.85 (s, 1H), 7.71 (s, 1H), 7.66 (s, 1H), 7.32 (d, J=8.9 Hz, 2H), 6.52-6.47 (m, 1H), 4.06-3.84 (m, 3H), 3.60-3.48 (m, 1H), 2.46 (t, J=7.0 Hz, 2H), 2.36 (t, J=6.8 Hz, 2H), 2.04-1.93 (m, 1H), 1.78-1.67 (m, 1H), 1.62-1.48 (m, 2H), 1.11 (d, J=6.8 Hz, 3H), 0.73 (d, J=6.4 Hz, 3H).

Example 40

Synthesis of N-(4-(chlorodifluoromethoxy)phenyl)-9-isopropyl-2-methyl-8-(1H-pyrazol-5-yl)-2,3,4,4a,9,9a-hexahydro-1H-pyrido[3,4-b]indole-6-carboxamide (Compound No. 40)

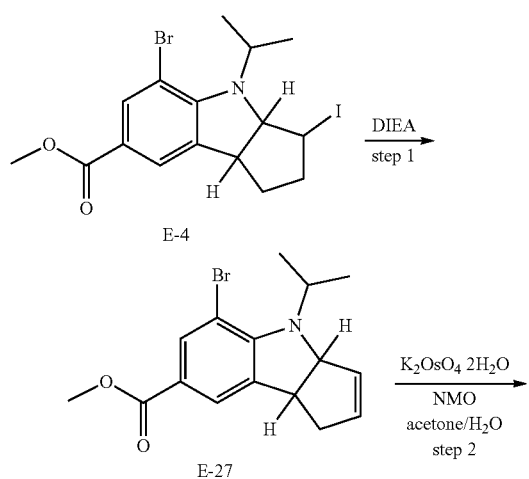

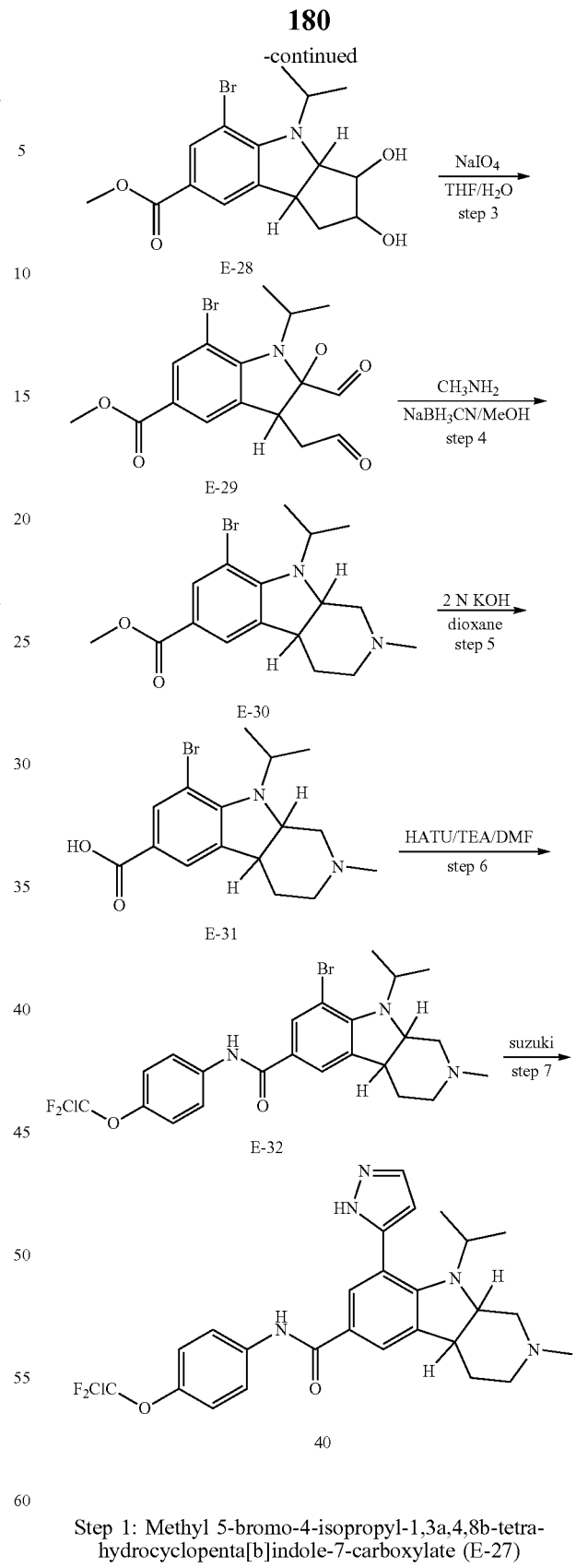

Step 1: Methyl 5-bromo-4-isopropyl-1,3a,4,8b-tetrahydrocyclopenta[b]indole-7-carboxylate (E-27)

Under nitrogen, the mixture of methyl 5-bromo-3-iodo-4-isopropyl-1,2,3,3a,4,8b-hexahydrocyclopenta[b]indole-7-carboxylate (4.86 g, 10.47 mmol) in DIEA (50 mL) was stirred at 120° C. for 3 h in a flushed 100 mL round-bottomed flask. After being cooled to room temperature, the mixture was concentrated to give a residue, which was added into water (50 mL), then extracted with ethyl acetate (50 mL×3). The combined organic layers were washed with brine, dried over $Na_2SO_4$, filtrated and concentrated to give a residue, which was purified by silica gel column chromatography (ethyl acetate/hexane from 10% to 50%) to give methyl 5-bromo-4-isopropyl-1,3a,4,8b-tetrahydrocyclopenta[b]indole-7-carboxylate (3.03 g, 86%) as a yellow oil. $^1$H NMR (400 MHz, Chloroform-d) δ 7.99-7.94 (m, 1H), 7.62 (s, 1H), 5.88 (m, 1H), 5.67 (m, 1H), 5.00-4.86 (m, 2H), 4.03 (t, J=8.6 Hz, 1H), 3.86 (s, 3H), 2.93 (m, 1H), 2.59 (m, 1H), 1.37 (d, J=6.8 Hz, 3H), 1.12 (d, J=6.6 Hz, 3H). MS: 335.9 $(M+H)^+$

Step 2: 5-bromo-2,3-dihydroxy-4-isopropyl-1,2,3,3a,4,8b-hexahydrocyclopenta[b]indole-7-carboxylate (E-28)

Under nitrogen, to a solution of methyl 5-bromo-4-isopropyl-1,3a,4,8b-tetrahydrocyclopenta[b]indole-7-carboxylate (5.73 g, 17.04 mmol) and 4-methylmorpholine 4-oxide (3.99 g, 34.1 mmol) in acetone (35 mL) was added potassium osmate dihydrate (0.628 g, 1.704 mmol) in water (11.67 mL) at room temperature in an oven-dried 100 mL two-necked round-bottomed flask, it was stirred for 2 h at room temperature. Water (50 mL) was added to the mixture, then extracted with ethyl acetate (50 mL×3). The combined organic layers were washed with brine, dried over $Na_2SO_4$, filtrated and concentrated to give a residue, which was purified by silica gel column chromatography (ethyl acetate/hexane from 40% to 50%) to give methyl 5-bromo-2,3-dihydroxy-4-isopropyl-1,2,3,3a,4,8b-hexahydrocyclopenta[b]indole-7-carboxylate (5.47 g, 87%) as a colorless solid. $^1$H NMR (400 MHz, Chloroform-d) δ 7.98 (s, 1H), 7.61 (s, 1H), 4.96-4.90 (m, 1H), 4.17-4.10 (m, 1H), 4.10-4.03 (m, 1H), 4.01-3.91 (m, 2H), 3.88 (s, 3H), 2.36-2.31 (m, 1H), 2.00-1.94 (m, 1H), 1.39 (d, J=6.9 Hz, 3H), 1.03 (d, J=6.5 Hz, 3H). MS: 369.9 $(M+H)^+$

Step 2: methyl 7-bromo-2-formyl-1-isopropyl-3-(2-oxoethyl)indoline-5-carboxylate (E-29)

Under nitrogen, the mixture of methyl 5-bromo-2,3-dihydroxy-4-isopropyl-1,2,3,3a,4,8b-hexahydrocyclopenta[b]indole-7-carboxylate (127 mg, 0.343 mmol) and sodium periodate (110 mg, 0.515 mmol) in THF (6 mL) and water (0.5 mL) was stirred at room temperature for 1 h. Water (20 mL) was added to the mixture, followed by extraction with dichloromethane (10 mL×3). The combined organic layers were dried over $Na_2SO_4$, filtrated and concentrated to give crude product (as yield 100%), which was used for the next step directly.

Step 4: 8-bromo-9-isopropyl-2-methyl-2,3,4,4a,9,9a-hexahydro-1H-pyrido[3,4-b]indole-6-carboxylate (E-30)

Under nitrogen, to a solution of methyl 7-bromo-2-formyl-1-isopropyl-3-(2-oxoethyl)indoline-5-carboxylate in methanol (5 mL) was added methylamine in MeOH (30%) (71.1 mg, 0.686 mmol), $NaBH_3CN$ (43.1 mg, 0.686 mmol) and acetic acid (20.60 mg, 0.343 mmol), it was stirred at room temperature for 2 h. Water (20 mL) was added to the mixture, followed extraction with dichloromethane (30 mL×3). The combined organic layers were dried over $Na_2SO_4$, filtrated and concentrated to give a residue, which was purified by silica gel column chromatography (methanol/dichloromethane from 0% to 10%) to give methyl 8-bromo-9-isopropyl-2-methyl-2,3,4,4a,9,9a-hexahydro-1H-pyrido[3,4-b]indole-6-carboxylat e (87 mg, 69.1%) as an oil. $^1$H NMR (400 MHz, Chloroform-d) δ 8.00 (t, J=1.2 Hz, 1H), 7.58 (t, J=1.7 Hz, 1H), 4.68 (m, 1H), 4.02 (m, 1H), 3.89 (s, 3H), 3.53 (m, 1H), 3.45-3.36 (m, 1H), 2.87 (m, 2H), 2.73 (d, J=11.0 Hz, 1H), 2.39 (m, 1H), 2.27 (s, 3H), 1.80 (m, 2H), 1.25 (d, J=6.6 Hz, 3H), 1.16 (d, J=6.6 Hz, 3H). MS: 366.9 $(M+H)^+$

Step 5: 8-bromo-9-isopropyl-2-methyl-2,3,4,4a,9,9a-hexahydro-1H-pyrido[3,4-b]indole-6-carboxylic acid (E-31)

Under nitrogen, to a solution of methyl 8-bromo-9-isopropyl-2-methyl-2,3,4,4a,9,9a-hexahydro-1H-pyrido[3,4-b]indole-6-carboxylat e (87 mg, 0.237 mmol) in 1,4-Dioxane (5 ml) and water (0.500 ml) was added 2N KOH (0.24 mL, 0.48 mmol) at room temperature, it was stirred at 50° C. for 2 h. After being cooled to room temperature, the mixture was acidified with 2N HCl to PH=4~5, followed by extraction with ethyl acetate (30 mL×3). The combined organic layers were washed with brine, dried over $Na_2SO_4$, filtrated and concentrated to give 8-bromo-9-isopropyl-2-methyl-2,3,4,4a,9,9a-hexahydro-1H-pyrido[3,4-b]indole-6-carboxylic acid (96 mg, 115%), which was used for the next step without purification as a yellow oil. MS: 352.9 $(M+H)^+$

Step 6: 8-bromo-N-(4-(chlorodifluoromethoxy)phenyl)-9-isopropyl-2-methyl-2,3,4,4a,9,9a-hexahydro-1H-pyrido[3,4-b]indole-6-carboxamide (E-32)

Under nitrogen, the mixture of 8-bromo-9-isopropyl-2-methyl-2,3,4,4a,9,9a-hexahydro-1H-pyrido[3,4-b]indole-6-carboxylic acid (148 mg, 0.419 mmol), 2-(3H-[1,2,3]triazolo[4,5-b]pyridin-3-yl)-1,1,3,3-tetramethylisouronium hexafluorophosphate(V) (239 mg, 0.628 mmol), triethylamine (63.6 mg, 0.628 mmol) and 4-(chlorodifluoromethoxy) aniline (97 mg, 0.503 mmol) in DMF (5 mL) was stirred at room temperature for overnight. Water (30 mL) was added to the mixture, followed by extraction with ethyl acetate (20 mL×3). The combined organic layers were washed with brine, dried over $Na_2SO_4$, filtrated and concentrated to give a residue, which was purified by silica gel column chromatography (methanol/dichloromethane from 15% to 25%) to give 8-bromo-N-(4-(chlorodifluoromethoxy)phenyl)-9-isopropyl-2-methyl-2,3,4,4a,9,9a-hexahydro-1H-pyrido[3,4-b]indole-6-carboxamide (118 mg, 53.3%) as an oil. MS: 527.9 $(M+H)^+$

Step 7: N-(4-(chlorodifluoromethoxy)phenyl)-9-isopropyl-2-methyl-8-(1H-pyrazol-5-yl)-2,3,4,4a,9,9a-hexahydro-1H-pyrido[3,4-b]indole-6-carboxamide (40)

The mixture of 8-bromo-N-(4-(chlorodifluoromethoxy) phenyl)-9-isopropyl-2-methyl-2,3,4,4a,9,9a-hexahydro-1H-pyrido[3,4-b]indole-6-carboxamide (118 mg, 0.223 mmol), 5-(4,4,5,5-tetramethyl-1,3,2-dioxaborolan-2-yl)-1H-pyrazole (64.9 mg, 0.335 mmol), sodium carbonate (70.9 mg, 0.669 mmol) and $Pd(PPh_3)_2Cl_2$ (16.33 mg, 0.022 mmol) in DME (2 mL)/water (0.667 mL) was stirred under microwave for 2 h at 120° C. After being cooled to room temperature, the mixture was poured into water (20 mL), followed by extraction with dichloromethane (20 mL×3). The combined organic layers were washed with brine, dried over $Na_2SO_4$, filtrated and concentrated to give a residue, which was purified by silica gel column chromatography (methanol/dichloromethane from 15% to 30%) to give N-(4-(chlorodifluoromethoxy)phenyl)-9-isopropyl-2-methyl-8-(1H-pyrazol-5-yl)-2,3,4,4a,9,9a-hexahydro-1H-pyrido[3,4-b]indole-6-carboxamide (50 mg, 43.4%) as a solid. $^1$H NMR (400 MHz, DMSO-d$_6$) δ 10.26 (s, 1H), 8.06 (s, 1H), 7.88 (d, J=9.1 Hz, 2H), 7.82-7.72 (m, 2H), 7.35 (d, J=8.9 Hz, 2H), 6.57 (d, J=1.9 Hz, 1H), 4.16-4.02 (m, 1H), 3.73-3.62 (m, 1H), 3.59-3.48 (m, 3H), 2.91-2.81 (m, 1H), 2.78 (s, 3H), 2.70-2.52 (m, 2H), 2.38-2.25 (m, 1H), 1.11 (d, J=6.7 Hz, 3H), 0.89 (d, J=6.5 Hz, 3H), MS: 516.1 (M+H)$^+$.

Example 41

Synthesis of N-(4-(chlorodifluoromethoxy)phenyl)-9-isopropyl-8-(1H-pyrazol-5-yl)-2-(2,2,2-trifluoroethyl)-2,3,4,4a,9,9a-hexahydro-1H-pyrido[3,4-b]indole-6-carboxamide (Compound No. 41)

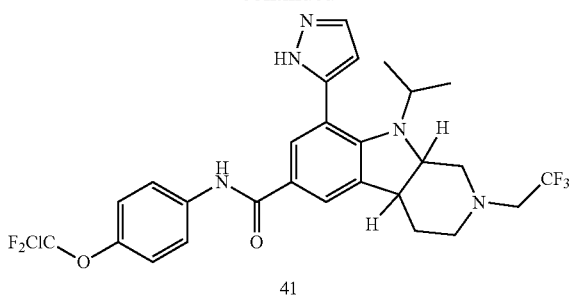

Compound 41 was prepared in a similar fashion as Compound 40 to afford a white solid. $^1$H NMR (400 MHz, DMSO-d$_6$)) δ 12.87 (s, 1H), 10.18 (s, 1H), 7.95 (s, 1H), 7.87 (d, J=9.1 Hz, 2H), 7.75 (s, 1H), 7.65 (s, 1H), 7.33 (d, J=8.8 Hz, 2H), 6.53 (s, 1H), 4.0-3.84 (m, 1H), 3.61-3.42 (m, 2H), 3.15 (q, J=10.2 Hz, 2H), 2.95 (dd, J=11.5, 6.4 Hz, 1H), 2.78 (d, J=11.0 Hz, 1H), 2.36-2.23 (m, 2H), 2.22-2.06 (m, 2H), 1.08 (d, J=6.7 Hz, 3H), 0.91 (d, J=6.5 Hz, 3H). MS: 584.1 (M+H)$^+$.

Example 42

Synthesis of 2-acetyl-N-(4-(chlorodifluoromethoxy)phenyl)-9-isopropyl-8-(1H-pyrazol-5-yl)-2,3,4,4a,9,9a-hexahydro-1H-pyrido[3,4-b]indole-6-carboxamide (Compound No. 42)

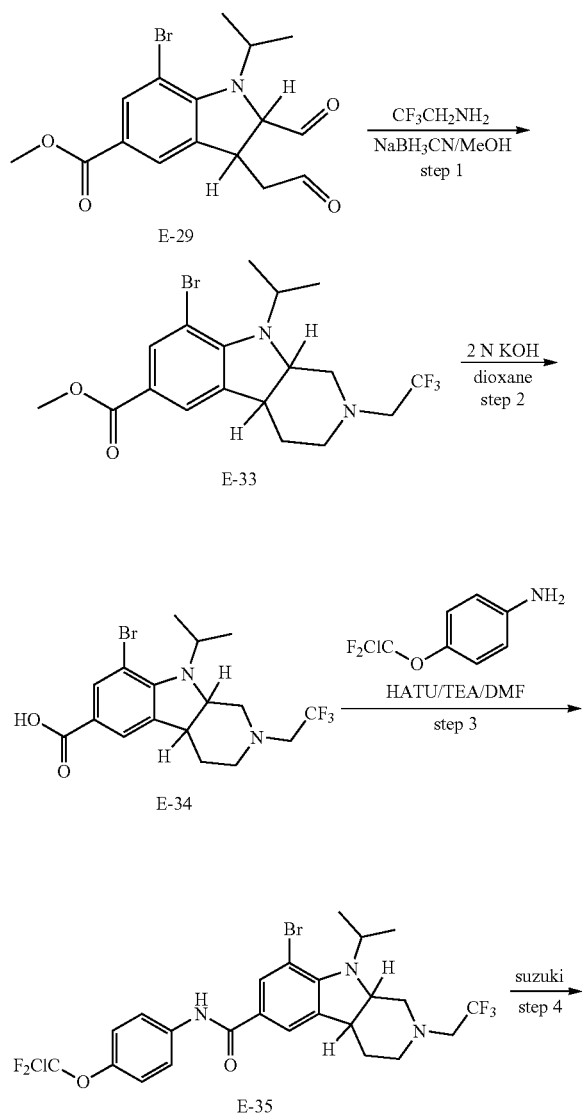

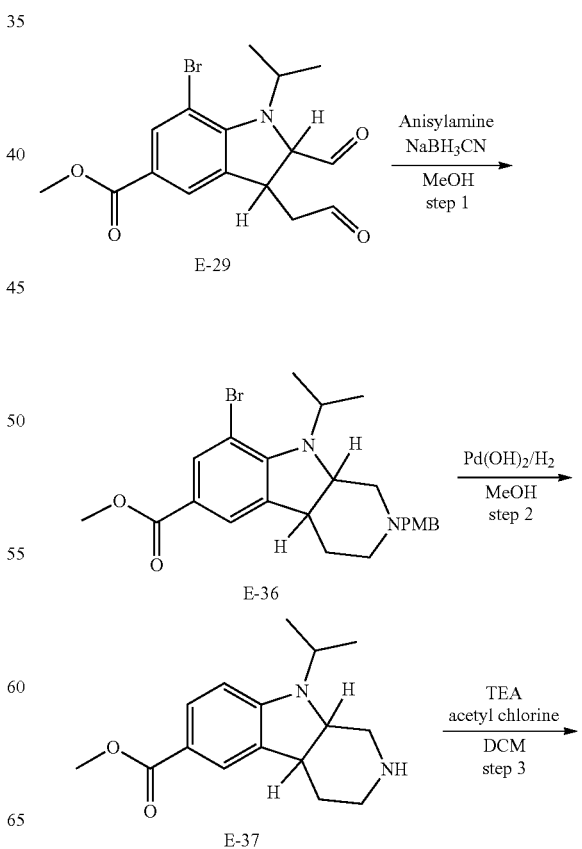

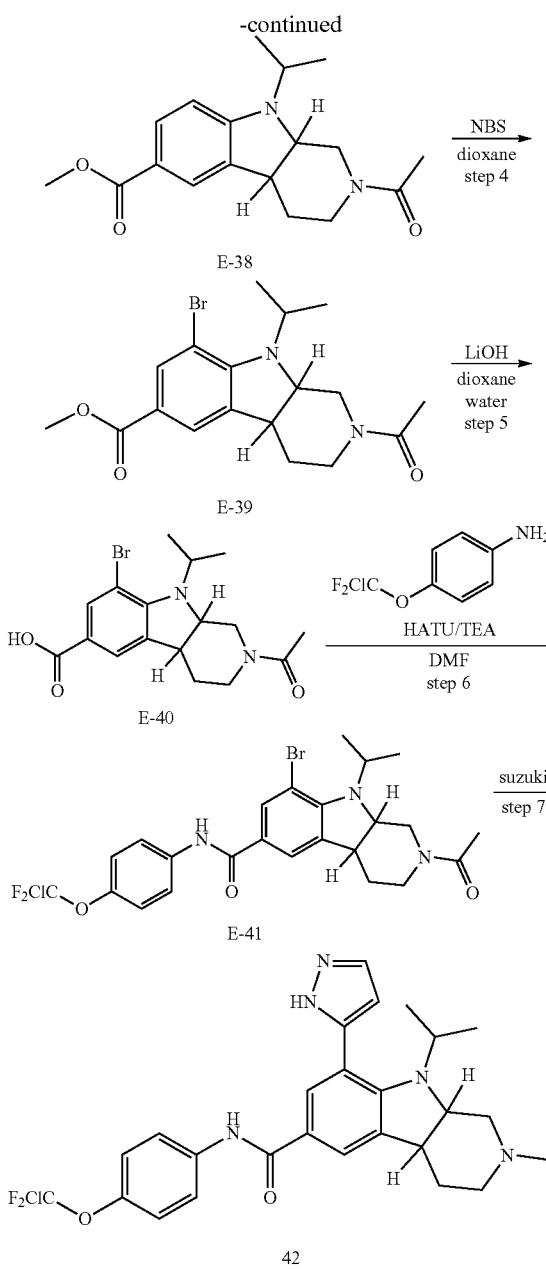

Step 1: Methyl 8-bromo-9-isopropyl-2-(4-methoxybenzyl)-2,3,4,4a,9,9a-hexahydro-1H-pyrido[3,4-b]indole-6-carboxylate (E-36)

Under nitrogen, to a solution of methyl 7-bromo-2-formyl-1-isopropyl-3-(2-oxoethyl)indoline-5-carboxylate (1.1 g, 2.99 mmol) and (4-methoxyphenyl)methanamine (0.410 g, 2.99 mmol) in methanol (15 mL) was added NaBH$_3$CN (0.375 g, 5.97 mmol) at room temperature in a nitrogen flushed 50 mL two-necked round-bottomed flask, it was stirred at room temperature for 1 h. Water (50 mL) was added to the mixture, followed by extraction with ethyl acetate (50 mL×3). The combined organic layers were washed with brine, dried over Na$_2$SO$_4$, filtrated and concentrated to give a residue, which was purified by silica gel column chromatography (ethyl acetate/hexane from 0% to 55%) to give methyl 8-bromo-9-isopropyl-2-(4-methoxybenzyl)-2,3,4,4a,9,9a-hexahydro-1H-pyrido[3,4-b]indole-6-carboxylate (720 mg, 50.9%) as a colorless oil. 1H NMR (400 MHz, Chloroform-d) δ 8.01-7.97 (m, 1H), 7.55 (t, J=1.6 Hz, 1H), 7.20 (d, J=8.6 Hz, 2H), 6.86 (d, J=8.6 Hz, 2H), 4.72-3.64 (m, 1H), 3.40-3.90 (m, 1H), 3.88 (s, 3H), 3.82 (s, 3H), 3.43 (d, J=13.0 Hz, 1H), 3.29 (d, J=13.0 Hz, 1H), 2.93-2.83 (m, 1H), 2.21 (d, J=15.2 Hz, 1H), 2.18-2.00 (m, 1H), 1.92-1.74 (m, 2H), 1.25 (d, J=6.7 Hz, 3H), 1.14 (d, J=6.5 Hz, 3H), 0.90 (t, J=6.7 Hz, 2H). MS: 473.0 (M+H)$^+$ Step 2: methyl 9-isopropyl-2,3,4,4a,9,9a-hexahydro-1H-pyrido[3,4-b]indole-6-carboxylate (E-37)

Under hydrogen, to a solution of methyl 8-bromo-9-isopropyl-2-(4-methoxybenzyl)-2,3,4,4a,9,9a-hexahydro-1H-pyrido[3,4-b]indole-6-carboxylate (500 mg, 1.056 mmol) in methanol (10 ml) was added dihydroxypalladium (74.2 mg, 0.528 mmol) at room temperature in an oven-dried 50 mL round-bottomed flask, it was stirred at refluxing temperature for 24 h. After being cooled to room temperature, the mixture was filtrated and the filtrate was concentrated to give crude product, which was used for the next step without purification. MS: 275.0 (M+H)$^+$ Step 3: Methyl 2-acetyl-9-isopropyl-2,3,4,4a,9,9a-hexahydro-1H-pyrido[3,4-b]indole-6-carboxylate Under nitrogen, to a solution of methyl 9-isopropyl-2,3,4,4a,9,9a-hexahydro-1H-pyrido[3,4-b]indole-6-carboxylate (550 mg, 2.005 mmol) and triethylamine (406 mg, 4.01 mmol) in dichloromethane (10 mL) was added acetyl chloride (315 mg, 4.01 mmol) at 0° C., it was stirred for 2 h at room temperature. Water (30 mL) was added to the mixture, followed by extraction with dichloromethane (30 mL×3). The combined organic layers were washed with brine, dried over Na$_2$SO$_4$, filtrated and concentrated to give a residue, which was purified by silica gel column chromatography (ethyl acetate/hexane from 50% to 80%) to give methyl 2-acetyl-9-isopropyl-2,3,4,4a,9,9a-hexahydro-1H-pyrido[3,4-b]indole-6-carboxylate (160 mg, 25.2%) as a yellow oil. MS: 317.1 (M+H)$^+$.

Step 4: Methyl 2-acetyl-8-bromo-9-isopropyl-2,3,4,4a,9,9a-hexahydro-1H-pyrido[3,4-b]indole-6-carboxylate (E-39)

Under nitrogen, to a solution of methyl 2-acetyl-9-isopropyl-2,3,4,4a,9,9a-hexahydro-1H-pyrido[3,4-b]indole-6-carboxylate (160 mg, 0.506 mmol) in dioxane (5 mL) was added 1-bromopyrrolidine-2,5-dione (95 mg, 0.531 mmol) in a nitrogen flushed 25 mL round-bottomed flask at room temperature, it was stirred for 1 h at room temperature. Water (30 mL) was added to the mixture, followed by extraction with ethyl acetate (30 mL×3). The combined organic layers were washed with brine, dried over Na$_2$SO$_4$, filtrated and concentrated to give a residue, which was purified by silica gel column chromatography (ethyl acetate/hexane from 50% to 70%) to give methyl 2-acetyl-8-bromo-9-isopropyl-2,3,4,4a,9,9a-hexahydro-1H-pyrido[3,4-b]indole-6-carboxylate (200 mg, 100%) as a colorless oil. MS: 394.9 (M+H)$^+$.

Step 5: 2-acetyl-8-bromo-9-isopropyl-2,3,4,4a,9,9a-hexahydro-1H-pyrido[3,4-b]indole-6-carboxylic acid (E-40)

Under nitrogen, to a solution of methyl 2-acetyl-8-bromo-9-isopropyl-2,3,4,4a,9,9a-hexahydro-1H-pyrido[3,4-b]indole-6-carboxylate (200 mg, 0.506 mmol) in dioxane (5 mL) and water (2 mL) was added potassium hydroxide (56.8 mg, 1.012 mmol) in an oven-dried 25 mL round-bottomed flask at room temperature, it was stirred for 2 h at 50° C. After being cooled to room temperature, the mixture was acidified with 1N HCl to pH=2, followed by extraction with ethyl acetate (30 mL×3). The combined organic layers were washed with brine, dried over Na$_2$SO$_4$, filtrated and concentrated to give a crude product (140 mg, 72.6%), which was used for the next step without purification. MS: 380.9 (M+H)$^+$.

Step 6: 2-acetyl-8-bromo-N-(4-(chlorodifluoromethoxy)phenyl)-9-isopropyl-2,3,4,4a,9,9a-hexahydro-1H-pyrido[3,4-b]indole-6-carboxamide (E-41)

Under nitrogen, a solution of 2-acetyl-8-bromo-9-isopropyl-2,3,4,4a,9,9a-hexahydro-1H-pyrido[3,4-b]indole-6-carboxylic acid (140 mg, 0.367 mmol), HATU (209 mg, 0.551 mmol) and triethylamine (74.3 mg, 0.734 mmol) in DMF (5 ml) was added 4-(chlorodifluoromethoxy)aniline (85 mg, 0.441 mmol) at room temperature in a nitrogen flushed 25 mL round-bottomed flask, it was stirred at room temperature for overnight. Water (30 mL) was added to the mixture, followed by extraction with ethyl acetate (30 mL×3). The combined organic layers were washed with brine, dried over Na$_2$SO$_4$, filtrated and concentrated to give a residue, which was purified by silica gel column chromatography (ethyl acetate/hexane from 10% to 50%) to give 2-acetyl-8-bromo-N-(4-(chlorodifluoromethoxy)phenyl)-9-isopropyl-2,3,4,4a,9,9a-hexahydro-1H-pyrido[3,4-b]indole-6-carboxamide (105 mg, 51.4%) as a yellow oil. MS: 555.9 (M+H)$^+$ Step 7: 2-acetyl-N-(4-(chlorodifluoromethoxy)phenyl)-9-isopropyl-8-(1H-pyrazol-5-yl)-2,3,4,4a,9,9a-hexahydro-1H-pyrido[3,4-b]indole-6-carboxamide (42)

The mixture of 2-acetyl-8-bromo-N-(4-(chlorodifluoromethoxy)phenyl)-9-isopropyl-2,3,4,4a,9,9a-hexahydro-1H-pyrido[3,4-b]indole-6-carboxamide (105 mg, 0.189 mmol), 5-(4,4,5,5-tetramethyl-1,3,2-dioxaborolan-2-yl)-1H-pyrazole (54.9 mg, 0.283 mmol), Pd(dppf)Cl$_2$·CH$_2$Cl$_2$ (15.40 mg, 0.019 mmol) and Na$_2$CO$_3$ (60.0 mg, 0.566 mmol, 3) in DME (2 mL)/water (0.6 mL) was stirred under microwave at 110° C. for 3 h. After being cooled to room temperature, it was poured into water (30 mL), followed by extraction with ethyl acetate (30 mL×3). The combined organic layers were washed with brine, dried over Na$_2$SO$_4$, filtrated and concentrated to give a residue, which was purified by silica gel column chromatography (ethyl acetate/hexane from 0% to 40%) to give 2-acetyl-N-(4-(chlorodifluoromethoxy)phenyl)-9-isopropyl-8-(1H-pyrazol-5-yl)-2,3,4,4a,9,9a-hexahydro-1H-pyrido[3,4-b]indole-6-carboxamide (46 mg, 44.8%) as a yellow oil. MS: 544.1 (M+H)$^+$ Example 43

Synthesis of 2-acetamido-N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (Compound No. 43)

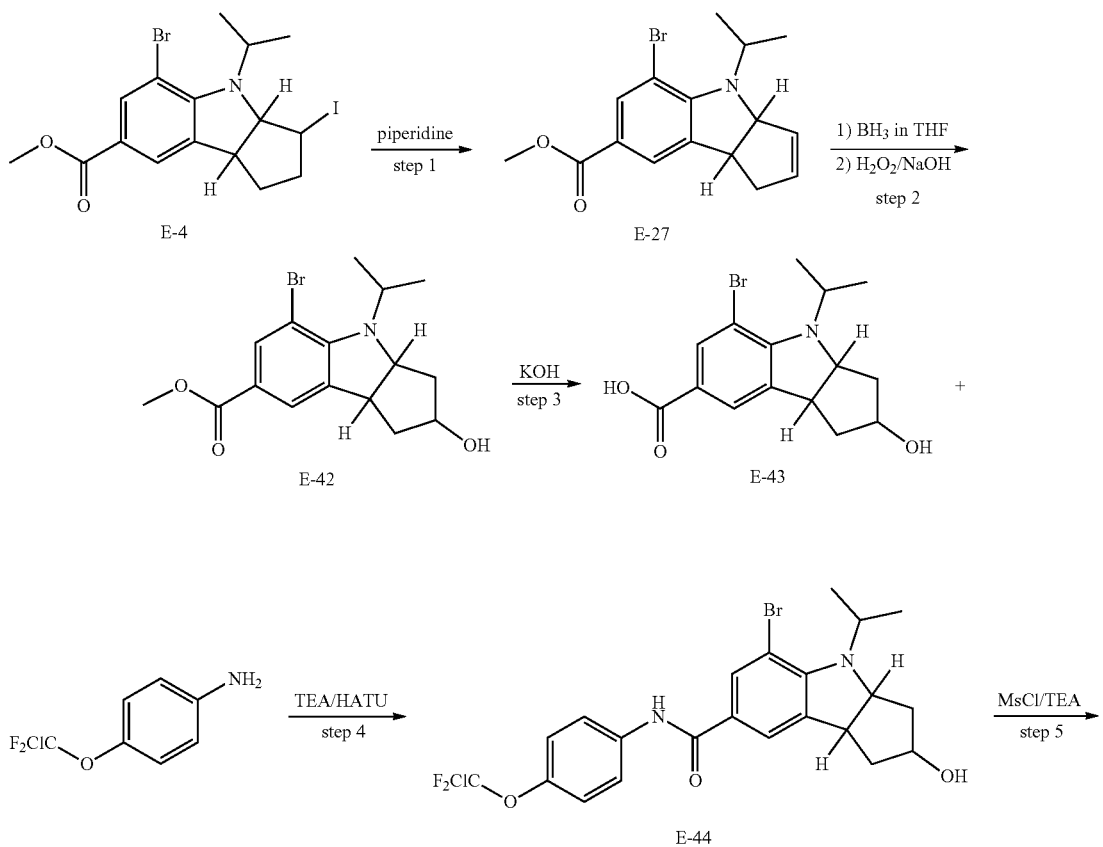

-continued

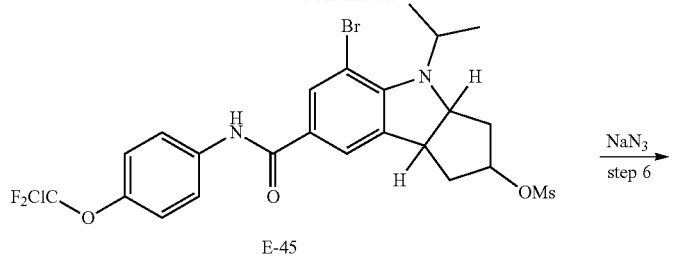
E-45

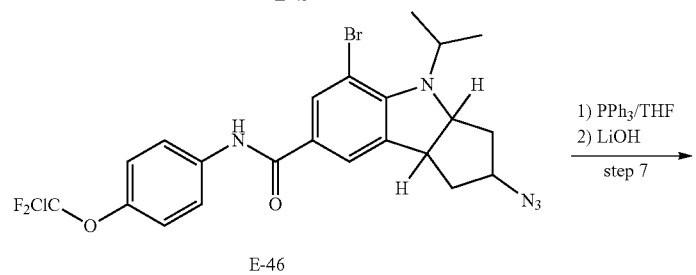
E-46

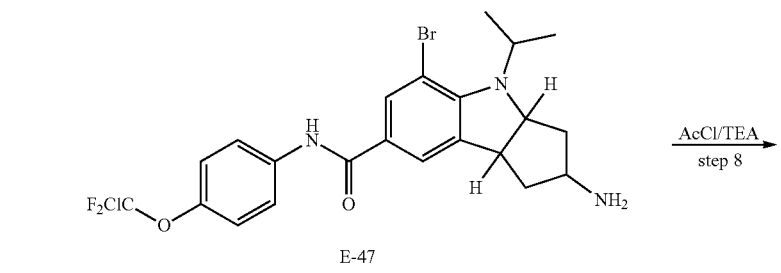
E-47

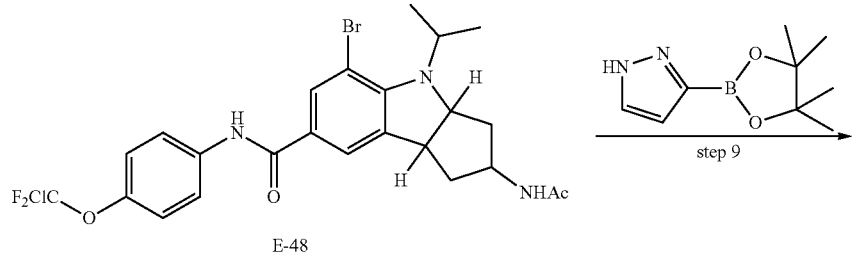
E-48

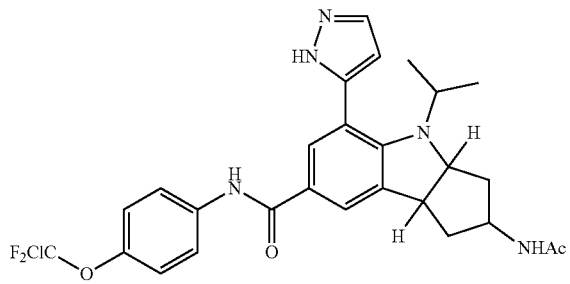
43

Step 1: Methyl 5-bromo-4-isopropyl-1,3a,4,8b-tetrahydrocyclopenta[b]indole-7-carboxylate (E-27)

Under nitrogen, the mixture of methyl 5-bromo-3-iodo-4-isopropyl-1,2,3,3a,4,8b-hexahydrocyclopenta[b]indole-7-carboxylate (4.86 g, 10.47 mmol) in DIEA (30 mL) was stirred at 120° C. for 3 h in a 100 mL round-bottomed flask. After being cooled to room temperature, water (50 mL) was added to the mixture, followed by extraction with ethyl acetate (50 mL×3). The combined organic layers were washed with brine, dried over $Na_2SO_4$, filtrated and concentrated to give a residue, which was purified by silica gel column chromatography (ethyl acetate/hexane from 0% to 25%) to give methyl 5-bromo-4-isopropyl-1,3a,4,8b-tetrahydrocyclopenta[b]indole-7-carboxylate (3.03 g, 86%) as a yellow oil. $^1$H NMR (400 MHz, Chloroform-d) δ 7.99-7.94 (m, 1H), 7.62 (s, 1H), 5.88 (m, 1H), 5.67 (m, 1H), 5.00-4.86 (m, 2H), 4.03 (t, J=8.6 Hz, 1H), 3.86 (s, 3H), 2.93 (m, 1H), 2.59 (m, 1H), 1.37 (d, J=6.8 Hz, 3H), 1.12 (d, J=6.6 Hz, 3H). MS: 335.9 (M+H)$^+$ Step 2: methyl 5-bromo-2-hydroxy-4-isopropyl-1,2, 3,3a,4,8b-hexahydrocyclopenta[b]indole-7-carboxylate (E-42)

Under nitrogen, to a solution of methyl 5-bromo-4-isopropyl-1,3a,4,8b-tetrahydrocyclopenta[b]indole-7-carboxylate (3.03 g, 9.01 mmol) in THF (5 mL) was added borane (0.374 g, 27.0 mmol) at 0° C., it was stirred for 1 h at room temperature. Then $H_2O_2$ (30%, 1.2 mL) aqueous and NaOH (3N, 1.2 mL) aqueous were added dropwise to the mixture at 0° C., stirred for 1 h at room temperature. The mixture was acidified with 1N HCl to Ph=7, followed by extraction with ethyl acetate (50 mL×3). The combined organic layers were washed with brine, dried over $Na_2SO_4$, filtrated and concentrated to give a residue, which was purified by silica gel column chromatography (ethyl acetate/hexane from 25% to 30%) to give methyl 5-bromo-2-hydroxy-4-isopropyl-1,2,3, 3a,4,8b-hexahydrocyclopenta[b]indole-7-carboxylate (539 mg, 16.93%) as a white oil. $^1$H NMR (400 MHz, $CDCl_3$) δ 7.94 (d, J=1.5 Hz, 1H), 7.59 (s, 1H), 5.02-4.89 (m, 1H), 4.17-4.11 (m, 1H), 4.02 (d, J=9.2 Hz, 1H), 3.94 (d, J=8.4 Hz, 1H), 3.93 (t, J=8.6 Hz, 1H), 3.85 (s, 3H), 2.40-2.26 (m, 1H), 1.88-1.76 (m, 1H), 1.71-1.61 (m, 1H), 1.57-1.49 (m, 1H), 1.48-1.42 (m, 1H), 1.37 (d, J=6.9 Hz, 3H), 1.01 (d, J=6.5 Hz, 3H).

Step 3: 5-bromo-2-hydroxy-4-isopropyl-1,2,3,3a,4, 8b-hexahydrocyclopenta[b]indole-7-carboxylic acid (E-43)

Under nitrogen, to a solution of methyl 5-bromo-2-hydroxy-4-isopropyl-1,2,3,3a,4,8b-hexahydrocyclopenta[b]indole-7-carboxylate (170 mg, 0.480 mmol) in dioxane (5 mL) was added potassium hydroxide (53.8 mg, 0.960 mmol) in water (2 mL) in a 50 mL round-bottomed flask at room temperature, it was stirred for 2 h at 50° C. After being cooled to room temperature, the mixture was acidified with 2N HCl to pH=3, followed by extraction with ethyl acetate (30 mL×3). The combined organic layers were washed with brine, dried over $Na_2SO_4$, filtrated and concentrated to give a crude product, which was used for the next step without purification. MS: 339.9 (M+H)$^+$ Step 4: 5-bromo-N-(4-(chlorodifluoromethoxy)phenyl)-2-hydroxy-4-isopropyl-1,2,3,3a,4,8b-hexahydrocyclopenta[b]indole-7-carboxamide (E-44)

Under nitrogen, to a solution of 5-bromo-2-hydroxy-4-isopropyl-1,2,3,3a,4,8b-hexahydrocyclopenta[b]indole-7-carboxylic acid (160 mg, 0.470 mmol) in DMF (5 mL) was added HATU (268 mg, 0.705 mmol) and triethylamine (95 mg, 0.941 mmol) and 4-(chlorodifluoromethoxy)aniline (109 mg, 0.564 mmol), it was stirred overnight at room temperature. Water (30 mL) was added to the mixture, followed by extraction with ethyl acetate (30 mL×3). The combined organic layers were washed with brine, dried over $Na_2SO_4$, filtrated and concentrated to give a residue, which was purified by silica gel column chromatography (ethyl acetate/hexane from 10% to 50%) to give 5-bromo-N-(4-(chlorodifluoromethoxy)phenyl)-2-hydroxy-4-isopropyl-1, 2,3,3a,4,8b-hexahydrocyclopenta[b]indole-7-carboxamide (160 mg, 66.0%) as a yellow solid. MS: 515.0 (M+H)

Step 5: 5-bromo-7-((4-(chlorodifluoromethoxy)phenyl)carbamoyl)-4-isopropyl-1,2,3,3a,4,8b-hexahydrocyclopenta[b]indol-2-yl methanesulfonate (E-45)

Under nitrogen, to a solution of 5-bromo-N-(4-(chlorodifluoromethoxy)phenyl)-2-hydroxy-4-isopropyl-1,2,3,3a,4, 8b-hexahydrocyclopenta[b]indole-7-carboxamide (450 mg, 0.872 mmol) and triethylamine (177 mg, 1.745 mmol) in dichloromethane (10 mL) was added methanesulfonyl chloride (200 mg, 1.745 mmol) dropwise at 0° C. in a 100 mL three-necked round-bottomed flask, it was stirred for 2 h at 0° C. Water (30 mL) was added to the mixture, followed by extraction with dichloromethane (30 mL×3). The combined organic layers were washed with brine, dried over $Na_2SO_4$, filtrated and concentrated to give a residue, which was purified by silica gel column chromatography (ethyl acetate/ hexane from 0% to 40%) to give 5-bromo-7-((4-(chlorodifluoromethoxy)phenyl)carbamoyl)-4-isopropyl-1,2,3,3a,4, 8b-hexahydrocyclopenta[b]indol-2-yl methanesulfonate (397 mg, 77%) as a white solid. $^1$H NMR (400 MHz, $CDCl_3$) δ 7.77 (s, 1H), 7.68 (s, 1H), 7.65 (d, J=9.0 Hz, 2H), 7.48 (s, 1H), 7.24 (d, J=9.0 Hz, 2H), 5.17-5.09 (m, 1H), 4.97 (m, 1H), 4.51-4.41 (m, 1H), 4.08-3.97 (m, 1H), 3.04 (s, 3H), 2.67-2.42 (m, 2H), 2.10-1.96 (m, 2H), 1.30 (d, J=6.8 Hz, 3H), 1.05 (d, J=6.5 Hz, 3H). MS: 592.9 (M+H)$^+$.

Step 6: 2-azido-5-bromo-N-(4-(chlorodifluoromethoxy)phenyl)-4-isopropyl-1,2,3,3a,4,8b-hexahydro cyclopenta[b]indole-7-carboxamide (E-46)

Under nitrogen, to a solution of 5-bromo-7-((4-(chlorodifluoromethoxy)phenyl)carbamoyl)-4-isopropyl-1,2,3,3a,4, 8b-hexahydrocyclopenta[b]indol-2-yl methanesulfonate (397 mg, 0.669 mmol) in acetone (10 mL) and water (1 mL) was added sodium azide (217 mg, 3.34 mmol) at room temperature in a 50 mL round-bottomed flask, it was stirred for 8 h at 80° C. After being cooled to room temperature, water (30 mL) was added to the mixture, followed by extraction with ethyl acetate (30 mL×3). The combined organic layers were washed with brine, dried over $Na_2SO_4$ and concentrated to give a residue, which was purified by silica gel column chromatography (ethyl acetate/hexane from 25% to 30%) o give 2-azido-5-bromo-N-(4-(chlorodifluoromethoxy)phenyl)-4-isopropyl-1,2,3,3a,4,8b-hexahydro cyclopenta[b]indole-7-carboxamide (250 mg, 69.2%) as a white solid. $^1$H NMR (400 MHz, $CDCl_3$) δ 7.74 (s, 1H), 7.68 (s, 1H), 7.65 (d, J=9.0 Hz, 2H), 7.47 (s, 1H), 7.23 (d, J=8.8 Hz, 2H), 5.01 (dt, J=13.3, 6.7 Hz, 1H), 4.36-4.21 (m, 1H), 4.02-3.93 (m, 1H), 3.92-3.80 (m, 1H), 2.47-2.23 (m, 2H), 2.1.96-1.83 (m, 2H), 1.32 (d, J=6.8 Hz, 3H), 1.05 (d, J=6.5 Hz, 3H).

Step 7: 2-amino-5-bromo-N-(4-(chlorodifluoromethoxy)phenyl)-4-isopropyl-1,2,3,3a,4,8b-hexahydrocyclopenta[b]indole-7-carboxamide (E-47)

Under nitrogen, to a solution of 2-azido-5-bromo-N-(4-(chlorodifluoromethoxy)phenyl)-4-isopropyl-1,2,3,3a,4,8b-hexahydro cyclopenta[b]indole-7-carboxamide (250 mg, 0.462 mmol) in THF (5 mL) was added triphenylphosphine (158 mg, 0.601 mmol) at room temperature in a 50 mL round-bottomed flask, it was stirred for 3 h at 50° C., then lithium hydroxide (22.14 mg, 0.925 mmol) in water (1 mL) was added to the mixture. The mixture was stirred for overnight at 50° C. Water (30 mL) was added to the mixture, followed by extraction with ethyl acetate (30 mL×3). The combined organic layers were washed with brine, dried over $Na_2SO_4$, filtrated and concentrated to give a residue, which was purified by silica gel column chromatography (ethyl acetate/hexane from 20% to 40%) to give 2-amino-5-bromo-N-(4-(chlorodifluoromethoxy)phenyl)-4-isopropyl-1,2,3,3a, 4,8b-hexahydrocyclopenta[b]indole-7-carboxamide (195 mg, 82%) as a white solid. $^1$H NMR (400 MHz, $CDCl_3$) δ

7.84 (s, 1H), 7.75 (s, 1H), 7.66 (d, J=8.3 Hz, 2H), 7.46 (s, 1H), 7.22 (d, J=8.7 Hz, 2H), 5.10-4.90 (m, 1H), 4.27-4.13 (m, 1H), 3.82-3.67 (m, 1H), 3.36-3.22 (m, 1H), 2.54-2.25 (m, 2H), 1.61-1.57 (m, 2H), 1.57-1.44 (m, 2H), 1.29 (d, J=6.7 Hz, 3H), 1.05 (d, J=6.3 Hz, 3H). 513.9 (M+H)+.

Step 8: 2-acetamido-5-bromo-N-(4-(chlorodifluoromethoxy)phenyl)-4-isopropyl-1,2,3,3a,4,8b-hexahydrocyclopenta[b]indole-7-carboxamide (E-48)

Under nitrogen, to a solution of 2-amino-5-bromo-N-(4-(chlorodifluoromethoxy)phenyl)-4-isopropyl-1,2,3,3a,4,8b-hexahydrocyclopenta[b]indole-7-carboxamide (190 mg, 0.369 mmol) and triethylamine (74.7 mg, 0.738 mmol) in dichloromethane (5 mL) was added acetyl chloride (57.9 mg, 0.738 mmol) dropwise at 0° C., it was stirred for 2 h at room temperature. Water (30 mL) was added to the mixture, followed by extraction with dichloromethane (30 mL×3). The combined organic layers were washed with brine, dried over Na$_2$SO$_4$, filtrated and concentrated to give a residue, which was purified by silica gel chromatography (methanol/dichloromethane from 5% to 15%) to give 2-acetamido-5-bromo-N-(4-(chlorodifluoromethoxy)phenyl)-4-isopropyl-1,2,3,3a,4,8b-hexahydrocyclopenta[b]indole-7-carboxamide (167 mg, 81%) as a white solid. $^1$H NMR (400 MHz, Chloroform-d) δ 7.93 (s, 1H), 7.83 (d, J=1.7 Hz, 1H), 7.74-7.65 (m, 2H), 7.48 (t, J=1.5 Hz, 1H), 7.29-7.21 (m, 2H), 5.65 (d, J=7.2 Hz, 1H), 5.03-4.97 (m, 1H), 4.37-4.32 (m, 1H), 4.29-4.23 (m, 1H), 3.89-3.84 (m, 1H), 2.44-2.26 (m, 2H), 1.90-1.76 (m, 2H), 1.74 (s, 3H), 1.34 (d, J=6.9 Hz, 3H), 1.05 (d, J=6.5 Hz, 3H). MS: 555.9 (M+H)+.

Step 9: 2-acetamido-N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (43)

The mixture of 2-acetamido-5-bromo-N-(4-(chlorodifluoromethoxy)phenyl)-4-isopropyl-1,2,3,3a,4,8b-hexahydrocyclopenta[b]indole-7-carboxamide (68 mg, 0.122 mmol), 5-(4,4,5,5-tetramethyl-1,3,2-dioxaborolan-2-yl)-1H-pyrazole (35.5 mg, 0.183 mmol), Pd(dppf)Cl$_2$·CH$_2$Cl$_2$ (9.97 mg, 0.012 mmol) and Na$_2$CO$_3$ (38.8 mg, 0.366 mmol) in DME (2 mL)/water (0.6 mL) was stirred under microwave at 110° C. for 3 h. After being cooled to room temperature, the mixture was concentrated to give a residue, which was purified by silica gel column chromatography (ethyl acetate/hexane from 0% to 60%) to give 2-acetamido-N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (10.5 mg, 15.81%) as a yellow oil.

Example 44

Synthesis of N-(4-(chlorodifluoromethoxy)phenyl)-4-isopropyl-3-(N-methylacetamido)-5-(1H-pyrazol-5-yl)-1,2,3,3a,4,8b-hexahydrocyclopenta[b]indole-7-carboxamide (Compound No. 44)

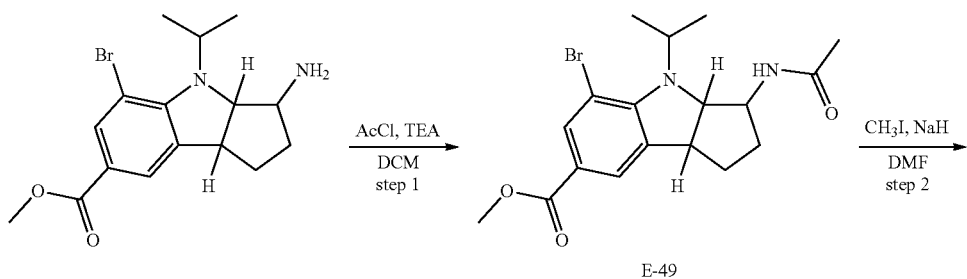

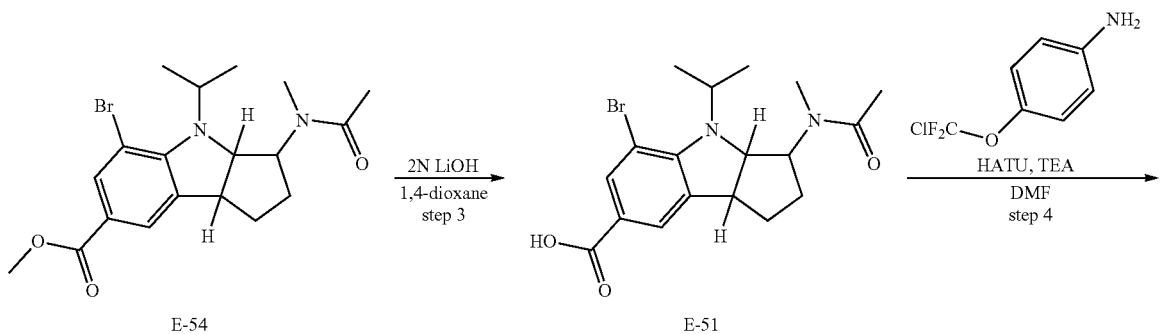

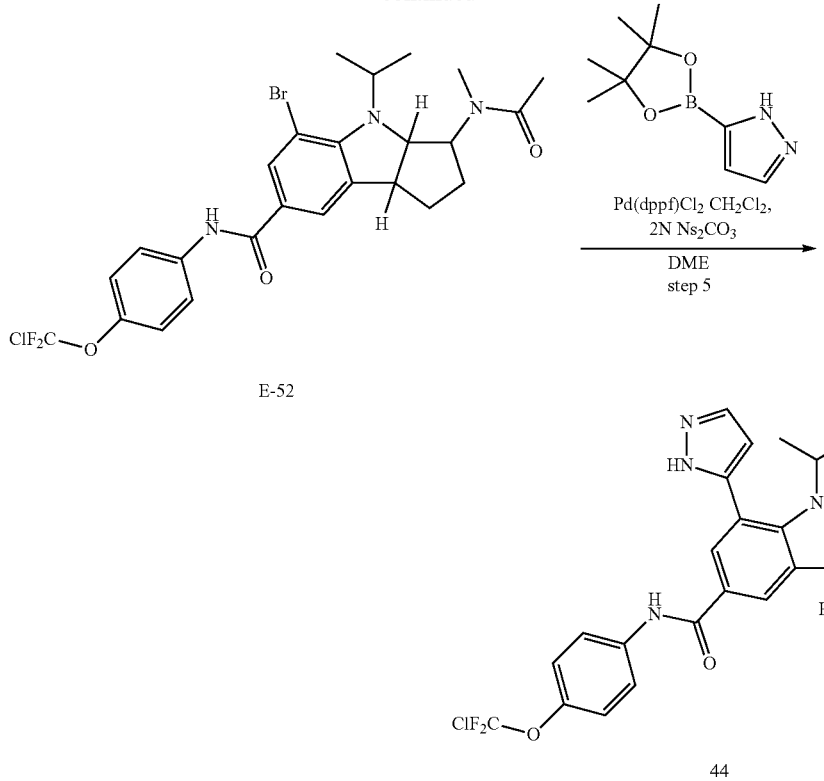

Step 1: Synthesis of Methyl 3-acetamido-5-bromo-4-isopropyl-1,2,3,3a,4,8b-hexahydrocyclopenta[b]indole-7-carboxylate (E-49)

Under Ar, to a solution of methyl 3-amino-5-bromo-4-isopropyl-1,2,3,3a,4,8b-hexahydrocyclopenta[b]indole-7-carboxylate (0.4 g, 1.132 mmol) in dichloromethane (10 mL) was added triethylamine (0.229 g, 2.265 mmol) and acetyl chloride (0.133 g, 1.698 mmol) at room temperature, it was stirred at room temperature for 2 h, then quenched with $Na_2CO_3$ aqueous solution, followed by extraction with dichloromethane (30 mL×3). The combined organic layers were washed with brine, dried $Na_2SO_4$, filtrated and concentrated to give a residue, which was purified by silica gel column chromatography (methanol/dichloromethane from 0% to 10%) to give methyl-3-acetamido-5-bromo-4-isopropyl-1,2,3,3a,4,8b-hexahydrocyclopenta[b]indole-7-carboxylat e (0.36 g, 80%) as a yellow oil.

Step 2: Synthesis of Methyl-5-bromo-4-isopropyl-3-(N-methylacetamido)-1,2,3,3a,4,8b-hexahydrocyclopenta[b]indole-7-carboxylate (E-50)

Under Ar, to a solution of methyl-3-acetamido-5-bromo-4-isopropyl-1,2,3,3a,4,8b-hexahydrocyclopenta[b]indole-7-carboxylate (200 mg, 0.506 mmol) in DMF (5 mL) was added sodium hydride (40.5 mg, 1.012 mmol) at room temperature, stirred at room temperature for 5 min. Iodomethane (144 mg, 1.012 mmol) was added to the mixture, and it was stirred at room temperature for 12 h, then quenched with $NH_4Cl$ aqueous solution, followed by extraction with ethyl acetate (30 mL×3). The combined organic layers were washed with brine, dried $Na_2SO_4$, filtrated and concentrated to give a residue, which was purified by silica gel column chromatography (ethyl acetate/hexane from 0% to 50%) to give methyl-5-bromo-4-isopropyl-3-(N-methylacetamido)-1,2,3,3a,4,8b-hexahydrocyclopenta[b]indole-7-carboxylate (130 mg, 62.8%) as a yellow oil.

Step 3: Synthesis of -5-bromo-4-isopropyl-3-(N-methylacetamido)-1,2,3,3a,4,8b-hexahydrocyclopenta[b]indole-7-carboxylic acid (E-51)

To a solution of methyl-5-bromo-4-isopropyl-3-(N-methylacetamido)-1,2,3,3a,4,8b-hexahydrocyclopenta[b]indole-7-carboxylate (130 mg, 0.318 mmol) in 1,4-dioxane (2.5 mL)/water (0.500 mL) was added lithium hydroxide (15.21 mg, 0.635 mmol) at room temperature, it was stirred at 45° C. for 12 h. The mixture was acidified with 1N HCl (2.0 mL) to Ph=4, followed by extraction with ethyl acetate (15 mL×3). The combined organic layers were washed with brine, dried $Na_2SO_4$, filtrated and concentrated to give a crude product (0.1 g, 80%), which was used for the next step without purification.

Step 4: Synthesis of -5-bromo-N-(4-(chlorodifluoromethoxy)phenyl)-4-isopropyl-3-(N-methylacetamido)-1,2,3,3a,4,8b-hexahydrocyclopenta[b]indole-7-carboxamide (E-52)

Under Ar, to a solution of -5-bromo-4-isopropyl-3-(N-methylacetamido)-1,2,3,3a,4,8b-hexahydrocyclopenta[b]indole-7-carboxylic acid (0.1 g, 0.253 mmol) in DMF (2 mL) was added triethylamine (0.051 g, 0.506 mmol), 4-(chlorodifluoromethoxy)aniline (0.098 g, 0.506 mmol) and HATU (0.115 g, 0.304 mmol) at room temperature, it was stirred at 45° C. for 10 h. After being cooled to room temperature, water (20 mL) was added to the mixture, followed by extraction with ethyl acetate (20 mL×3). The combined organic layers were washed with brine, dried Na$_2$SO$_4$, filtrated and concentrated to give a residue, which was purified by silica gel column chromatography (ethyl acetate/hexane from 0% to 50%) to give -5-bromo-N-(4-(chlorodifluoromethoxy)phenyl)-4-isopropyl-3-(N-methylacetamido)-1,2,3,3a,4,8b-hexahydrocyclopenta[b]indole-7-carboxamide (0.127 g, 88%) as a yellow oil.

Step 5: Synthesis of —N-(4-(chlorodifluoromethoxy)phenyl)-4-isopropyl-3-(N-methylacetamido)-5-(1H-pyrazol-5-yl)-1,2,3,3a,4,8b-hexahydrocyclopenta[b]indole-7-carboxamide (44)

The mixture of 5-(4,4,5,5-tetramethyl-1,3,2-dioxaborolan-2-yl)-1H-pyrazole (68.0 mg, 0.350 mmol), PdCl$_2$(dppf)-CH$_2$Cl$_2$ adduct (28.6 mg, 0.035 mmol) and -5-bromo-N-(4-(chlorodifluoromethoxy)phenyl)-4-isopropyl-3-(N-methylacetamido)-1,2,3,3a,4,8b-hexahydrocyclopenta[b]indole-7-carboxamide (100 mg, 0.175 mmol) in DME (0.9 ml)/2N Na$_2$CO$_3$ (0.300 mL) in microwave tube was stirred under microwave at 100° C. for 30 min. After being cooled to room temperature, the mixture was poured into water (20 mL), followed by extraction with ethyl acetate (20 mL×3). The combine organic layers were washed with brine, dried over Na$_2$SO$_4$, filtrated and concentrated to give a residue, which was purified using Prep HPLC to give —N-(4-(chlorodifluoromethoxy)phenyl)-4-isopropyl-3-(N-methylacetamido)-5-(1H-pyrazol-5-yl)-1,2,3,3a,4,8b-hexahydrocyclopenta[b]indole-7-carboxamide (21.6 mg, 22.10%) as a white solid. $^1$H NMR (400 MHz, dimethylsulfoxide-d$_6$)) δ 10.25-10.21 (m, 1H), 8.11-7.93 (m, 1H), 7.88 (d, J=9.0 Hz, 2H), 7.84-7.61 (m, 2H), 7.34 (d, J=9.0 Hz, 2H), 6.67-6.51 (m, 1H), 4.69-3.90 (m, 2H), 3.88-3.74 (m, 1H), 3.56-3.52 (m, 1H), 2.98-2.82 (m, 3H), 2.46-2.33 (m, 1H), 2.12-2.04 (m, 3H), 1.85-1.62 (m, 3H), 0.94-0.92 (m, 3H), 0.72-0.70 (m, 3H). MS: 558.2 (M+H)$^+$.

Example 45

Preparation of (3R,3aR,8bS)-3-acetamido-N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (Compound No. 4-A)

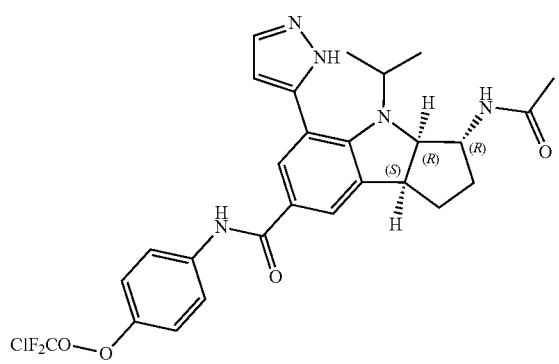

Compound No. 4 was separated through Prep-SFC by the following separation condition to give pure optical stereoisomer 4-A:

| Column | CHIRALPAK IH |
|---|---|
| Column size | 2 cm × 25 cm, 5 um |
| Injection | 1.5 mL |
| Mobile phase | CO2:MeOH = 80:20 |
| Flow rate | 50 mL/min |
| Wave length | UV 220 nm |
| Temperature | 35° C. |
| Sample solution | 29 mg/ml in MeOH |
| Retention time | 1.319 min |

Example 46

Preparation of (3S,3aS,8bR)-3-acetamido-N-(4-(chlorodifluoromethoxy)phenyl)-4-isopropyl-5-(1H-pyrazol-5-yl)-1,2,3,3a,4,8b-hexahydrocyclopenta[b]indole-7-carboxamide (Compound No. 4-B)

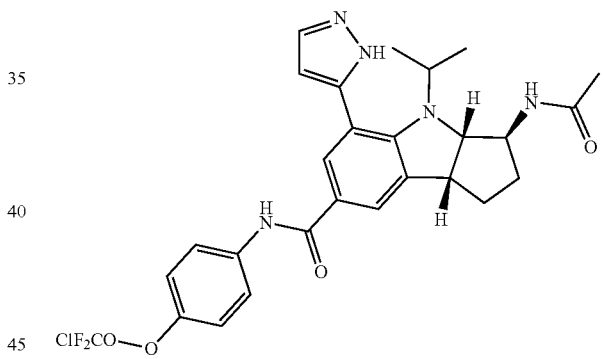

Compound No. 4 was separated through Prep-SFC by the following separation condition to give pure optical stereoisomer 4-B:

| Column | CHIRALPAK IH |
|---|---|
| Column size | 2 cm × 25 cm, 5 um |
| Injection | 1.5 mL |
| Mobile phase | CO2:MeOH = 80:20 |
| Flow rate | 50 mL/min |
| Wave length | UV 220 nm |
| Temperature | 35° C. |
| Sample solution | 29 mg/ml in MeOH |
| Retention time | 1.866 min |

Example 47

Preparation of (3R,3aR,8bS)-3-acetamido-N-(4-(chlorodifluoromethoxy)phenyl)-4-isopropyl-5-(pyrimidin-5-yl)-1,2,3,3a,4,8b-hexahydrocyclopenta[b]indole-7-carboxamide (Compound No. 20-A)

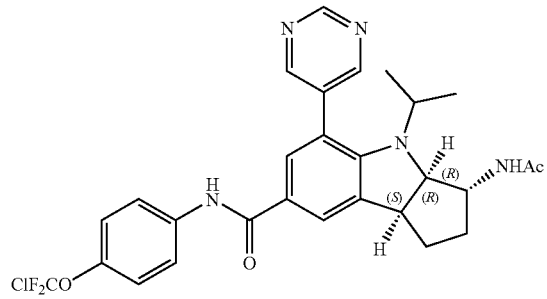

Compound No. 20 was separated through Prep-Chiral HPLC by the following separation condition to give pure optical stereoisomer 20-A:

| | |
|---|---|
| Column | CHIRALPAK IC |
| Column size | 2 cm × 25 cm, 5 um |
| Injection | 1.0 mL |
| Mobile phase | Hex:EtOH = 70:30 |
| Flow rate | 20 mL/min |
| Wave length | UV 220 nm |
| Temperature | 25° C. |
| Sample solution | 20 mg/ml in EtOH |
| Retention time | 1.221 min |

Example 48

Preparation of (3S,3aS,8bR)-3-acetamido-N-(4-(chlorodifluoromethoxy)phenyl)-4-isopropyl-5-(pyrimidin-5-yl)-1,2,3,3a,4,8b-hexahydrocyclopenta[b]indole-7-carboxamide (Compound No. 20-B)

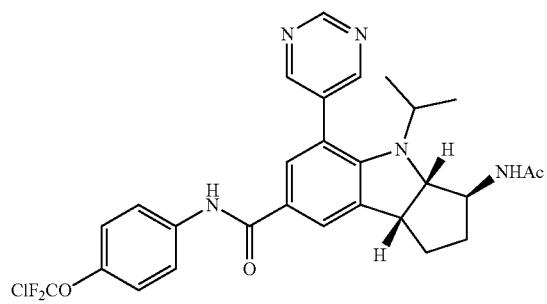

Compound No. 20 was separated through Prep-Chiral HPLC by the following separation condition to give pure optical stereoisomer 20-B:

| | |
|---|---|
| Column | CHIRALPAK IC |
| Column size | 2 cm × 25 cm, 5 um |
| Injection | 1.0 mL |
| Mobile phase | Hex:EtOH = 70:30 |
| Flow rate | 20 mL/min |
| Wave length | UV 220 nm |
| Temperature | 25° C. |
| Sample solution | 20 mg/ml in EtOH |
| Retention time | 2.453 min |

Example 49

Preparation of (3R,3aR,8bS)-3-acetamido-N-(4-(chlorodifluoromethoxy)phenyl)-4-neopentyl-5-(1H-pyrazol-5-yl)-1,2,3,3a,4,8b-hexahydrocyclopenta[b]indole-7-carboxamide (Compound No. 22-A)

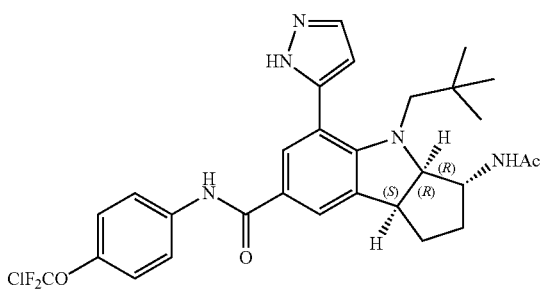

Compound No. 22 was separated through Prep-SFC by the following separation condition to give pure optical stereoisomer 22-A:

| | |
|---|---|
| Column | CHIRALPAK IG |
| Column size | 3 cm × 25 cm, 5 um |
| Injection | 1.5 mL |
| Mobile phase | CO2:MeOH = 75:25 |
| Flow rate | 55 mL/min |
| Wave length | UV 220 nm |
| Temperature | 35° C. |
| Sample solution | 5.6 mg/ml in MeOH |
| Retention time | 2.414 min |

Example 50

Preparation of (3S,3aS,8bR)-3-acetamido-N-(4-(chlorodifluoromethoxy)phenyl)-4-neopentyl-5-(1H-pyrazol-5-yl)-1,2,3,3a,4,8b-hexahydrocyclopenta[b]indole-7-carboxamide (Compound No. 22-B)

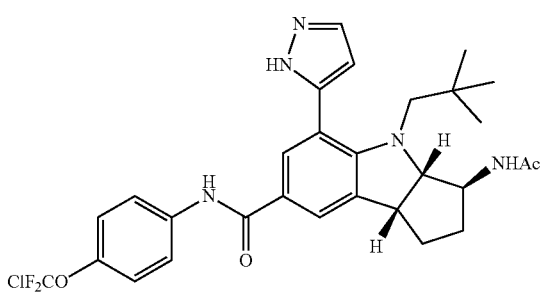

Compound No. 22 was separated through Prep-SFC by the following separation condition to give pure optical stereoisomer 22-B:

| Column | CHIRALPAK IG |
|---|---|
| Column size | 3 cm × 25 cm, 5 um |
| Injection | 1.5 mL |
| Mobile phase | CO2:MeOH = 75:25 |
| Flow rate | 55 mL/min |
| Wave length | UV 220 nm |
| Temperature | 35° C. |
| Sample solution | 5.6 mg/ml in MeOH |
| Retention time | 1.753 min |

Example 51

Preparation of (3R,3aR,8bS)-3-acetamido-N-(4-(chlorodifluoromethoxy)phenyl)-4-isopropyl-5-(pyridin-3-yl)-1,2,3,3a,4,8b-hexahydrocyclopenta[b]indole-7-carboxamide (Compound No. 26-A)

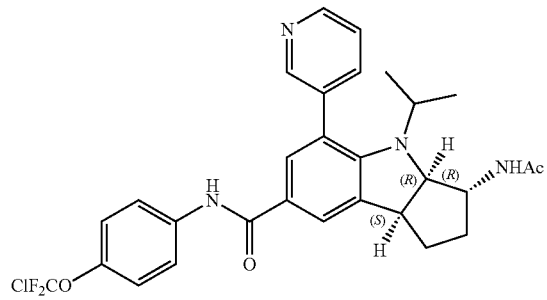

Compound No. 26 was separated through Prep-Chiral HPLC by the following separation condition to give pure optical stereoisomer 26-A:

| Column | CHIRALPAK IC |
|---|---|
| Column size | 2 cm × 25 cm, 5 um |
| Injection | 1.0 mL |
| Mobile phase | Hex:EtOH = 70:30 |
| Flow rate | 20 mL/min |
| Wave length | UV 220 nm |
| Temperature | 25° C. |
| Sample solution | 20 mg/ml in EtOH |
| Retention time | 2.988 min |

Example 52

Preparation of (3S,3aS,8bR)-3-acetamido-N-(4-(chlorodifluoromethoxy)phenyl)-4-isopropyl-5-(pyridin-3-yl)-1,2,3,3a,4,8b-hexahydrocyclopenta[b]indole-7-carboxamide (Compound No. 26-B)

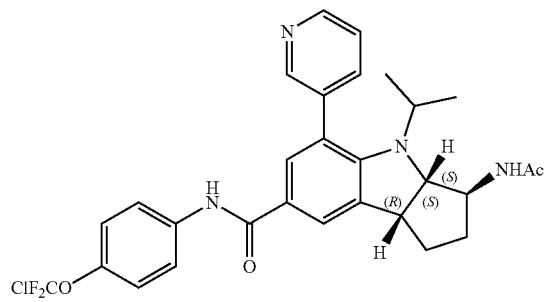

Compound No. 26 was separated through Prep-Chiral HPLC by the following separation condition to give pure optical stereoisomer 26-B:

| Column | CHIRALPAK IC |
|---|---|
| Column size | 2 cm × 25 cm, 5 um |
| Injection | 1.0 mL |
| Mobile phase | Hex:EtOH = 70:30 |
| Flow rate | 20 mL/min |
| Wave length | UV 220 nm |
| Temperature | 25° C. |
| Sample solution | 20 mg/ml in EtOH |
| Retention time | 4.010 min |

Example 54

Synthesis of (4aS,9aR)-N-(4-(chlorodifluoromethoxy)phenyl)-9-isopropyl-8-(1H-pyrazol-5-yl)-1,3,4,4a,9,9a-hexahydrothiopyrano[3,4-b]indole-6-carboxamide 2,2-dioxide (Compound No. 54 and Compound No. 54-A)

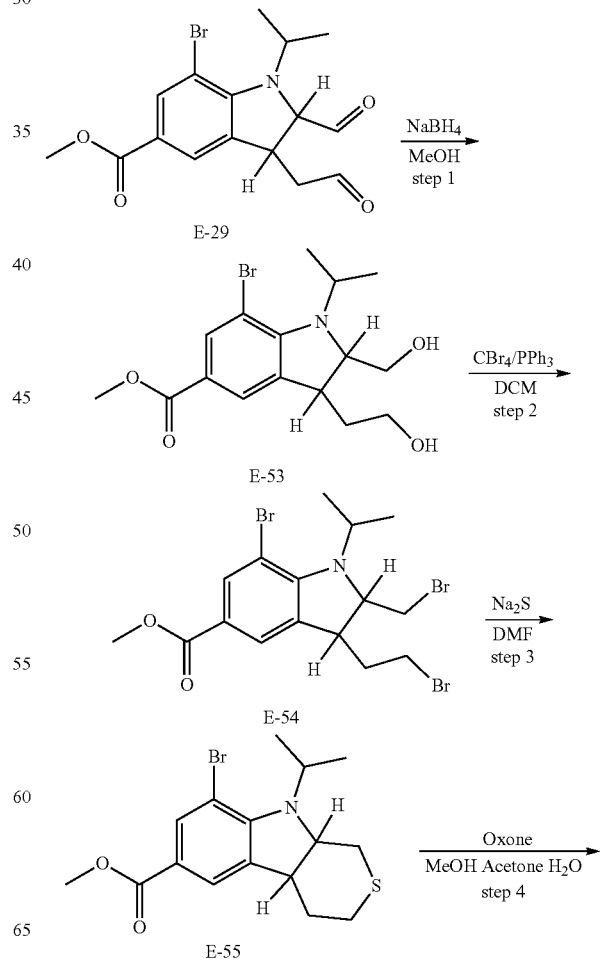

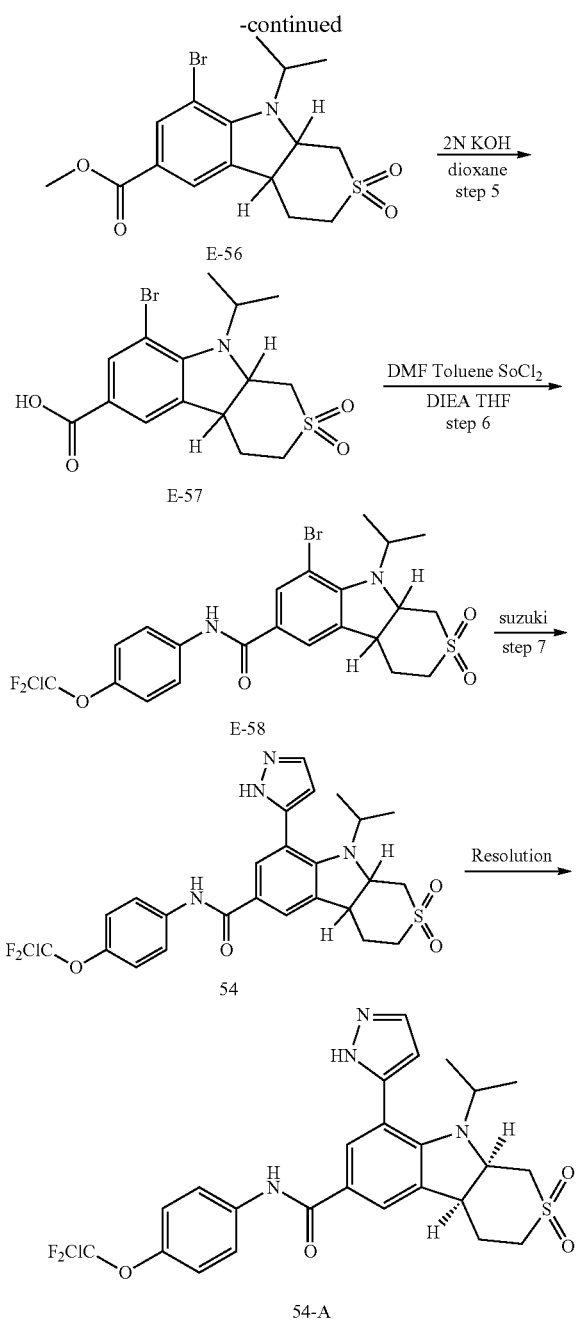

methyl 7-bromo-3-(2-hydroxyethyl)-2-(hydroxymethyl)-1-isopropylindoline-5-carboxylate (650 mg, 78%) as an oil. MS: 372.9 (M+H+). $^1$H NMR (400 MHz, Chloroform-d) δ 8.05-8.00 (m, 1H), 7.65 (t, J=1.6 Hz, 1H), 4.50-4.40 (m, 1H), 3.97-2.87 (m, 3H), 3.91 (s, 3H), 3.77-3.69 (m, 1H), 3.64 (dd, J=11.1, 5.3 Hz, 1H), 3.38 (dd, J=11.0, 7.6 Hz, 1H), 2.15 (d, J=4.9 Hz, 1H), 2.00-1.82 (m, 1H), 1.35 (d, J=6.8 Hz, 3H), 1.08 (d, J=6.6 Hz, 3H).

Step 2: Methyl 7-bromo-3-(2-bromoethyl)-2-(bromomethyl)-1-isopropylindoline-5-carboxylate (E-54)

In an oven-dried 50 mL round-bottomed flask, methyl 7-bromo-3-(2-hydroxyethyl)-2-(hydroxymethyl)-1-isopropylindoline-5-carboxylate (560 mg, 1.504 mmol) was dissolved in DCM (5 mL) under nitrogen to give a colorless solution. The reaction mixture was cooled in an ice/water bath at 0° C. CBr$_4$ (1247 mg, 3.76 mmol) and triphenylphosphine (986 mg, 3.76 mmol) were added to the reaction mixture in one portion. The mixture was stirred at room temperature for 2 hours, then eluted directly with ethyl acetate/hexane to give methyl 7-bromo-3-(2-bromoethyl)-2-(bromomethyl)-1-isopropylindoline-5-carboxylate (380 mg, 50.7%) as an oil. MS: 499.0 (M+H+). $^1$H NMR (400 MHz, Chloroform-d) δ 8.02 (t, J=1.8 Hz, 1H), 7.60-7.56 (m, 1H), 4.68-4.56 (m, 1H), 4.16-4.06 (m, 1H), 3.92-3.80 (m, 2H), 3.88 (s, 3H), 3.77-3.62 (m, 2H), 3.48-3.32 (m, 2H), 2.57-2.35 (m, 1H), 1.39 (d, J=6.8 Hz, 3H), 1.12 (d, J=6.6 Hz, 3H).

Step 3: Methyl 8-bromo-9-isopropyl-1,3,4,4a,9,9a-hexahydrothiopyrano[3,4-b]indole-6-carboxylate (E-55)

In an oven-dried 50 mL round-bottomed flask, methyl 7-bromo-3-(2-bromoethyl)-2-(bromomethyl)-1-isopropylindoline-5-carboxylate (380 mg, 0.763 mmol) was dissolved in DMF (5 mL) under nitrogen to give a colorless solution. To the solution was added Na$_2$S (126 mg, 2.289 mmol) in one portion. The reaction mixture was heated in an oil bath at 50° C., then quenched with water, followed by extraction with ethyl acetate. The combined organic layers were dried over Na$_2$SO$_4$, filtered and concentrated. The crude product was eluted with ethyl acetate/hexane to give methyl 8-bromo-9-isopropyl-1,3,4,4a,9,9a-hexahydrothiopyrano[3,4-b]indole-6-carboxylate (160 mg, 56.6%) as an oil. MS: 371.1 (M+H+).

Step 4: Methyl 8-bromo-9-isopropyl-1,3,4,4a,9,9a-hexahydrothiopyrano[3,4-b]indole-6-carboxylate 2,2-dioxide (E-56)

In an oven-dried 50 mL round-bottomed flask, methyl 8-bromo-9-isopropyl-1,3,4,4a,9,9a-hexahydrothiopyrano[3,4-b]indole-6-carboxylate (160 mg, 0.432 mmol) and 8-bromo-9-isopropyl-1,3,4,4a,9,9a-hexahydrothiopyrano[3,4-b]indole-6-carboxylic acid (50 mg, 0.140 mmol) was dissolved in MeOH (5 mL), Acetone (0.2 mL) and Water (0.2 mL) under nitrogen to give a colorless solution. Oxone (145 mg, 0.864 mmol) was bubbled to the reaction mixture while stirring at room temperature, then quenched by water, and followed by extraction with ethyl acetate. The combined organic layers were dried over Na$_2$SO$_4$, filtered and concentrated. The resulting crude product was used in next step without purification. MS: 403.0 (M+H+).

Step 1: methyl 7-bromo-3-(2-hydroxyethyl)-2-(hydroxymethyl)-1-isopropylindoline-5-carboxylate (E-53)

In an oven-dried 50 mL round-bottomed flask, methyl 7-bromo-2-formyl-1-isopropyl-3-(2-oxoethyl)indoline-5-carboxylate (Intermediate E-29) (826 mg, 2.243 mmol) was dissolved in MeOH (10 mL) under nitrogen to give a colorless solution. To the reaction mixture cooled in an ice/water bath at 0° C., was added NaBH$_4$ (170 mg, 4.49 mmol) in one portion. The mixture was stirred at room temperature for 2 hrs, then quenched by water, followed by extraction with ethyl acetate. The combined organic layers were dried over Na$_2$SO$_4$, filtered and concentrated. The crude product was eluted with ethyl acetate/hexane to give

Step 5: 8-bromo-9-isopropyl-1,3,4,4a,9,9a-hexahydrothiopyrano[3,4-b]indole-6-carboxylic acid 2,2-dioxide (E-57)

In an oven-dried 50 mL round-bottomed flask, methyl 8-bromo-9-isopropyl-1,3,4,4a,9,9a-hexahydrothiopyrano[3,4-b]indole-6-carboxylate 2,2-dioxide (150 mg, 0.373 mmol) was dissolved in 1,4-Dioxane (5 mL) under nitrogen to give a colorless solution. KOH (41.8 mg, 0.746 mmol) was added to the reaction mixture in one portion. The reaction mixture was heated in an oil bath to 45° C., then quenched with 1N HCl, followed by extraction with ethyl acetate. The combined organic layers were dried over $Na_2SO_4$, filtered and concentrated. The resulting crude product was eluted with ethyl acetate/hexane (from 60% to 80%) to give 8-bromo-9-isopropyl-1,3,4,4a,9,9a-hexahydrothiopyrano[3,4-b]indole-6-carboxylic acid 2,2-dioxide (70 mg, 48.4%) as an oil. MS: 388.9 (M+H$^+$).

Step 6: 8-bromo-N-(4-(chlorodifluoromethoxy)phenyl)-9-isopropyl-1,3,4,4a,9,9a-hexahydrothiopyrano[3,4-b]indole-6-carboxamide 2,2-dioxide (E-58)

In an oven-dried 50 mL round-bottomed flask, 8-bromo-9-isopropyl-1,3,4,4a,9,9a-hexahydrothiopyrano[3,4-b]indole-6-carboxylic acid 2,2-dioxide (70 mg, 0.180 mmol) and DMF were dissolved in Toluene (5 mL) under nitrogen to give a colorless solution. The reaction mixture was heated in an oil bath at 80° C. for 1 h. the solvent was evaporated off under reduced pressure and the residue was dissolved in THF (0.4 mL), DIEA (46.6 mg, 0.361 mmol) was added to the reaction mixture in one portion. To the resulting mixture was dropped a solution of 4-(chlorodifluoromethoxy)aniline (38.4 mg, 0.198 mmol) in THF (1 mL) at 0° C. The mixture was stirred at 0° C. for another 2 h, then diluted with ethyl acetate, followed by washing with 1N HCl and 1N NaOH. The organic layer was dried over $Na_2SO_4$, filtered and concentrated. The crude product was eluted with ethyl acetate/hexane (from 20% to 40%) to give 8-bromo-N-(4-(chlorodifluoromethoxy)phenyl)-9-isopropyl-1,3,4,4a,9,9a-hexahydrothiopyrano[3,4-b]indole-6-carboxamide 2,2-dioxide (90 mg, 89%) as a solid. MS: 564.0 (M+H$^+$). $^1$H NMR (400 MHz, Chloroform-d) δ 7.88 (s, 1H), 7.81 (s, 1H), 7.70 (d, J=2.2 Hz, 1H), 7.68 (d, J=2.3 Hz, 1H), 7.57 (t, J=1.7 Hz, 1H), 7.27 (d, J=8.7 Hz, 2H), 4.70-4.57 (m, 1H), 4.48-4.35 (m, 1H), 3.79-3.69 (m, 1H), 3.20-2.83 (m, 4H), 2.77-2.56 (m, 2H), 1.35 (d, J=6.8 Hz, 3H), 1.17 (d, J=6.6 Hz, 3H).

Step 7: N-(4-(chlorodifluoromethoxy)phenyl)-9-isopropyl-8-(1H-pyrazol-5-yl)-1,3,4,4a,9,9a-hexahydrothiopyrano[3,4-b]indole-6-carboxamide 2,2-dioxide (Compound 54)

In an oven-dried 5 mL round-bottomed flask, 8-bromo-N-(4-(chlorodifluoromethoxy)phenyl)-9-isopropyl-1,3,4,4a,9,9a-hexahydrothiopyrano[3,4-b]indole-6-carboxamide 2,2-dioxide (45 mg, 0.080 mmol), 5-(4,4,5,5-tetramethyl-1,3,2-dioxaborolan-2-yl)-1H-pyrazole (23.23 mg, 0.120 mmol), sodium carbonate (25.4 mg, 0.239 mmol) and Pd(dppf)Cl$_2$·CH$_2$Cl$_2$ (5.84 mg, 7.98 μmol) were dissolved in DME (1.5 mL) and Water (0.500 ml) under nitrogen to give a colorless solution. After LCMS showed the reaction was complete, the mixture was eluted with ethyl acetate/hexane (from 30% to 60%) to give N-(4-(chlorodifluoromethoxy)phenyl)-9-isopropyl-8-(1H-pyrazol-5-yl)-1,3,4,4a,9,9a-hexahydrothiopyrano[3,4-b]indole-6-carboxamide 2,2-dioxide (9 mg, 20.47%) as a solid. MS: 552.0 (M+H$^+$). $^1$H NMR (400 MHz, DMSO-d$_6$) δ 12.96 (s, 1H), 10.24 (s, 1H), 8.00 (s, 1H), 7.89 (d, J=2.3 Hz, 1H), 7.87 (d, J=2.3 Hz, 1H), 7.77-7.71 (m, 2H), 7.35 (dt, J=7.9, 1.1 Hz, 2H), 6.58 (d, J=2.1 Hz, 1H), 4.37-4.31 (m, 1H), 3.79-3.71 (m, 1H), 3.57-3.44 (m, 1H), 3.27 (dd, J=14.4, 5.4 Hz, 1H), 3.14 (t, J=6.5 Hz, 2H), 3.03 (dd, J=14.3, 10.9 Hz, 1H), 2.62-2.51 (m, 2H), 1.12 (d, J=6.8 Hz, 3H), 0.90 (d, J=6.5 Hz, 3H).

Step 8: (4aS,9aR)-N-(4-(chlorodifluoromethoxy)phenyl)-9-isopropyl-8-(1H-pyrazol-5-yl)-1,3,4,4a,9,9a-hexahydrothiopyrano[3,4-b]indole-6-carboxamide 2,2-dioxide (Compound 54-A)

N-(4-(chlorodifluoromethoxy)phenyl)-9-isopropyl-8-(1H-pyrazol-5-yl)-1,3,4,4a,9,9a-hexahydrothiopyrano[3,4-b]indole-6-carboxamide 2,2-dioxide (Compound 54) was separated through Prep-Chiral HPLC by the following separation condition to give pure optical stereoisomer 54-A.

| | |
|---|---|
| Column | CHIRAL Cellulose-SB |
| Colum size | 4.6 × 100 mm 3 um |
| Flow rate | 1.0 ml/min |
| Mobile phase | Hex(0.1% DEA):EtOH = 50:50 |
| Temperature | 25° C. |
| Retention time | 4.85 min |

Example 55

Synthesis of N-(4-(chlorodifluoromethoxy)phenyl)-9-neopentyl-8-(1H-pyrazol-5-yl)-1,3,4,4a,9,9a-hexahydrothiopyrano[3,4-b]indole-6-carboxamide 2,2-dioxide (Compound No. 55)

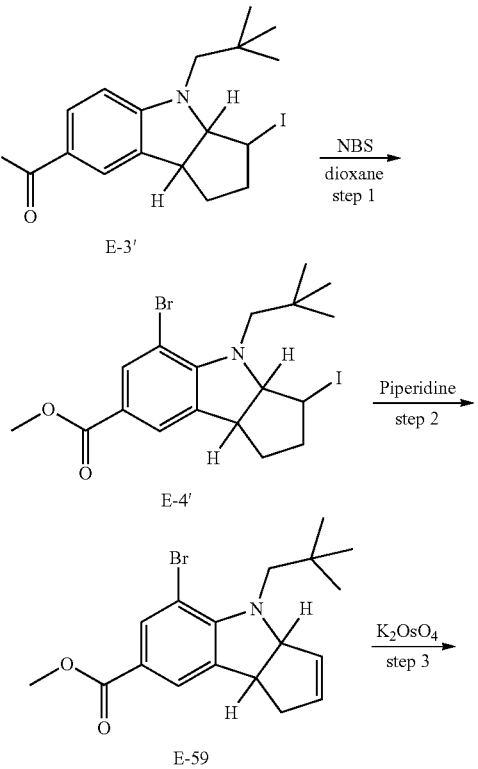

-continued

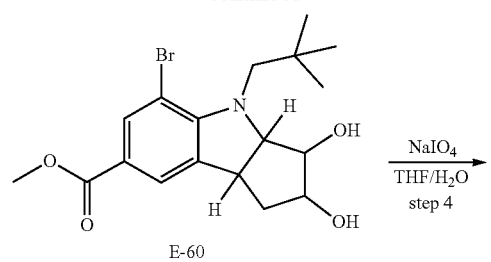

E-60

NaIO₄
THF/H₂O
step 4

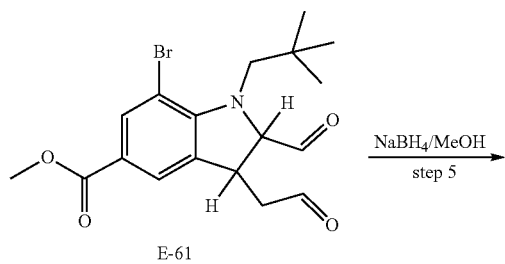

E-61

NaBH₄/MeOH
step 5

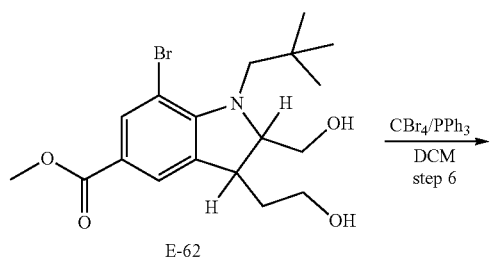

E-62

CBr₄/PPh₃
DCM
step 6

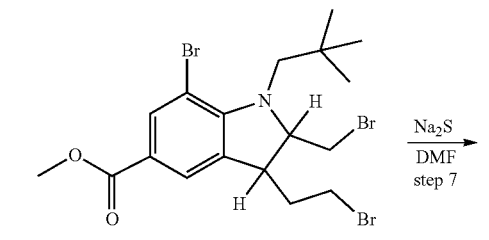

E-63

Na₂S
DMF
step 7

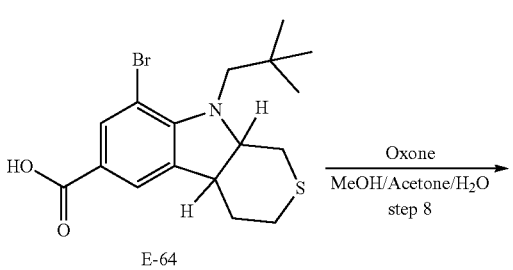

E-64

Oxone
MeOH/Acetone/H₂O
step 8

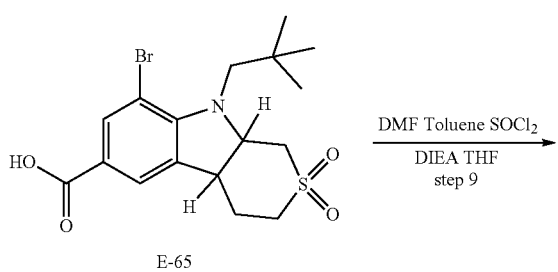

E-65

DMF Toluene SOCl₂
DIEA THF
step 9

-continued

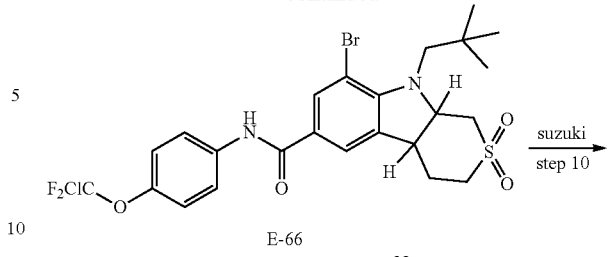

E-66 suzuki
step 10

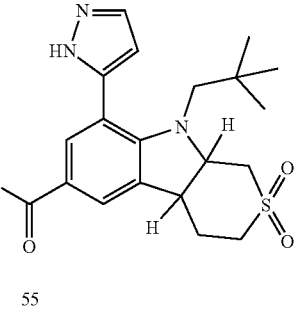

55

Step 1: Methyl 5-bromo-3-iodo-4-neopentyl-1,2,3,3a,4,8b-hexahydrocyclopenta[b]indole-7-carboxylate (E-4')

In an oven-dried 10 mL round-bottomed flask, methyl-3-iodo-4-neopentyl-1,2,3,3a,4,8b-hexahydrocyclopenta[b]indole-7-carboxylate (8 g, 19.36 mmol), which was prepared through the same procedure as described in the synthesis of Intermediate E-10'-A, was dissolved in 1,4-Dioxane (4 mL) under nitrogen to give a yellow solution. 1-bromopyrrolidine-2,5-dione (10.34 g, 58.1 mmol) was added to the reaction mixture in one portion. Then the mixture was stirred at room temperature for 2 hrs, then quenched with saturated NaHCO₃, followed by extraction with ethyl acetate. The combined organic layers were dried over Na₂SO₄, filtered and concentrated. The crude product was eluted with ethyl acetate/hexane (from 0% to 20%) to give methyl 5-bromo-3-iodo-4-neopentyl-1,2,3,3a,4,8b-hexahydrocyclopenta[b]indole-7-carboxylate (6 g, 69.6%) as a yellow oil.

Step 2: Methyl 5-bromo-4-neopentyl-1,3a,4,8b-tetrahydrocyclopenta[b]indole-7-carboxylate (E-59)

In an oven-dried 100 mL round-bottomed flask, methyl 5-bromo-3-iodo-4-neopentyl-1,2,3,3a,4,8b-hexahydrocyclopenta[b]indole-7-carboxylate (6 g, 13.48 mmol, 1.000) was dissolved in piperidine (50 mL) under nitrogen to give a yellow solution. The reaction mixture was heated in an oil bath at 120° C. for overnight, then quenched with water, followed by extraction with ethyl acetate. The combined organic layers were dried over Na₂SO₄, filtered and concentrated. The crude product was eluted with ethyl acetate/hexane (from 0% to 25%) to give methyl 5-bromo-4-neopentyl-1,3a,4,8b-tetrahydrocyclopenta[b]indole-7-carboxylate (2 g, 40.7%) as a yellow oil. MS: 364.08 (M+H⁺).

Step 3: Methyl 5-bromo-2,3-dihydroxy-4-neopentyl-1,2,3,3a,4,8b-hexahydrocyclopenta[b]indole-7-carboxylate (E-60)

In an oven-dried 50 mL two-necked round-bottomed flask, to a solution of methyl 5-bromo-4-neopentyl-1,3a,4, 8b-tetrahydrocyclopenta[b]indole-7-carboxylate (2 g, 5.49 mmol) and 4-methylmorpholine 4-oxide (1.286 g, 10.98 mmol) in acetone (30 ml) under nitrogen, was added the solution of potassium tetrahydroxydioxidoosmium (0.202 g, 0.549 mmol) in water (10.00 mL). The mixture was stirred at room temperature for 2 hours, then quenched with water, followed by extraction with ethyl acetate. The combined organic layers were dried over $Na_2SO_4$, filtered and concentrated. The resulting crude product was eluted with ethyl acetate/hexane (from 10% to 20%) to give methyl 5-bromo-2,3-dihydroxy-4-neopentyl-1,2,3,3a,4,8b-hexahydrocyclopenta[b]indole-7-carboxylate (1.9 g, 87%) as a yellow solid. MS: 398.09 (M+H$^+$).

Step 4: methyl 7-bromo-2-formyl-1-neopentyl-3-(2-oxoethyl)indoline-5-carboxylate (E-61)

In an oven-dried 50 mL round-bottomed flask, methyl 5-bromo-2,3-dihydroxy-4-neopentyl-1,2,3,3a,4,8b-hexahydrocyclopenta[b]indole-7-carboxylate (1.9 g, 4.77 mmol) and sodium periodate (1.530 g, 7.16 mmol) were dissolved in THF (25 mL) and Water (2 mL) under nitrogen to give a yellow solution. The mixture was stirred at room temperature for 1 hour. TLC showed the reaction was complete, then water was added to the reaction mixture, followed by extraction with dichloromethane. The combined organic layers were dried over $Na_2SO_4$, filtered and concentrated to give methyl 7-bromo-2-formyl-1-neopentyl-3-(2-oxoethyl) indoline-5-carboxylate (1.80 g), which was used in the next step without purification. MS: 396.07 (M+H$^+$).

Step 5: Methyl 7-bromo-3-(2-hydroxyethyl)-2-(hydroxymethyl)-1-neopentylindoline-5-carboxylate (E-62)

In an oven-dried 50 mL round-bottomed flask, to a solution of methyl 7-bromo-2-formyl-1-neopentyl-3-(2-oxoethyl)indoline-5-carboxylate (1.8 g, 4.54 mmol) in MeOH (10 mL) under nitrogen at 0° C., was added sodium tetrahydroborate (0.344 g, 9.08 mmol). The mixture was stirred at room temperature for 2 h, then quenched with water, followed by extraction with ethyl acetate. The combined organic layers were dried over $Na_2SO_4$, filtered and concentrated. The crude product was eluted with ethyl acetate/hexane to give methyl 7-bromo-3-(2-hydroxyethyl)-2-(hydroxymethyl)-1-neopentylindoline-5-carboxylate (1.2 g, 66.0%) as a yellow oil. MS: 400.1 (M+H$^+$). $^1$H NMR (400 MHz, Chloroform-d) δ 7.92 (dd, J=1.7, 0.9 Hz, 1H), 7.55 (t, J=1.7 Hz, 1H), 4.54 (d, J=15.0 Hz, 1H), 4.05-3.93 (m, 2H), 3.89-3.80 (m, 1H), 3.86 (s, 3H), 3.73-3.66 (m, 2H), 3.60 (m, 1H), 2.88 (d, J=15.1 Hz, 1H), 2.33-2.21 (m, 1H), 2.14-1.99 (m, 1H), 1.01 (s, 9H).

Step 6: Methyl 7-bromo-3-(2-bromoethyl)-2-(bromomethyl)-1-neopentylindoline-5-carboxylate (E-63)

In an oven-dried 50 mL round-bottomed flask, to a solution of methyl 7-bromo-3-(2-hydroxyethyl)-2-(hydroxymethyl)-1-neopentylindoline-5-carboxylate (1.5 g, 3.75 mmol) in DCM (15 ml), was added perbromomethane (3.11 g, 9.37 mmol) and triphenylphosphine (2.457 g, 9.37 mmol). The mixture was stirred at room temperature for 2 hours, then directly eluted with ethyl acetate/hexane (from 0% to 20%) to give methyl 7-bromo-3-(2-bromoethyl)-2-(bromomethyl)-1-neopentylindoline-5-carboxylate (500 mg, 25.4%) as a yellow oil. MS: 523.94 (M+H$^+$).

Step 7: 8-bromo-9-neopentyl-1,3,4,4a,9,9a-hexahydrothiopyrano[3,4-b]indole-6-carboxylic acid (E-64)

In an oven-dried 50 mL round-bottomed flask, to a solution of methyl 7-bromo-3-(2-bromoethyl)-2-(bromomethyl)-1-neopentylindoline-5-carboxylate (500 mg, 0.950 mmol) in DMF (5 ml), was added sodium sulfide (223 mg, 2.85 mmol). The reaction mixture was heated in an oil bath at 50° C. for overnight, then diluted with water, followed by extraction with ethyl acetate. The combined organic layers were dried over $Na_2SO_4$, filtered and concentrated. The crude product was eluted with ethyl acetate/hexane (from 0% to 80%) to give 8-bromo-9-neopentyl-1,3,4,4a,9,9a-hexahydrothiopyrano[3,4-b]indole-6-carboxylic acid (320 mg, 88%) as a yellow oil. MS: 384.0 (M+H$^+$). $^1$H NMR (400 MHz, Chloroform-d) δ 8.02 (s, 1H), 7.58 (s, 1H), 4.69 (d, J=15.0 Hz, 2H), 3.97-3.84 (m, 2H), 2.75-2.25 (m, 6H), 1.04 (s, 9H).

Step 8: 8-bromo-9-neopentyl-1,3,4,4a,9,9a-hexahydrothiopyrano[3,4-b]indole-6-carboxylic acid 2,2-dioxide (E-65)

In an oven-dried 50 mL round-bottomed flask, 8-bromo-9-neopentyl-1,3,4,4a,9,9a-hexahydrothiopyrano[3,4-b]indole-6-carboxylic acid (160 mg, 0.416 mmol) was dissolved in MeOH (10 mL), Acetone (1 mL) and Water (1 mL) under nitrogen to give a solution. Oxone (140 mg, 0.832 mmol) was added to the reaction mixture in one portion. The mixture was stirred at room temperature for 20 hours, then diluted with, followed by extraction with ethyl acetate. The combined organic layers were dried over $Na_2SO_4$, filtered and concentrated. The crude product was eluted with ethyl acetate/hexane (from 50% to 65%) to give 8-bromo-9-neopentyl-1,3,4,4a,9,9a-hexahydrothiopyrano[3,4-b]indole-6-carboxylic acid 2,2-dioxide (160 mg, 92%) as a yellow solid. MS: 416.05 (M+H$^+$).

Step 9: 8-bromo-N-(4-(chlorodifluoromethoxy)phenyl)-9-neopentyl-1,3,4,4a,9,9a-hexahydrothiopyrano [3,4-b]indole-6-carboxamide 2,2-dioxide (E-69)

In an oven-dried 50 mL round-bottomed flask, 8-bromo-9-neopentyl-1,3,4,4a,9,9a-hexahydrothiopyrano[3,4-b]indole-6-carboxylic acid 2,2-dioxide (320 mg, 0.769 mmol) was dissolved in DMF (2 drops) and Toluene (5 mL) under nitrogen to give a yellow solution. Sulfurous dichloride (457 mg, 3.84 mmol) was added to the reaction mixture in one portion. The reaction mixture was heated in an oil bath at 80° C. for 2 hrs. The mixture was evaporated off under reduced pressure and the residue was dissolved in THF (10 mL), then were added 4-(chlorodifluoromethoxy)aniline (164 mg, 0.845 mmol) and N-ethyl-N-isopropylpropan-2-amine (199 mg, 1.537 mmol). The mixture was stirred at rt for another 2 hrs, then diluted with ethyl acetate, followed by washing with water. The organic layer was dried over $Na_2SO_4$, filtered and concentrated. The crude product was eluted with ethyl acetate/hexane from (0% to 40%) to give 8-bromo-N-(4-(chlorodifluoromethoxy)phenyl)-9-neopentyl-1,3,4,4a,9, 9a-hexahydrothiopyrano[3,4-b]indole-6-carboxamide 2,2-dioxide (240 mg, 52.8%) as a yellow solid. MS: 591.05 (M+H$^+$).

Step 10: N-(4-(chlorodifluoromethoxy)phenyl)-9-neopentyl-8-(1H-pyrazol-5-yl)-1,3,4,4a,9,9a-hexahydrothiopyrano[3,4-b]indole-6-carboxamide 2,2-dioxide (Compound 55)

The mixture of 8-bromo-N-(4-(chlorodifluoromethoxy)phenyl)-9-neopentyl-1,3,4,4a,9,9a-hexahydrothiopyrano[3,4-b]indole-6-carboxamide 2,2-dioxide (240 mg, 0.405 mmol), 5-(4,4,5,5-tetramethyl-1,3,2-dioxaborolan-2-yl)-1H-pyrazole (157 mg, 0.811 mmol), sodium carbonate (129 mg, 1.216 mmol) and Pd(dppf)Cl$_2$·CH$_2$Cl$_2$ (29.7 mg, 0.041 mmol) in DME (1.5 mL) and Water (0.5 mL) was stirred under microwave at 110° C. for 3 hrs, then concentrated. The crude product was purified by Prep-HPLC to give N-(4-(chlorodifluoromethoxy)phenyl)-9-neopentyl-8-(1H-pyrazol-5-yl)-1,3,4,4a,9,9a-hexahydrothiopyrano[3,4-b]indole-6-carboxamide 2,2-dioxide (110 mg, 46.8%) as a white solid. MS: 579.16 (M+H$^+$). $^1$H NMR (400 MHz, DMSO-d$_6$) δ 12.95 (s, 1H), 10.08 (s, 1H), 7.91-7.75 (m, 3H), 7.78 (s, 1H), 7.69 (d, J=2.0 Hz, 1H), 7.35 (d, J=8.7 Hz, 2H), 6.38 (s, 1H), 4.26-4.18 (m, 1H), 3.74-3.64 (m, 1H), 3.52 (d, J=14.9 Hz, 1H), 3.20-3.02 (m, 2H), 3.00-2.89 (m, 1H), 2.86-2.70 (m, 4H), 0.68 (s, 9H).

Example 56—Biological Activity

WST Assay

The anti-proliferative effect of representative compounds of the present disclosure was determined by a water-soluble tetrazolium (WST)-based assay using Cell Counting Kit-8 (CCK-8). Cells were seeded in 96-well plates and treated with different concentrations of test articles for 72 h. Each treatment was tested in triplicate. Briefly, a series of 9 concentrations were chosen for each test article and added at 100 μl/well into a 96-well plate. Each concentration was tested in triplicate. 100 μl of diluent was added into 3-6 wells in the same plate for cell control group, and another set of 3-6 wells was used as a blank control.

In each well, 100 μl of cell suspension (containing optimal cell numbers, which creates approximately 100% confluence of cells in control wells based on by the absorbance (OD) value) was dispensed into the same 96-well plate except for the blank well. The plate was then cultured at 37° C. in an incubator in an atmosphere with 5% CO$_2$ for 72 h. At the end of the treatments, 20 μl/well of CCK-8 reagent was directly added to each well. The plate was then incubated at 37° C. in an incubator in an atmosphere with 5% CO$_2$ for 2-4 hours. The OD value was then detected at 450 nm on a microplate reader (SpectraMax Plus 384, Molecular Devices, LLC. US).

The cells viability was calculated using the mean OD value of triplicated wells following the equation below: (OD sample−OD blank)/(OD cell control−OD blank)×100 IC$_{50}$ values were calculated with Graphpad Prism 6.0 software using nonlinear regression (curve fitting) type data analysis.

In this assay, ABL04 ((R)-N-(4-(chlorodifluoromethoxy)phenyl)-6-(3-hydroxypyrrolidin-1-yl)-5-(1H-pyrazol-5-yl)nicotinamide) was used as control reference. ABL001 is the first allosteric BCR-ABL inhibitor in clinical trial that selectively inhibits growth of BCR-ABL1-driven cells, and is commercially available.

The results of cell-based assays are provided in Table 15.

TABLE 15

| Example NO. | BaF3(WT, nM) | BaF3 (T315I mutant, nM) |
|---|---|---|
| ABL001 | 42 | 294 |
| 1 | 17 | 192 |
| 2 | 15 | 354 |
| 3 | 36 | 177 |
| 4 | 14 | 71 |
| 5 | 34 | 144 |
| 6 | 67 | 154 |
| 7 | 14 | 142 |
| 8 | 21 | 179 |
| 9 | 17 | 206 |
| 4A | 3 | 35 |
| 4b | 535 | 1273 |
| 10 | 31 | 29 |
| 11 | 53 | 64 |
| 12 | 10 | 216 |
| 13 | 12 | 122 |
| 14 | 41 | 208 |
| 15 | 35 | 346 |
| 16 | 12 | 252 |
| 17 | 1064 | 1666 |
| 18 | 13 | 126 |
| 19 | 6 | 97 |
| 20 | 9 | 44 |
| 21 | 27 | 176 |
| 22 | 3 | 21 |
| 23 | 10 | 81 |
| 24 | 17 | 114 |
| 25 | 15 | 183 |
| 26 | 12 | 65 |
| 27 | 1241 | 5065 |
| 28 | 19 | 168 |
| 29 | 177 | 1259 |
| 30 | 16 | 64 |
| 31 | 15 | 40 |
| 32 | 491 | 2109 |
| 33 | 14 | 109 |
| 34 | 17 | 411 |
| 35 | 12 | 55 |
| 36 | 9 | 84 |
| 37 | 25 | 245 |
| 38 | 18 | 77 |
| 39 | 2758 | 5708 |
| 40 | 358 | 1109 |
| 41 | 120 | 850 |
| 42 | 38 | 115 |
| 43 | 190 | 768 |
| 44 | 36 | 122 |
| 22-A | 3 | 21 |
| 22-B | 482 | 1009 |
| 20-A | 42 | 29 |
| 20-B | 365 | 1384 |
| 26-A | 6 | 41 |
| 26-B | 186 | 956 |
| 4-A | 3 | 35 |
| 4-B | 535 | 1273 |
| 45 | 18 | 111 |
| 46-A | 2 | 8 |
| 47-A | 5 | 13 |
| 48-A | 2 | 14 |
| 49 | 72 | 125 |
| 50-A | 4 | 39 |
| 51-A | 12 | 116 |
| 52-A | 3 | 47 |
| 53-A | 3 | 16 |
| 54-A | 8 | 45 |
| 55-A | 28 | 123 |
| 56-A | 56 | 440 |
| 57-A | 97 | 316 |
| 58-A | 18 | 80 |
| 59-A | 65 | 122 |
| 60-A | 13 | 92 |
| 61-A | 11 | 56 |
| 62 | 21 | 41 |

TABLE 15-continued

| Example NO. | BaF3(WT, nM) | BaF3 (T315I mutant, nM) |
|---|---|---|
| 63 | 41 | 52 |
| 64 | 8 | 43 |
| 65 | 9 | 119 |
| 66-A | 3 | 29 |
| 67-A | 6 | 59 |

We claim:

1. A compound of formula I:

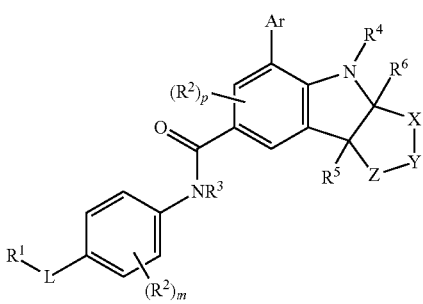

I or an enantiomer or diastereomer, or a pharmaceutically acceptable salt thereof, wherein: $R^1$ is —$C_{1-6}$alkyl, cycloalkyl, or heterocycloalkyl;
each $R^2$ is independently —H, -halo, —OH, —CN, —$NH_2$, —$NO_2$, —$C_{1-6}$alkyl, or —$C_{1-6}$alkoxy; wherein m is 0, 1, 2, 3, or 4; p is 0, 1 or 2;
$R^3$ is —H or —$C_{1-6}$alkyl;
$R^4$ is —H, cycloalkyl, or —$C_{1-6}$alkyl;
$R^5$ and $R^6$ are each independently —H or —$C_{1-6}$alkyl;
Ar is aryl or heteroaryl;
X is —C($R^7R^{7'}$)—;
Y is —C($R^8R^{8'}$)—, —O—, —N($R^{10}$)—, —C(=O)—, —$SO_2$;
Z is —[C($R^9R^{9'}$)]$_n$—; wherein n is 1, 2, 3, or 4;
or X and Y together form —($R^7$)C=C($R^8$)—;
L is —S—, —O—, —N($R^{11}$)—, —C(=O)N($R^{11}$)—, —C(=O)N($R^{11}$)—$C_{1-4}$alkyl-, —N($R^{11}$)C(=O)—, —N($R^{11}$)C(=O)—$C_{1-4}$alkyl-, —$SO_2$N($R^{11}$)—, or —N($R^{11}$)$SO_2$—;
each $R^7$, $R^{7'}$, $R^8$, $R^{8'}$, $R^9$ and $R^{9'}$ independently comprises:
1) —H,
2) —$C_{1-6}$alkyl,
3) -cycloalkyl,
4) -heterocycloalkyl,
5) —$OR^{12}$,
6) —N($R^{12}$)$_2$,
7) —$NR^{11}$C(=O)$R^{12}$,
8) —$NR^{11}$C(=O)$OR^{12}$,
9) —$NR^{11}$C(=O)N($R^{12}$)$_2$,
10) —$NR^{11}SO_2R^{12}$,
11) —$NR^{11}SO_2N(R^{12})_2$,
12) —C(=O)$R^{12}$,
13) —C(=O)O($C_{1-6}$ alkyl),
14) —C(=O)N($R^{12}$)$_2$,
15) —$SO_2R^{12}$,
16) —$SO_2N(R^{12})_2$,
17) -aryl, and
18) -heteroaryl;

$R^{10}$ is —H, —$C_{1-6}$alkyl, -cycloalkyl, heterocycloalkyl, —C(=O)$R^{12}$, —C(=O)$OR^{12}$, —C(=O)N($R^{12}$)$_2$, —$SO_2R^{12}$, —$SO_2N(R^{12})_2$, aryl, or heteroaryl;
each $R^{11}$ is independently —H or —$C_{1-6}$alkyl; and
each $R^{12}$ is independently —H, —$C_{1-6}$alkyl, —$C_{1-6}$alkoxy, -cycloalkyl, heterocycloalkyl, aryl, or heteroaryl;
wherein at each occurrence alkyl is substituted with 0, 1, 2, 3, or 4 substituents comprising halo, -oxo, —OH, —CN, —$NH_2$, —$NO_2$, —$SO_2$($C_{1-6}$alkyl), —$C_{1-6}$alkoxy, -cycloalkyl, -heterocycloalkyl, aryl, and heteroaryl;
wherein at each occurrence cycloalkyl and heterocycloalkyl are substituted with 0, 1, 2, 3, or 4 substituents comprising halo, -oxo, —OH, —CN, —$NH_2$, —$NO_2$, —$C_{1-6}$alkyl, —$SO_2$($C_{1-6}$alkyl), —CO($C_{1-6}$alkyl), —$C_{1-6}$ alkoxy, aryl, and heteroaryl;
wherein at each occurrence aryl and heteroaryl are substituted with 0, 1, 2, or 3 substituents comprising halo, —OH, —CN, —$NH_2$, $NO_2$, —NH($C_{1-6}$alkyl), —N($C_{1-6}$alkyl)$_2$, —$C_{1-6}$alkyl, -cycloalkyl, -heterocycloalkyl, and —$C_{1-6}$ alkoxy.

2. The compound of claim 1 which is a compound of formula II:

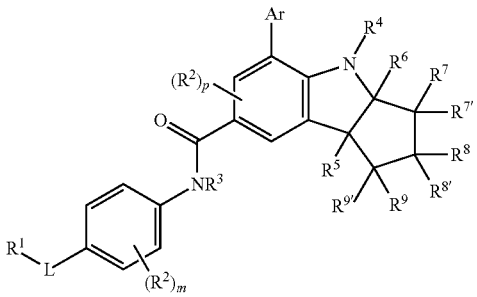

II or an enantiomer or diastereomer, or a pharmaceutically acceptable salt thereof, wherein:
$R^1$ is —$C_{1-6}$alkyl;
each $R^2$ is independently —H, -halo, —OH, —CN, —$NH_2$, —$NO_2$, —$C_{1-6}$alkyl, or —$C_{1-6}$alkoxy; wherein m is 0, 1, or 2 p is 0, 1 or 2;
$R^3$ is —H or —$C_{1-6}$alkyl;
$R^4$ is —H, cycloalkyl, or —$C_{1-6}$alkyl;
$R^5$ and $R^6$ are —H;
Ar is aryl or heteroaryl;
L is —S—, —O—, —N($R^{11}$)—, —C(=O)N($R^{11}$)—, —C(=O)N($R^{11}$)—$C_{1-4}$alkyl-, —N($R^{11}$)C(=O)—, —N($R^{11}$)C(=O)—$C_{1-4}$alkyl-, —$SO_2$N($R^{11}$)—, or —N($R^{11}$)$SO_2$—;
each $R^7$, $R^{7'}$, $R^8$, $R^{8'}$, $R^9$ and $R^{9'}$ independently comprises:
1) —H,
2) —$C_{1-6}$alkyl,
3) -cycloalkyl,
4) -heterocycloalkyl,
5) —$OR^{12}$,
6) —N($R^{12}$)$_2$,
7) —$NR^{11}$C(=O)$R^{12}$,
8) —$NR^{11}$C(=O)$OR^{12}$,
9) —$NR^{11}$C(=O)N($R^{12}$)$_2$,
10) —$NR^{11}SO_2R^{12}$,
11) —$NR^{11}SO_2N(R^{12})_2$,
12) —C(=O)$R^{12}$, 13) —C(=O)O($C_{1-6}$ alkyl),
14) —C(=O)N($R^{12}$)$_2$,
15) —SO$_2$$R^{12}$,
16) —SO$_2$N($R^{12}$)$_2$,
17) -aryl, and
18) -heteroaryl;
or $R^{7'}$ and $R^{8'}$ form a bond:
each $R^{11}$ is independently —H or —$C_{1-6}$alkyl; and
each $R^{12}$ is independently —H, —$C_{1-6}$alkyl, —$C_{1-6}$alkoxy, -cycloalkyl, heterocycloalkyl, aryl, or heteroaryl;
wherein at each occurrence alkyl is substituted with 0, 1, 2, 3, or 4 substituents comprising halo, —OH, —CN, —NH$_2$, —NO$_2$, —SO$_2$($C_{1-6}$alkyl), —$C_{1-6}$alkoxy, -cycloalkyl, -heterocycloalkyl, aryl, and heteroaryl;
wherein at each occurrence cycloalkyl and heterocycloalkyl are substituted with 0, 1, 2, 3, or 4 substituents comprising halo, -oxo, —OH, —CN, —NH$_2$, —NO$_2$, —$C_{1-6}$alkyl, —SO$_2$($C_{1-6}$alkyl), —CO($C_{1-6}$alkyl), —$C_{1-6}$alkoxy, aryl, and heteroaryl;
wherein at each occurrence aryl and heteroaryl are substituted with 0, 1, 2, or 3 substituents comprising halo, —OH, —CN, —NH$_2$, —NO$_2$, —NH($C_{1-6}$alkyl), —N($C_{1-6}$alkyl)$_2$, —$C_{1-6}$alkyl, -cycloalkyl, -heterocycloalkyl, and —$C_{1-6}$alkoxy.

3. The compound of claim 2, or an enantiomer or diastereomer, or a pharmaceutically acceptable salt thereof, wherein $R^1$ is —$C_{1-6}$alkyl substituted with 1, 2, or 3 F or Cl.

4. The compound of claim 3, or an enantiomer or diastereomer, or a pharmaceutically acceptable salt thereof, wherein $R^1$ is difluorochloromethyl.

5. The compound of claim 2, or an enantiomer or diastereomer, or a pharmaceutically acceptable salt thereof, wherein L is —O—.

6. The compound of claim 2, or an enantiomer or diastereomer, or a pharmaceutically acceptable salt thereof, wherein $R^2$ is —H.

7. The compound of claim 2, or an enantiomer or diastereomer, or a pharmaceutically acceptable salt thereof, wherein $R^3$ is —H.

8. The compound of claim 2, or an enantiomer or diastereomer, or a pharmaceutically acceptable salt thereof, wherein $R^4$ is —$C_{1-6}$alkyl.

9. The compound of claim 2, or an enantiomer or diastereomer, or a pharmaceutically acceptable salt thereof, wherein $R^4$ is methyl, ethyl, propyl, iso-propyl, butyl, neopentyl, or pentyl.

10. The compound of claim 2, or an enantiomer or diastereomer, or a pharmaceutically acceptable salt thereof, wherein Ar is pyridinyl, pyrimidinyl, or pyrazinyl.

11. The compound of claim 2, or an enantiomer or diastereomer, or a pharmaceutically acceptable salt thereof, wherein Ar is phenyl, pyridinyl, pyrimidinyl, pyridazinyl, or pyrazinyl, any of which is substituted with 0, 1, 2, or 3 substituents comprising halo, —CN, —$C_{1-6}$alkyl, and —$C_{1-6}$alkoxy.

12. The compound of claim 2, or an enantiomer or diastereomer, or a pharmaceutically acceptable salt thereof, wherein Ar is pyrazolyl.

13. The compound of claim 2, or an enantiomer or diastereomer, or a pharmaceutically acceptable salt thereof, wherein Ar is 1H-pyrazol 5-yl.

14. The compound of claim 2, or an enantiomer or diastereomer, or a pharmaceutically acceptable salt thereof, wherein:

$R^1$ is —$C_{1-3}$alkyl substituted with 1, 2, or 3 halo;
each $R^2$ is independently —H, -halo, —$C_{1-3}$alkyl, or —$C_{1-3}$alkoxy;
wherein m is 0, 1, or 2; p is 0, 1 or 2;
$R^3$ is —H;
$R^4$ is —$C_{1-6}$alkyl or -cycloalkyl;
$R^5$ and $R^6$ are —H;
Ar is a 5- or 6-membered monocyclic aromatic ring systems having 0, 1, 2, or 3 heteroatoms including nitrogen, oxygen and sulfur atoms, wherein Ar is substituted with 0, 1, 2, or 3 substituents comprising halo, —OH, —CN, —$C_{1-6}$alkyl, -cycloalkyl, -heterocycloalkyl, and —$C_{1-6}$alkoxy;
L is —O— or —S—;
each $R^7$, $R^{7'}$, $R^8$, $R^{8'}$, $R^9$ and $R^{9'}$ independently comprises:
1) —H,
2) —$C_{1-6}$alkyl,
3) -cycloalkyl,
4) -heterocycloalkyl,
5) —OR$^{12}$,
6) —N(R$^{12}$)$_2$,
7) —NR$^{11}$C(=O)R$^{12}$,
8) —NR$^{11}$C(=O)OR$^{12}$,
9) —NR$^{11}$C(=O)N(R$^{12}$)$_2$,
10) —NR$^{11}$SO$_2$R$^{12}$,
11) —NR$^{11}$SO$_2$N(R$^{12}$)$_2$,
12) —C(=O)R$^{12}$,
13) —C(=O)O($C_{1-6}$ alkyl),
14) —C(=O)N(R$^{12}$)$_2$,
15) —SO$_2$R$^{12}$, and
16) —SO$_2$N(R$^{12}$)$_2$;
each $R^{11}$ or $R^{12}$ are the same as defined.

15. The compound of claim 14, or an enantiomer or diastereomer, or a pharmaceutically acceptable salt thereof, wherein $R^1$ is —$C_{1-6}$alkyl substituted with 1, 2, or 3-F or Cl.

16. The compound of claim 15, or an enantiomer or diastereomer, or a pharmaceutically acceptable salt thereof, wherein $R^1$ is difluorochloromethyl.

17. The compound of claim 14, or an enantiomer or diastereomer, or a pharmaceutically acceptable salt thereof, wherein $R^7$, $R^{7'}$, $R^8$, $R^{8'}$, $R^9$ and $R^{9'}$ are H.

18. The compound of claim 14, or an enantiomer or diastereomer, or a pharmaceutically acceptable salt thereof, wherein $R^9$ and $R^{9'}$ are H; $R^7$, $R^{7'}$, $R^8$, and $R^{8'}$ are each independently
1) —H,
2) -heterocycloalkyl,
3) —OR$^{12}$,
4) —N(R$^{12}$)$_2$,
5) —NR$^{11}$C(=O)R$^{12}$,
6) —NR$^{11}$C(=O)OR$^{12}$,
7) —NR$^{11}$C(=O)N(R$^{12}$)$_2$,
8) —NR$^{11}$SO$_2$R$^{12}$,
9) —NR$^1$SO$_2$N(R$^{12}$)$_2$,
10) —C(=O)R$^{12}$,
11) —C(=O)O($C_{1-6}$ alkyl), or
12) —C(=O)N(R$^{12}$)$_2$; wherein
$R^{11}$ is H; each $R^{12}$ is independently —$C_{1-6}$alkyl, —$C_{1-6}$alkoxy, heterocycloalkyl, or heteroaryl; wherein at each occurrence heterocycloalkyl is substituted with 0, 1, or 2, substituents comprising halo, -oxo, and —$C_{1-6}$alkyl.

19. The compound of 14, or an enantiomer or diastereomer, or a pharmaceutically acceptable salt thereof, wherein $R^7$, $R^{7'}$, $R^8$, and $R^{8'}$ are each independently H or comprises:

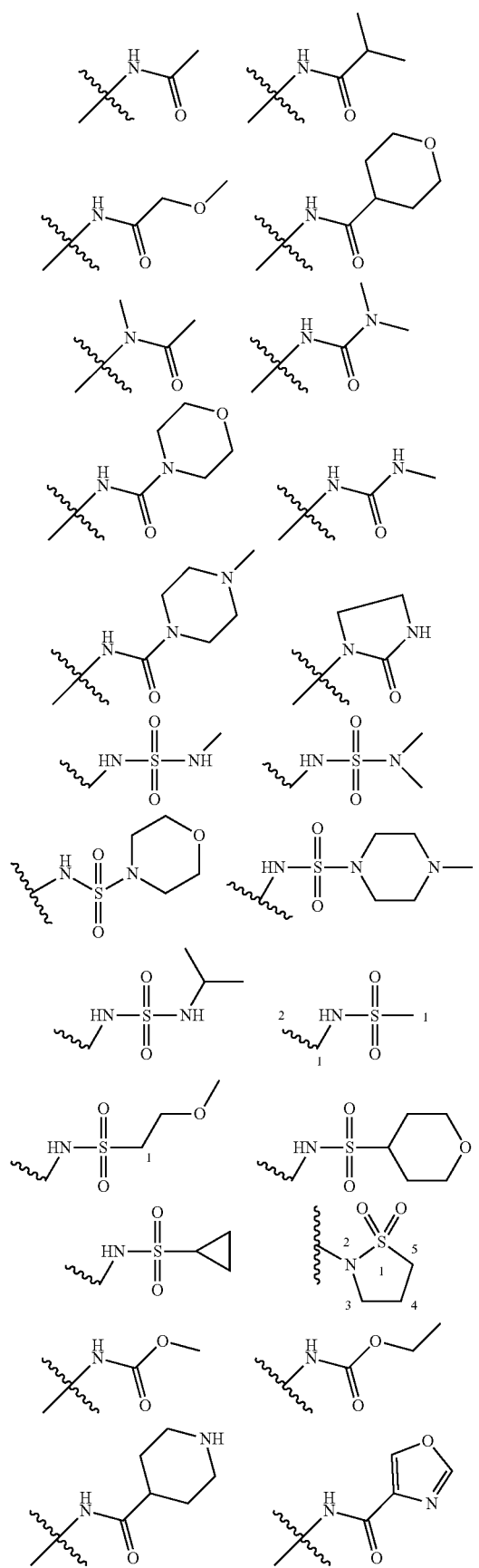
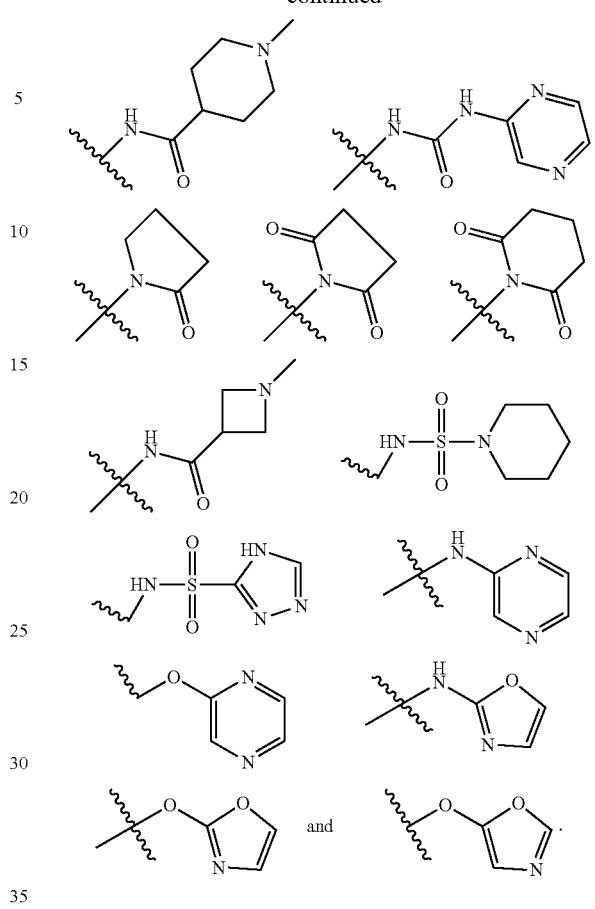
20. The compound of claim 19 an enantiomer or diastereomer, or a pharmaceutically acceptable salt thereof, wherein $R^1$ is difluorochloromethyl; $R^2$ is —H; $R^3$ is —H; $R^4$ is —$C_{1-6}$alkyl or -cycloalkyl; $R^5$ and $R^6$ are —H; L is —O—; and Ar is:
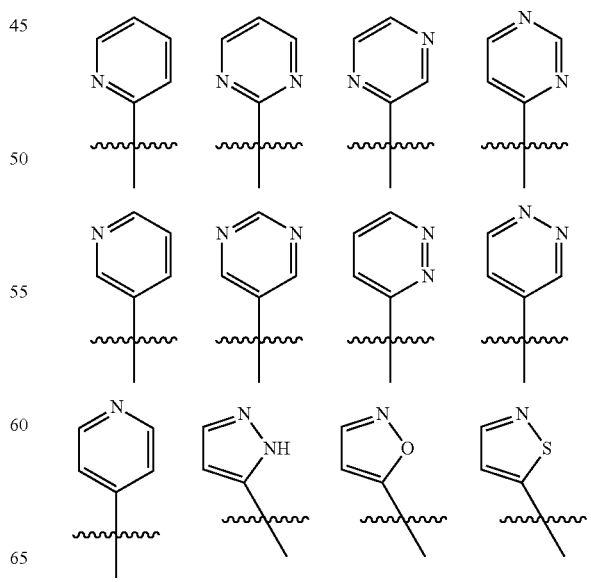

-continued

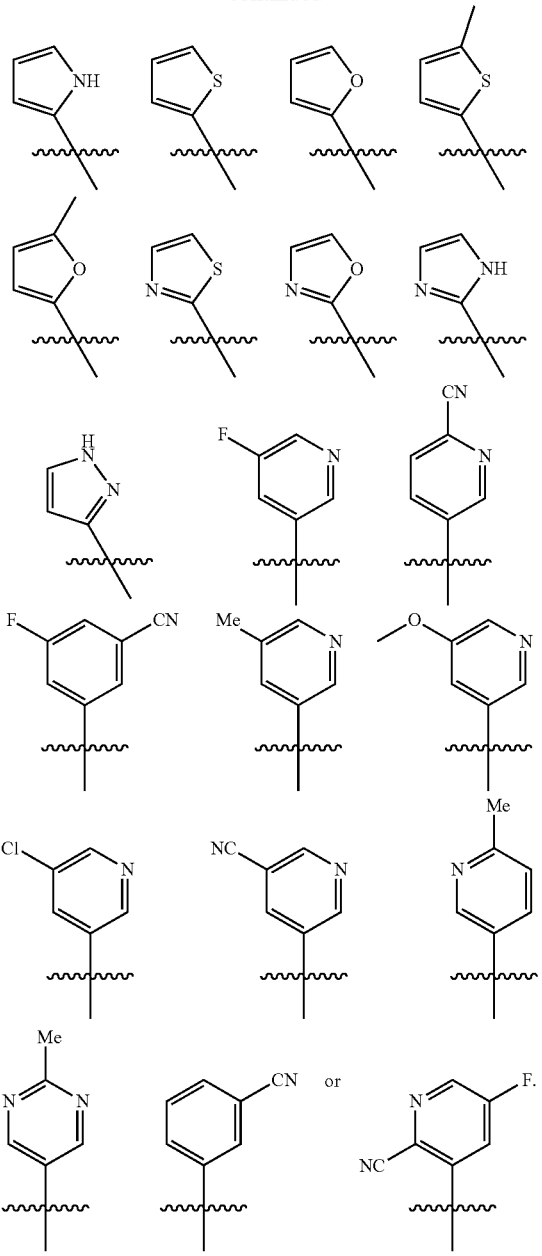

21. The compound of claim 20, or an enantiomer or diastereomer, or a pharmaceutically acceptable salt thereof, wherein each $R^7$, $R^{7'}$, $R^8$, and $R^{8'}$ is independently H, and Ar is phenyl, pyrazoly, pyridinyl, pyrimidinyl, pyridazinyl, or pyrazinyl, any of which is substituted with 0, 1, 2, or 3 substituents comprising halo, —CN, —$C_{1-6}$alkyl, and —$C_{1-6}$alkoxy.

22. The compound of claim 20, or an enantiomer or diastereomer, or a pharmaceutically acceptable salt thereof, wherein each $R^7$, $R^{7'}$, $R^8$, and $R^{8'}$ is independently H, and Ar is pyrazolyl.

23. The compound of claim 22, or an enantiomer or diastereomer, or a pharmaceutically acceptable salt thereof, wherein pyrazolyl is 1H-pyrazol-5yl.

24. The compound of claim 14, or an enantiomer or diastereomer, or a pharmaceutically acceptable salt thereof, wherein each $R^7$, $R^{7'}$, $R^8$, and $R^{8'}$ is independently —H,
—$OR^{12}$, —$C(=O)R^{12}$, or —$C(=O)O(C_{1-6}alkyl)$-, or —$N(R^{12})_2$, wherein each $R^{12}$ is independently H, $C_{1-6}$alkyl, heterocycloalkyl, or heteroaryl.

25. The compound of claim 14, or an enantiomer or diastereomer, or a pharmaceutically acceptable salt thereof, wherein each $R^7$, $R^{7'}$, $R^8$, and $R^{8'}$ are independently —H, —$NR^{11}C(=O)R^{12}$, —$NR^{11}SO_2R_{12}$, or —$NR^{11}C(=O)N(R^{12})_2$, wherein $R^{11}$ is H, and each $R^{12}$ is independently $C_{1-6}$alkyl, —$C_{1-6}$alkoxy, heterocycloalkyl, or heteroaryl.

26. The compound of claim 14 which is a compound of formula IB-11:

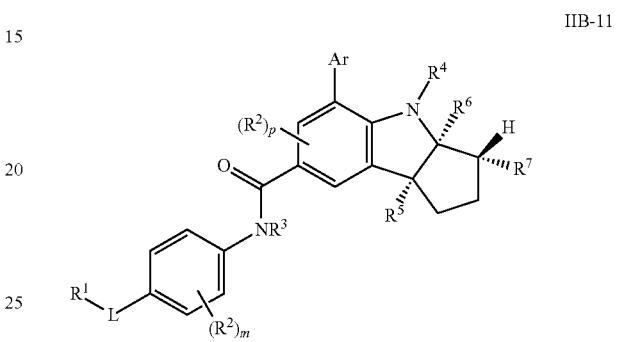

or a pharmaceutically acceptable salt thereof.

27. The compound of claim 1 which is a compound of formula I:

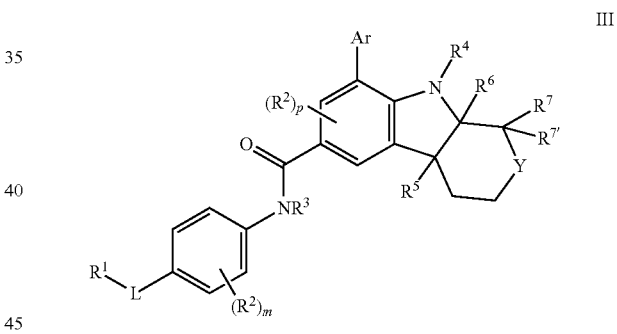

or an enantiomer or diastereomer, or a pharmaceutically acceptable salt thereof, wherein:
$R^1$ is —$C_{1-6}$alkyl, cycloalkyl, or heterocycloalkyl;
each $R^2$ is independently —H, -halo, —OH, —CN, —$NH_2$, —$NO_2$, —$C_{1-6}$alkyl, or —$C_{1-6}$alkoxy;
wherein m is 0, 1, 2, 3, or 1 p is 0, 1 or 2;
$R^3$ is —H or —$C_{1-6}$alkyl;
$R^4$ is —H or —$C_{1-6}$alkyl;
$R^5$ and $R^6$ are each independently —H or —$C_{1-6}$alkyl;
Ar is aryl or heteroaryl;
L is —S—, —O—, —$N(R^{11})$—, —$C(=O)N(R^{11})$—, —$C(=O)N(R^{11})$—$C_{1-4}$alkyl-, —$N(R^{11})C(=O)$—, —$N(R^{11})C(=O)$—$C_{1-4}$alkyl-, —$SO_2N(R^{11})$—, or —$N(R^{11})SO_2$—;
Y is —$C(R^8R^{8'})$—, —O—, —$N(R^{10})$—, $C(=O)$—, —$SO_2$—;
$R^7$, $R^{7'}$, $R^8$, and $R^{8'}$ each independently comprises:
1) —H,
2) —$C_{1-6}$alkyl,
3) -cycloalkyl,
4) -heterocycloalkyl, 5) —OR¹²,
6) —N(R¹²)₂,
7) —NR¹¹C(=O)R¹²,
8) —NR¹¹C(=O)OR¹²,
9) —NR¹¹C(=O)N(R¹²)₂,
10) —NR¹¹SO₂R¹²,
11) —NR¹¹SO₂N(R¹²),
12) —C(=O)R¹²,
13) —C(=O)O(C₁-C₆ alkyl),
14) —C(=O)N(R¹²)₂,
15) —SO₂R¹²,
16) —SO₂N(R¹²)₂,
17) -aryl, or
18) -heteroaryl;

R¹⁰ is —H, —C₁₋₆alkyl, -cycloalkyl, heterocycloalkyl, —C(=O)R¹², —C(=O)OR¹²—, —C(=O)N(R¹²)₂, —SO₂R¹², —SO₂N(R¹²)₂, aryl, or heteroaryl;

each R¹¹ is independently —H or —C₁₋₆alkyl; and
each R¹² is independently —H, —C₁₋₆alkyl, —C₁₋₆alkoxy, -cycloalkyl, heterocycloalkyl, aryl, or heteroaryl;

wherein at each occurrence alkyl is substituted with 0, 1, 2, 3, or 4 substituents comprising halo, -oxo, —OH, —CN, —NH₂, —NO₂, —SO₂(C₁₋₆alkyl), —C₁₋₆alkoxy, -cycloalkyl, -heterocycloalkyl, aryl, and heteroaryl;

wherein at each occurrence cycloalkyl and heterocycloalkyl are substituted with 0, 1, 2, 3, or 4 substituents comprising halo, -oxo, —OH, —CN, —NH₂, —NO₂, —C₁₋₆alkyl, —SO₂(C₁₋₆alkyl), —CO(C₁₋₆alkyl), —C₁₋₆alkoxy, aryl, and heteroaryl;

wherein at each occurrence aryl and heteroaryl are substituted with 0, 1, 2, or 3 substituents comprising halo, —OH, —CN, —NH₂, NO₂, —NH(C₁₋₆alkyl), —N(C₁₋₆alkyl)₂, —C₁₋₆alkyl, -cycloalkyl, -heterocycloalkyl, and —C₁₋₆alkoxy.

28. A compound, which is

| Compound No. | Compound Structure |
| --- | --- |
| 1 | 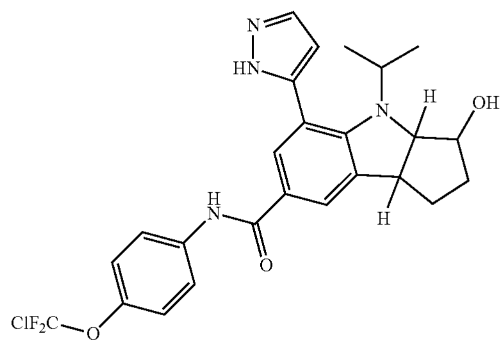 |
| 2 | 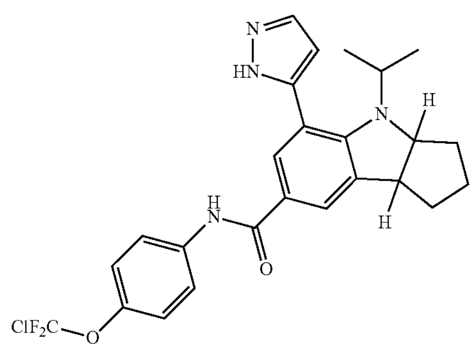 |
| 3 | 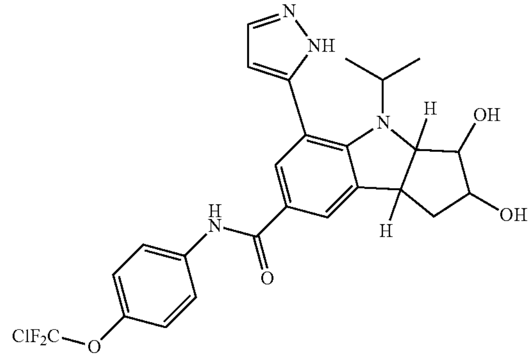 |

| Compound No. | Compound Structure |
|---|---|
| 4 | 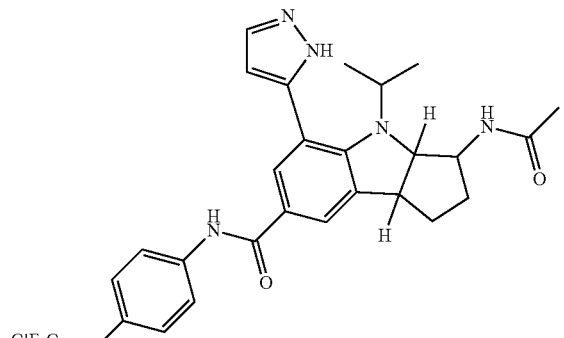 |
| 5 | 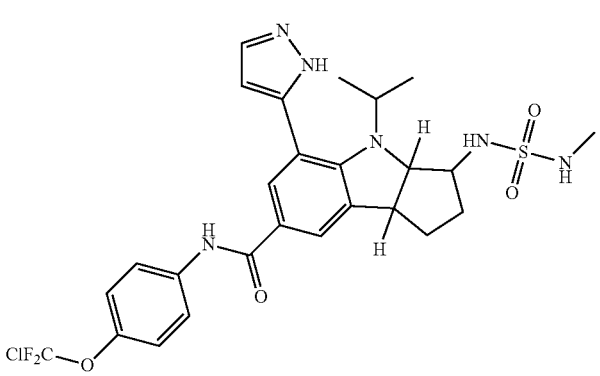 |
| 6 | 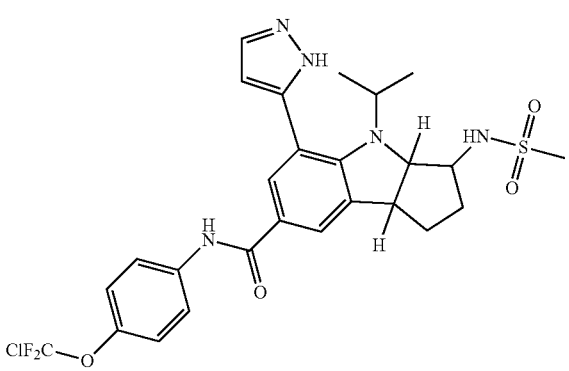 |
| 7 | 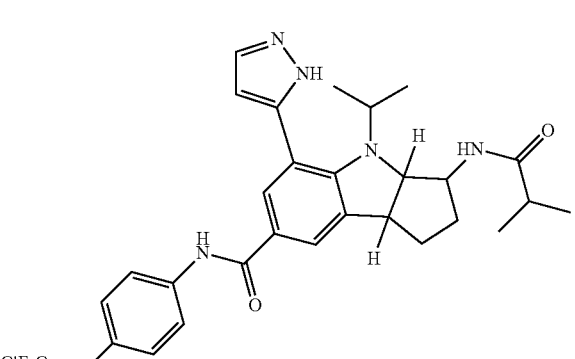 |

-continued

| Compound No. | Compound Structure |
|---|---|
| 8 | 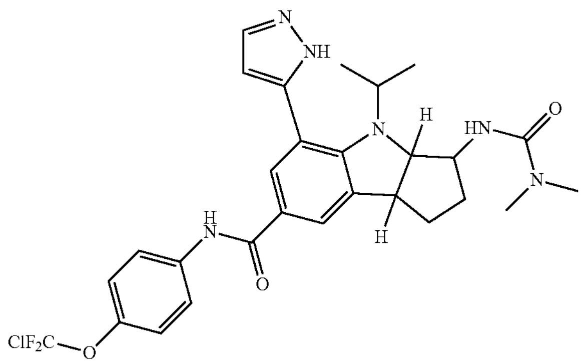 |
| 9 | 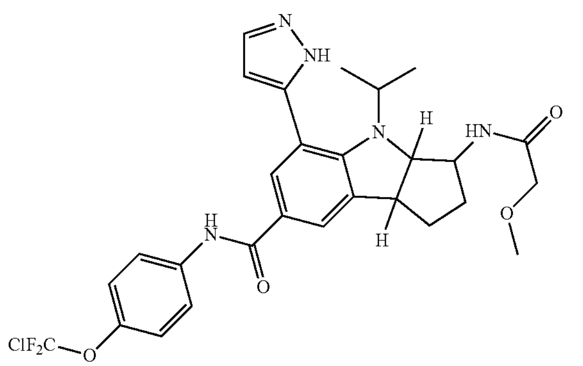 |
| 10 | 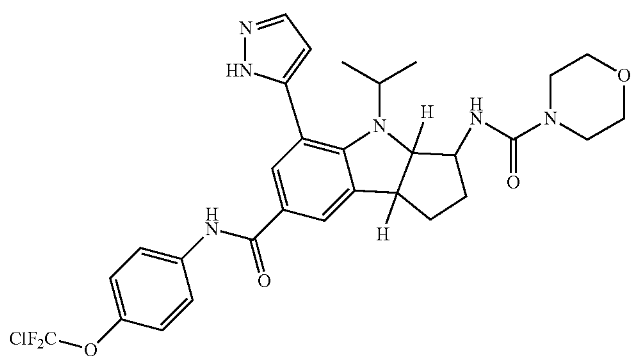 |
| 11 | 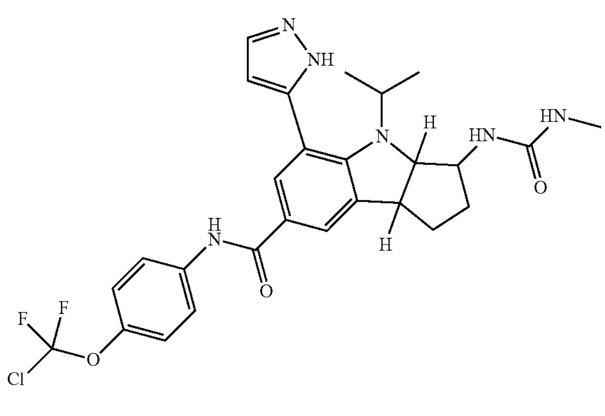 [SMILES: CNC(=O)NC1CCC2c3cc(C(=O)Nc4ccc(OC(F)(F)Cl)cc4)cc(-c4ccn[nH]4)c3N(C(C)C)C12] |

-continued
| Compound No. | Compound Structure |
|---|---|
| 12 | 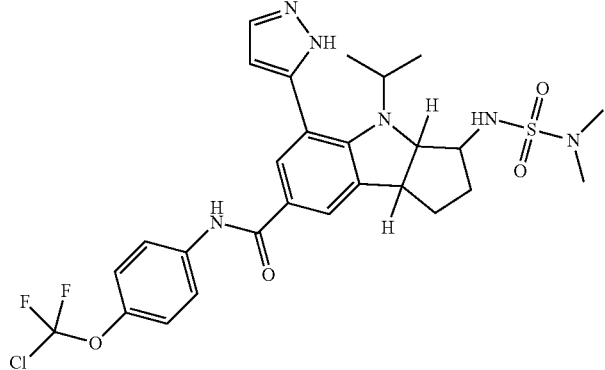 [SMILES: CC(C)N1c2c(-c3ccn[nH]3)cc(C(=O)Nc3ccc(OC(F)(F)Cl)cc3)cc2C2CCC(NS(=O)(=O)N(C)C)C21] |
| 13 | 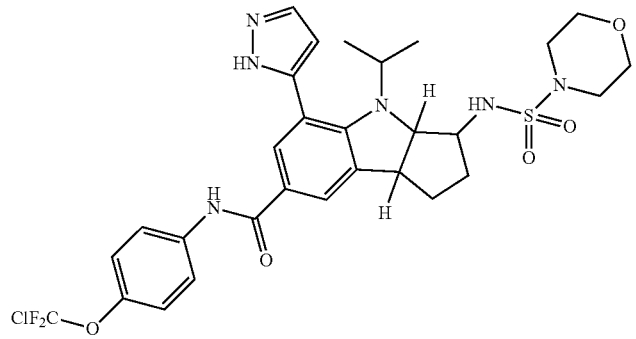 |
| 14 | 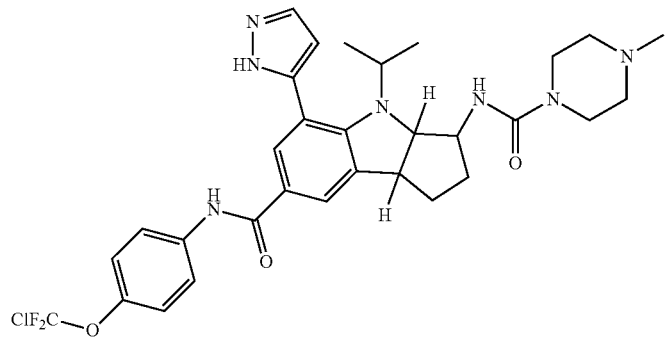 |
| 15 | 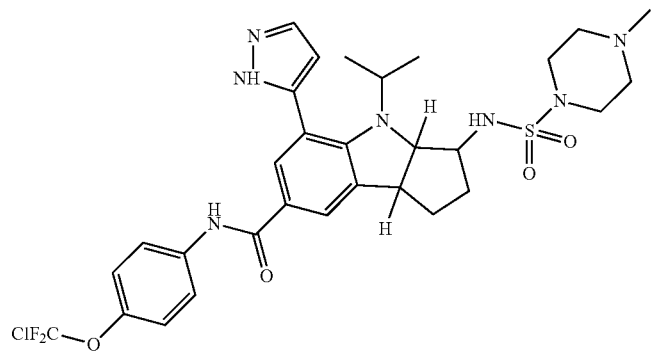 |

-continued
| Compound No. | Compound Structure |
|---|---|
| 16 | 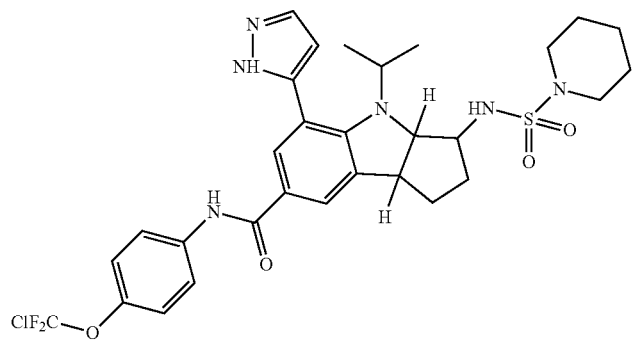 |
| 17 | 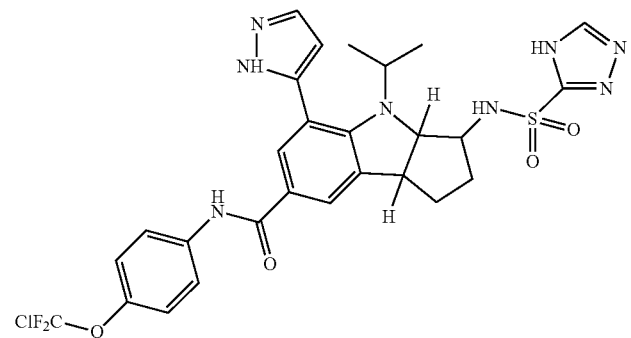 |
| 18 | 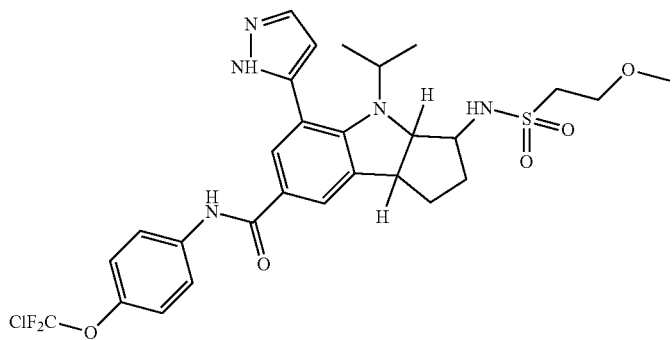 |
| 19 | 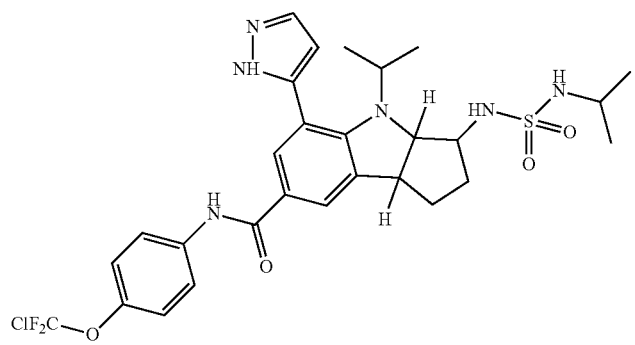 |

| Compound No. | Compound Structure |
|---|---|
| 20 | 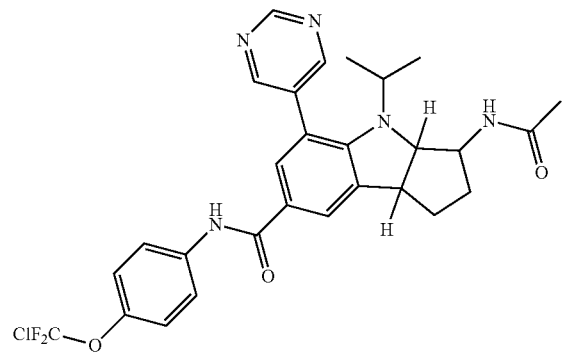 |
| 21 | 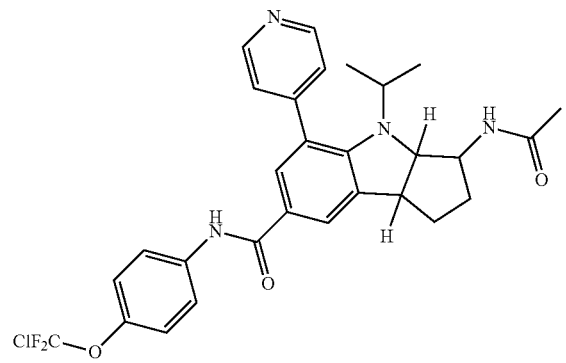 |
| 22 | 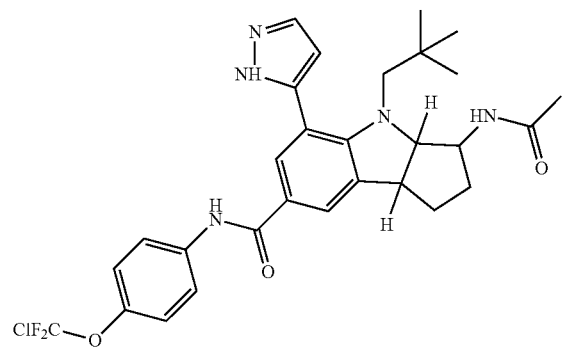 |
| 23 | 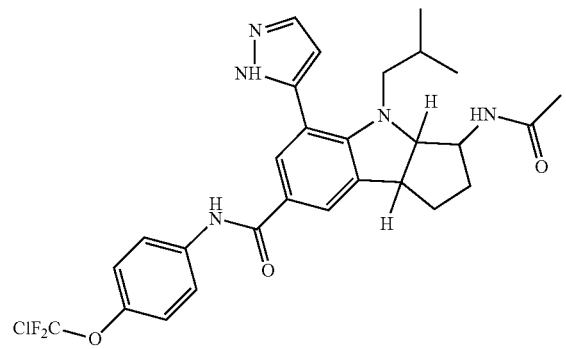 |

-continued

| Compound No. | Compound Structure |
|---|---|
| 24 | 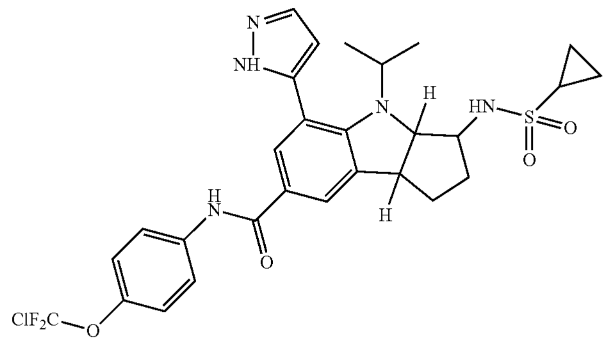 |
| 25 | 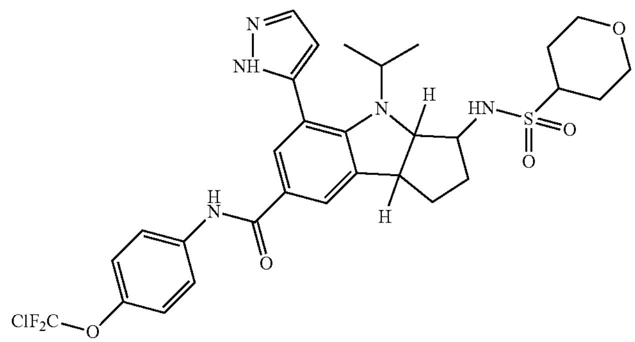 |
| 26 | 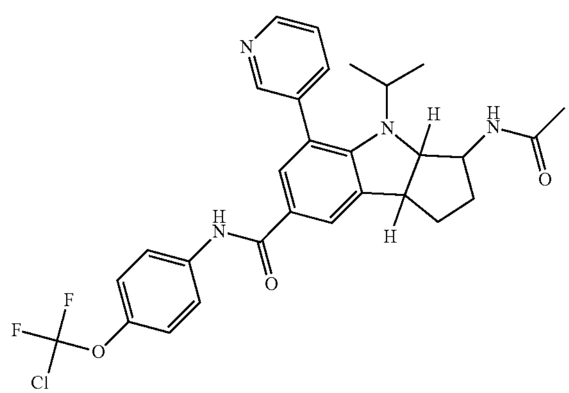 [SMILES: CC(=O)NC1CCC2c3cc(C(=O)Nc4ccc(OC(F)(F)Cl)cc4)cc(-c4cccnc4)c3N(C(C)C)C12] |
| 27 | 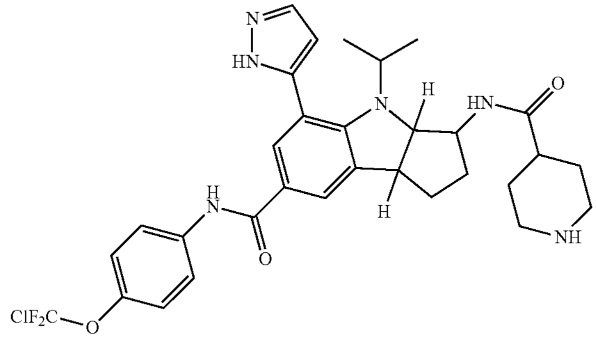 |

| Compound No. | Compound Structure |
|---|---|
| 28 | 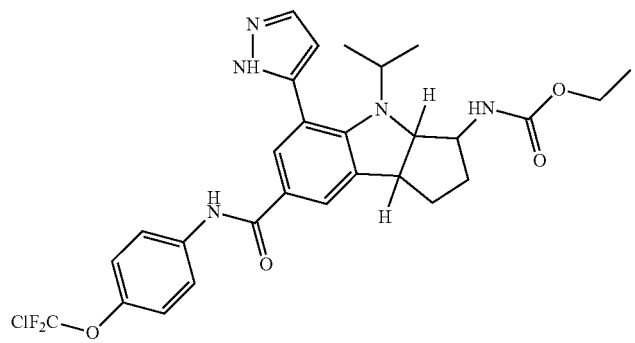 |
| 29 | 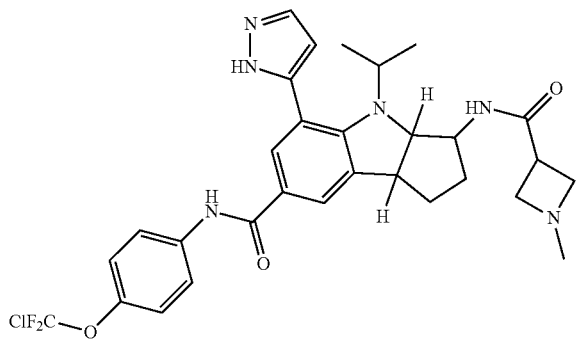 |
| 30 | 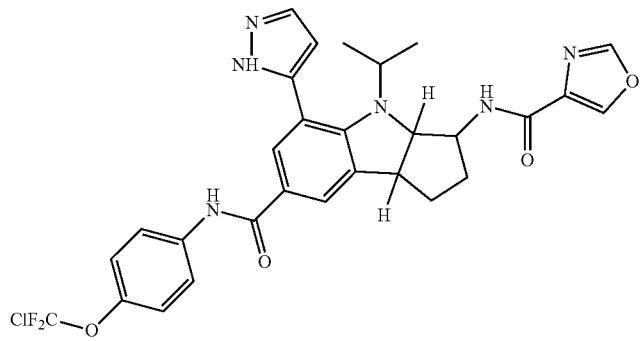 |
| 31 | 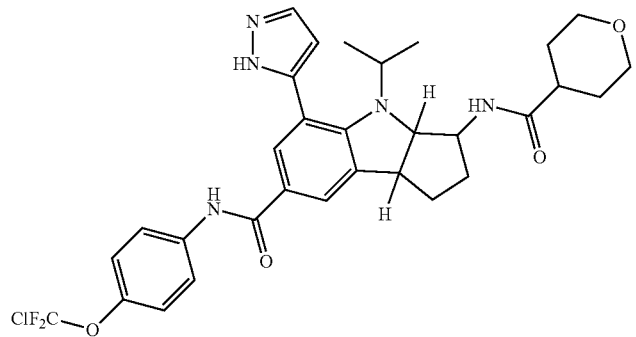 |

| Compound No. | Compound Structure |
|---|---|
| 32 | 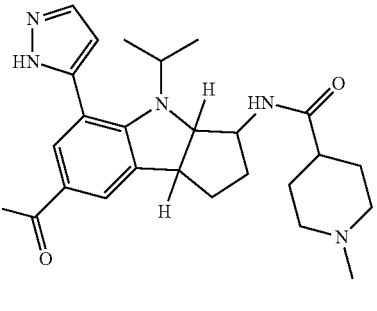 |
| 33 | 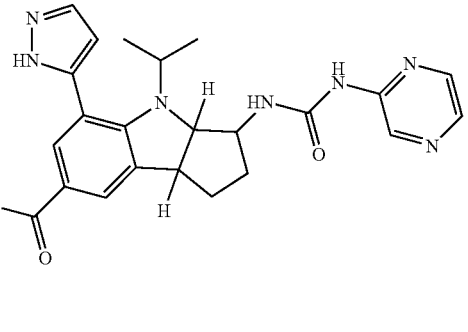 |
| 34 | 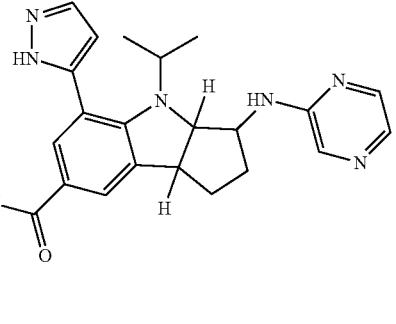 |
| 35 | 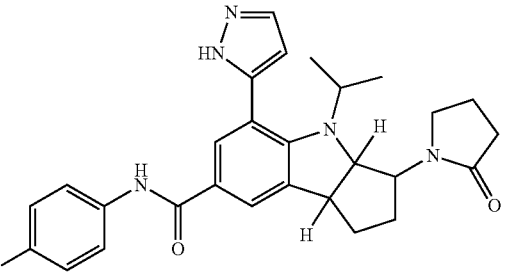 |
| 36 | 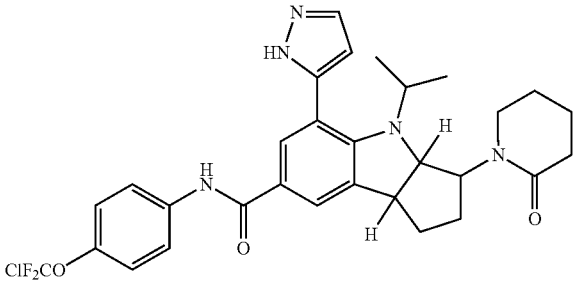 |

| Compound No. | Compound Structure |
|---|---|
| 37 | 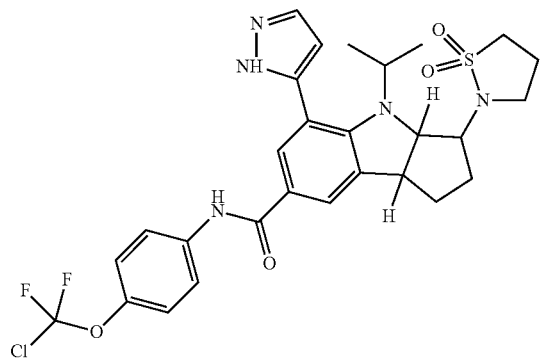 [SMILES: CC(C)N1c2c(-c3ccn[nH]3)cc(C(=O)Nc3ccc(OC(F)(F)Cl)cc3)cc2C2CCC(N3CCCS3(=O)=O)C21] |
| 38 | 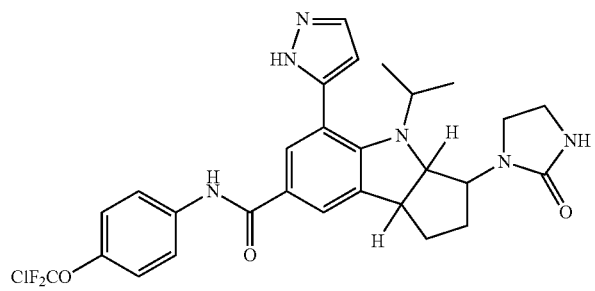 |
| 39 | 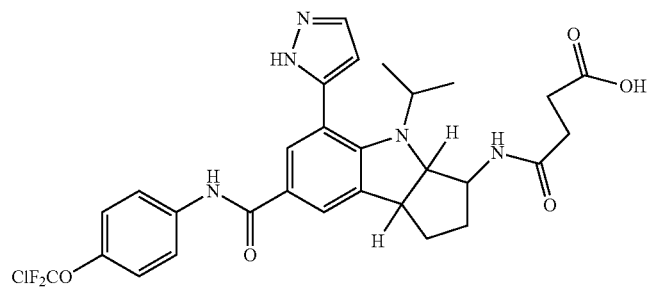 |
| 40 | 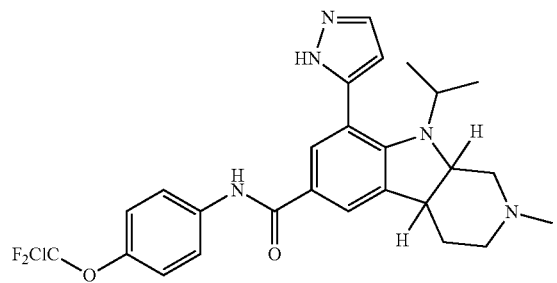 |
| 41 | 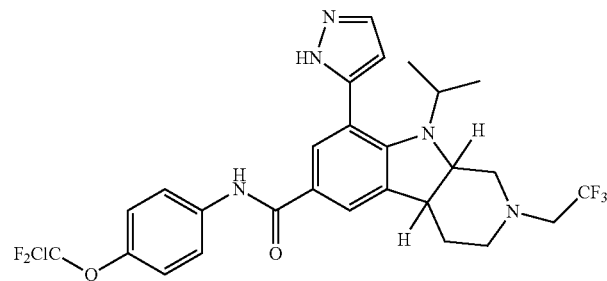 |

-continued
| Compound No. | Compound Structure |
|---|---|
| 42 | 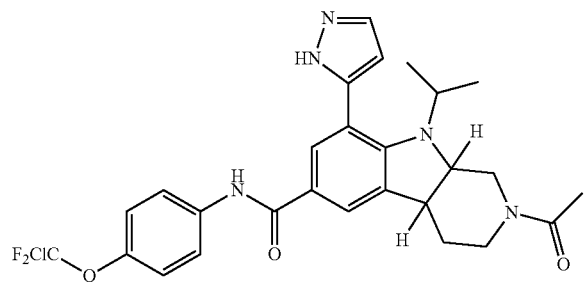 |
| 43 | 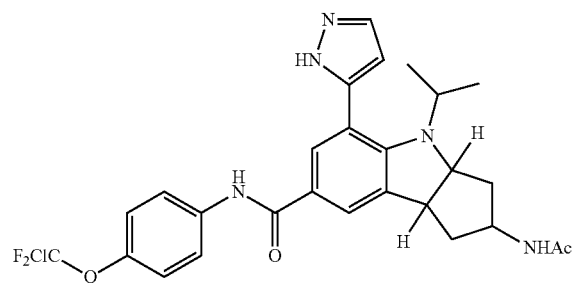 |
| 44 | 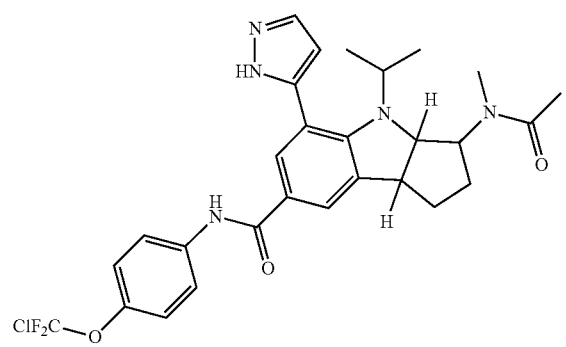 |
| 45 | 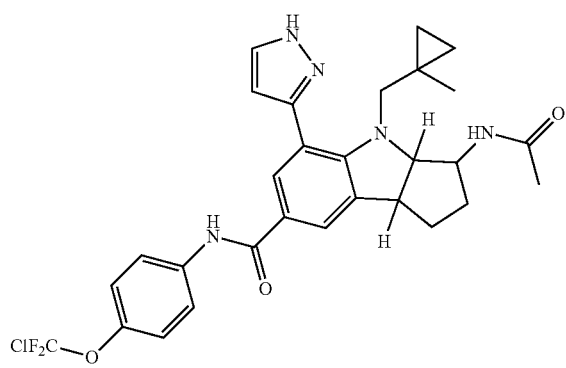 |

-continued
| Compound No. | Compound Structure |
|---|---|
| 46 | 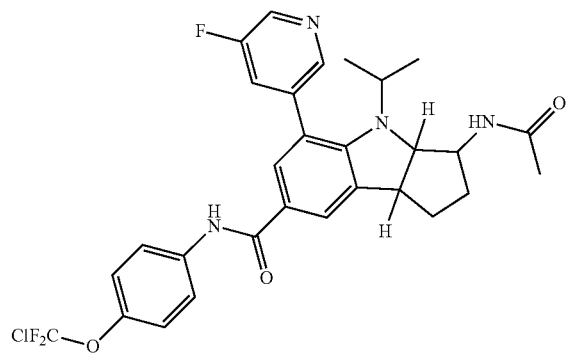 |
| 47 | 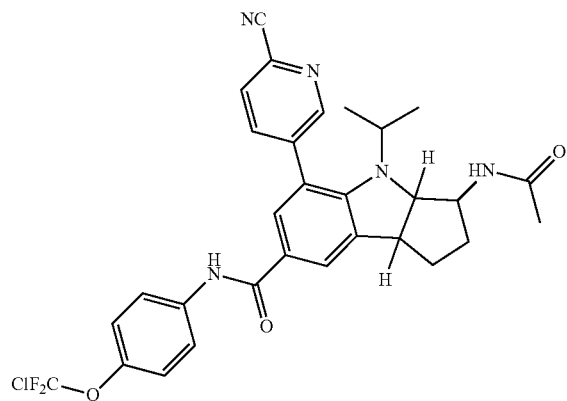 |
| 48 | 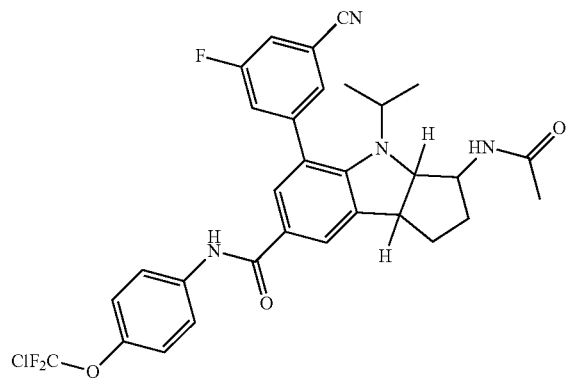 |
| 49 | 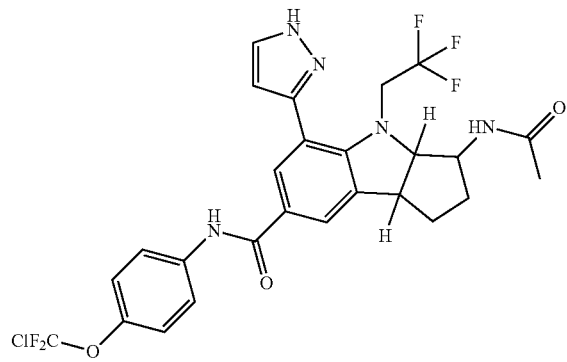 |

-continued
| Compound No. | Compound Structure |
|---|---|
| 50 | 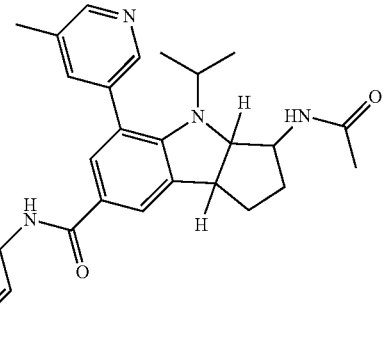 |
| 51 | 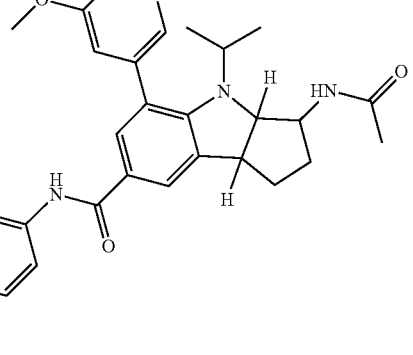 |
| 52 | 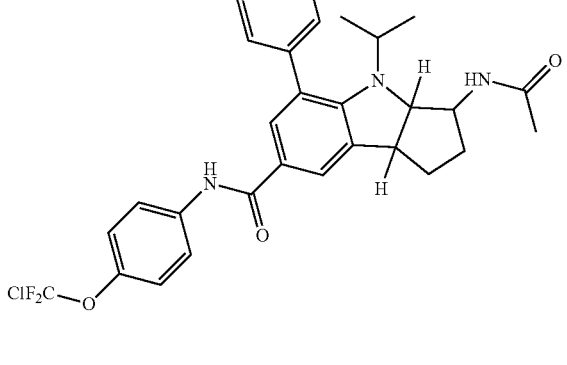 |
| 53 | 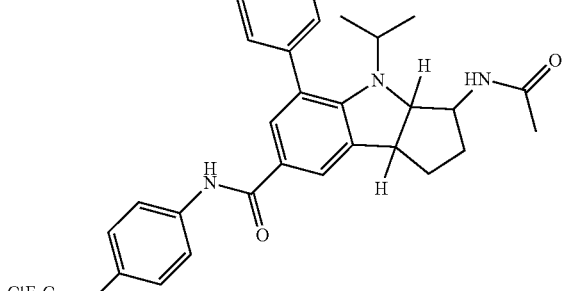 |

US 11,987,575 B2
247                                                                 248
-continued
| Compound No. | Compound Structure |
|---|---|
| 54 | 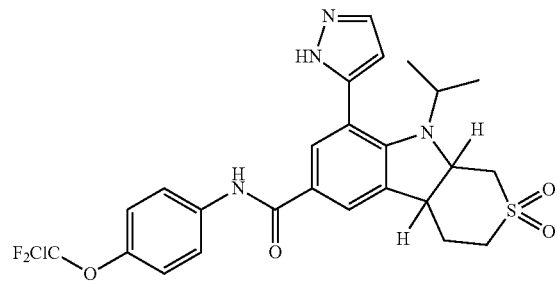 |
| 55 | 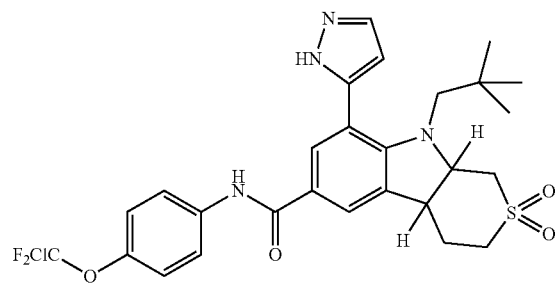 |
| 56 | 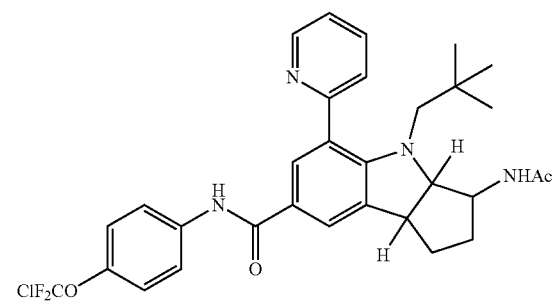 |
| 57 | 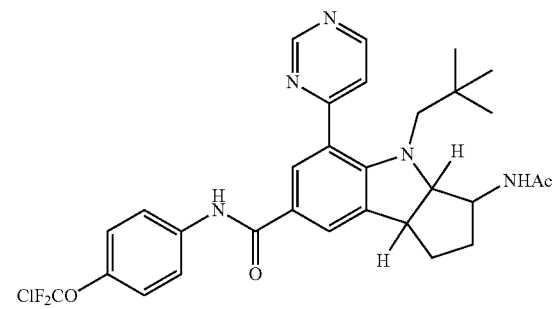 |
| 58 | 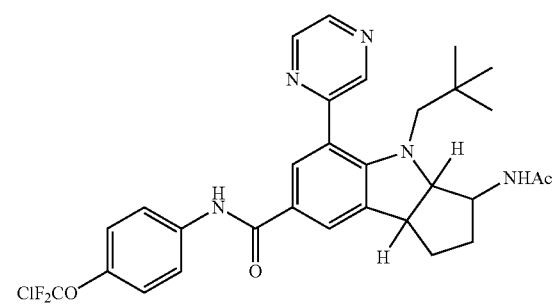 |

-continued
| Compound No. | Compound Structure |
|---|---|
| 59 | 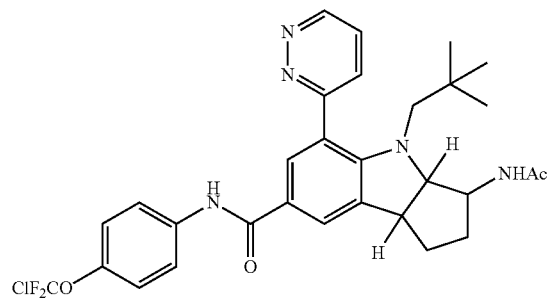 |
| 60 | 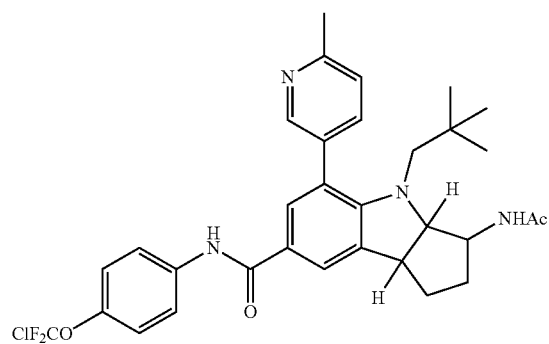 |
| 61 | 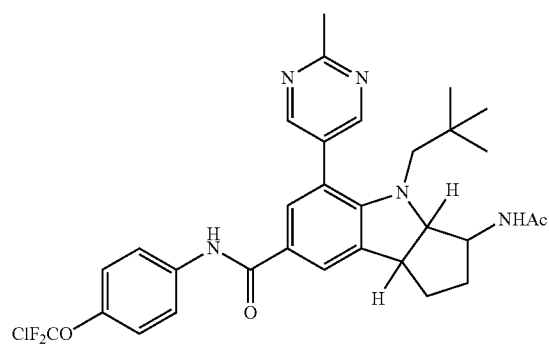 |
| 62 | 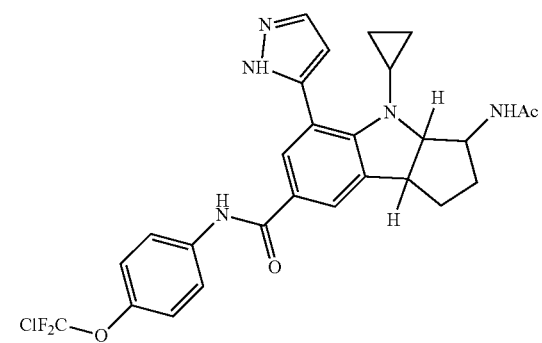 |

-continued

| Compound No. | Compound Structure |
| --- | --- |
| 63 | 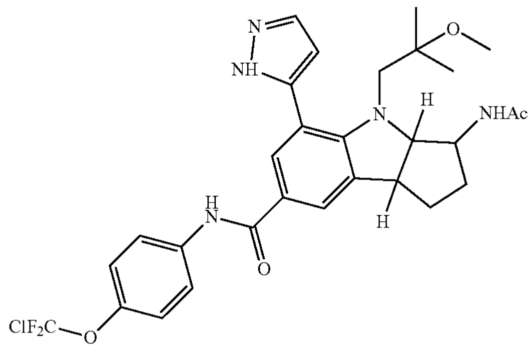 |
| 64 | 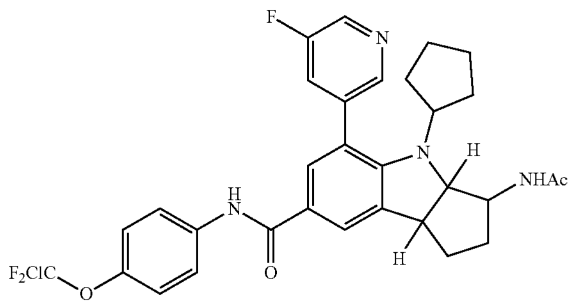 |
| 65 | 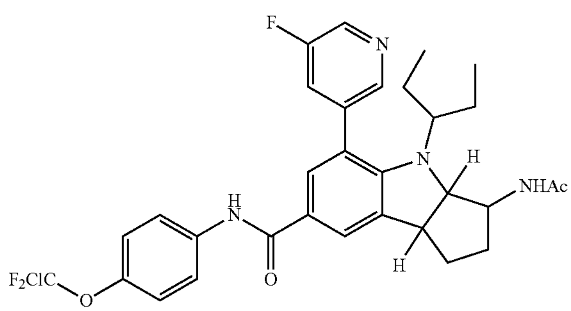 |
| 66 | 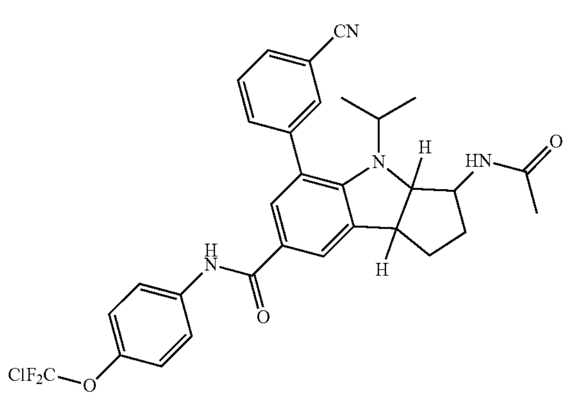 |

-continued
| Compound No. | Compound Structure |
|---|---|
| 67 | 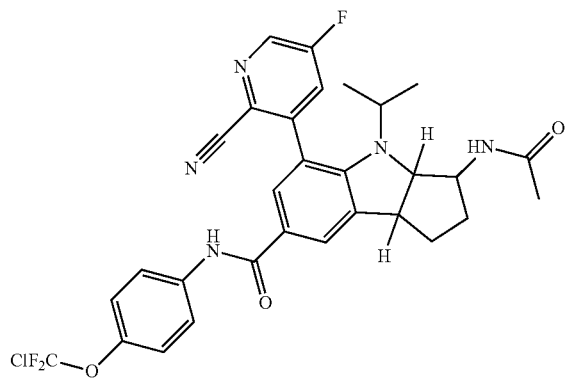 |
or an enantiomer or diastereomer, or a pharmaceutically acceptable salt thereof.
29. A compound, which is
| Compound No. | Compound Structure |
|---|---|
| 4-A | 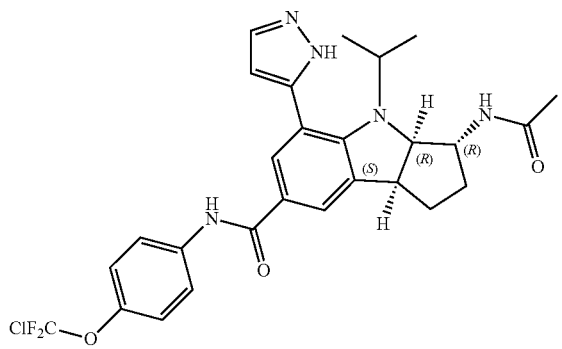 |
| 20-A | 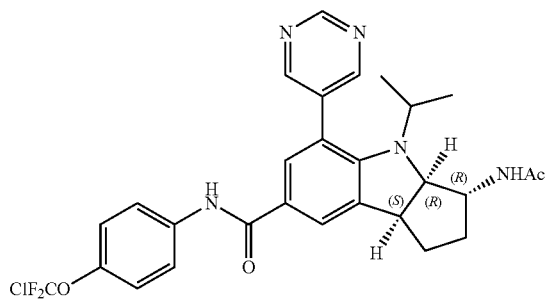 |
| 22-A | 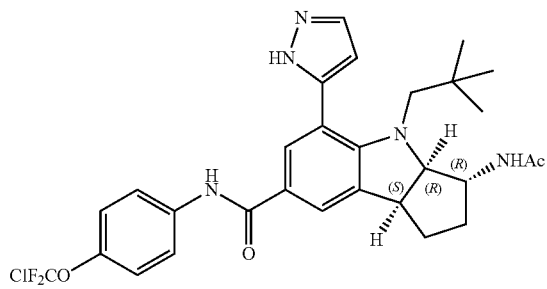 |

-continued

| Compound No. | Compound Structure |
|---|---|
| 26-A | 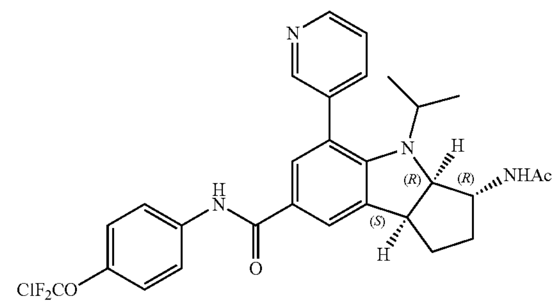 |
| 46-A | 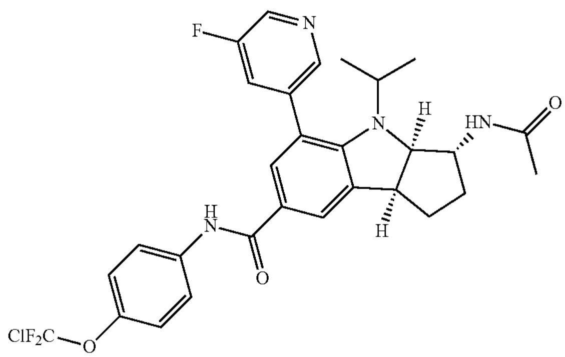 |
| 47-A | 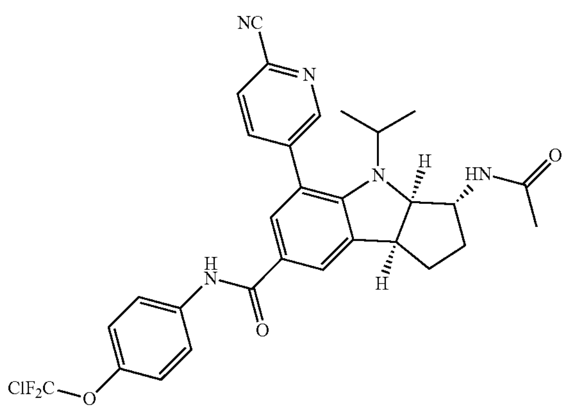 |
| 48-A | 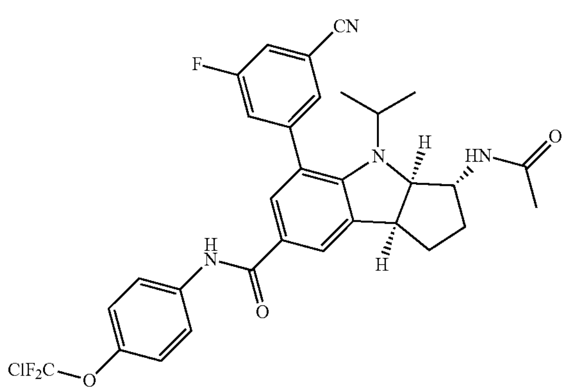 |

| Compound No. | Compound Structure |
|---|---|
| 50-A | 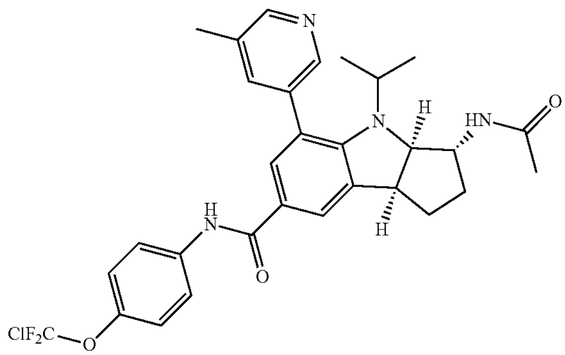 |
| 51-A | 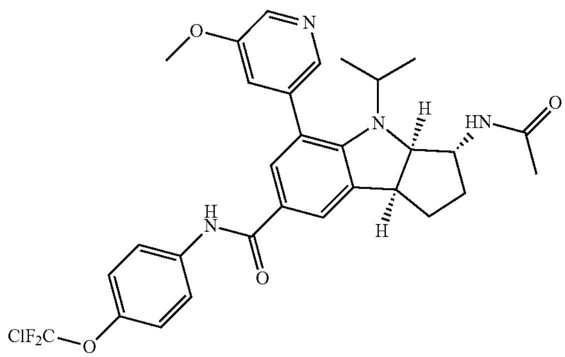 |
| 52-A | 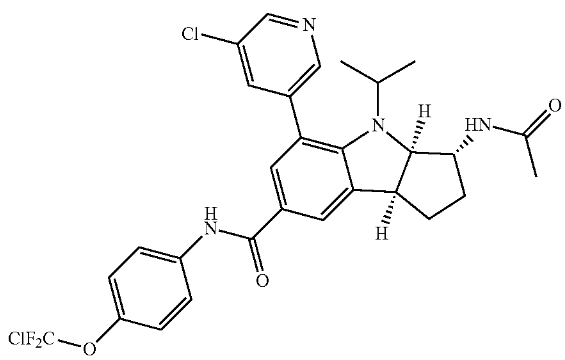 |
| 53-A | 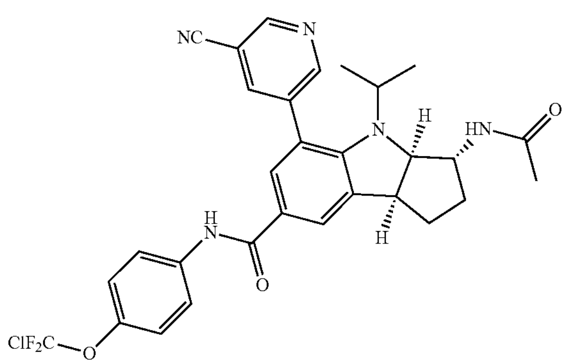 |

| Compound No. | Compound Structure |
|---|---|
| 54-A | 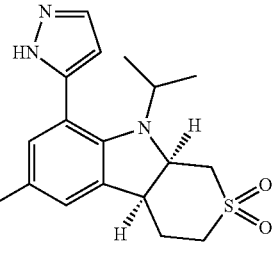 |
| 56-A | 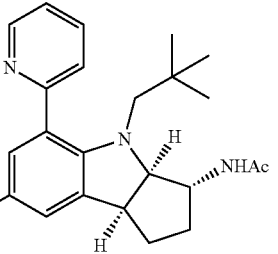 |
| 57-A | 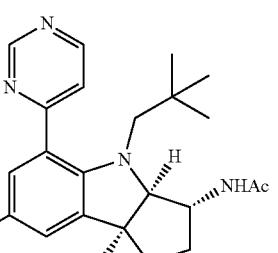 |
| 58-A | 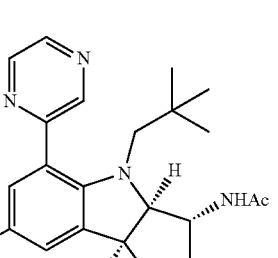 |
| 59-A | 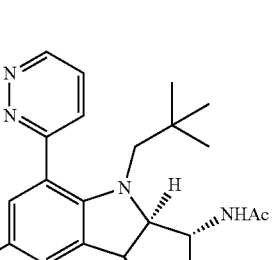 |

-continued

| Compound No. | Compound Structure |
|---|---|
| 60-A | 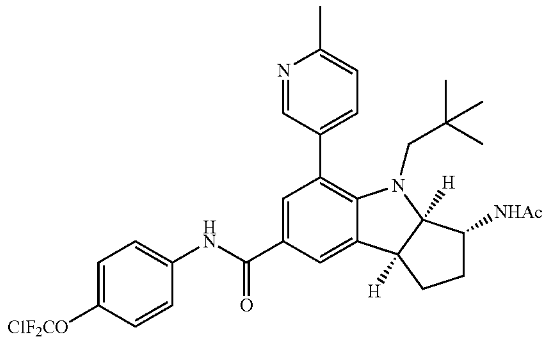 |
| 61-A | 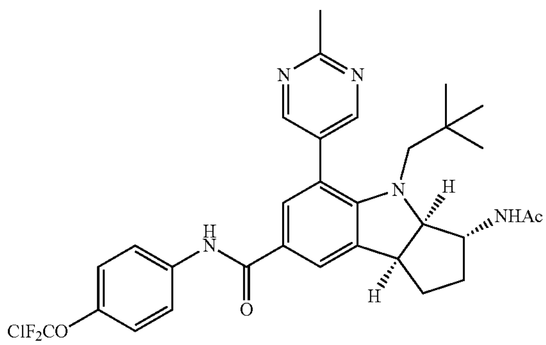 |
| 66-A | 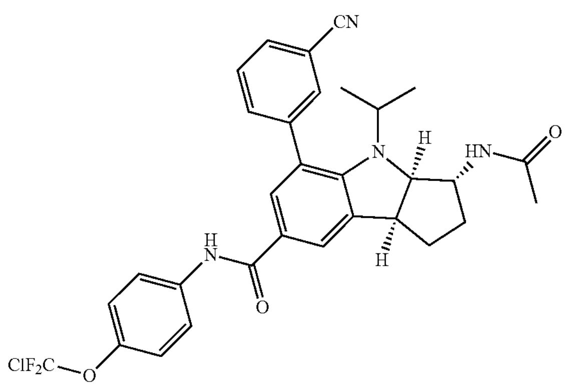 |
| 67-A | | or a pharmaceutically acceptable salt thereof.

30. A method of treating or conditions or diseases associated with enzymatic activity of BCR-ABL1, ABL1 or ABL2 in a subject in need thereof, the method comprising administering to the subject a therapeutically effective amount of the compound of claim 1, or a pharmaceutically acceptable salt thereof.

* * * * *